(12) United States Patent
Jogalekar et al.

(10) Patent No.: US 8,067,424 B2
(45) Date of Patent: Nov. 29, 2011

(54) SELECTIVE INHIBITORS FOR CYCLIN-DEPENDENT KINASES

(75) Inventors: Ashutosh S. Jogalekar, Decatur, GA (US); James P. Snyder, Atlanta, GA (US); Dennis C. Liotta, Atlanta, GA (US); Anthony G. M. Barrett, London (GB); Raoul Charles Dalmedo Stuart Coombes, London (GB); Simak Ali, London (GB); Aleksandra Siwicka, Warsaw (PL); Jan Brackow, Suhr (CH); Bodo Scheiper, Frankfurt am Main (DE)

(73) Assignees: Emory University, Atlanta, GA (US); Imperial College of Science and Technology, London (GB)

( * ) Notice: Subject to any disclaimer, the term of this patent is extended or adjusted under 35 U.S.C. 154(b) by 0 days.

(21) Appl. No.: 12/631,373

(22) Filed: Dec. 4, 2009

(65) Prior Publication Data
US 2010/0261683 A1 Oct. 14, 2010

Related U.S. Application Data

(63) Continuation of application No. PCT/US2008/065988, filed on Jun. 5, 2008.

(60) Provisional application No. 60/942,198, filed on Jun. 5, 2007.

(51) Int. Cl.
*C07D 487/00* (2006.01)
*A01N 43/90* (2006.01)
*C12N 9/12* (2006.01)

(52) U.S. Cl. ........... 514/259.3; 544/281; 435/194

(58) Field of Classification Search ............... None
See application file for complete search history.

(56) References Cited

U.S. PATENT DOCUMENTS
2004/0209878 A1* 10/2004 Guzi et al. ............ 514/234.5

FOREIGN PATENT DOCUMENTS
WO WO 2005/077954 A2 8/2005

OTHER PUBLICATIONS

Bour, G., "Cyclin H binding to the RARalpha activation function (AF)-2 domain directs phosphorylation of the AF-1 domain by cyclin-dependent kinase 7," *Proc. Natl. Acad. Sci., U.S.A.*, 102(46): 16608-16613 (2005).
Chen, D., et al., "Activation of estrogen receptor alpha by S118 phosphorylation involves a ligand-dependent interaction with TFIIH and participation of CDK7," *Mol. Cell.*, 6(1): 127-137 (2000).
Devault, A., et al., "MAT1 (menage á trois) a new RING finger protein subunit stabilizing cyclin H-cdk7 complexes in starfish and Xenopus CAK," *EMBO J.*, 14(20): 5027-36 (1995).
Fischer, P.M., "The use of CDK inhibitors in oncology: a pharmaceutical perspective," *Cell Cycle*, 3(6): 742-6 (2004).
Fisher, R.P., et al., "Alternative mechanisms of CAK assembly require an assembly factor or an activating kinase," *Cell*, 83(1): 47-57 (1995).
Fisher, R.P., "Secrets of a double agent: CDK7 in cell-cycle control and transcription," *J. Cell Sci.*, 118(22): 5171-5180 (2005).
Iben, S., et al., "TFIIH plays an essential role in RNA polymerase I transcription," *Cell*, 109(3): 297-306 (2002).
Lolli, G., and Johnson, L.N., "CAK-Cyclin-dependent Activating Kinase: a key kinase in cell cycle control and a target for drugs?" *Cell Cycle*, 4(4): 572-577 (2005).
Losiewicz, M.D., et al., "Potent inhibition of CDC2 kinase activity by the flavonoid L86-8275," *Biochem. Biophys. Res. Commmun.*, 201(2): 589-595 (1994).
Knockaert, M., et al., "Pharmacological inhibitors of cyclin-dependent kinases," *Trends Pharmacol. Sci.*, 23(9): 417-425 (2002).
Wang, S., et al., "Synthesis and configuration of the cyclin-dependent kinase inhibitor roscovitine and its enantiomer," *Tetrahedron: Asymmetry*, 12(20): 2891-2894 (2001).
Williamson, D.S., et al., "Structure-guided design of pyrazolo[1,5-a]pyrimidines as inhibitors of human cyclin-dependent kinase 2," *Bioorg. Med. Chem. Lett.*, 15(4): 863-867 (2005).

* cited by examiner

*Primary Examiner* — Brandon Fetterolf
*Assistant Examiner* — Anna Pagonakis
(74) *Attorney, Agent, or Firm* — King & Spalding

(57) ABSTRACT

This invention provides a class of compounds which are useful for specifically inhibiting cyclin-dependent kinases. This class of compounds finds use in treating diseases resulting from inappropriate activity of cyclin-dependent kinases, including cancer, viral infections (e.g., HIV) neurodegenerative disorders (e.g. Alzheimer's disease), and cardiovascular disorders (e.g. atherosclerosis). Moreover, certain members of this class are particularly useful for inhibiting cyclin-dependent kinase 7 and are especially useful for the treatment of breast cancer.

16 Claims, 9 Drawing Sheets

SEQUENCE LISTING

<160> NUMBER OF SEQ ID NOS: 37

<210> SEQ ID NO 1
<211> LENGTH: 21
<212> TYPE: PRT
<213> ORGANISM: Artificial Sequence
<220> FEATURE:
<223> OTHER INFORMATION: Synthetic

<400> SEQUENCE: 1

Tyr Ser Pro Thr Ser Pro Ser Tyr Ser Pro Thr Ser Pro Ser Tyr Ser
1               5                   10                  15

Pro Thr Ser Pro Ser
            20

<210> SEQ ID NO 2
<211> LENGTH: 25
<212> TYPE: PRT
<213> ORGANISM: Artificial Sequence
<220> FEATURE:
<223> OTHER INFORMATION: Synthetic

<400> SEQUENCE: 2

Tyr Ser Pro Thr Ser Pro Ser Tyr Ser Pro Thr Ser Pro Ser Tyr Ser
1               5                   10                  15

Pro Thr Ser Pro Ser Lys Lys Lys Lys
            20                  25

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Lys Lys Leu Asn Arg Thr Leu Ser Val Ala
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic

<400> SEQUENCE: 4

Gly Arg Pro Arg Thr Ser Ser Phe Ala Glu Gly Lys Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic

<400> SEQUENCE: 5

Lys Lys Leu Arg Arg Thr Leu Ser Val Ala
1               5                   10

<210> SEQ ID NO 6
<211> LENGTH: 7
<212> TYPE: PRT
<213> ORGANISM: Artificial Sequence

```
<220> FEATURE:
<223> OTHER INFORMATION: Synthetic

<400> SEQUENCE: 6

Leu Arg Arg Ala Ser Leu Gly
1               5

<210> SEQ ID NO 7
<211> LENGTH: 39
<212> TYPE: PRT
<213> ORGANISM: Artificial Sequence
<220> FEATURE:
<223> OTHER INFORMATION: Synthetic

<400> SEQUENCE: 7

Lys Thr Phe Cys Gly Thr Pro Glu Tyr Leu Ala Pro Glu Val Arg Arg
1               5                   10                  15

Glu Pro Arg Ile Leu Ser Glu Glu Gln Glu Met Phe Arg Asp Phe
            20                  25                  30

Asp Tyr Ile Ala Asp Trp Cys
        35

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Lys Lys Arg Asn Arg Thr Leu Thr Val
1               5

<210> SEQ ID NO 9
<211> LENGTH: 27
<212> TYPE: PRT
<213> ORGANISM: Artificial Sequence
<220> FEATURE:
<223> OTHER INFORMATION: Synthetic

<400> SEQUENCE: 9

Tyr Arg Arg Ala Ala Val Pro Pro Ser Pro Ser Leu Ser Arg His Ser
1               5                   10                  15

Ser Pro His Gln Ser Pro Glu Asp Glu Glu Glu
            20                  25

<210> SEQ ID NO 10
<211> LENGTH: 32
<212> TYPE: PRT
<213> ORGANISM: Artificial Sequence
<220> FEATURE:
<223> OTHER INFORMATION: Synthetic

<400> SEQUENCE: 10

Lys Glu Ala Lys Glu Lys Arg Gln Glu Gln Ile Ala Lys Arg Arg Arg
1               5                   10                  15

Leu Ser Ser Leu Arg Ala Ser Thr Ser Lys Ser Gly Gly Ser Gln Lys
            20                  25                  30

<210> SEQ ID NO 11
<211> LENGTH: 15
<212> TYPE: PRT
<213> ORGANISM: Artificial Sequence
<220> FEATURE:
<223> OTHER INFORMATION: Synthetic
```

```
<400> SEQUENCE: 11

His Met Arg Ser Ala Met Ser Gly Leu His Leu Val Lys Arg Arg
1               5                   10                  15

<210> SEQ ID NO 12
<211> LENGTH: 23
<212> TYPE: PRT
<213> ORGANISM: Artificial Sequence
<220> FEATURE:
<223> OTHER INFORMATION: Synthetic

<400> SEQUENCE: 12

Lys Lys Lys Val Ser Arg Ser Gly Leu Tyr Arg Ser Pro Ser Met Pro
1               5                   10                  15

Glu Asn Leu Asn Arg Pro Arg
            20

<210> SEQ ID NO 13
<211> LENGTH: 10
<212> TYPE: PRT
<213> ORGANISM: Artificial Sequence
<220> FEATURE:
<223> OTHER INFORMATION: Synthetic

<400> SEQUENCE: 13

Arg Arg Arg Asp Asp Ser Asp Asp Asp
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic

<400> SEQUENCE: 14

Lys Arg Lys Gln Ile Ser Val Arg Gly Leu
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Synthetic

<400> SEQUENCE: 15

Lys Val Glu Lys Ile Gly Glu Gly Thr Tyr Gly Val Val Tyr Lys
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: Synthetic

<400> SEQUENCE: 16

Lys Lys Ile Ser Gly Arg Leu Ser Pro Ile Met Thr Glu Gln
1               5                   10

<210> SEQ ID NO 17
<211> LENGTH: 18
<212> TYPE: PRT
<213> ORGANISM: Artificial Sequence
<220> FEATURE:
<223> OTHER INFORMATION: Synthetic
```

```
<400> SEQUENCE: 17

Arg Arg Lys Asp Leu His Asp Asp Glu Glu Asp Glu Ala Met Ser Ile
1               5                   10                  15

Thr Ala

<210> SEQ ID NO 18
<211> LENGTH: 15
<212> TYPE: PRT
<213> ORGANISM: Artificial Sequence
<220> FEATURE:
<223> OTHER INFORMATION: Synthetic

<400> SEQUENCE: 18

Phe Leu Ala Lys Ser Phe Gly Ser Pro Asn Arg Ala Tyr Lys Lys
1               5                   10                  15

<210> SEQ ID NO 19
<211> LENGTH: 9
<212> TYPE: PRT
<213> ORGANISM: Artificial Sequence
<220> FEATURE:
<223> OTHER INFORMATION: Synthetic

<400> SEQUENCE: 19

Arg Phe Arg Arg Ser Arg Arg Met Ile
1               5

<210> SEQ ID NO 20
<211> LENGTH: 17
<212> TYPE: PRT
<213> ORGANISM: Artificial Sequence
<220> FEATURE:
<223> OTHER INFORMATION: Synthetic

<400> SEQUENCE: 20

Leu Asp Asp Arg His Asp Ser Gly Leu Asp Ser Met Lys Asp Glu Glu
1               5                   10                  15

Tyr

<210> SEQ ID NO 21
<211> LENGTH: 13
<212> TYPE: PRT
<213> ORGANISM: Artificial Sequence
<220> FEATURE:
<223> OTHER INFORMATION: Synthetic

<400> SEQUENCE: 21

Lys Lys Pro Pro Gln Arg Ala Thr Ser Asn Val Phe Ala
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic

<400> SEQUENCE: 22

Tyr Leu Arg Arg Arg Leu Ser Asp Ser Asn Phe
1               5                   10

<210> SEQ ID NO 23
<211> LENGTH: 11
<212> TYPE: PRT
<213> ORGANISM: Artificial Sequence
```

```
<220> FEATURE:
<223> OTHER INFORMATION: Synthetic

<400> SEQUENCE: 23

Arg Ser Arg His Ser Ser Tyr Pro Ala Gly Thr
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Synthetic

<400> SEQUENCE: 24

Phe Leu Ala Lys Ser Phe Gly Ser Pro Asn Arg Ala Tyr Lys Lys
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic

<400> SEQUENCE: 25

Arg Ser Arg Ser Arg Ser Arg Ser Arg Ser Arg Ser Arg Ser Arg
1               5                   10                  15

<210> SEQ ID NO 26
<211> LENGTH: 28
<212> TYPE: PRT
<213> ORGANISM: Artificial Sequence
<220> FEATURE:
<223> OTHER INFORMATION: Synthetic

<400> SEQUENCE: 26

Leu Arg Arg Leu Ser Leu Gly Leu Arg Arg Leu Ser Leu Gly Leu Arg
1               5                   10                  15

Arg Leu Ser Leu Gly Leu Arg Arg Leu Ser Leu Gly
            20                  25

<210> SEQ ID NO 27
<211> LENGTH: 15
<212> TYPE: PRT
<213> ORGANISM: Artificial Sequence
<220> FEATURE:
<223> OTHER INFORMATION: Synthetic

<400> SEQUENCE: 27

Arg Lys Lys Phe Gly Glu Ser Lys Thr Lys Thr Lys Glu Phe Leu
1               5                   10                  15

<210> SEQ ID NO 28
<211> LENGTH: 18
<212> TYPE: PRT
<213> ORGANISM: Artificial Sequence
<220> FEATURE:
<223> OTHER INFORMATION: Synthetic

<400> SEQUENCE: 28

Ile Ser Asp Glu Leu Met Asp Ala Thr Phe Ala Asp Gln Glu Ala Lys
1               5                   10                  15

Lys Lys

<210> SEQ ID NO 29
```

```
<211> LENGTH: 14
<212> TYPE: PRT
<213> ORGANISM: Artificial Sequence
<220> FEATURE:
<223> OTHER INFORMATION: Synthetic

<400> SEQUENCE: 29

Lys Lys Ile Ser Gly Arg Leu Ser Pro Ile Met Thr Glu Gln
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic

<400> SEQUENCE: 30

Arg Arg Arg Leu Ser Phe Ala Glu Pro Gly
1               5                   10

<210> SEQ ID NO 31
<211> LENGTH: 23
<212> TYPE: PRT
<213> ORGANISM: Artificial Sequence
<220> FEATURE:
<223> OTHER INFORMATION: Synthetic

<400> SEQUENCE: 31

Ala Lys Pro Lys Gly Asn Lys Asp Tyr His Leu Gln Thr Cys Cys Gly
1               5                   10                  15

Ser Leu Ala Tyr Arg Arg Arg
            20

<210> SEQ ID NO 32
<211> LENGTH: 19
<212> TYPE: PRT
<213> ORGANISM: Artificial Sequence
<220> FEATURE:
<223> OTHER INFORMATION: Synthetic

<400> SEQUENCE: 32

Asp Gly Glu Phe Leu Arg Thr Ser Cys Gly Ser Pro Asn Tyr Ala Ala
1               5                   10                  15

Arg Arg Arg

<210> SEQ ID NO 33
<211> LENGTH: 13
<212> TYPE: PRT
<213> ORGANISM: Artificial Sequence
<220> FEATURE:
<223> OTHER INFORMATION: Synthetic

<400> SEQUENCE: 33

Lys Lys Leu Asn Arg Thr Leu Ser Phe Ala Glu Pro Gly
1               5                   10

<210> SEQ ID NO 34
<211> LENGTH: 15
<212> TYPE: PRT
<213> ORGANISM: Artificial Sequence
<220> FEATURE:
<223> OTHER INFORMATION: Synthetic

<400> SEQUENCE: 34

Glu Arg Met Arg Pro Arg Lys Arg Gln Gly Ser Val Arg Arg Val
1               5                   10                  15
```

```
<210> SEQ ID NO 35
<211> LENGTH: 14
<212> TYPE: PRT
<213> ORGANISM: Artificial Sequence
<220> FEATURE:
<223> OTHER INFORMATION: Synthetic

<400> SEQUENCE: 35

Lys Lys Lys Ser Pro Gly Glu Tyr Val Asn Ile Glu Phe Gly
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Synthetic

<400> SEQUENCE: 36

Lys Lys Ser Arg Gly Asp Tyr Met Thr Met Gln Ile Gly
1               5                   10

<210> SEQ ID NO 37
<211> LENGTH: 23
<212> TYPE: PRT
<213> ORGANISM: Artificial Sequence
<220> FEATURE:
<223> OTHER INFORMATION: Synthetic

<400> SEQUENCE: 37

Lys Lys Lys Lys Glu Arg Leu Leu Asp Asp Arg His Asp Ser Gly Leu
1               5                   10                  15

Asp Ser Met Lys Asp Glu Glu
                20
```

SELECTIVE INHIBITORS FOR CYCLIN-DEPENDENT KINASES

CROSS REFERENCE TO RELATED APPLICATIONS

This application is a continuation application of International Patent Application No. PCT/US2008/065988, filed Jun. 5, 2008, which claims priority to U.S. Provisional Patent Application No. 60/942,198, filed Jun. 5, 2007, which are hereby incorporated by reference in their entirety.

FIELD OF THE INVENTION

This invention relates to compounds that inhibit or modulate the activity of cyclin-dependent kinases (e.g., CDK7) and to the use of these compounds in the treatment and prophylaxis of the diseases mediated by the kinases, such as breast cancer.

BACKGROUND OF THE INVENTION

The process of cell growth and division is divided into four stages that make up the cell cycle: G1, S (DNA synthesis), G2 and M (mitosis). Progression through the cell cycle is a tightly regulated process, and critical to the cell cycle progression are cyclin-dependent kinases (CDKs). CDKs are the catalytic subunits of a large family of serine/threonine protein kinases. Activation of specific CDKs is required for the appropriate progression through a given stage of the cell cycle and into the next stage in the cell cycle. Hence, regulation of CDK activity is pivotal for the correct timing of cell cycle progression and CDK activity is tightly regulated at many levels, including complex formation with cyclins and CDK inhibitors (CDKI), in particular CIP/KIP and INK-type CDKIs, as well as phosphorylation and dephosphorylation. Central to the activation of a given CDK is the requirement for association with cyclins and phosphorylation at a threonine residue in the activation loop (T-loop). Cyclins are synthesized and degraded during the cell cycle (hence their name), so that activation of a particular CDK occurs only when its cyclin partner(s) becomes available. Additionally, many CDKs require phosphorylation of a threonine residue in the activation loop (T-loop) for their activation. In the case of CDK1, CDK2, CDK4 and CDK6 T-loop phosphorylation is mediated by the CDK activating kinase (CAK).

Deregulation of CDK activity forms an important part of many disease states, generally through elevated and/or inappropriate activation, as CDKs are infrequently mutated. Important mechanisms of CDK deregulation include cyclin overexpression. For example, the cyclin D1 gene is frequently amplified in cancer (Fu et al. *Endocrinology* 145: 5439-5447 (2004)). CDKI expression is frequently lost, for example, through mutational or epigenetic alterations in genes encoding INK4, CIP or KIP CDKIs in cancer (Malumbres and Barbacid, *Nature Reviews Cancer* 1, 223-231 (2001)).

CDKs are important targets for the design of drugs with antimimotic, antineurodegenerative, antiviral and antitumor effects. A few specific and high-affinity inhibitors of some CDKs have been developed using CDK2 as a model system. One of these is flavopiridol (clinical phase I/II), which has modest selectivity for CDKs over other kinases and inhibits many members of the CDK family (M. D. Losiewicz et al., *Biochem. Biophys. Res. Commun.*, 201, 589-595 (1994)). One compound class that has yielded many CDK-selective ATP antagonists is 2,6,9-trisubstituted purines. Within this group, roscovitine shows good biological and pharmacological properties (clinical phase I/II) (S. Wang et al., *Tetrahedron: Asymmetry*, 12, 2891-2894 (2001); M. Mapelli et al., *J. Med. Chem.*, 48, 671-679 (2005)). Recently, another class of compounds having a pyrazolo[1,5-a]pyrimidine skeleton has been developed. These compounds show a high potency for inhibiting CDK2, and in some cases were shown to inhibit the growth of human colon tumor cells (D. S. Williamson et al., *Bioorg. Med. Chem. Lett.*, 15, 863-867 (2005)). However, most CDK inhibitors that have been described do not specifically inhibit one CDK. For example, most CDK2 inhibitors also inhibit CDK1, CDKS, as well as CDK7 and CDK9 (P. M. Fischer, *Cell Cycle* 3: 742-746). It has also been noted, however, that some inhibitors of structurally similar kinases CDK1, CDK2 and CDKS do not inhibit CDK4 and CDK6 (M. Knockaert et al., *Trends Pharmacol. Sci.*, 23, 417-425 (2002)).

CDK7

While CDK1, CDK2, CDK4 and CDK6 are primarily involved in cell-division control, other cyclin-dependent kinases, such as CDK8 and CDK9, largely regulate transcription. CDK7 is unusual in that it is important in transcription, but also acts as the CDK-activating kinase (CAK) (Lolli and Johnson *Cell Cycle* 4: 572-577 (2005)). The CDK7 CAK complex comprises cyclin H and the ring finger protein MAT1 and is unusual in that its phosphorylation in the T-loop is not required for its activity (R. P. Fisher et al. *Cell* 83: 47-57 (1995); Devault et al. *EMBO J.* 14: 5027-5036 (1995)). In transcription regulation, CDK7/Cyclin H/MAT1 are components of the general transcription factor TFIIH, which is required for initiation of transcription of RNA polymerase II-directed genes. As part of the TFIIH complex, CDK7 phosphorylates the C-terminal domain of the largest subunit of RNA polymerase II (R. P. Fisher *J. Cell Sci.* 118: 5171-5180 (2005)). Additionally, TFIIH plays a role in RNA polymerase I-mediated transcription (Iben et al. *Cell* 109: 297-306 (2002)). Further, CAK or TFIIH-associated CAK phosphorylate several transcription factors to regulate their activities (see, e.g., Chen et al *Mol Cell* 6: 127-137 (2000); Bour et al *PNAS* 102: 16608-16613 (2005)). With respect to cell cycle regulation, the CDK7 CAK complex phosphorylates the cell cycle CDKs in the activation segment (T-loop), required for the activation of CDKs involved in cell cycle regulation (Lolli and Johnson *Cell Cycle* 4: 572-577 (2005)).

SUMMARY OF THE INVENTION

The present invention relates to the application of a class of pyrazolo[1,5-a]pyrimidine-derived compounds as highly specific cyclin-dependent kinase inhibitors. The compounds are suitable for the treatment of diseases resulting from inappropriate activity of cyclin-dependent kinases. Non-limiting examples of such diseases include cancer, viral infections (e.g., HIV) neurodegenerative disorders (e.g., Alzheimer's disease), and cardiovascular disorders (e.g., atherosclerosis).

In certain preferred embodiments, the compounds of the invention are highly specific towards the inhibition of CDK7, and thus may be used in the treatment any disease where abnormal CDK7 activity is implicated, such as refractory breast cancer. In other preferred embodiments, the compounds of the invention are capable of specifically inhibiting more than one cyclin-dependent kinase (e.g., both CDK2 and CDK7).

One aspect of this invention is the recognition that CAK is required for cell cycle progression and is therefore a potential target for therapies, such as in the treatment of cancer. Another aspect of this invention is the recognition that the role of CAK in transcription suggests that CDK7 may be a therapeutic target in HIV (e.g., see M. Knockaert et al., *Trends Pharmacol. Sci.* 23: 417-425 (2002)).

Yet another aspect of this invention is the recognition that 7-amino 3-isopropyl-pyrazolo[1,5-a]pyrimidine derivatives with benzylic substituents on the amino group are particularly effective as specific inhibitors of CDK7.

One object of this invention is to provide a composition comprising a compound with the following structure:

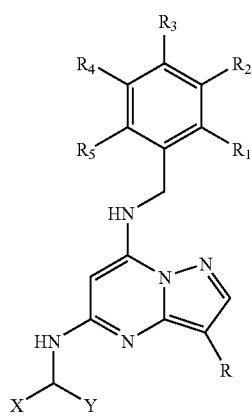

(I)

wherein

R represents a hydrocarbyl containing from 1 to 6 carbon atoms;

$R^1$ represents a hydroxyl, alkoxy, hydrogen, or halogen;

$R^2$ represents a hydrogen, an alkanyl, —$NR_aR_b$ where $R_a$ and $R_b$ are independently optionally substituted hydrocarbyls having up to six carbon atoms, an alkoxy chain having from 1 to 6 carbon atoms, —$SR_c$ where $R_c$ is a hydrocarbyl containing from one to six carbon atoms, —$SO_2R_d$ where Rd is a hydrocarbyl containing from one to six carbon atoms, or a halogen;

$R^3$ is hydrogen, —$SO_2NH_2$, —$SO_2NR_eR_f$ where $R_e$ and $R_f$ are independently optionally substituted hydrocarbyls having up to 6 carbon atoms, halogen or a group -$(A)_a$-$Alk^1$ wherein a is 0 or 1, and when a is 1, A is —O—, —S—, or —$NR^6$ wherein $R^6$ is hydrogen or a $C_1$-$C_5$ alkanyl chain, and $Alk^1$ is an optionally substituted divalent hydrocarbyl chain containing from 1 to 6 carbon atoms in length and optionally unsaturated bonds between at least two carbon atoms of $Alk^1$ when $Alk^1$ contains at least two carbon atoms;

$R^4$ represents hydrogen, halogen, alkoxy, hydroxy, or an optionally substituted hydrocarbyl group containing up to 6 carbon atoms;

$R^5$ represents a hydrogen, hydroxyl, alkoxy, a linear, branched, or cyclic chain with between 1 and 8 carbon atoms, or halogen;

X represents a hydrogen, a group -$Alk^2$-Z, $C_1$-$C_4$ hydrocarbyl group or halogen, wherein $Alk^2$ is an optionally substituted divalent alkanyl, alkenyl, or alkynyl chain containing from 1 to 6 carbon atoms in length; and Z represents an —OH, —$OR^7$, —SH, $SR^7$, —CN, —$NH_2$, or $NHR^7$ group, wherein $R^7$ is a $C_1$-$C_6$ hydrocarbyl or heterocyclic group optionally substituted by halogen or alkoxy;

Y represents a group -$Alk^3$-$(Q)_a$-$Alk^4$-B, wherein a is 0 or 1, and wherein $Alk^3$ represents a hydrocarbyl chain containing from 2 to 7 carbon atoms in length, wherein said hydrocarbyl chain optionally comprises double and/or triple bonds in between carbon atoms of said hydrocarbyl chain, and wherein said hydrocarbyl chain is optionally substituted with a halogen, alkoxy, or an alkyl chain that itself is optionally substituted with halogen, hydroxyl, or alkoxy groups;

Q is selected from the group consisting of —$CH_2$—, —O—, —S—, —NR—, —$S(O_2)$—, —$C(=O)$—, and —$S(O)$—;

$Alk^4$ is an alkanyl chain; and

B is hydroxyl, alkoxy, halogen, alkylthio, nitro, cyano, amine, an optionally substituted carbocyclic group, an optionally substituted heterocyclic group, and wherein X and Y, along with the carbon atom joining X and Y, do not form an unsubstituted $C_1$ to $C_6$ alkyl.

Another object of this invention is to provide a composition comprising a compound with the following structure:

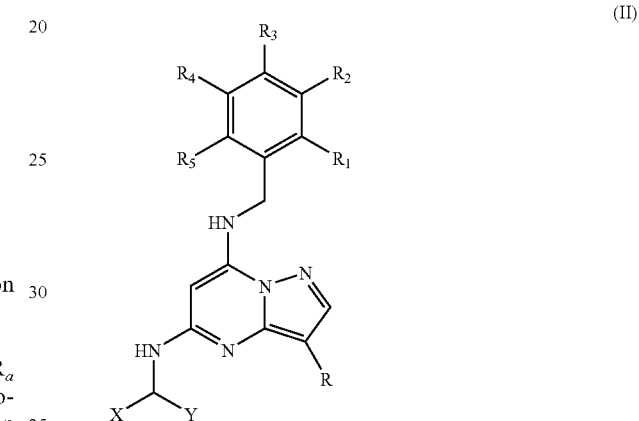

(II)

wherein

R represents a hydrocarbyl containing from 1 to 6 carbon atoms;

$R^1$ represents a hydroxyl, alkoxy, hydrogen, or halogen;

$R^2$ represents a hydrogen, an alkanyl, —$NR_aR_b$ where $R_a$ and $R_b$ are independently optionally substituted hydrocarbyls having up to six carbon atoms, an alkoxy chain having from 1 to 6 carbon atoms, —$SR_c$ where $R_c$ is a hydrocarbyl containing from one to six carbon atoms, —$SO_2R_d$ where Rd is a hydrocarbyl containing from one to six carbon atoms, or a halogen;

$R^3$ is hydrogen, —$SO_2NH_2$, —$SO_2NR_eR_f$ where $R_e$ and $R_f$ are independently optionally substituted hydrocarbyls having up to 6 carbon atoms, halogen or a group -$(A)_a$-$Alk^1$ wherein a is 0 or 1, and when a is 1, A is —O—, —S—, or —$NR^6$ wherein $R^6$ is hydrogen or a $C_1$-$C_5$ alkanyl chain, and $Alk^1$ is an optionally substituted divalent hydrocarbyl chain containing from 1 to 6 carbon atoms in length and optionally unsaturated bonds between at least two carbon atoms of $Alk^1$ when $Alk^1$ contains at least two carbon atoms;

$R^4$ represents hydrogen, halogen, alkoxy, hydroxy, or an optionally substituted hydrocarbyl group containing up to 6 carbon atoms;

$R^5$ represents a hydrogen, hydroxyl, alkoxy, a linear, branched, or cyclic chain with between 1 and 8 carbon atoms, or halogen;

X represents a hydrogen, a group -$Alk^2$-Z, $C_1$-$C_4$ hydrocarbyl group or halogen, wherein $Alk^2$ is an optionally substituted divalent alkanyl, alkenyl, or alkynyl chain containing from 1 to 6 carbon atoms in length; and Z represents an —OH, —OR$^7$, —SH, SR$^7$, —CN, —NH$_2$, or NHR$^7$ group, wherein R$^7$ is a C$_1$-C$_6$ hydrocarbyl or heterocyclic group optionally substituted by halogen or alkoxy;

Y represents a group -Alk$^3$-(Q)$_a$-(Alk$^4$)$_b$-B, wherein a and b are independently 0 or 1, and wherein Alk$^3$ represents a hydrocarbyl chain containing from 2 to 7 carbon atoms in length, wherein said hydrocarbyl chain optionally comprises double and/or triple bonds in between carbon atoms of said hydrocarbyl chain, and wherein said hydrocarbyl chain is optionally substituted with a halogen, hydroxyl, alkoxy, or an alkyl chain that itself is optionally substituted with halogen, hydroxyl, or alkoxy groups;

Q is selected from the group consisting of —CH$_2$—, —O—, —S—, NR—, —S(O$_2$)—, —C(═O)—, and —S(O)—;

Alk$^4$ is an alkanyl chain; and

B is hydroxyl, alkoxy, halogen, alkylthio, nitro, cyano, amine, an optionally substituted carbocyclic group, an optionally substituted heterocyclic group, and wherein X and Y, along with the carbon atom joining X and Y, do not form an unsubstituted C$_1$ to C$_6$ alkyl.

Yet another aspect of this invention is to provide a composition comprising a compound with the following structure:

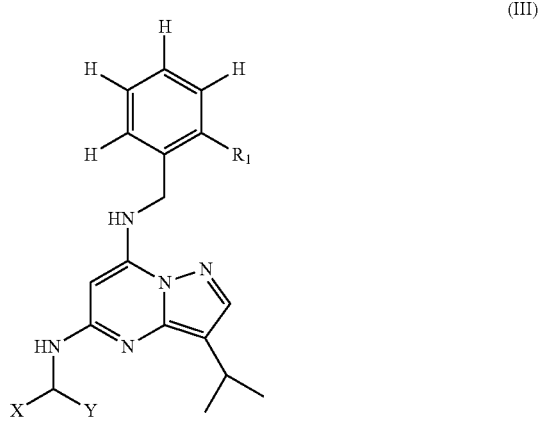

(III)

wherein

R$^1$ is either fluorine or hydrogen;

X represents a hydrogen or a group -Alk$^2$-Z, wherein Alk$^2$ is an alkanyl containing one or two carbon atoms; and Z represents an —OH group;

Y represents a group -Alk$^5$, wherein Alk$^5$ comprises one or two carbons, with proviso that Alk$^5$ may be aliphatic or olefinic when it comprises two carbons, and wherein Alk$^5$ is optionally substituted with one hydroxyl group on each carbon atom when Alk$^5$ is not olefinic;

and wherein X and Y, along with the carbon atom joining X and Y, do not form an unsubstituted C$_1$ to C$_6$ alkyl.

One aspect of this invention is to provide a method of inhibiting the activity of a cyclin-dependent kinase involving exposing the cyclin-dependent kinase to a composition as described above. In certain embodiments, the cyclin-dependent kinase is selected from the group consisting of CDK 2, CDK 4, CDK 5, CDK 7, and CDK 9.

Another aspect of this invention is to provide a method of treating a patient with cancer. The method comprises exposing cells of the cancer to a therapeutically effective amount of a composition as described above. In preferred embodiments, the cancer is selected from the group consisting of breast cancer, leukemia, melanoma, prostate cancer, lung cancer, central nervous system cancer, colorectal cancer, renal cancer, and ovarian cancer.

BRIEF DESCRIPTION OF THE FIGURES

FIG. 1.

FIG. 3.

FIG. 4.

DETAILED DESCRIPTION OF THE INVENTION

Figure 1A:
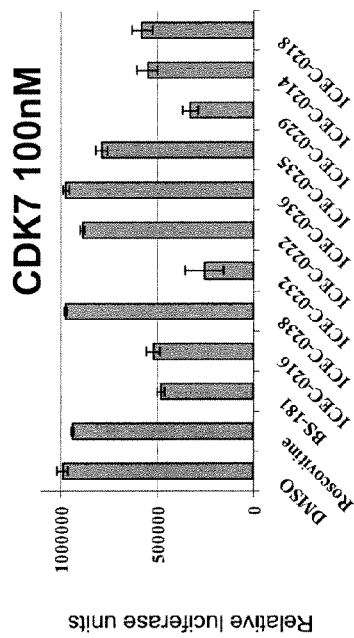
FIG. 1(a) shows kinase inhibition by compound at 100 nM.

One aspect of this invention is to provide pharmaceutical compositions for specifically inhibiting cyclin-dependent kinases using the compounds described herein. Generally, the pharmaceutical compositions of this invention may be used to treat any disease or disorder where inhibition of one or more cyclin-dependent kinases brings therapeutic relief.

For example, in certain embodiments, the disease to be treated is a cancer. By way of example only, the cancer to be treated may be selected from the group consisting of breast cancer, leukemia, melanoma, prostate cancer, lung cancer, central nervous system cancer, colorectal cancer, renal cancer, and ovarian cancer. In certain preferred embodiments, the cancer to be treated is breast cancer, particularly refractory breast cancer in which one or more tumors have developed a resistance towards common chemotherapeutic agents, such as tamoxifen.

Another aspect of the invention is to provide a method for treating diseases or disorders by specifically inhibiting one or more of the eleven known cyclin-dependent kinases (viz., CDK 1, CDK 2, CDK 3, CDK 4, CDK 5, CDK 6, CDK 7, CDK 8, CDK 9, CDK 10, and CDK 11). For example, in one particularly preferred embodiment, the compositions according to the invention are used to specifically inhibit CDK 7 in order to treat diseases for which abnormal CDK 7 activity is implicated, such as refractory breast cancer. Alternatively, this invention also contemplates the use of pharmaceutical compositions as described herein that are capable of specifically inhibiting two or more cyclin-dependent kinases simultaneously. By way of example only, the two or more cyclin-dependent kinases may be selected from the group consisting of CDK2, CDK4, CDK 5, CDK 7 and CDK 9. Particularly preferred are those compositions which are capable of inhibiting CDK 2 and CDK 7 simultaneously or CDK 5 and CDK 9 simultaneously.

As used herein, the term "specific inhibition" and similar terms refer to an enhanced potency for inhibiting the activity of one or more cyclin-dependent kinases with respect to another or other cyclin-dependent kinases. In certain non-limiting embodiments, the degree of specific inhibition is measured by comparing $IC_{50}$ values. In such embodiments, for a given inhibitor, the $IC_{50}$ value corresponding to a specifically inhibited kinase may be at least 2, 3, 5, 10, 20, 30, 40, 50, 60, 70, 80, 90, or 100-fold less than the $IC_{50}$ value corresponding to a reference kinase.

Generally, the pharmaceutical compositions of the invention may be administered in via any method known in the art. Preferred routes of administration include oral administration (e.g, in the form of capsules, tablets, lozengers, powders, solutions, or emulsions) or parenteral administration by bolus injection (either intramuscularly or intravenously) or continuous intravenous infusion. As will be appreciated, the precise formulation of the pharmaceutical composition will depend on the method of delivery. For example, when the chosen route of administration is injection, the active agents of the invention may be added to a composition that comprises a pharmaceutically acceptable buffer, such as saline. However, when active agents of the invention are to be administered orally, they may be combined with one or more excipients, non-limiting examples of which include fillers (e.g., cellulose or starch), stabilizers, sugars, flavors or colors. Of course, other common routes of administration of pharmaceutical compounds are contemplated by the invention, including, but not limited to, buccal, rectal, sublingual, intra-nasal, or topical administration.

The administered dosages of the pharmaceutical compositions will depend on many factors, including the specific disease or disorder to be treated, the particular composition used, the route of administration, and the age, weight, and physical condition of the patient to be treated. In certain embodiments where the compounds of the invention are administered orally to humans, the dosage of those compounds is in the range of 0.001 to 1000 mg/kg/day, preferably in the range of 0.01-500 mg/kg/day, more preferably in the range of 0.1 to 30 mg/kg/day, and most preferably in the range of 1-10 mg/kg/day.

In the description presented below, the following general definitions shall apply to all moieties R, $R^1$, $R^2$, $R^3$, $R^4$, $R^5$, X, Y and subgroups of atoms set forth below, unless the context indicates otherwise.

As used herein, "hydrocarbyl" is a generic term encompassing aliphatic, alicyclic, and aromatic groups having a carbon backbone and consisting of carbon and hydrogen atoms, except where otherwise stated.

As used herein "$C_a$-$C_b$" refers to chemical compounds having from a to b carbon atoms, where a and b are integers. Thus, for example, a $C_1$-$C_4$ alkanyl chain refers to straight, branched, or cyclic alkanyl chains having from one to four carbon atoms. Specifically, the term "$C_1$-$C_4$ alkanyl chain" includes methyl, ethyl, propyl, isopropyl, cyclopropyl, n-butyl, iso-butyl, sec-butyl, tert-butyl, cyclobutyl, 1-methyl cyclopropyl, and 2-methyl cyclopropyl.

The term "alkoxyl" (or "alkoxy") refers to an alkyl group linked to an oxygen. Unless otherwise specified, it is preferred that the alkoxyl contains not more than six carbon atoms. The alkyl group of the alkoxyl may be a linear or branched chain, or may be a carbocyclic or a heterocyclic ring system without aromatic character. In some embodiments, the carbon-containing portion of the alkoxyl group may contain unsaturated bonds. For example, the carbon-containing portion could have aromatic character (e.g., a benzyloxyl or 1-2-phenyl ethoxyl group).

The term "carbocyclic ring" refers to a cyclic group of carbon and hydrogen atoms. The term includes both aromatic and non-aromatic rings. Non-limiting examples of carbocyclic rings includes cyclopropyl, cyclobutyl and phenyl. As used herein, a "heterocyclic ring" refers to a cyclic group of carbon and hydrogen atoms which contains at least one other non-carbon atom as a part of the ring. A heterocyclic ring may possess aromatic character (i.e., heteroaryl) or non-aromatic character. Carbocyclic and heterocyclic rings according to the invention may be substituted unless stated otherwise, and typically with halogen, alkyl or alkoxy groups. The term "non-aromatic character" includes unsaturated ring systems without aromatic character, as well as partially or fully saturated carbocyclic or heterocyclic ring systems. The term "unsaturated" or "partially saturated" refers to groups of atoms that share more than one valence bond, such that the overall structure contains at least one multiple bond (e.g. a C=C or C=N bond). Examples of "partially saturated" chemical groups includes alkenyl, alkynyl, cycloalkenyl and cycloalkynyl groups (e.g., vinyl or cyclohexenyl.) The term "fully saturated" refers to a group of atoms connected with single bonds and include alkyls and cycloalkyls, (e.g., methyl or cyclohexyl). As used herein "alkenyl" is a generic term that refers to a carbon chain containing at least one double bond and preferably containing 2-6 carbon atoms. The carbon chain might be straight or branched and, if it is not stated otherwise in the context, may be substituted with halogen or other substituents such as hydroxyl, alkoxyl, amino or substituted amino.

Heteroaryl groups contemplated by the invention include monocyclic or bicyclic structures containing usually up to 12 ring members with heteroatoms selected from S, N or O. The bicyclic moieties are formed from fused rings (usually 5-6 membered rings) and typically contain up to four heteroaroms. Non-limiting examples of five-membered monocyclic heteroaryl groups include imidazole, pyrrole, furan, thiophene, oxazole, and pyrazole. Non-limiting examples of six-membered monocyclic heteroaryl groups include pyridine, pyrimidine, and pyrazine. Furthermore, non-limiting examples of bicyclic heteroaryls include indole, quinoline, and benzothiazole.

Non-aromatic carbocyclic rings include substituted or unsubstituted cycloalkyl, or cycloalkenyl systems, wherein cycloalkyl refers to a fully saturated ring, and cycloalkenyl refers to a ring containing at least one double bond. Most typically, these are monocyclic groups containing up to 6 ring members. The carbocyclic rings can be substituted with at least one "substituent" as defined herein.

The term "substituent" refers to any chemical moiety that can take the place of hydrogen or hydrogens in satisfying the valence of a carbon atom. Non-limiting examples of substituents contemplated by the invention include straight or branched alkyl, straight or branched alkenyl, straight or branched alkynyl, hydroxy, alkoxy, halogen, alkylmercapto, nitro, cyano, carbocyclic, heterocyclic, benzyl, trifluoromethyl. Moreover, a "substituent" according to the invention may include —COOH, —COOR$^x$, —COR$^x$, —SO$_2$R$^x$, —CONH$_2$, —CONHR$^x$, —CONHR$^x$R$^y$, —NH$_2$, —NHR$^x$, —NHR$^x$R$^y$, —CH=NNH$_2$, —OCONH$_2$, —OCONHR$^x$, —OCONHR$^x$R$^y$, wherein R$^x$ and R$^y$ are independently hydrocarbyls.

When there are two substituents, one on each of two vicinal carbon atoms in a carbocyclic or heterocyclic ring, the two substituents themselves may be linked to form a heteroaryl ring, non-aromatic carbocyclic ring or non-aromatic heterocyclic ring. Alternatively, in some embodiments where two substituents are in the 1,3-positions with respect to each other, the substituents may also be linked to form a carbocyclic or non-aromatic heterocyclic ring. The heteroatoms within such rings are usually selected from O, N and S. Rings formed in this manner have typically up to 6 members and up to 3 heteroatoms. A few representative examples of such rings are shown below:

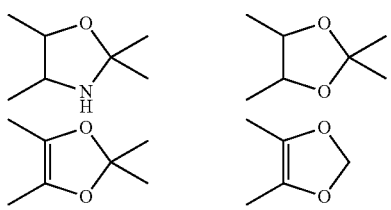

The invention includes all the compounds described herein as well as their salts. The term "salt" refers to an ionic form of these compounds obtained by addition of base (e.g. sodium hydroxide, magnesium hydroxide) or acid. If acid is used, the acid may be an organic acid (e.g. citric acid or acetic acid) or an inorganic acid (e.g. hydrochloric acid or sulphuric acid).

Since some of the compounds have chiral centers, it is possible to have several diastereoisomers bearing R or S stereochemistry at each center. This invention covers all possible diastereoisomers and their mixtures.

One aspect of the invention provides compounds of formula (I) (or derived salts, enantiomers, N-oxides, hydrates or solvates thereof), that are specific inhibitors of enzymes known as cyclin-dependent kinases, such as CDK7:

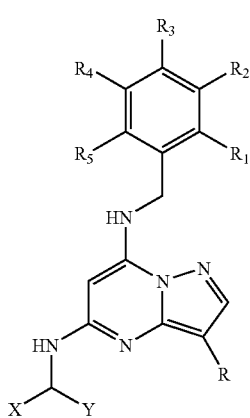

(I)

wherein R represents a hydrocarbyl containing from 1 to 6 carbon atoms. R may be optionally substituted with at least one "substituent" as defined herein. In certain embodiments, R is methyl, ethyl, n-propyl, isopropyl, n-butyl, iso-butyl, sec-butyl, tert-butyl, cyclopropyl, or cyclobutyl. R may also be a straight, branched or cyclic group bearing unsaturated bonds, non-limiting examples of which include vinyl, allyl, and cyclopentenyl. The invention also contemplates stereoisomers of compounds with R having one or more chiral centers (e.g. (R) or (S)-isobutyl). In one particularly preferred embodiment, R is isopropyl.

$R^1$ represents a hydroxyl, hydrocarbyl, alkoxyl, hydrogen, halogen, —$NR_mR_n$, or $SO_2NR_mR_n$, where $R_m$ and $R_n$ are independently optionally substituted hydrocarbyl groups having up to six carbons. When $R^1$ is an alkoxyl, it may be a $C_1$-$C_6$ alkoxyl, preferably a $C_1$-$C_4$ alkoxyl, even more preferably a $C_1$-$C_2$ alkoxyl, and most preferably methoxyl. When $R^1$ is a halogen, it is preferably chlorine or fluorine. In some particularly preferred embodiments, $R^1$ is hydrogen, hydroxyl or fluorine. When $R^1$ is a hydrocarbyl, it is preferably a fully saturated, $C_1$-$C_6$ straight or branched chain hydrocarbyl, optionally with a chiral center and optionally with one or more attached substituents as defined herein. In certain preferred embodiments, $R^1$ is methyl, ethyl, propyl, isopropyl, n-butyl, isobutyl, tert-butyl, n-pentyl, or n-hexyl and the optional substituents are selected from the group consisting of hydrogen, hydroxyl and alkoxyl. In certain preferred embodiments, the number of substituents is limited to three or less. The number of substituents is not particularly limited in principle, although practical issues such as commercial availability of reagents and steric effects may make some embodiments more desirable than others. For example, when the substituent is halogen, the number of substituents may be up to three, whereas when the substituent is hydroxyl or alkoxyl, typically there is only one such substituent. The substituents might be linked to one or several carbon atoms in hydrocarbyl group.

$R^2$ represents a hydrogen, —$SO_2NR_gR_h$, —$OSO_2R_i$, a halogen, an alkanyl, or an alkoxyl, where $R_g$, $R_h$, and $R_i$ are independently optionally substituted hydrocarbyl groups having up to six carbon atoms. When $R^2$ is an alkanyl or alkoxyl, it may contain from one to ten carbon atoms, but in certain preferred embodiments, it will be either a $C_1$-$C_6$ alkanyl or $C_1$-$C_6$ alkoxyl. In other preferred embodiments, $R^2$ is a $C_1$-$C_3$ alkoxyl, but more preferably methoxyl. When $R^2$ is a halogen, it is preferably fluorine, chlorine, or bromine. In one particularly preferred embodiment, $R^2$ is hydrogen.

$R^3$ represents a hydrogen, —$SO_2NH_2$, a halogen, or a chemical moiety with the following structure:

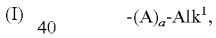

-$(A)_a$-$Alk^1$, wherein a can be 0 or 1. When $R^3$ is a halogen, it is preferably fluorine, chlorine, or bromine Additionally, when $R^3$ is -$(A)_a$-$Alk^1$ and a is 1, A is a linking group, non-limiting examples of which include —O—, —S—, —SO—, —$SO_2$—, —C═O—, —$CONR^6$—, and $NR^6$. If A is —$NR^6$—, $R^6$ is either hydrogen or a fully saturated $C_1$-$C_5$ alkanyl chain, which may be straight or branched, but preferably contains from 1 to 3 carbon atoms. In one embodiment, $R^6$ is methyl. $Alk^1$ may be an optionally substituted divalent hydrocarbyl chain containing from one to six carbon atoms. The hydrocarbyl chain of $Alk^1$ may optionally contain one or more unsaturated bonds. $Alk^1$ also may be represent carbocyclic groups bearing aromatic or non-aromatic character. These carbocylic groups can be substituted by halogen, hydroxyl, alkoxyl or an alkyl chain preferably with up to 3 carbon atoms. Some non-limiting examples of $Alk^1$ include methyl, ethyl, propyl, isopropyl, cyclopropyl, hexyl, cyclopentyl, and phenyl. When $Alk^1$ is substituted by two substituents they may be linked to form 5 or 6-membered heterocyclic ring. In such cases, the heteroatoms are usually selected from the group consisting of O, N, S. The heterocyclic ring may contain two heteroatoms (e.g. 1,4-dioxane). When a is 0, $Alk^1$ is directly connected to a phenyl ring. In especially preferred embodiments, $R^3$ is halogen selected from chlorine, bromine and fluorine, most preferably fluorine.

$R^4$ represents hydrogen, a halogen, alkoxyl, hydroxyl or an optionally substituted $C_1$-$C_6$ hydrocarbyl group, which may be linear, branched or cyclic. The hydrocarbyl group may be fully saturated or may have one or more double or triple bonds. When $R^4$ is a halogen, it is preferably fluorine, chlorine, or bromine. When $R^4$ is alkoxyl, the alkoxyl can be a $C_1$-$C_6$ alkoxyl, but preferably is a $C_1$-$C_3$ alkoxyl, and most preferably is methoxyl. Furthermore, the alkoxy group optionally can be substituted by halogen, hydroxyl or alkoxy moieties (e.g., to form species such as methoxymethoxyl). In one especially preferred embodiment, $R^4$ represents hydrogen.

$R^5$ represents a hydrogen, halogen, hydroxyl, alkoxyl, or a $C_1$-$C_8$ hydrocarbyl, which may be a linear, branched or cyclic chain of carbon atoms. The $C_1$-$C_8$ hydrocarbyl may be optionally substituted with a "substituent" as defined herein. When $R^5$ is a halogen, it may be any of the five known halogens, but is preferably fluorine, chlorine, or bromine. When $R^5$ is alkoxyl, the alkoxyl may contain up to, and including six carbon atoms, but in certain preferred embodiments is just methoxyl. In one especially preferred embodiment, $R^5$ represents hydrogen.

X represents a hydrogen, a halogen, a $C_1$-$C_4$ hydrocarbyl group, or a chemical moiety having the structure -Alk$^2$-Z. When X is a halogen, it is preferably fluorine, chlorine, or bromine, and most preferably fluorine. When X is $C_1$-$C_4$ hydrocarbyl, it may be, for example, any of the hydrocarbyl groups listed in Table 1.

TABLE 1

Examples of the group X when it is $C_1$-$C_4$ hydrocarbyl

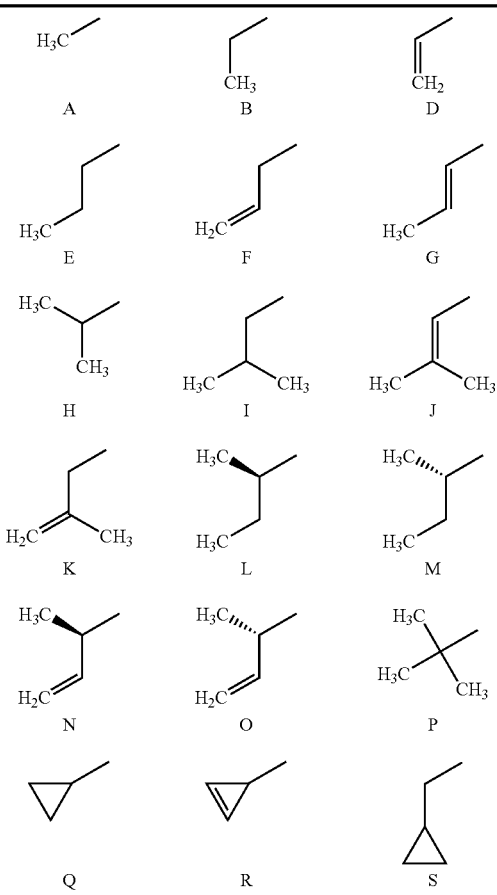

TABLE 1-continued

Examples of the group X when it is $C_1$-$C_4$ hydrocarbyl

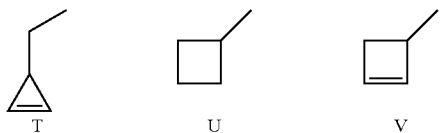

In certain preferred embodiments, X is hydrogen and the corresponding compounds are represented by formula (IA):

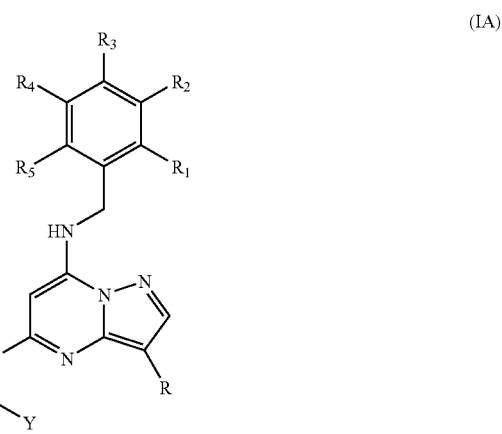

(IA)

When X is a chemical moiety having the structure -Alk$^2$-Z, the corresponding compounds are represented by formula (IB):

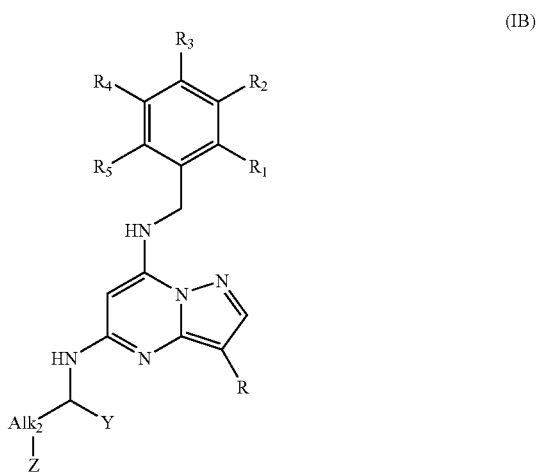

(IB)

Here, Alk$^2$ is an optionally substituted divalent alkanyl, alkenyl or alkynyl chain containing from 1 to 6 carbon atoms, preferably not more than four carbon atoms, and most preferably two carbon atoms or less (e.g. —CH$_2$—). In certain embodiments, Alk$^2$ preferably does not contain more than one double or triple bond. Alk$^2$ can be linear or branched and can be optionally substituted by a "substituent" as defined herein. Z represents —OH, —OR$^7$, —SH, —SR$^7$, —CN, —NH$_2$, —NHR$^7$, wherein R$^7$ is a $C_1$-$C_6$ hydrocarbyl or heterocyclic group optionally substituted by halogen or alkoxy. R$^7$ can also be a saturated or unsaturated carbon chain, aryl, heteroaryl, a carbocyclic ring without aromatic character, or a heterocyclic ring without aromatic character. Non-limiting examples of $R^7$ groups contemplated by this invention include methyl, ethyl, iso-propyl, cyclohexyl, phenyl, pyrroldinyl, and piperidinyl. Additionally, the $R^7$ hydrocarbyl may be optionally substituted with a "substituent" as defined herein.

Y represents a group of atoms with the structure -$Alk^3$-$(Q)_a$-$Alk^4$-B, wherein a is 0 or 1. Here, $Alk^3$ represents a $C_2$-$C_7$ hydrocarbyl chain that optionally may contain double and/or triple bonds. For example, in certain embodiments, $Alk^3$ is a linear or branched saturated chain optionally substituted with a "substituent" as described herein. Non-limiting examples of linear alkyl groups include methyl, ethyl, propyl, n-butyl, n-pentyl, and n-hexyl. Furthermore, non-limiting examples of branched alkyl groups include isopropyl, iso-butyl, tert-butyl, and 2,2-dimethylpropyl. In other embodiments, $Alk^3$ is a linear or branched chain bearing up to three unsaturated bonds (which can be double or triple bonds), preferably two unsaturated bonds, and most preferably one unsaturated bond. The presence of double bonds gives rise to geometric isomers with Z and E geometry. The invention includes all such geometric isomers and the mixtures thereof. Non-limiting examples of $Alk^3$ having unsaturated bonds include —CH=CH—, —CH$_2$CH=CH—, —C≡C—, —CH$_2$C=C—CH$_2$—, —CH$_2$C≡C—, —CH$_2$C(CH$_3$)=CH—, —CH=CHCH=CH—, and —C≡CCH$_2$—.

Generally, $Alk^3$, whether saturated or unsaturated, may be substituted by at least one "substituent" as defined herein. In some embodiments, the $Alk^3$ $C_2$-$C_7$ hydrocarbyl chain is substituted with one or more substituents selected from halogen, hydroxy, $C_1$-$C_4$ alkoxy, amino, hydrocarbylamino, hydrocarbyl or a heterocyclic group. The alkoxy, hydrocarbyl, and heterocyclic substituents can be further substituted, typically by halogen, hydroxy or a $C_1$-$C_4$ alkoxy group.

In one preferred embodiment, the heterocyclic substituent on $Alk^3$ is heteroaryl. Heteroaryls include monocyclic rings with between 3 and 7 ring members and up to 3 heteroatoms and bicyclic rings with up to 2 heteroatoms in one ring. Heteroatoms are preferably selected from O, S, N. Non-limiting examples of heteroaryl groups contemplated by the invention include furanyl, pyrazolyl, imidazolyl, thienyl, quinolinyl, pyridyl, indolyl, and pyrrolyl.

In another preferred embodiment, the heterocyclic substituent on $Alk^3$ is a mono- or bicyclic group without aromatic character. Non-limiting examples of such groups include morpholino, piperazino, thiomorpholino, pyrrolidino, and piperidino.

The hydrocarbyl substituent on $Alk^3$ can be a carbocyclic or an acyclic group consisting of up to 12 carbon atoms in length. Non-limiting examples of carbocyclic groups bearing aromatic character include phenyl and naphthyl. Furthermore, non-limiting examples of non-aromatic carbocyclic systems include cyclopropyl, cyclobutyl, cyclopentyl, cyclohexyl. Additionally, the non-aromatic carbocycles can be partially unsaturated (e.g. 2-cyclohexenyl.)

In Y, the chemical moiety denoted by Q is a linker between hydrocarbyl $Alk^3$ and $Alk^4$. Non-limiting examples of suitable chemical linkers includes —O—, —S—, —NH—, —NR—, —S(O$_2$)—, —C(=O)—, and —S(O)—, wherein the R in —NR— may be a hydrocarbyl, cycloalkyl, or heterocycle, any of which may be optionally substituted. In certain preferred embodiments, R is $C_1$-$C_6$ hydrocarbyl or heterocyclic group optionally substituted by at least one halogen or alkoxyl group.

In Y, $Alk^4$ is a $C_1$-$C_6$ alkanyl chain, more preferably a $C_1$-$C_4$ alkanyl chain, and most preferably a —CH$_2$— group.

In some embodiments, the subscript "a" in the formula for Y (i.e., -$Alk^3$-$(Q)_a$-$Alk^4$-B) is equal to zero. In this case, $Alk^3$ is directly connected with $Alk^4$, and the corresponding compounds have the general formula given by Formula (IC):

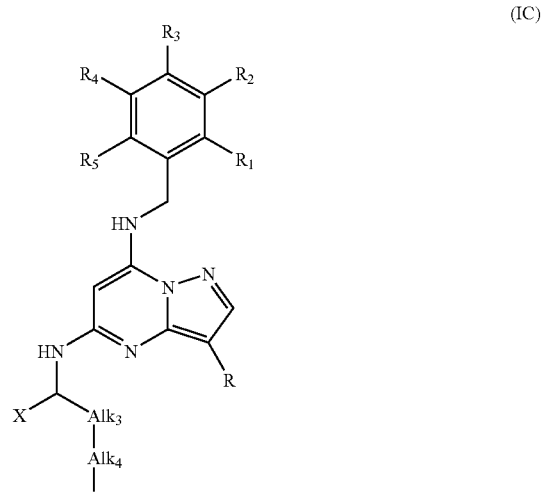

(IC)

In Y, the chemical moiety denoted by B can be a hydroxyl, alkoxyl, halogen, alkylthio, alkylmercapto, nitro, cyano, carbocyclic, heterocyclic, benzyl, or trifluoromethyl group. When B is a carbocyclic or heterocyclic group, it can be optionally substituted by one or more substituents selected from the group consisting of halogen, hydroxyl or alkoxyl groups. Additionally, non-limiting examples of carbocyclic groups contemplated by the invention include aromatic and non-aromatic rings with up to 7 carbon atoms in one ring. The group can be monocyclic (e.g., cyclopropyl, phenyl) or bicyclic (e.g., naphthyl). When B is a heterocyclic group, the heterocyclic group may be a heteroaryl or a heterocyclic system without aromatic character. The heteroaryls can be monocyclic with up to 3 heteroatoms in ring, or bicyclic with up to 2 heteroatoms in each ring, wherein both of the rings have to be aromatic. The monocyclic heteroaryls have preferably five or six members in ring, whereas bicyclic heteroaryls are typically formed from a five-membered ring fused with a six-membered ring or a six-membered ring fused with another six-membered ring. Heteroatoms are selected from O, N, S. Non-limiting examples of heteroaryls include pyridyl, imidazole, pyrazole, thiazole, isothiazole, pyrimidine, furyl, quinoline, isoquinoline, indole.

Additionally, in some embodiments, B can also be —COOH, CN, NHSO$_2$R$^x$, —COOR$^x$, —COR$^x$, —SO$_2$R$^x$, —CONH$_2$, —CONHR$^x$, —CONHR$^x$R$^y$, —NH$_2$, —NHR$^x$, —NHR$^x$R$^y$, —CH=NNH$_2$, —OCONH$_2$, OCONHR$^x$, —OCONHR$^x$R$^y$, wherein R$^x$ and R$^y$ are independently hydrocarbyls.

EXAMPLES

The invention will now be illustrated, but not limited, by the reference to the specific embodiments described in the following examples. Compounds of formulas (I), (IA), (IB), (IC), (II), (III) and their sub-groups can be prepared according to methodologies well known to those trained in the art. All the procedures presented in this section are applicable to compounds with formulas corresponding to formulas (I), (IA), (IB), (IC), (II), and (III) unless it is stated otherwise. Below are presented several, non-limiting examples of the compounds of the invention.

All the prepared compounds in the Examples were characterized by proton and carbon magnetic resonance and most of them by mass spectroscopy (chemical ionization). The purification was performed by column chromatography on silica gel. Unless otherwise stated, reaction solvents were dried by distillation under $N_2$ from $CaH_2$ (toluene, dichloromethane), $K_2CO_3$ (methanol) or obtained commercially anhydrous (ethanol). Reactions were performed in oven-dried glassware under nitrogen atmosphere unless otherwise stated.

Example 1

Compounds of formula (I), wherein $R^2$, $R^3$, $R^4$ and $R^5$ are hydrogen can be prepared accordingly to the Scheme 1.

example, selected from carbamates (e.g. tert-butyl carbamate, benzyl carbamate) or amides (e.g. formamide, acetamide, benzamide). In a particularly preferred embodiment, the protecting grup is a carbamate, most preferably tert-butylcarbamate (Boc).

The protection reaction to synthesize compound (V) can be carried out in several ways that are well documented in litterature and known to those trained in the art. When Boc is chosen as a protective group, the reaction is typically carried out with the use of di-tert-butyl dicarbonate in a non-aqueous solvent such as acetonitrile, dimethyl sulfoxide, dichloromethane or in an aqueous solvent optionally together with a miscible or non-miscible co-solvent. The reaction can be carried out in a presence of base such as sodium hydroxide or triethylamine.

Compound (VII) is obtained from the cross coupling reaction of chloride (V) with amine (VI). The amination reaction

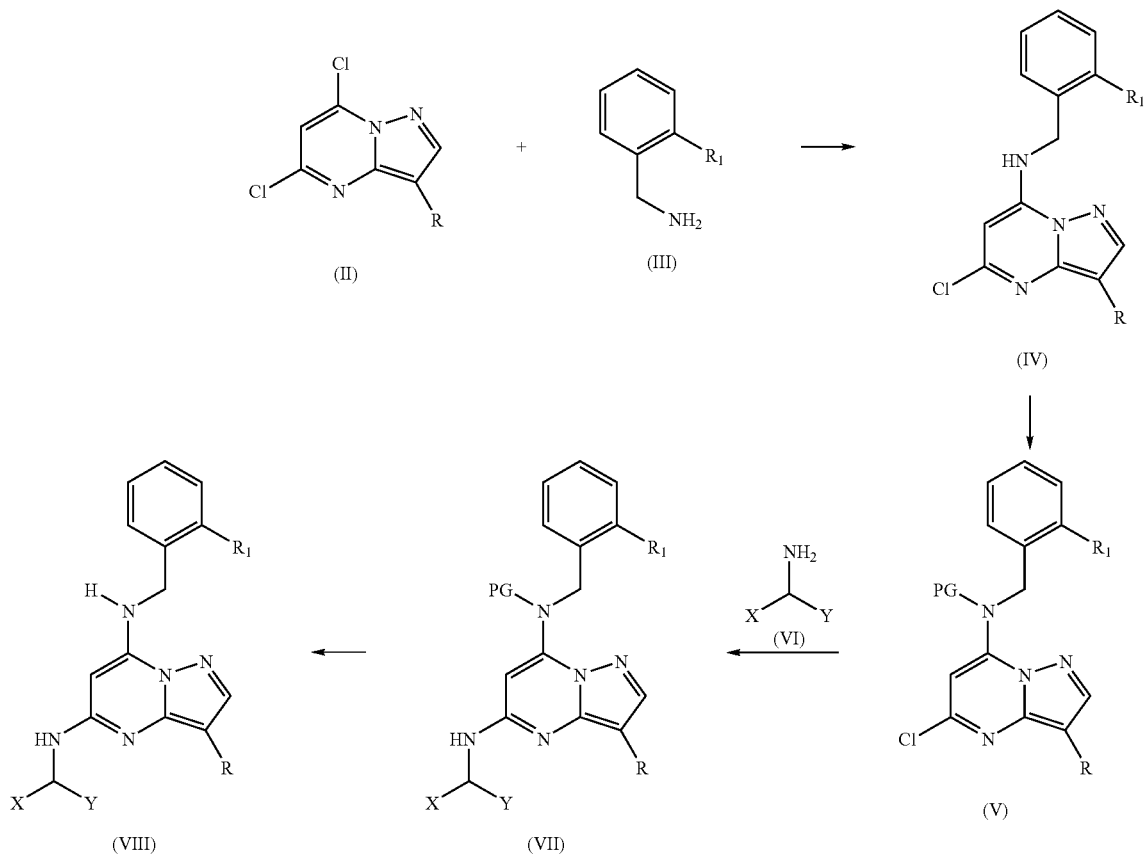

Scheme 1

Dichloro heterocycle (II) is allowed to react with the amine of formula (III) to give chloro-pyrazolo[1,5-a]-pyrimidinamine (IV). The reaction can be carried out in a protic solvent such as an alcohol, in the presence of a tertiary amine or equivalent organic base (e.g., triethylamine, di-iso-propylethylamine or N''-tert-butyl-N',N',N,N-tetramethylguanidine; see D. S. Williamson et al., *Bioorg. Med. Chem. Lett.*, 15, 863-867 (2005)).

The amine of formula (III) can be obtained from commercial sources or can be prepared by a large number of synthetic methods when known to those trained in the art.

The amine (IV) is next protected with a protection group PG. The type of PG is not particularly limited and can be, for can be carried out with the use of palladium complex or salt as a catalyst and in the presence of a ligand or ligands for palladium such as phosphine ligands (e.g., BINAP). Typically the process is carried out in an aprotic anhydrous solvent, preferable toluene, in the presence of an appropriate base such as sodium tert-butoxide. The reaction mixture is usually subjected to heating, for example to a temperature around 100° C.

Deprotection of the nitrogen protecting group PG in compound (VII) carried out under standard conditions well known to those trained in the art and which yields the desired compound (VIII).

Amines of the formula (VI) are synthesized accordingly to synthetic methods well known to those trained in the art. For example, in the class of compounds represented by formula (IA), when a is 0 and Alk⁴ is —CH₂—, the final compounds can be obtained from amine of formula (VIA).

Example 2

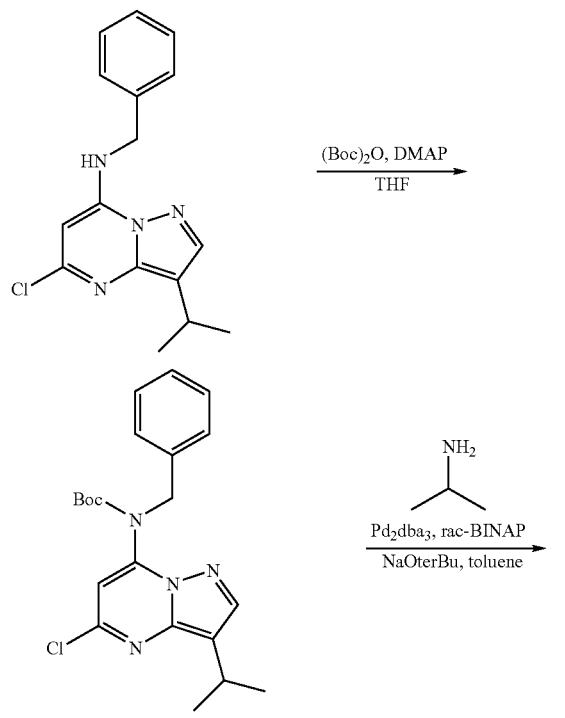

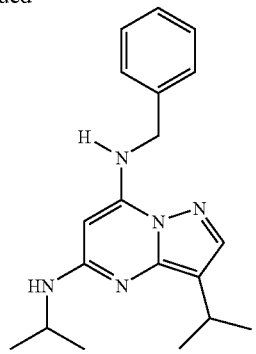

Step 1

N-Benzyl-5-chloro-3-isopropylpyrazolo[1,5-a]pyrimidin-7-amine

A solution of 3-isopropyl-5,7-dichloropyrazolo[1,5-c]pyrimidine (500 mg, 2.17 mmol) and the benzyl amine (0.52 mL, 4.78 mmol) in ethanol (20 mL) was heated under reflux for 3 h. The reaction mixture was cooled to room temperature and concentrated in vacuo. The remaining residue was purified by column chromatography on silica (methanol/ethyl acetate) to yield the desired products as a white solid (630 mg, 97%).

M.p. 74-75° C. (CHCl₃). IR (neat) $v_{max}$=1617, 1583, 1455, 1168, 740. ¹H NMR (CDCl₃, 300 MHz) δ 7.82 (m, 1H), 7.32 (m, 5H), 7.01 (m, 1H), 5.90 (m, 1H), 4.53 (m, 2H), 3.27 (hep, J=6.9 Hz, 1H), 1.32 (d, J=6.9 Hz, 6H). ¹³C (CDCl₃, 300 MHz) δ 150.1, 146.8, 144.1, 141.5, 135.7, 129.0, 128.1, 127.1, 116.9, 84.6, 46.0, 23.4, 23.3. MS m/z (CI) 301 (M+H), 267, 177, 52. HRMS (CI) Calc.: 301.1220. Found: 301.1230. Microanalysis Calc: C, 63.89; H, 5.70; N, 18.63. Found: C, 63.95; H, 5.78; N, 18.59.

Step 2 tert-Butyl benzyl-5-chloro-3-isopropylpyrazolo[1,5-a]pyrimidin-7-yl carbamate A flask was charged with the amine (300 mg, 1 mmol), Boc₂O (284 mg, 1.3 mmol), DMAP (24 mg, 0.2 mmol) and THF (6 mL). The mixture was stirred for 1.5 h at room temperature. Ethyl acetate (10 mL) was added and the organic phase washed with water (3×20 mL), saturated aqueous sodium hydrogencarbonate (20 mL) and dried over anhydrous sodium sulfate. The crude product was purified after concentration by column chromatography on silica (ethyl acetate:hexanes=1:20) to yield the product as a pale yellow solid (385 mg, 96%).

M.P. 93-94° C. (ethyl acetate). IR (neat) $v_{max}$=2967, 1727, 1612, 1518, 1454, 1154, 699. ¹H NMR (CDCl₃, 300 MHz) δ 8.03 (s, 1H), 7.25 (m, 5H), 6.49 (s, 1H), 5.04 (s, 2H), 3.31 (hep, J=6.8 Hz, 1H), 1.37 (d, J=6.8 Hz, 6H). ¹³C NMR (CDCl₃, 300 MHz) δ 152.6, 147.9, 144.9, 144.0, 142.5, 136.7, 128.5, 127.7, 127.6, 118.2, 106.1, 82.9, 51.3, 27.8, 23.5, 23.3. MS m/z (CI) 401 (M+H), 301, 179, 123, 52. HRMS (CI) Calc.: 401.1744. Found: 401.1747. Microanalysis Calc: C, 62.91; H, 6.29; N, 13.98. Found: C, 62.87; H, 6.19; N, 13.94.

Step 3 tert-Butyl benzyl-3-isopropyl-5-(isopropylamino)pyrazolo[1,5-a]pyrimidin-7-yl carbamate The heteroaryl chloride (50 mg, 0.12 mmol), Pd$_2$ dba$_3$ (6 mg, 5 mol %), rac-BINAP (11 mg, 15 mol %), and sodium tert-butoxide (17 mg, 0.18 mmol) were suspended in toluene (0.5 mL). After 5 min of stirring, isopropylamine (13 μL, 0.15 mmol) was added and the red mixture heated for 12 h at 100° C. in a sealed tube. The reaction mixture was cooled to room temperature and poured into water (10 mL). The aqueous phase was extracted with ethyl acetate (3×10 mL) and the combined organic phases were dried over anhydrous sodium sulfate. After concentration by rotary evaporation, the crude product was purified by column chromatography on silica (ethyl acetate:hexanes=10:1) to yield the product as a yellow syrup (39 mg, 77%).

IR (neat) $v_{max}$=3361, 2966, 2870, 1719, 1698, 1644, 1580, 1520, 1158. $^1$H NMR (CDCl$_3$, 300 MHz) δ 7.74 (s, 1H) 7.26 (m, 5H), 5.66 (s, 1H), 4.93 (s, 2H), 4.52 (m, 1H), 4.03 (m, 1H), 3.11 (hep, J=6.8 Hz, 1H), 1.41 (s, 9H), 1.33 (d, J=6.8 Hz, 6H), 1.16 1.33 (d, J=6.8 Hz, 6H). $^{13}$C(CDCl$_3$, 300 MHz) δ 154.0, 146.3, 141.5, 137.8, 128.4, 127.9, 127.4, 113.1, 97.0, 82.1, 51.3, 43.0, 28.0, 23.8, 23.2, 22.6. MS m/z (CI) 424 (M+H). HRMS (CI) Calc.: 424.2713. Found: 424.2706.

Step 4 N$^7$-Benzyl-N$^5$, 3-diisopropylpyrazolo[1,5-a]pyrimidine-5,7-diamine The carbamate (39 mg, 0.09 mmol) was dissolved in hydrogen chloride in methanol (5 mL, 1.25M) and stirred at room temperature for 2 h. The solvent was evaporated and the residue dissolved in dichloromethane (10 mL) and washed with saturated aqueous sodium hydrogencarbonate (10 mL). The organic phase was dried over anhydrous sodium sulfate and the solvent removed in vacuo to yield a light yellow solid (29 mg, 97%).

IR (neat) $v_{max}$=3263, 2961, 2867, 1634, 1578, 1441, 1220. $^1$H NMR (CDCl$_3$, 300 MHz) δ 7.65 (s, 1H), 7.33 (m, 5H), 6.51 (s, 1H), 5.01 (s, 1H), 4.47 (m, 3H), 3.93 (m, 1H), 3.10 (m, 1H), 1.31 (m, 6H), 1.18 (m, 6H). $^{13}$C (CDCl$_3$, 300 MHz) δ 156.0, 146.7, 140.6, 136.9, 128.8, 127.7, 127.1, 112.4, 72.2, 46.1, 43.1, 23.7, 23.3, 22.9. MS m/z (CI) 324 (M+H). HRMS (CI) Calc.: 324.2188. Found: 324.2187.

Example 3

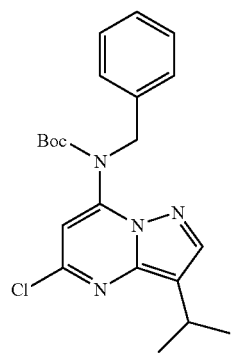 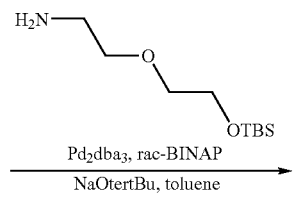

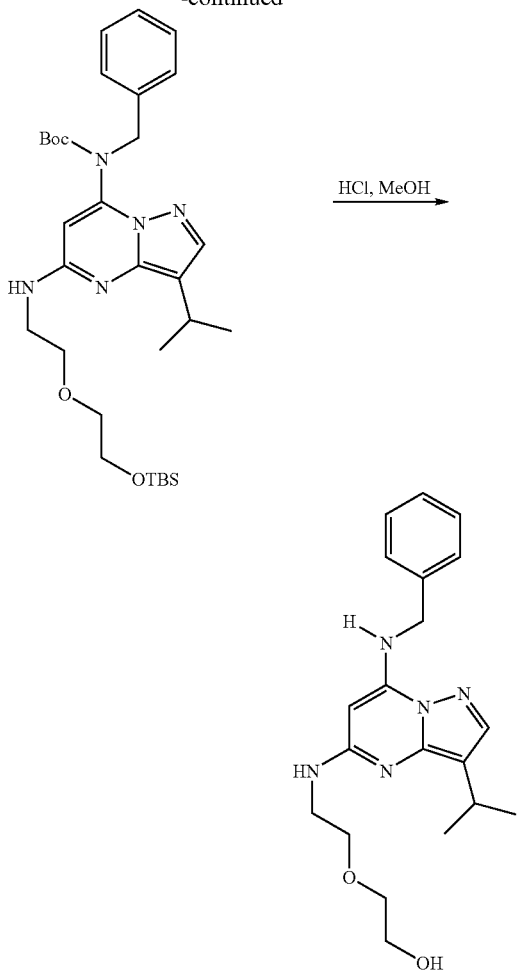

Step 1 tert Butyl Benzyl-(5-{2-[2-(tert-butyldimethylsilyloxy)-ethoxy]ethylamino}-3-isopropylpyrazolo[1,5-a]pyrimidin-7-yl)-carbamate The heteroaryl chloride (100 mg, 0.25 mmol), Pd$_2$ dba$_3$ (11 mg, 5 mol %), rac-BINAP (23 mg, 15 mol %), and sodium tert-butoxide (36 mg, 0.36 mmol) were suspended in toluene (0.5 mL). After 5 min of stirring, the amine (66 mg, 0.30 mmol) was added and the red mixture heated for 12 h at 100° C. The reaction mixture was cooled to room temperature and poured into water (10 mL). The aqueous phase was extracted with ethyl acetate (3×10 mL) and the combined organic phases were dried over anhydrous sodium sulfate. After concentration by rotary evaporation, the crude product was purified by column chromatography on silica (hexanes:ethyl acetate=4:1) to yield the product as a yellow syrup (84 mg, 58%).

IR (neat) $v_{max}$=3374, 2955, 2929, 2860, 1721, 1644, 1582, 1524, 1455, 835, 777. $^1$H NMR (CDCl$_3$, 300 MHz) δ 7.75 (s, 1H), 7.26 (m, 5H), 5.68 (s, 1H), 5.05-4.93 (m, 3H), 3.78-3.53 (m, 9H), 3.13 (hep, J=6.8 Hz, 1H), 1.40 (s, 9H), 1.33 (d, J=6.8 Hz, 6H), 0.07 (s, 6H). $^{13}$C (CDCl$_3$, 300 MHz) δ 154.4, 153.5, 146.2, 142.6, 141.4, 137.7, 128.4, 127.8, 127.4, 113.3, 97.4, 82.0, 72.4, 69.4, 62.6, 51.3, 41.0, 28.0, 25.9, 23.8, 23.2, 23.1, 18.3. MS m/z (CI) 584 (M+H). HRMS (CI) Calc.: 584.3632. Found: 584.3626.

Step 2

2-(2-(7-(Benzylamino)-3-isopropylpyrazolo[1,5-a]pyrimidin-5-ylamino)ethoxy)ethanol The carbamate (20 mg, 0.034 mmol) was dissolved in hydrogen chloride in methanol (5 mL, 1.25M) and stirred at room temperature for 2 h. The solvent was evaporated and the residue dissolved in dichloromethane (10 mL) and washed with saturated aqueous sodium hydrogencarbonate (10 mL). The organic phase was dried over anhydrous sodium sulfate and the solvent removed in vacuo to yield a light yellow solid (12 mg, 96%).

IR (neat) $v_{max}$=3334, 2955, 2866, 1637, 1578, 1446, 1223, 1063. $^1$H NMR (CDCl$_3$, 300 MHz) δ 7.66 (s, 1H), 7.33 (m, 5H), 6.44 (s, 1H), 5.03 (m, 2H), 4.44 (m, 2H), 3.73-3.58 (m, 9H), 3.11 (hep, J=6.8 Hz, 1H), 1.32 (d, J=6.8 Hz, 6H). $^{13}$C (CDCl$_3$, 300 MHz) δ 156.5, 146.7, 140.7, 136.8, 128.8, 127.8, 127.2, 112.8, 72.6, 72.2, 69.9, 61.7, 46.1, 41.3, 23.7, 23.3. MS m/z (CI) 370 (M+H). HRMS (CI) Calc.: 370.2243. Found: 370.2241.

Example 4

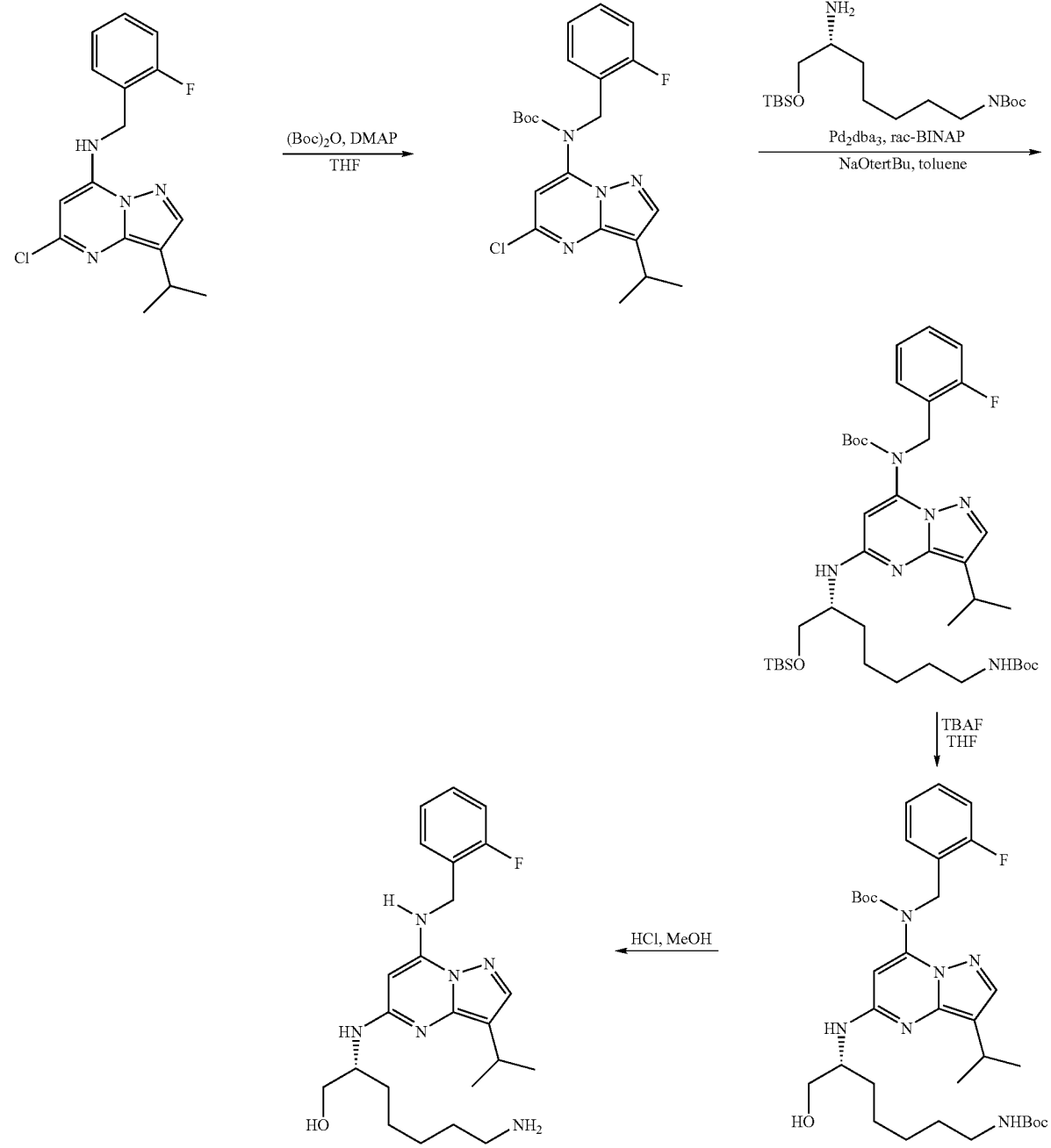

Step 1: N-(2-Fluorobenzyl)-5-chloro-3-isopropylpyrazolo[1,5-a]pyrimidin-7-amine A solution of 3-isopropyl-5,7-dichloropyrazolo[1,5-a]pyrimidine (500 mg, 2.17 mmol) and ortho-fluorobenzylamine (0.5 mL, 4.34 mmol) in ethanol (20 mL) was heated under reflux for 3 h. The reaction mixture was cooled to room temperature and concentrated in vacuo. The remaining residue was purified by column chromatography on silica (methanol/ethyl acetate) to yield the desired products as a light yellow solid (681 mg, 98%).

M.P. 83-84° C. (CHCl$_3$). IR (neat) $v_{max}$=1616, 1601, 1491, 1458, 1225, 757. $^1$H NMR (CDCl$_3$, 300 MHz) δ 7.84 (s, 1H), 7.30 (m, 2H), 7.11 (m, 2H), 6.86 (m, 1H), 5.95 (s, 1H), 4.61 (m, 2H), 3.27 (hep, J=6.9 Hz, 1H), 1.32 (d, J=6.9 Hz, 6H). $^{13}$C (CDCl$_3$, 300 MHz) δ 160.7 (J=247.5 Hz), 150.1, 146.7, 144.1, 141.6, 130.1 (J=8.3 Hz), 129.2, 129.1, 124.6 (J=3.2 Hz), 122.9 (J=14.2 Hz), 117.0, 115.8 (J=21.2 Hz), 84.5, 40.0, 23.5, 23.3. MS m/z (CI) 319 (M+H), 285, 211, 177, 124. HRMS (CI) Calc.: 319.1126. Found: 319.1123. Microanalysis Calc: C, 60.28; H, 5.06; N, 17.58. Found: C, 60.36; H, 4.94; N, 17.57.

Step 2: tert-Butyl-2 fluorobenzyl-5-chloro-3-isopropylpyrazolo[1,5-a]pyrimidin-7-yl carbamate A flask was charged with the amine (644 mg, 2.02 mmol), Boc$_2$O (573 g, 2.63 mmol), 4-(dimethylamino)pyridine (49 mg, 0.40 mmol) and THF (12 mL). The mixture was stirred for 1.5 h at room temperature. Ethyl acetate (20 mL) was added and the organic phase washed with water (3×20 mL), saturated aqueous sodium hydrogencarbonate (40 mL) and dried over anhydrous sodium sulfate. The crude product, after concentration by rotary evaporation, was purified by column chromatography on silica (ethyl acetate:hexanes=1:20) to yield the product as a pale yellow solid (837 mg, 99%).

M.p. 120-121° C. (ethyl acetate). IR (neat) $v_{max}$=2967, 1728, 1613, 1456, 1155, 877, 758. $^1$H NMR (CDCl$_3$, 300 MHz) δ 8.02 (s, 1H), 7.28, (m, 2H), 7.03 (m, 2H), 6.57 (s, 1H), 5.12 (s, 2H), 3.31 hep, J=6.8 Hz, 1H), 1.40 (s, 9H), 1.37 (d, J=6.8 Hz, 6H). $^{13}$C (CDCl$_3$, 300 MHz) δ 162.3, 159.0, 152.5, 148.0, 145.0, 143.9, 142.5, 130.1, 130.1, 129.7, 129.6, 124.1, 124.1, 123.7, 123.5, 118.2, 115.5, 115.2, 106.2, 83.0, 45.4, 27.8, 23.5, 23.3. MS m/z (CI) 419 (M+H), 363, 319, 303, 211, 126, 109. HRMS (CI) Calc.: 419.1650. Found: 419.1635. Microanalysis Calc: C, 60.21; H, 5.77; N, 13.37. Found: C, 60.37; H, 5.68; N, 13.30.

Step 3: tert-Butyl {5-[(R)-6-tert-butoxycarbonylamino-(tert-butyldimethylsilyloxymethyl)-hexylamino]-3-isopropylpyrazolo[1,5-a]pyrimidin-7-yl}-(2-fluorobenzyl)-carbamate The heteroaryl chloride (50 mg, 0.12 mmol), Pd$_2$ dba$_3$ (6 mg, 10 mol %), rac-BINAP (12 mg, 30 mol %), and sodium tert-butoxide (19 mg, 0.20 mmol) were suspended in toluene (0.5 mL). After 5 min of stirring. the amine (50 mg, 0.14 mmol) was added and the red mixture heated for 12 h at 100° C. The reaction mixture was cooled to room temperature and poured into water (10 mL). The aqueous phase was extracted with ethyl acetate (3×10 mL) and the combined organic phases were dried over anhydrous sodium sulfate. After concentration by rotary evaporation, the crude product was purified by column chromatography on silica (ethyl acetate:hexanes=10:1) to yield the product as a yellow syrup (41 mg, 46%).

$[α]_D$ (c 1.90, CH$_2$Cl$_2$): +14.0. IR (neat) $v_{max}$=3371, 2955, 2930, 2858, 1720, 1644, 1518, 1390, 1366, 1160, 837, 757. $^1$H NMR (CDCl$_3$, 300 MHz) δ 7.70 (s, 1H), 7.33 (m, 1H), 7.21 (m, 1H), 7.02 (m, 2H), 5.72 (s, 1H), 4.98 (m, 2H), 4.70 (m, 1H), 4.48 (m, 1H), 4.00 (m, 1H), 3.64 (m, 2H), 3.05 (m, 3H), 1.40-1.27 (m, 32H), 0.85 (s, 9H), 0.04 (s, 6H). $^{13}$C (CDCl$_3$, 300 MHz) δ 155.9, 154.3, 153.4, 146.3, 142.7, 141.4, 130.2, 129.2, 129.1, 124.7, 124.5, 124.0, 124.0, 115.4, 113.1, 97.2, 82.1, 64.1, 52.0, 48.3, 45.7, 40.4, 31.3, 29.9, 28.4, 28.1, 28.0, 26.7, 25.9, 23.8, 23.2, 23.1, 18.3, −5.4. MS m/z (CI) 744 (M+H).

Step 4 tert-Butyl [5-(R)-6-tert-Butoxycarbonylamino-hydroxymethyl-heptylamino]-3-isopropylpyrazolo[1,5-a]pyrimidin-7-yl)-(2-fluorobenzyl)-carbamate The silyl-ether (40 mg, 0.054 mmol) was dissolved in THF (5 mL) and tetrabutylammonium fluoride in THF (1M; 0.07 mL, 0.065 mmol) was added at room temperature. The resulting solution was stirred until TLC showed complete conversion. The reaction was quenched by the addition of saturated aqueous ammonium chloride (5 mL). The aqueous phase was extracted with ethyl acetate (3×10 mL) and the combined organic phases dried over anhydrous sodium sulfate. After concentration by rotary evaporation, the crude product purified by column chromatography on silica (hexanes:ethyl acetate=4:1) to yield the product as a light yellow oil (24 mg, 71%).

$[α]_D$ (c 1.20, CH$_2$Cl$_2$): +12.8. IR (neat) $v_{max}$=2974, 2932, 2867, 1716, 1698, 1646, 1557, 1520, 1366, 1161, 758. $^1$H NMR (CDCl$_3$, 300 MHz) δ 7.74 (s, 1H), 7.36 (m, 1H), 7.25 (m, 1H), 7.03 (m, 2H), 5.91 (m, 1H), 5.13 (m, 3H), 4.64 (m, 1H), 3.95 (m, 1H), 3.76 (m, 1H), 3.61 (m, 1H), 3.09 (m, 3H), 1.43-1.29 (m, 33H). $^{13}$C (CDCl$_3$, 300 MHz) δ 156.1, 155.2, 153.4, 143.1, 141.5, 130.2, 130.1, 129.3, 124.1, 124.0, 115.4, 115.1, 113.4, 97.4, 83.8, 82.4, 67.3, 54.7, 45.8, 39.9, 31.3, 29.7, 28.4, 28.0, 23.7, 23.2.

Step 5 (R)-2-(7-(2-Fluorobenzylamino)-3-isopropylpyrazolo[1,5-a]pyrimidin-5-ylamino)-7-aminoheptanol The carbamate (23 mg, 0.037 mmol) was dissolved in MeOH/HCl (5 mL, 1.25M) and stirred at room temperature for 2 h. The solvent was evaporated and the residue dissolved in dichloromethane (10 mL) and washed with saturated aqueous sodium hydrogencarbonate (10 mL). The organic phase was dried over anhydrous sodium sulfate and the solvent removed in vacuo to yield a colorless solid (14 mg, 88%).

$[α]_D$ (c 0.70, CH$_2$Cl$_2$): +27.4. IR (neat) $v_{max}$=3287, 2926, 2857, 1638, 1579, 1491, 1445, 1227, 757. $^1$H NMR (CDCl$_3$, 300 MHz) δ 7.65 (s, 1H), 7.32 (m, 2H), 7.11 (m, 2H), 6.47 (m, 1H), 5.10 (m, 1H), 4.63 (m, 1H), 4.53 (m, 2H), 3.95 (m, 1H), 3.80 (m, 1H), 3.59 (m, 1H), 3.07 (m, 1H), 2.68 (m, 3H), 1.57-1.25 (m, 16H). $^{13}$C (CDCl$_3$, 300 MHz) δ 157.0, 146.6, 140.8, 129.7, 129.6, 129.0, 129.0, 124.5, 115.7, 115.4, 113.1, 72.8, 68.4, 55.1, 42.0, 39.7, 39.7, 33.3, 31.9, 26.8, 26.2, 23.6, 23.3. MS m/z (CI) 429 (M+H).

Examples 5-12

The compounds of Examples 5-12 were prepared accordingly to the procedures described above. All of them were tested as inhibitors of CDK7, and for their activities against other kinases including CDK2 and CDK9. Table 2 shows the obtained results, including Examples 2, 3 and 4.

TABLE 2

Comparison of IC$_{50}$ data for CDK2, CDK7, and CDK9. "N.D." stands for "not determined"

| Example No. | Structure | Prepared using method analogous to Example No. | CDK2 IC$_{50}$ (nM) | CDK7 IC$_{50}$ (nM) | CDK9 IC$_{50}$ (nM) | m/z |
|---|---|---|---|---|---|---|
| 2 | (structure) | 2 | ~100 | >1000 | >1000 | 324 [M + H] |
| 3 | (structure) | 3 | >1000 | 32 | ~100 | 370 [M + H] |
| 4 | (structure) | 4 | N.D. | 180 | N.D. | 429 [M + H] |

TABLE 2-continued

Comparison of IC$_{50}$ data for CDK2, CDK7, and CDK9. "N.D." stands for "not determined"

| Example No. | Structure | Prepared using method analogous to Example No. | CDK2 IC$_{50}$ (nM) | CDK7 IC$_{50}$ (nM) | CDK9 IC$_{50}$ (nM) | m/z |
|---|---|---|---|---|---|---|
| 5 | 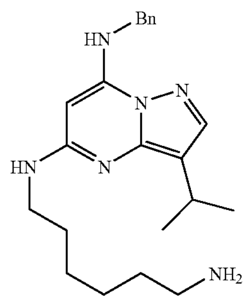 | 2 | >1000 | 18 | >1000 | 381 [M + H] |
| 6 | 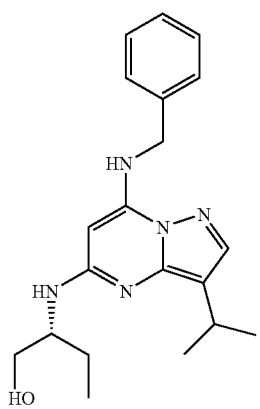 | 2 | >1000 | 70 | ~100 | 354 [M + H] |
| 7 | 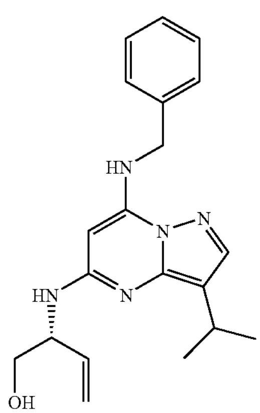 | 3 | N.D. | >1000 | N.D. | 352 [M + H] |

TABLE 2-continued

Comparison of IC$_{50}$ data for CDK2, CDK7, and CDK9. "N.D."stands for "not determined"

| Example No. | Structure | Prepared using method analogous to Example No. | CDK2 IC$_{50}$ (nM) | CDK7 IC$_{50}$ (nM) | CDK9 IC$_{50}$ (nM) | m/z |
| --- | --- | --- | --- | --- | --- | --- |
| 8 | 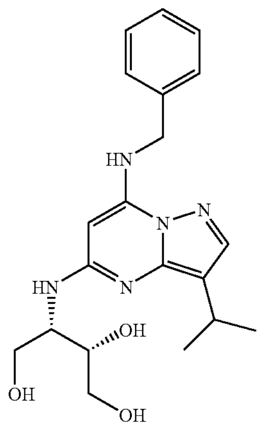 | 4 | N.D. | 350 | 10-100 | |
| 9 | 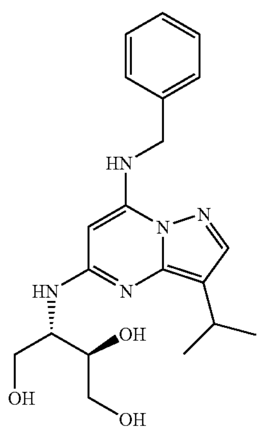 | 2 | N.D. | >300 | 10-100 | |
| 10 | 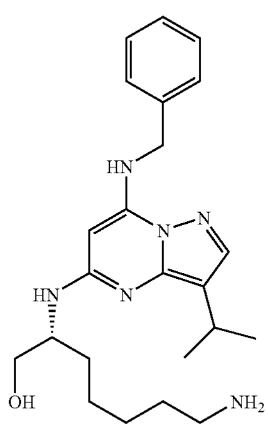 | 2 | N.D. | 100-1000 | N.D. | 411 [M + H] |

TABLE 2-continued
Comparison of IC$_{50}$ data for CDK2, CDK7, and CDK9. "N.D." stands for "not determined"
| Example No. | Structure | Prepared using method analogous to Example No. | CDK2 IC$_{50}$ (nM) | CDK7 IC$_{50}$ (nM) | CDK9 IC$_{50}$ (nM) | m/z |
|---|---|---|---|---|---|---|
| 11 | 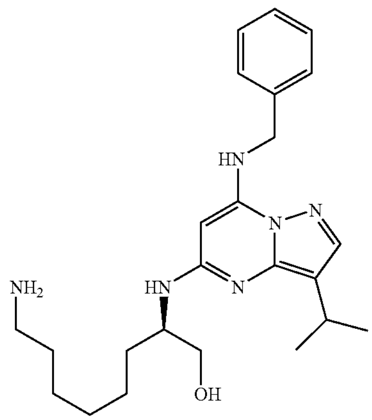 | 2 | N.D. | 100-1000 | N.D. | 426 [M + H] |
| 12 | 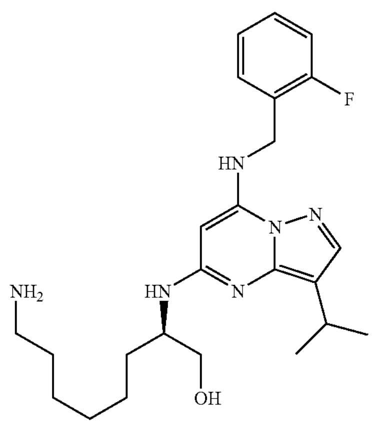 | 3 | >1000 | ~100 | 100-1000 | |
Example 13
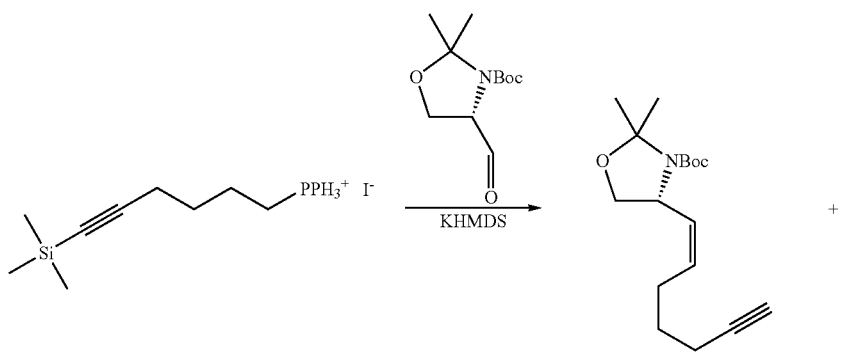

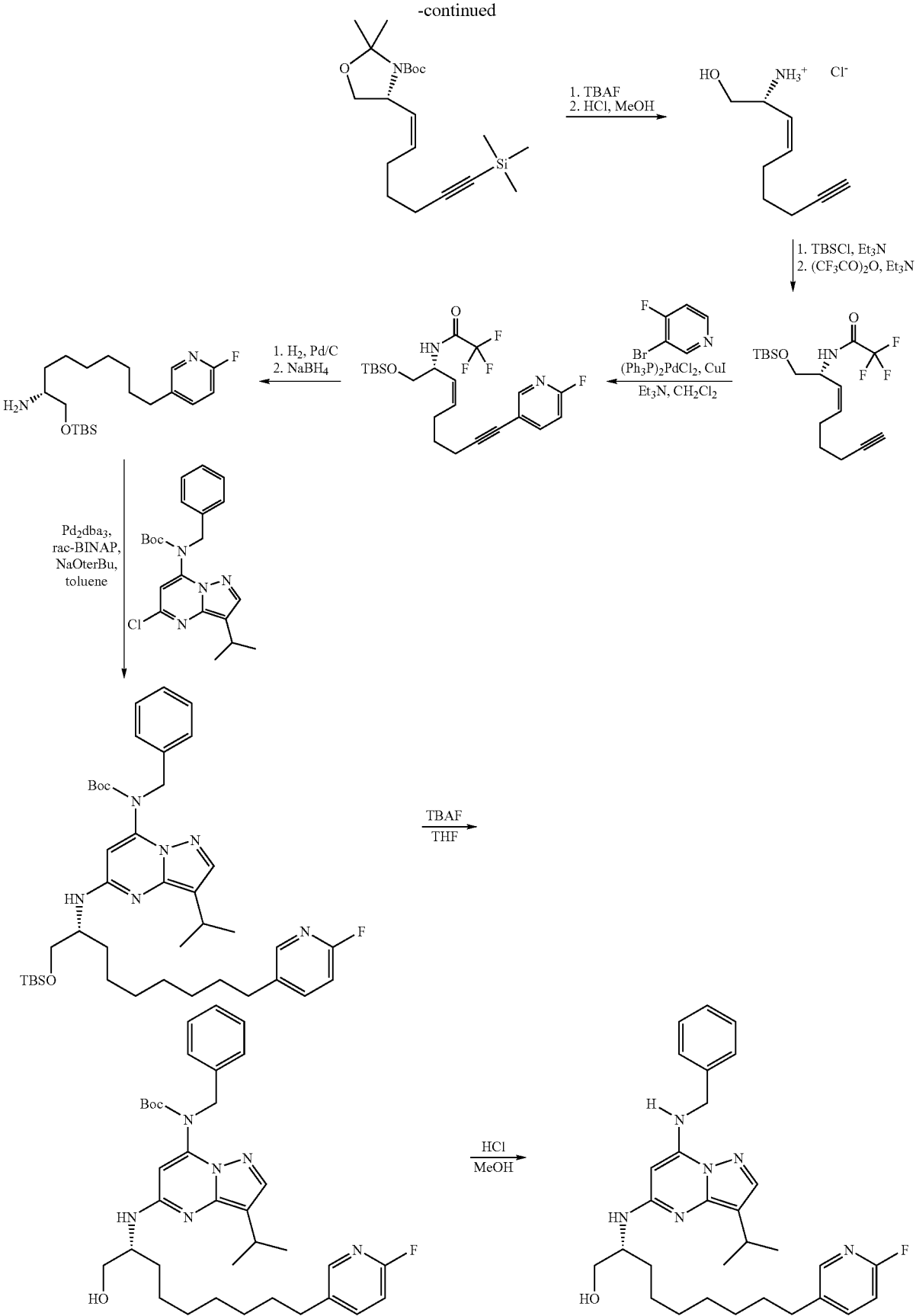

Step 1

Trimethylsilyl-1-hexenyl-6-(triphenyl)phosphonium iodide

A solution of trimethylsilylacetylene (7.2 mL, 51 mmol) in THF (50 mL) was cooled to −20° C. and n-butyllithium (20.4 mL, 51 mmol, 2.5 M in hexanes) was added dropwise. The mixture was stirred for 30 minutes and 1-chloro-4-iodobutane (5 mL, 41 mmol) was added. The mixture was warmed to room temperature and stirred for 72 hours. The reaction mixture was poured into saturated aqueous sodium hydrogencarbonate (50 mL) and the aqueous phase extracted with diethyl ether (5×40 mL). The combined organic phases were washed with brine, dried over anhydrous sodium sulfate and concentrated by rotary evaporation.

The crude product and sodium iodide (9.3 g, 62 mmol) were heated under reflux in acetone (80 mL) until GC-MS (give conditions) showed complete conversion to product. The reaction mixture was cooled to room temperature, filtered through celite and concentrated in vacuo. The remaining residue was dissolved in pentane (100 mL) and added to a saturated aqueous solution of saturated aqueous sodium hydrogencarbonate (100 mL). The water layer was extracted with pentane (3×50 mL) and the combined organic phases were dried over anhydrous sodium sulfate. After concentration by rotary evaporation, the crude product was purified by distillation at b.p. 120-123° C. and 20 mbar (10.28 g, 89% over two steps).

B.p. 120-123° C., 20 mbar. $^1$H NMR (CDCl$_3$, 300 MHz) δ 3.21 (m, 2H), 2.25 (m, 2H), 1.93 (m, 2H), 1.60 (m, 2H), 0.14 (s, 9H). $^{13}$C (CDCl$_3$, 300 MHz) δ 106.4, 83.7, 32.4, 29.2, 18.8, 6.1, 0.1. MS m/z (CI) 280 (M).

The iodide (10.16 g, 36 mmol) and triphenylphosphine (9.5 g, 36 mmol) were dissolved in toluene (22 mL, 0.6 mL/mmol) and heated at 90° C. for 4 days. The reaction mixture was filtered and the remaining solid washed with hexanes (3×50 mL). The solid was dried in high vacuum to leave the product was obtained as a white solid (19.65 g, 100%).

$^1$H NMR (CDCl$_3$, 300 MHz) δ 7.78-7.62 (m, 15H), 3.67 (m, 2H), 2.23 (m, 2H), 1.76 (m, 4H), −0.06 (s, 9H). $^{13}$C (CDCl$_3$, 300 MHz) δ 135.1, 133.7, 133.6, 130.6, 130.4, 128.2, 118.6, 106.0, 83.4, 28.5, 28.3, 21.3, 19.2, 0.06. MS m/z (FAB+) 415 (M). HRMS (CI) Calc.: 415.2011. Found: 415.2004.

Step 2

(R)-tert-Butyl 2,2-dimethyl-4-((Z)-7-(trimethylsilyl)hepten-6-ynyl)oxazolidine-3-carboxylate The phosphonium salt (4.5 g, 8.3 mmol) was suspended in THF (40 mL) at room temperature and a 0.5 M solution of potassium hexamethylsilazide in toluene (16.4 mL, 8.2 mmol) was added. The resultant suspension was stirred at room temperature for 1 hour, then cooled to −78° C. and a solution of (S)-tert-Butyl 2,2-dimethyl-4-formyloxazolidine-3-carboxylate (6.9 mmol) in THF (10 mL) was added dropwise. The cooling bath was removed and the mixture was stirred for further 2 h. The reaction was quenched with MeOH (3 mL) and the resulting mixture poured into a mixture of saturated aqueous potassium sodium tartrate and water (1:1, 50 mL). Extraction with diethyl ether (2×25 mL), drying (anhydrous magnesium sulfate) and evaporation of the solvent in vacuo gave a colorless oil which was purified by column chromatography on silica (hexanes:ethyl acetate=9:1) to give the alkene as a colorless oil (762 mg, 30%), along with the corresponding desilylated alkene (455 mg, 22%).

[α]$_D$ (c 1.12, CH$_2$Cl$_2$): +49.6. IR (neat) ν$_{max}$=2978, 2935, 2868, 2174, 1699, 1384, 1250, 1175, 1086, 843, 760. $^1$H NMR (CDCl$_3$, 300 MHz) δ 5.43 (m, 2H), 4.64 (m, 1H), 4.06 (m, 1H), 3.63 (m, 1H), 2.36-2.12 (m, 4H), 1.58-1.42 (m, 18H), 0.14 (s, 9H). $^{13}$C(CDCl$_3$, 300 MHz) δ 151.9, 131.5, 130.4, 129.3, 84.7, 79.6, 69.0, 54.4, 28.5, 26.2, 24.0, 19.1, 0.12. MS m/z (CI) 366 (M+H). HRMS (CI) Calc.: 366.2464. Found: 366.2457.

Step 3

(R,Z)-2-Aminonon-3-en-8-yn-1-ol hydrochloride

The carbamate (760 mg, 2.08 mmol) was dissolved in hydrochloric acid (6 M; 3 mL) and stirred at room temperature for 2 h. The solvent was evaporated to yield a colorless solid (394 mg, 100%).

M.p. 96-97° C. (MeOH). [α]$_D$ (c 1.14, CH$_2$Cl$_2$): −7.5. IR (neat) ν$_{max}$=3390, 3286, 3194, 2928, 2915, 1599, 1487, 1051. $^1$H NMR (CD$_3$OD, 300 MHz) δ 5.82 (m, 1H), 5.42 (m, 1H), 4.15 (m, 1H), 3.69 (m, 1H), 3.53 (m, 1H), 2.34-2.15 (m, 5H), 1.64 (m, 2H). $^{13}$C (CD$_3$OD, 300 MHz) δ 138.1, 123.8, 70.3, 63.2, 51.9, 29.0, 27.6, 18.4. MS m/z (CI) 154 (M+). HRMS (CI) Calc.: 154.1232. Found: 154.1227.

Step 4

N-[(Z)-(R)-1-(tert-Butyldimethylsilyloxy)-non-3en-8yn-2yl]-2,2,2-trifluoroacetamide To a solution of the aminoalcohol hydrochloride (511 mg, 2.69 mmol) in dichloromethane (20 mL) was added anhydrous magnesium sulfate (0.83 mL, 5.93 mmol), 4-(dimethylamino)pyridine (2 mg) and tert-butyldimethylsilyl chloride (446 mg, 2.96 mmol). The mixture was stirred over night at room temperature. Water (20 mL) was added and the mixture vigorously stirred for 10 min. The organic layer was separated, washed with water (20 mL), brine (20 mL) and dried over anhydrous sodium sulfate. Evaporation in vacuo gave the amine analytically pure (607 mg, 84%).

[α]$_D$ (c 1.14, CH$_2$Cl$_2$): −24.3. IR (neat) ν$_{max}$=3375, 3312, 2951, 2930, 2857, 2118, 1470, 1462, 1254, 1088, 837, 777. $^1$H NMR (CDCl$_3$, 300 MHz) δ 5.34 (m, 2H), 3.75 (m, 1H), 3.53 (m, 1H), 3.34 (m, 1H), 2.19 (m, 4H), 1.93 (m, 1H), 1.57 (m, 4H), 0.88 (s, 9H), 0.04 (s, 6H). $^{13}$C (CDCl$_3$, 300 MHz) δ 131.7, 130.6, 84.0, 68.6, 67.7, 50.3, 28.3, 26.6, 25.9, 18.3, 17.7, −5.3. MS m/z (CI) 268 (M+H). HRMS (CI) Calc.: 268.2097. Found: 268.2088.

A solution of the amine (200 mg, 075 mmol) and triethylamine (0.84 mL, 6.00 mmol) in dichloromethane (5 mL) was cooled to −20° C. and a solution of trifluoroacetic anhydride (0.42 mL, 2.99 mmol) in dichloromethane (1 mL) was added dropwise. The reaction mixture was allowed to warm to room temperature over night. After dilution with dichloromethane (10 mL) was the organic phase washed with saturated aqueous sodium hydrogencarbonate (10 mL) and dried over anhydrous sodium sulfate. The crude product was purified after concentration by column chromatography on silica (hexanes: ethyl acetate=10:1) to yield the product as a light yellow oil (241 mg, 88%).

[α]$_D$+6.4 (c 1.15 CH$_2$Cl$_2$); IR (neat) ν$_{max}$=3313, 2952, 2932, 2859, 2119, 1704, 1551, 1471, 1258, 1205, 1121, 838, 778. $^1$H NMR (CDCl$_3$, 300 MHz) δ 6.70 (m, 1H), 5.61 (m, 1H), 5.47 (m, 1H), 4.79 (m, 1H), 3.76 (m, 1H), 3.62 (m, 1H), 2.30 (m, 2H), 2.21 (m, 2H), 1.96 (m, 1H), 1.64 (m, 2H), 0.9 (s, 9H), 0.07 (s, 6H). $^{13}$C (CDCl$_3$, 300 MHz) δ 156.0, 133.8, 125.9, 115.9, 83.8, 68.7, 64.6, 48.7, 28.0, 26.7, 25.7, 18.2, 17.8, −5.6. MS m/z (CI) 364 (M+H). HRMS (CI) Calc.: 364.1920. Found: 364.1903.

Step 5

(N)-[(Z)-(R)-1-(tert-Butyldimethylsilyloxy)-9-(6-fluoro-pyridin-3-yl)-non-3-en-8yn-2-yl]-2,2,2-trifluoro-acetamide To a flask equipped with alkene (291 mg, 0.8 mmol) was added freshly distilled dichloromethane (1 mL), 5-bromo-2-fluoropyrimidine (0.25 mL, 2.4 mmol, 3 equivalents), (Ph$_3$P)$_2$PdCl$_2$ (11 mg, 0.016 mmol, 0.02 equivalents), CuI (1 mg, 0.008 mmol, 0.01 equivalents) and Et$_3$N (0.7 mL, 4.8 mmol, 6 equivalents). The resulting solution was stirred under reflux for 13 h, cooled to room temperature and quenched with saturated aqueous sodium hydrogencarbonate. The mixture was extracted with dichloromethane, combined organic layers dried (anhydrous magnesium sulfate) and evaporated in vacuo. Purification by column chromatography (silica gel, hexanes/ethyl acetate 20/1) gave the amide as a yellow oil (249 mg, 68%).

$[α]_D$+4.4 (c 1.23, CH$_2$Cl$_2$). IR (neat) $ν_{max}$=2952, 2932, 2858, 1706, 1543, 1483, 1255, 1206, 1183, 837, 779. $^1$H NMR (400 MHz, CDCl$_3$): $δ_H$ 0.04 (s, 6H), 0.87 (s, 9H), 1.68 (m, 2H), 2.34 (m, 4H), 3.63 (m, 1H), 3.71 (m, 1H), 4.82 (m, 1H), 5.48 (m, 1H), 5.61 (m, 1H), 6.84 (m, 1H), 6.90 (m, 1H), 7.78 (m, 1H), 8.22 (s, 1H); $^{13}$C (100 MHz, CDCl$_3$): $δ_C$ −5.65, 18.13, 18.78, 25.65, 26.92, 28.08, 48.76, 64.61, 76.48, 92.97, 109.12, 114.46, 125.97, 127.64, 133.74, 143.75, 150.22, 156.21, 162.19. MS (CI): m/z 459 (M+H), 486 (M+NH$_4$). HRMS (CI) Calc.: 459.2095. Found: 459.2097.

Step 6

(R)-(1-(tert-Butyldimethylsilyloxy))-9-(6-fluoropyridin-3-yl)-2-octylamine

A flask was charged with pyridine (235 mg, 0.51 mmol), palladium on carbon (65 mg, 10 mol %) and ethyl acetate (10 mL) and stirred vigorously in Parr apparatus under hydrogen atmosphere for 13 h. The mixture was filtrated through Celite, concentrated and dried in vacuo to give analytically pure product (165 mg, 70%). $[α]_D$+12.7 (c 1.45, CH$_2$Cl$_2$). IR (neat) $ν_{max}$=3306, 3091, 2930, 2858, 1706, 1593, 1558, 1472, 1393, 1253, 1184, 1162, 837, 778. $^1$H NMR (400 MHz, CDCl$_3$): $δ_H$ 0.05 (s, 6H), 0.88 (s, 9H), 1.30 (m, 9H), 1.57 (m, 3H), 2.57 (m, 2H), 3.64 (m, 2H), 3.96 (m, 1H), 6.66 (m, 1H), 6.83 (m, 1H), 7.58 (m, 1H), 7.98 (s, 1H); $^{13}$C (100 MHz, CDCl$_3$): $δ_C$-5.67, 18.15, 25.70, 28.88, 29.18, 30.95, 31.13, 31.93, 51.30, 63.55, 108.95, 115.94, 135.44, 141.03, 146.78, 156.65, 162.23. MS (CI): m/z 465 (M+H). HRMS (CI) Calc.: 465.2547. Found: 465.2547.

To a solution of amide (165 mg, 0.35 mmol) in ethanol (3 mL) sodium borohydride (161 mg, 4.26 mmol, 12 equivalents) was carefully added. The mixture was stirred for 1 hour at room temperature and then heated to reflux for another 1 hour. Evaporation of solvent, dilution with dichloromethane, washing with saturated aqueous sodium hydrogencarbonate, drying (anhydrous magnesium sulfate) and concentration by rotary evaporation gave the analytically pure amine (141 mg, 100%).

$[α]_D$−1.3 (c 1.15, CH$_2$Cl$_2$). IR (neat) $ν_{max}$=3368, 2928, 2855, 1721, 1593, 1483, 1391, 1360, 1251, 1091, 1025, 837, 776. $^1$H NMR (400 MHz, CDCl$_3$): $δ_H$ 0.02 (s, 6H), 0.87 (s, 9H), 1.28 (m, 10H), 1.56 (m, 2H), 2.01 (v br. s, 2H), 2.55 (m, 2H), 2.75 (m, 1H), 3.28 (m, 1H), 3.52 (m, 1H), 6.80 (m, 1H), 7.54 (m, 1H), 7.97 (m, 1H); $^{13}$C (100 MHz, CDCl$_3$): $δ_C$ −5.41, 18.26, 25.71, 25.89, 26.09, 28.95, 29.25, 29.63, 31.16, 31.94, 33.64, 52.87, 68.31, 108.95, 135.46, 140.93, 146.82, 163.33. MS (CI): m/z 369 (M+H). HRMS (CI) Calc.: 369.2737. Found: 369.2733.

Step 7 tert-Butyl Benzyl-{5-[(R)-(1-(tert-butyl-dimethylsilyloxy))-9-(6-fluoropyridin-3-yl)-nonyl-2-amino]-3-isopropyl-pyrazolo[1,5-a]pyrimidin-7-yl}-carbamate The chloride (49 mg, 0.12 mmol), Pd$_2$dba$_3$ (5.5 mg, 5 mol %), rac-BINAP (11 mg, 15 mol %), and sodium tert-butoxide (17 mg, 0.18 mmol, 1.5 equivalents) were suspended in toluene (0.5 mL). After 5 min of stirring, the amine (50 mg, 0.14 mmol, 1.1 equivalents) was added and the red mixture heated for 13 h at 100° C. The reaction mixture was cooled to room temperature and evaporated. After concentration the crude product was purified by column chromatography on silica (hexanes/ethyl acetate 10/1) yielding the product as a yellow oil (30.6 mg, 35%).

$[α]_D$+8.17 (c 1.53, CH$_2$Cl$_2$). IR (neat) $ν_{max}$=3366, 2928, 2856, 2237, 1720, 1643, 1582, 1518, 1391, 1368, 1250, 1157, 836. $^1$H NMR (400 MHz, CDCl$_3$): $δ_H$ 0.05 (s, 6H), 0.90 (s, 9H), 1.35 (m, 9H), 1.43 (s, 9H), 1.60 (m, 3H), 2.60 (m, 2H), 3.13 (hep, J=2.8 Hz, 1H), 3.68 (m, 2H), 4.95 (m, 2H), 5.70 (m, 1H), 6.86 (m, 1H), 7.29 (m, 7H), 7.60 (m, 1H), 7.76 (s, 1H), 8.02 (s, 1H); $^{13}$C (100 MHz, CDCl$_3$): $δ_C$ −5.36, 18.34, 23.13, 23.23, 23.82, 25.93, 26.04, 28.07, 29.02, 29.30, 29.49, 29.73, 31.23, 31.34, 32.00, 51.47, 64.18, 82.21, 108.79, 109.16, 113.12, 127.49, 127.95, 128.48, 135.46, 137.82, 140.95, 141.02, 141.53, 141.65, 146.84, 146.98, 153.61, 154.28, 161.03, 163.38.

Step 8

(R)-tert-butyl benzyl-(5-(9-(6-fluoropyridin-3-yl)-1-hydroxynonan-2-ylamino)-3-isopropylpyrazolo[1,5-a]pyrimidin-7-yl)carbamate To a solution of carbamate (30 mg, 0.04 mmol) in dry THF (1 mL) tetrabutylammonium fluoride (1M solution, 0.16 mL) was added. The reaction mixture was stirred at room temperature for 2 h. A saturated solution of ammonium chloride was added and the mixture was washed with ethyl acetate. The combined organic fractions were dried over magnesium sulphate and concentrated in vacuo. The product was purified on silica gel with 50% ethyl acetate in hexanes, to give the product as a yellow oil (17 mg, 69%).

$[α]_D$+8.5 (c 0.89, CH$_2$Cl$_2$). IR (neat) $ν_{max}$=3355, 2927, 2855, 1717, 1645, 1519, 1484, 1392, 1368, 1248, 1157, 855. $^1$H NMR (400 MHz, CDCl$_3$): $δ_H$ 1.33 (d, J=6.8 Hz, 6H), 1.35 (m, 9H), 1.43 (s, 9H), 1.58 (m, 3H), 2.60 (m, 2H), 3.17 (hep, J=2.8 Hz, 1H), 3.63 (m, 1H), 3.81 (m, 1H), 3.96 (m, 1H), 4.96 (m, 2H), 5.79 (s, 1H), 6.86 (m, 1H), 7.28 (m, 5H), 7.58 (m, 1H), 7.77 (s, 1H), 8.02 (s, 1H); $^{13}$C (100 MHz, CDCl$_3$): $δ_C$ −20.18, 22.71, 23.20, 23.65, 26.18, 28.94, 29.20, 29.39, 29.72, 31.16, 31.58, 31.96, 51.66, 54.94, 67.17, 82.53, 108.82, 109.19, 113.49, 127.57, 127.81, 128.55, 135.43, 137.60, 140.97, 143.57, 146.83, 146.97, 153.48, 155.08, 163.40. MS (CI): m/z 619 (M+H). HRMS (CI) Calc.: 619.3772. Found: 619.3753.

Example 14

CDK7/CycH/MAT1 Trimeric Complex: Kinase Assay 1050

In vitro inhibition of CDK7 activity was achieved by incubation of 150 ng of purified recombinant CDK7 complex (CDK7, Cyclin H, MAT1; purchased from Proqinase GmbH, Germany) with compounds according to the following procedure.

1. To 10 µl of CDK7 Assay Buffer (150 mM Hepes-NaOH (pH7.5), added 3 mM DTT, 7.5 mM $MgCl_2$, 7.5 $MnCl_2$, 7.5 µM sodium orthovanadate, 125 µg/ml $PEG_{20,000}$), 2.5 µl of 500 µM CDK7/9tide peptide (sequence: YSPTSPSYSPTSPS) (SEQ ID NO: 1) per reaction (500 µM) and 150 ng CDK7 complex.
2. Prepared test compounds, prepared at concentrations of 1000, 100, 10, 1 and 0.1 µM. Diluted 1 in 40 in $ddH_2O$ and added 1 µl of test compound or DMSO (controls).
3. Incubated at 30° C. for 30 mins in a water bath.
4. Added 10 µl of ATP (0.5 µM) per reaction to get a final concentration of 2 µM ATP.
5. Made up to 25 µl total volume with $ddH_2O$
6. Incubated for 20 min at 30° C. in a water bath
7. Used the PKLight Kinase assay (Cambrex, UK), add to each reaction 10 µl of stop reaction and mix thoroughly. Incubated at room temp for 10 min.
8. Added 20 µl Luciferase reaction mixture (Cambrex, UK) per reaction, and further incubated at room temp for 10 mins and determined luciferase activities according to manufacturer's methods. Kinase reactions were added to 96 well microplates and luciferase activities determined using a Packard TopCount NXT™ luminescent counter (TopCount 9904). The luminometer was programmed to take a read time of 0.1 integrated reading and emission of light was detectable at 560 nm.
9. All kinase inhibition assays were carried out in triplicate. As the bioluminescent signal is inversely proportional to kinase activity, all values were deducted from the no enzyme control. These values were then plotted utilizing the enzyme control as a reference to 100% activity and compared to all other values. The IC50 was determined as the inhibitor concentration at which kinase activity was 50% of the activity obtained in the presence of the solvent (DMSO).

Inhibition of CDK2 was assessed using 50 ng CDK2/cyclin A complex (Proqinase GmbH, Germany), as above for CDK7 Inhibition of CDK9 was assessed using 100 ng CDK9/cyclin T complex (Proqinase GmbH, Germany), as above for CDK7.

TABLE 3

Structure, formmula, and molecular weight of compounds examined in this example.

| Ref. No. | Structure | Formula | Mol. Weight [g mol$^{-1}$] |
|---|---|---|---|
| ICEC0232 | 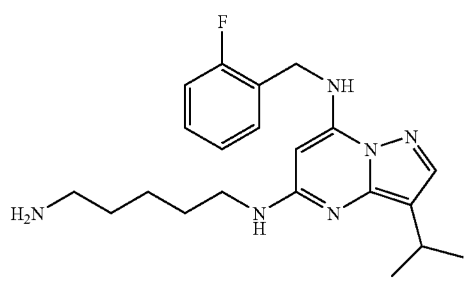 | $C_{21}H_{29}FN_6$ | 384.49 |
| ICEC0229 | 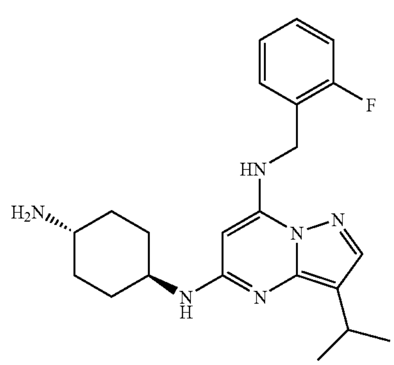 | $C_{22}H_{29}FN_6$ | 396.50 |

TABLE 3-continued

Structure, formmula, and molecular weight of compounds examined in this example.

| Ref. No. | Structure | Formula | Mol. Weight [g mol$^{-1}$] |
|---|---|---|---|
| ICEC0222 | 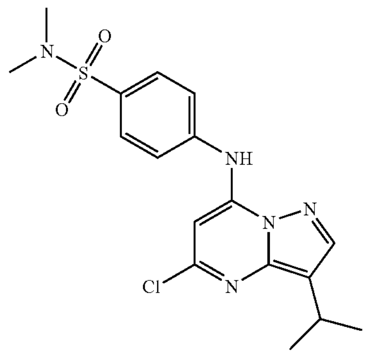 | $C_{22}H_{28}ClN_5O_4S$ | 494.01 |
| ICEC0218 | 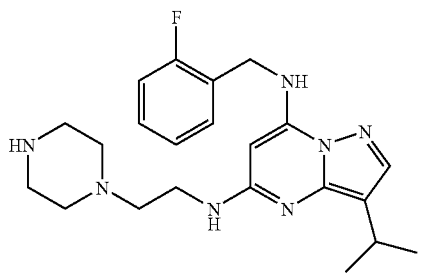 | $C_{22}H_{30}FN_7$ | 411.52 |
| ICEC0214 | 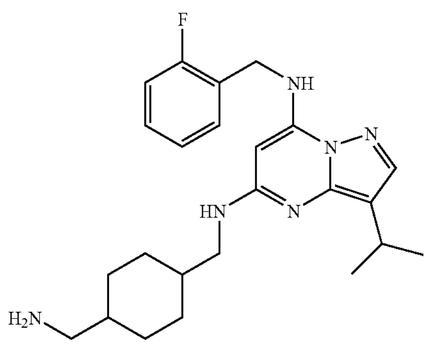 | $C_{24}H_{33}FN_6$ | 424.56 |
| ICEC0216 | 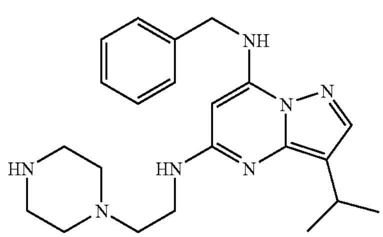 | $C_{22}H_{31}N_7$ | 393.5284 |
| ICEC0238 | 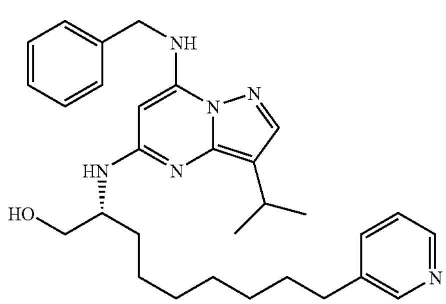 | $C_{30}H_{40}N_6O$ | 500.6782 |

TABLE 3-continued

Structure, formmula, and molecular weight of compounds examined in this example.

| Ref. No. | Structure | Formula | Mol. Weight [g mol⁻¹] |
|---|---|---|---|
| ICEC0235 | 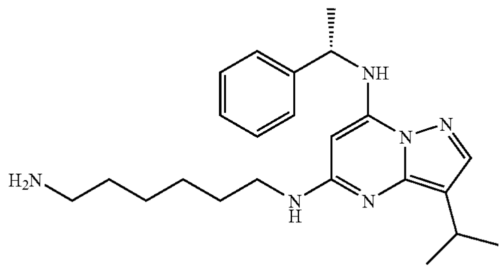 | $C_{22}H_{32}N_6$ | 380.54 |
| ICEC0236 | 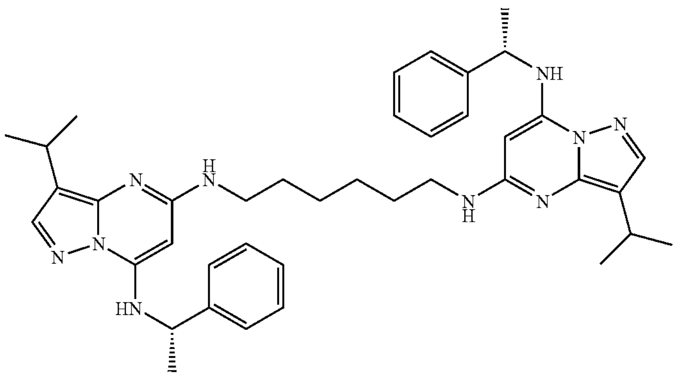 | $C_{40}H_{52}N_{10}$ | 672.9079 |
| BS-181 | 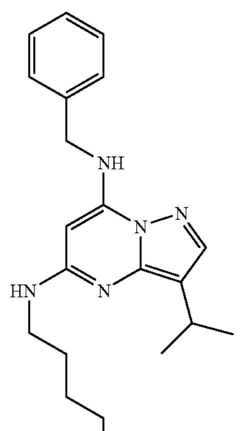 | $C_{23}H_{34}N_6$ | 394.56 |

Figure 1B:
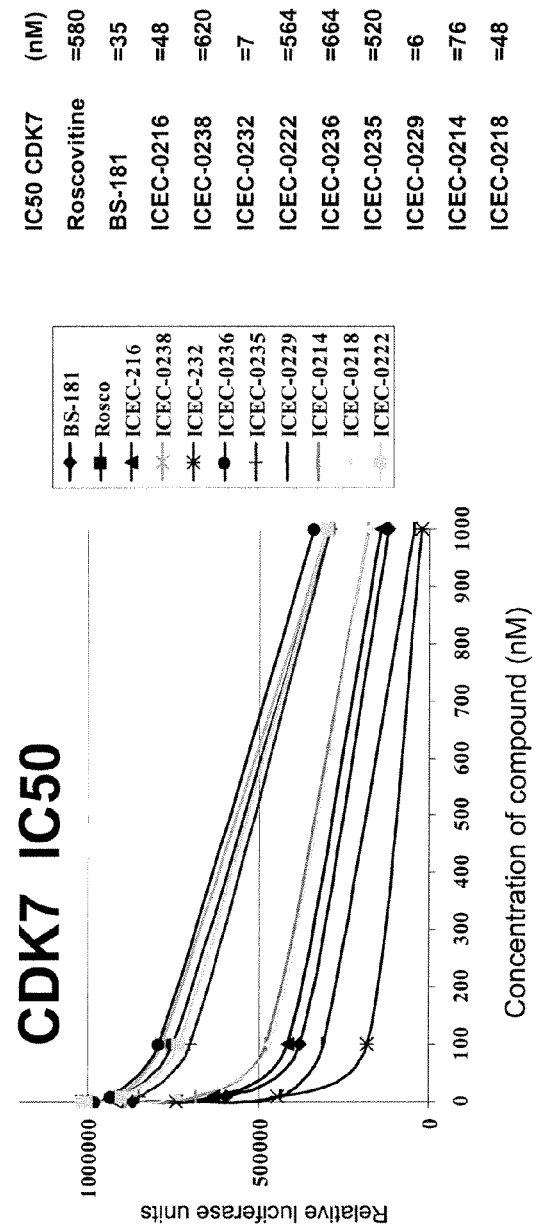
FIG. 1(b) shows the results of a kinase inhibition assay comparing compounds listed in Table 3.

FIG. 1(a) shows kinase inhibition by compound at 100 nM. FIG. 1(b) shows the results of a kinase inhibition assay comparing compounds listed in Table 3.

Example 15

In Vitro Assay for Inhibition of Protein Kinase Activity

Various compounds according to the invention were prepared for assay studies. Table 4 provides structures for the compounds that were used for the assay studies.

The assays of this example determined kinase activity by measuring incorporation of $^{32}P$ on substrate peptide, following incubation of substrate peptide with [γ-$^{32}$P]-ATP, in the presence of 0, 1, 10, 100 or 1000 nM of each compound solubilised in DMSO. Purified recombinant CAK was purchased from Proqinase GmbH (Germany), 150 ng being used per assay. Purified, recombinant CDK2, CDK4 and CDK9 were purchased from New England Biolabs (UK) Ltd, 200 ng being used per assay. The substrate peptide used for assaying CDK2, CDK9 and CAK had the sequence YSPTSP-SYSPTSPSYSPTSPSKKKK (SEQ ID NO: 2) and was synthesized by the Advanced Biotechnology Centre, Imperial College London, UK). The substrate peptide for the CDK4 assay was purchased from New England Biolabs (UK) Ltd and comprised sequences around serine 795 of the retinoblastoma (Rb) protein. 1 Ci/ml [γ-$^{32}$P]-ATP was prepared by dilution of 10 μl of [γ-$^{32}$P]-ATP (3000 Ci/mmol; Amersham/GE Healthcare, UK) with 90 μl of Magnesium/ATP cocktail (75 mM MgCl$_2$ and 500 μM cold ATP in 20 mM MOPS pH 7.2, 25 mM β-glycerol phosphate, 5 mM EGTA, 1 mM sodium orthovanadate, 1 mM DTT.

The kinase assay was carried out by the addition of 5 μl of 5× Reaction Buffer (300 mM HEPES pH 7.5, 15 mM MgCl$_2$, 15 mM MnCl$_2$, 15 μM sodium orthovanadate, 6 mM DTT, 12.5 μg/50 μl PEG20,000), 2.5 μl of 500 μM substrate peptide, 1.5 μl kinase and diluted compound (or DMSO), together with double distilled deionised H$_2$O to a final volume of 15 μl. Following incubation at 30° C. for 10 min., 10 μl of 1 Ci/ml [γ-$^{32}$P]-ATP was added and the reactions were incubated at 30° C. for 80 min. 45 μl of ice-cold 10% trichloroacetic acid (TCA) was added to the reactions, the tubes were vortexed and centrifuged for 2 min. at 10,000 rpm. 35 μl was spotted on p81 cellulose paper, allowed to dry and washed ×3 with 0.75% phosphoric acid, followed by a single wash with acetone. Radioactivity was measured following the addition of 5 ml scintillation fluid, using a scintillation counter. The kinase activities in the presence of different concentrations of each example were plotted and inhibition of kinase activity by 50% is represented as the IC50 in Table 4.

Growth assay: The cell lines (MCF-7 and MDA-MB-231; purchased from ATCC, USA) were routinely passaged in Dulbecco's Modified Eagle's Medium (DMEM), supplemented with 10% fetal calf serum (FCS) and kept in a 37° C. incubator with 5% CO$_2$. For the growth assay, 6000 cells were seeded into each well of 96-well plates in DMEM containing 10% FCS. Compounds prepared in DMSO were added to the medium at concentrations ranging from 0.4-100 μM. The cells were incubated for a further 72 hours, at which time they were fixed by the addition of 100 μl/well of ice-cold 40% TCA. The plates were left for 1 hour, washed in water and 100 μl of 0.4% (w/v) sulphorhodamine (SRB; Sigma-Aldrich, UK) prepared in 1% acetic acid was added. Plates were washed in 1% acetic acid to remove excess SRB reagent, air dried and bound dye was solubilized by the addition of 100 μl of 10 mM Tris base. The plates were read at 492 nm using a plate reader. The optical densities (OD) at 492 nm were plotted to determine the concentration of compounds at which 50% inhibition of growth is observed. Table 4 shows the results for the MCF-7 cell line.

TABLE 4

| Compound Name | Formula | Kinase Inhibition in vitro | | | | Growth Inhibition MCF7 | | |
|---|---|---|---|---|---|---|---|---|
| | | CDK7 (IC50) [nM] | CDK2 (IC50) [nM] | CDK4 (IC50) | CDK9 (IC50) | LC50 (μM) | TGI (μM) | IC50 (μM) |
| ICEC0167 (AS-540) | 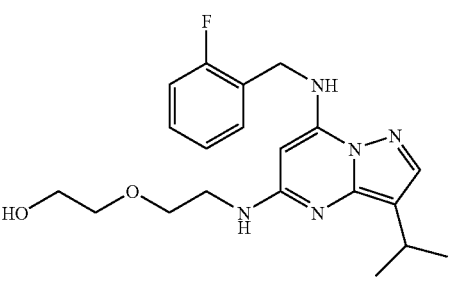 | 18 nM | ND | >1000 nM | ND | >100 | 54 | 25 |
| ICEC0179 (JAB-012) | 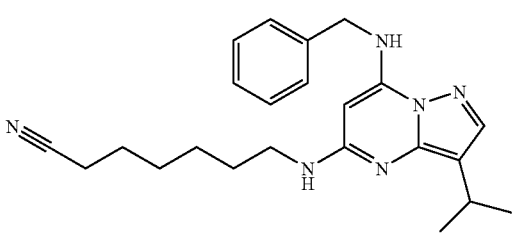 | 20 nM | ND | >1000 nM | ND | >100 | >100 | 35 |
| ICEC0159 (AS-524) | 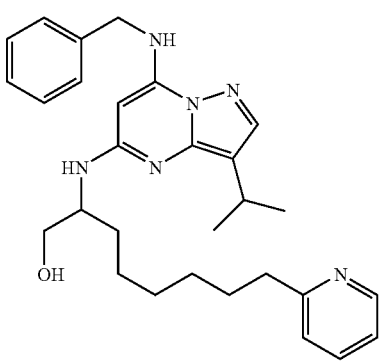 | 42 nM | ND | >1000 nM | ND | >100 | >100 | 87 |

TABLE 4-continued
| Compound Name | Formula | Kinase Inhibition in vitro ||||  Growth Inhibition MCF7 |||
|---|---|---|---|---|---|---|---|---|
| | | CDK7 (IC50) [nM] | CDK2 (IC50) [nM] | CDK4 (IC50) | CDK9 (IC50) | LC50 (μM) | TGI (μM) | IC50 (μM) |
| ICEC0160 (AS-525) | 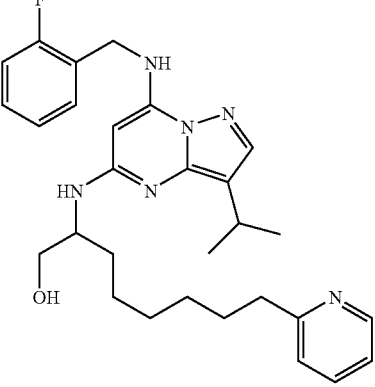 | 44 nM | ND | >1000 nM | ND | >100 | >100 | 55 |
| ICEC0138 (AS-473) | 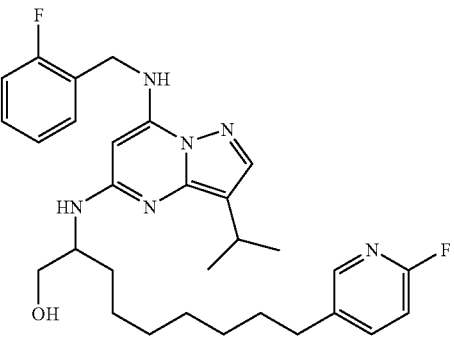 | 46 nM | ND | >1000 nM | ND | >100 | >100 | 69 |
| ICEC0161 (AS-528) | 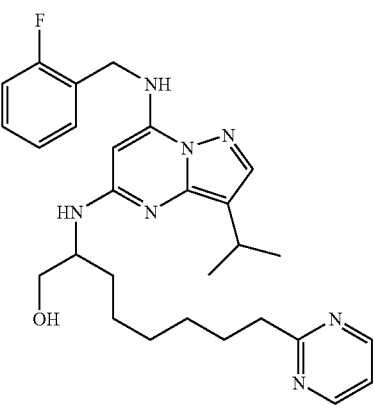 | 55 nM | ND | >1000 nM | ND | >100 | 36 | 23 |
| ICEC0141 (AS-481) | 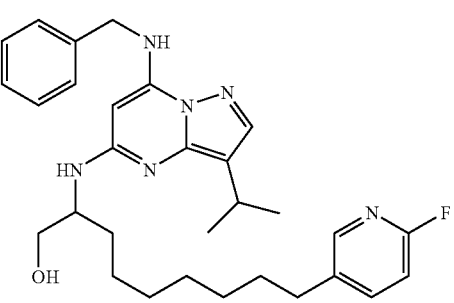 | 80 nM | ND | >1000 nM | ND | 42 | >100 | >100 |

TABLE 4-continued

| Compound Name | Formula | Kinase Inhibition in vitro | | | | Growth Inhibition MCF7 | | |
| --- | --- | --- | --- | --- | --- | --- | --- | --- |
| | | CDK7 (IC50) [nM] | CDK2 (IC50) [nM] | CDK4 (IC50) | CDK9 (IC50) | LC50 (µM) | TGI (µM) | IC50 (µM) |
| ICEC0168 (AS-541) | 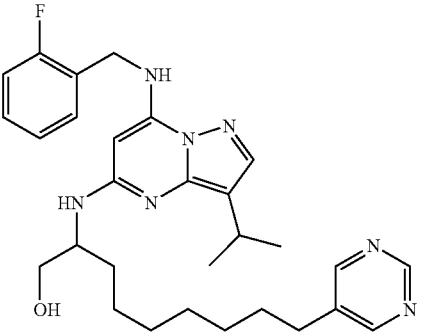 | 120 nM | ND | >1000 nM | ND | 35 | >100 | >100 |

Example 16

Inhibition of Phosphorylation of RNA Polymerase II by BS-181

Figure 2:
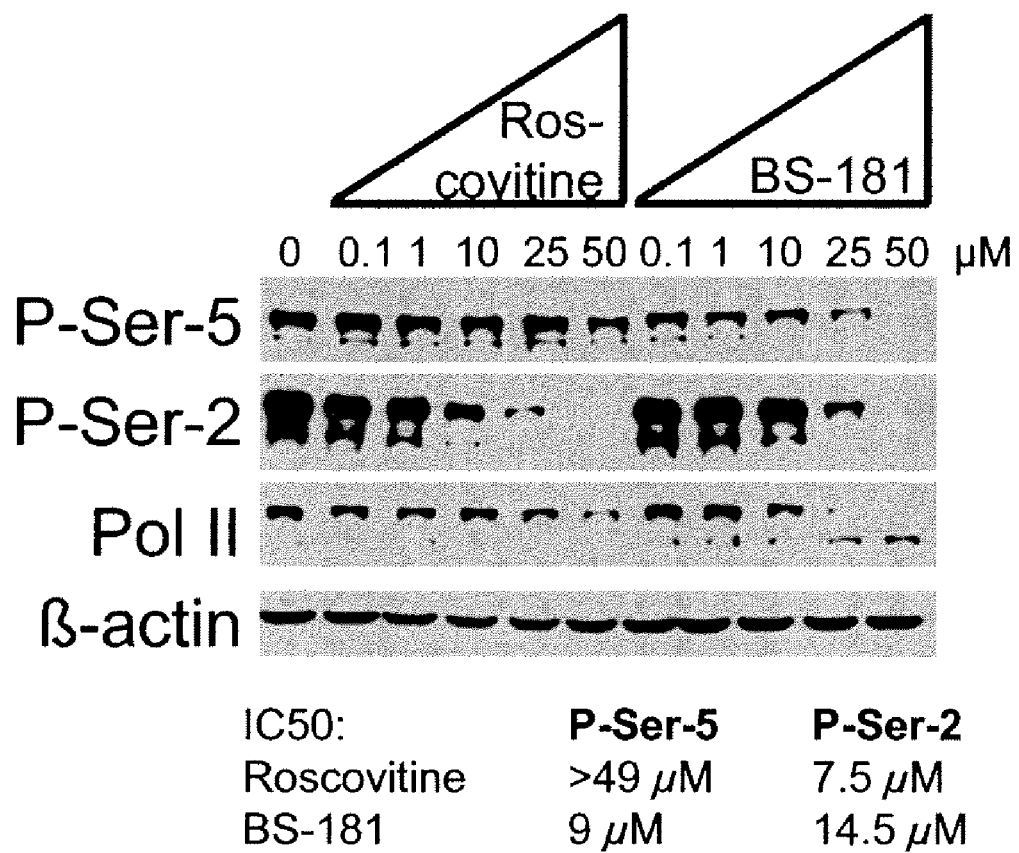
FIG. 2: Immunoblots comparing the inhibition of phosphorylation of RNA polymerase II by BS-181 and by Roscovitine.

This example demonstrates that the compound denoted BS-181 (see Table 3) is capable of inhibiting phosphorylation of RNAPolymerase II. MCF-7 breast cancer cells were treated with BS-181 or Roscovitine at the concentrations shown in FIG. 2 for 4 hours prior to harvesting of cells. FIG. 2 shows immunoblots for RNA polymerase II (Pol II), PolII phosphorylated at serine 2 in the C-terminal domain (P-Ser-2), or serine 5 (P-Ser-5). Immunblotting for β-actin was used as loading control for protein content. Also shown in FIG. 2 are the concentrations of Roscovitine and BS-181 at which serine 2 and serine 5 phosphorylation was inhibited by 50% (IC50).

Example 17

Inhibition of MCF-7 Tumor Growth in Nude Mice by BS-181

This example illustrates that BS-181 is capable of inhibiting MCF-7 tumor growth in nude mice. The following protocol was used in these mouse xenograft experiments. Female, 7-week-old, nu/nu-BALB/c athymic nude mice were purchased from Harlan Olac Ltd. The animals were housed in isolated ventilator cages (IVC) in a 12-h light/dark cycle. The animals received sterilized water and sterile rodent food ad libitum. All procedures were approved by the CBS, Imperial College London Ethics Committee and were covered by a Government Home Office project license for these specific studies. Before inoculation of animal with cells, a 0.72 mg 17β Estradiol 60-day release pellet was implanted subcutaneously (Innovative Research of America, USA). For insertion, animals were anaesthetised, an incision was made to the flank of the animals under aseptic conditions and pellets were implanted. The wound was closed with stainless steel sutures. MCF-7 cells ($5 \times 10^6$ cells) were injected subcutaneously in not more than 0.1 ml volume into the flank of the animals. Tumor measurements were performed twice per week, and volumes were calculated using the formula ½ [length (mm)]× [width (mm)]². The animals were randomized and when tumors had reached a volume of 100-200 mm³, animals were entered into the various treatment groups of 13 mice each and treatment with test drug or vehicle control was initiated. Animals were treated with compound twice daily by i.p. injection for a total of 14 days. The compounds were prepared in the vehicle of 10% DMSO, 50 mM HCl, 5% Tween 20, and 85% Saline. Compounds were administered by exact body weight, with the injection volume being not more than 0.2 ml. At the end of the treatment period (14 days), the mice were sacrificed. Throughout the 14-day treatment period animal weights were determined each day and tumor volume every 48 hours.

Figure 3A:
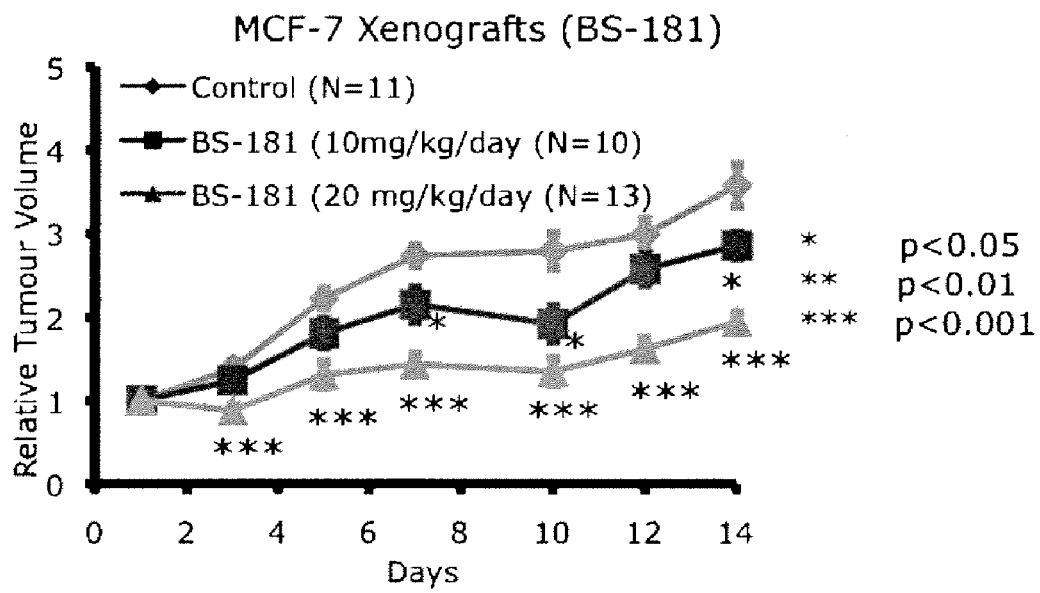
FIG. 3a shows the tumour volume increases over the 14-day course of BS-181 injection, relative to the tumour volume on day 1.
Figure 3B:
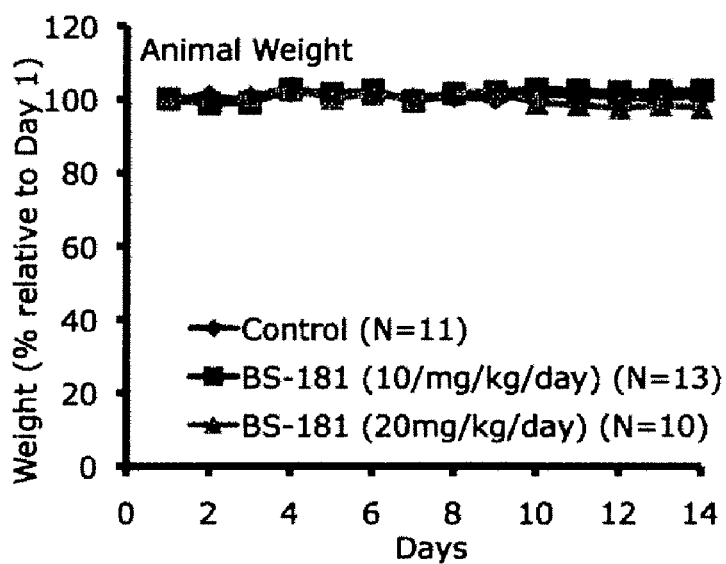
FIG. 3b shows changes in animal weight relative to animal weight on day 1 of the study. Control refers to injections carried out with the solvent alone. The unpaired Student's t-test was used to determine statistical significance. The significance of the differences between the control group and each of the BS-181 treatment groups is depicted by asterisks.

FIG. 3a shows the increase in tumor volume over a 14-day course of BS-181 injection, at different doses relative to the tumor volume on day one. The control curve refers to injections carried out with the solvent alone. FIG. 3b shows the corresponding change in animal weight during the same 14-day course of BS-181 injection. From these data, it is evident that the tumor volume increased more slowly with increasing dosage of BS-181, indicating that BS-181 is capable of inhibiting the growth of MCF-7 tumors. Furthermore, the corresponding animal weight was nearly constant during the 14-day course of BS-181 injection.

Example 18

Kinase Screen for Specificity of BS-181

In this example, recombinant kinases were tested in duplicate for enzyme activity. Table 5 shows the mean activities remaining (as a percentage of the original activity) following the addition of 10 µM of BS-181. The values on the right hand column represent the standard deviation. From these experiments, the three kinases that showed the greatest degree of inhibition were determined to be CDK2, CK1, and DYRK1A. The $IC_{50}$ values of these three kinases with respect to BS-181 were determined to be 750 nM, 7.4 µM, and 2.3 µM, respectively.

TABLE 5

Mean Remaining Enzyme Activities of Recombinant Kinases following addition BS-181

| Recombinant Kinase | Mean Remaining Enzyme Activity (%) | Std. Dev. |
|---|---|---|
| MKK1 | 96 | 7 |
| ERK1 | 108 | 10 |
| ERK2 | 86 | 10 |
| JNK1 | 100 | 6 |
| JNK2 | 90 | 8 |
| JNK3 | 128 | 9 |
| p38α MAPK | 95 | 1 |
| P38β MAPK | 115 | 2 |
| p38γ MAPK | 108 | 1 |
| p38σ MAPK | 96 | 2 |
| ERK8 | 32 | 1 |
| RSK1 | 67 | 9 |
| RSK2 | 55 | 2 |
| PDK1 | 80 | 8 |
| PKBα | 82 | 14 |
| PKBβ | 81 | 8 |
| SGK1 | 42 | 10 |
| S6K1 | 95 | 10 |
| PKA | 110 | 13 |
| ROCK 2 | 76 | 0 |
| PRK2 | 90 | 9 |
| PKCα | 98 | 2 |
| PKC zeta | 114 | 7 |
| PKD1 | 53 | 5 |
| MSK1 | 65 | 10 |
| MNK1 | 105 | 7 |
| MNK2 | 105 | 11 |
| MAPKAP-K2 | 88 | 7 |
| MAPKAP-K3 | 119 | 9 |
| PRAK | 115 | 2 |
| CAMKKα | 57 | 5 |
| CAMKKβ | 67 | 0 |
| CAMK1 | 48 | 8 |
| SmMLCK | 35 | 4 |
| PHK | 49 | 12 |
| CHK1 | 80 | 4 |
| CHK2 | 36 | 2 |
| GSK3β | 112 | 8 |
| CDK2-Cyclin A | 9 | 1 |
| PLK1 | 100 | 13 |
| PLK1 (Okadaic Acid) | 108 | 13 |
| AURORA B | 95 | 7 |
| AURORA C | 98 | 5 |
| AMPK | 122 | 8 |
| MARK3 | 104 | 0 |
| BRSK2 | 98 | 6 |
| MELK | 63 | 0 |
| CK1 | 29 | 6 |
| CK2 | 108 | 8 |
| DYRK1A | 17 | 1 |
| DYRK2 | 94 | 7 |
| DYRK3 | 87 | 1 |
| NEK2a | 92 | 9 |
| NEK6 | 85 | 2 |
| NEK7 | 97 | 9 |
| IKKβ | 96 | 1 |
| PIM1 | 88 | 6 |
| PIM2 | 102 | 3 |
| PIM3 | 78 | 10 |
| SRPK1 | 44 | 2 |
| MST2 | 112 | 8 |
| EFK2 | 119 | 13 |
| HIPK2 | 88 | 1 |
| HIPK3 | 90 | 8 |
| PAK4 | 75 | 8 |
| PAK5 | 80 | 8 |
| PAK6 | 95 | 9 |
| Src | 88 | 8 |
| Lck | 95 | 9 |
| CSK | 89 | 9 |

The following are protocols used for the kinase screening reported in Table 5. Generally, the same procedure was used for all assays. Since the total assay volume was 25.5 microliters, 0.5 microliters of inhibitors at 51× assay concentration were added to the plates before any other addition. For $IC_{50}$ analyses, half log dilutions (again all at 51×) were made and 0.5 microliters were added to the assay plates before any other addition.

The basic procedure was to add 0.5 microliters inhibitor/control in DMSO to plate. Fifteen microliters of enzyme/substrate/buffer mix were added and incubated for 5 min. Ten microliters MgATP at the relevant concentration were added and incubated for 30 min. The assay was stopped by adding 5 microliters of 3% orthophosphoric acid. The assay was transferred to a p81 filter plate and read in a scintillation counter of 30 sec/well. Note that this assay procedure was not followed for MKK1, which instead involved a two-step assay, and PKC alpha, which required the addition of lipid vesicles.

Assay Methodologies

MKK1 assay: This was a two-step assay where inactive MAPK (0.06 mg/ml) was activated by MKK1 (diluted in 25 mM Tris, 0.1 mM EGTA, 0.1% b-mercaptoethanol, 0.01% Brij35, 1 mg/ml BSA) in 25.5 μl containing 25 mM Tris, 0.1 mM EGTA, 0.01% Brij35, 10 mM magnesium acetate and 0.005 mM ATP. After incubating at room temperature for 30 min, 5 μl from the first reaction was pipetted into 20 μl of the second reaction mix containing (final concentration) 25 mM Tris pH 7.5, 0.1 mM EGTA, 0.1 mM Na3VO4, 0.66 mg/ml myelin basic protein (MBP), 10 mM magnesium acetate and 0.05 mM [33P-g-ATP] (500-1000 cpm/pmole) and incubated for 30 min at room temperature. Assays were stopped by addition of 5 μl of 0.5 M (3%) orthophosphoric acid and then harvested onto P81 Unifilter plates with a wash buffer of 50 mM orthophosphoric acid.

MAPK2/ERK2 assay: MAPK/ERK2 (5-20 mU diluted in 50 mM Tris pH 7.5, 0.1 mM EGTA, 0.1 mM Na3VO4, 0.1% b-mercaptoethanol, 1 mg/ml BSA) was assayed against MBP in a final volume of 25.5 μl in 25 mM Tris pH 7.5, 0.1 mM EGTA, 0.33 mg/ml MBP, 10 mM magnesium acetate and 0.05 mM [33P-g-ATP] (500-1000 cpm/pmole) and incubated for 30 min at room temperature. Assays were stopped by addition of 5 μl of 0.5 M (3%) orthophosphoric acid and then harvested onto P81 Unifilter plates with a wash buffer of 50 mM orthophosphoric acid.

JNK1a1/SAPK1c assay: JNK1a1/SAPK1c (5-20 mU diluted in 50 mM Tris pH 7.5, 0.1 mM EGTA, 1 mg/ml BSA, 0.1% b-mercaptoethanol) was assayed against ATF2 (activating transcription factor in a final volume of 25.5 μl in 50 mM Tris pH 7.5, 0.1 mM EGTA, 0.1% b-Mercaptoethanol, ATF2 (3 μM), 10 mM magnesium acetate and 0.02 mM [33P-g-ATP] (500-1000 cpm/pmole) and incubated for 30 min at room temperature. Assays were stopped by addition of 5 μl of 0.5 M (3%) orthophosphoric acid and then harvested onto P81 Unifilter plates with a wash buffer of 50 mM orthophosphoric acid.

SAPK 2a/p38 assay: SAPK 2a/p38 (5-20 mU diluted in 50 mM Tris pH 7.5, 0.1 mM EGTA, 0.1 mM Na3VO4, 0.1% b-mercaptoethanol, 1 mg/ml BSA) was assayed against MBP in a final volume of 25.5 μl containing 25 mM Tris pH 7.5, 0.1 mM EGTA, 0.33 mg/ml MBP, 10 mM magnesium acetate and 0.05 mM [33P-g-ATP] (50-1000 cpm/pmole) and incubated for 30 min at room temperature. Assays were stopped by addition of 5 μl of 0.5 M (3%) orthophosphoric acid and then harvested onto P81 Unifilter plates with a wash buffer of 50 mM orthophosphoric acid.

SAPK 2b/p38β2 assay: SAPK 2b/p38β2 (5-20 mU diluted in 50 mM Tris pH 7.5, 0.1 mM EGTA, 0.1 mM Na3VO4, 0.1% b-mercaptoethanol, 1 mg/ml BSA) was assayed against MBP in a final volume of 25.5 μl containing 25 mM Tris pH 7.5, 0.1 mM EGTA, 0.33 mg/ml MBP, 10 mM magnesium acetate and 0.02 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

SAPK 3/p38g assay: SAPK 3/p38g (5-20 mU diluted in 50 mM Tris pH 7.5, 0.1 mM EGTA, 0.1 mM Na3VO4, 0.1% b-mercaptoethanol, 1 mg/ml BSA) was assayed against MBP in a final volume of 25.5 µl containing 25 mM Tris pH 7.5, 0.1 mM EGTA, 0.33 mg/ml MBP, 10 mM magnesium acetate and 0.005 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

SAPK 4/p38d assay: SAPK 4/p38d (5-20 mU diluted in 50 mM Tris pH 7.5, 0.1 mM EGTA, 0.1 mM Na3VO4, 0.1% b-mercaptoethanol, 1 mg/ml BSA) was assayed against MBP in a final volume of 25.5 µl containing 25 mM Tris pH 7.5, 0.1 mM EGTA, 0.33 mg/ml MBP, 10 mM magnesium acetate and 0.005 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

MAPKAP-K1a assay: MAPKAP-K1a (5-20 mU diluted in 20 mM MOPS pH 7.5, 1 mM EDTA, 0.01% Brij35, 5% glycerol, 0.1% b-mercaptoethanol, 1 mg/ml BSA) was assayed against KKLNRTLSVA (SEQ ID NO: 3) in a final volume of 25.5 µl containing 50 mM Na-b-glycerophosphate pH 7.5, 0.5 mM EDTA, 30 µM substrate peptide, 10 mM magnesium acetate and 0.05 mM [33P-g-ATP] (50-1000 cpm/pmole) and incubated for 40 min at room temperature. Assays were stopped by addition of 5 µl of 0.5 M (3%) orthophosphoric acid and then harvested onto P81 Unifilter plates with a wash buffer of 50 mM orthophosphoric acid.

MAPKAP-K2 assay: MAPKAP-K2 (5-20 mU diluted in 20 mM MOPS pH 7.5, 1 mM EDTA, 0.01% Brij35, 5% glycerol, 0.1% b-mercaptoethanol, 1 mg/ml BSA) was assayed against KKLNRTLSVA (SEQ ID NO: 3) in a final volume of 25.5 l containing 50 mM Na-b-glycerophosphate pH 7.5, 0.5 mM EDTA, 30 µM substrate peptide, 10 mM magnesium acetate and 0.02 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

MSK1 assay: MSK1 (5-20 mU diluted in 20 mM MOPS pH 7.5, 1 mM EDTA, 0.01% Brij35, 0.1% b-mercaptoethanol, 1 mg/ml BSA) was assayed against a modified Crosstide peptide GRPRTSSFAEGKK (SEQ ID NO: 4) in a final volume of 25.5 µl containing 8 mM MOPS pH7.0, 0.2 mM EDTA, 30 µM substrate peptide, 10 mM magnesium acetate and 0.02 mM [33P-g-ATP] (50-1000 cpm/pmole) and incubated for 30 min at room temperature Assays were stopped by addition of 5 µl of 0.5 M (3%) orthophosphoric acid and then harvested onto P81 Unifilter plates with a wash buffer of 50 mM orthophosphoric acid.

PRAK assay: PRAK (5-20 mU diluted in 50 mM Na-b-glycerophosphate pH 7.5, 0.1 mM EGTA, 0.1% b-mercaptoethanol, 1 mg/ml BSA) was assayed against KKLRRTLSVA (SEQ ID NO: 5) in a final volume of 25.5 µl containing 50 mM Na-b-glycerophosphate pH 7.5, 0.1 mM EGTA, 30 µM substrate peptide, 10 mM magnesium acetate and 0.02 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

PKA assay: PKA (5-20 mU diluted in 20 mM MOPS pH 7.5, 1 mM EDTA, 0.01% Brij35, 0.1% b-mercaptoethanol, 1 mg/ml BSA) was assayed against Kemptide (LRRASLG) (SEQ ID NO: 6) in a final volume of 25.5 µl containing 8 mM MOPS pH 7.5, 0.2 mM EDTA, 30 µM substrate peptide, 10 mM magnesium acetate and 0.005 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

PKCa assay: PKCa (5-20 mU diluted in 20 mM Hepes pH 7.4, 0.03% Triton X-100) was assayed against Histone H1 in the presence of PtdSerine and DAG (0.1 mg/ml. and 10 µg/ml) and 0.1 mM CaCl2. The assay was carried out in a final volume of 25.5 µl containing 20 mM Hepes pH 7.4, 0.03% Triton X-100, 0.1 mg/ml Histone H1, 10 mM magnesium acetate and 0.02 mM[33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

PtdSer/DAG preparation: PtdSer stock was 10 mg/ml in MeOH/Chloroform (1:2). The required amount was dried down and re-suspended in an appropriate volume of 10 mM Hepes pH 7.4, vortexed, and briefly sonicated ($2 \times 10^{-15}$ seconds at 10-15 seconds apart). DAG stock was 10 mg/ml in MeOH/chloroform (1:2). The required amount was dried down and sonicated PtdSer solution was added, vortexed and sonicated.

PDK1 assay: PDK1 (5-20 mU diluted in 50 mM Tris pH 7.5, 0.05% b-mercaptoethanol, 1 mg/ml BSA) was assayed against PDKtide (KTFCGTPEYLAPEVRREPRILSEEEQ-EMFRDFDYIADWC) (SEQ ID NO: 7) in a final volume of 25.5 µl containing 50 mM Tris pH 7.5, 0.05% b-mercaptoethanol, 100 µM substrate peptide, 10 mM magnesium acetate and 0.02 mM [33P-g-ATP] (50-1000 cpm/pmole) and incubated for 30 min at room temperature Assays were stopped by addition of 5 µl of 0.5 M (3%) orthophosphoric acid and then harvested onto P81 Unifilter plates with a wash buffer of 50 mM orthophosphoric acid.

APH-PKBa-S473D assay: APH-PKBa-S473D (5-20 mU diluted in 50 mM Tris pH 7.5, 0.1 mM EGTA, 0.1% b-mercaptoethanol, 1 mg/ml BSA) was assayed against a modified Crosstide peptide GRPRTSSFAEGKK (SEQ ID NO: 4) in a final volume of 25.5 µl containing 50 mM Tris pH 7.5, 0.05% b-mercaptoethanol, 30 µM substrate peptide, 10 mM magnesium acetate and 0.005 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

SGK assay: SGK (5-20 mU diluted in 20 mM MOPS pH 7.5, 1 mM EDTA, 0.01% Brij35, 5% glycerol, 0.1% b-mercaptoethanol, 1 mg/ml BSA) was assayed against a modified Crosstide peptide GRPRTSSFAEGKK (SEQ ID NO: 4) in a final volume of 25.5 µl containing 8 mM MOPS pH 7.0, 0.2 mM EDTA, 30 µM substrate peptide, 10 mM magnesium acetate and 0.02 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

S6K1/P70 S6K assay: S6K1/P70 S6K (5-20 mU diluted in 20 mM MOPS pH 7.5, 1 mM EDTA, 0.01% Brij35, 5% glycerol, 0.1% b-mercaptoethanol, 1 mg/ml BSA) was assayed against substrate peptide (KKRNRTLTV) (SEQ ID NO: 8) in a final volume of 25.5 μl containing 8 mM MOPS pH 7.0, 0.2 mM EDTA, 10 mM substrate peptide, 10 mM magnesium acetate and 0.02 mM [33P-g-ATP] (50-1000 cpm/pmole) and incubated for 30 min at room temperature. Assays were stopped by addition of 5 μl of 0.5 M (3%) orthophosphoric acid and then harvested onto P81 Unifilter plates with a wash buffer of 50 mM orthophosphoric acid.

GSK3b assay: GSK3b (5-20 mU diluted in 20 mM MOPS pH 7.5, 1 mM EDTA, 0.01% Brij35, 5% glycerol, 0.1% b-mercaptoethanol, 1 mg/ml BSA) was assayed against Phospho-GS2 peptide (YRRAAVPPSPSLSRHSSPHQS(PO4)EDEEE) (SEQ ID NO: 9) in a final volume of 25.5 μl containing 8 mM MOPS pH 7.0, 0.2 mM EDTA, 20 μM Phospho GS2 peptide, 10 mM magnesium acetate and 0.005 mM [33P-g-ATP] (50-1000 cpm/pmole) and incubated for 30 min at room temperature. Assays were stopped by addition of 5 μl of 0.5 M (3%) orthophosphoric acid and then harvested onto P81 Unifilter plates with a wash buffer of 50 mM orthophosphoric acid.

ROCK-II (ROKa) assay: ROCK-II (ROKa) (5-20 mU diluted in 50 mM Tris pH 7.5, 0.1 mM EGTA, 0.1% b-mercaptoethanol, 1 mg/ml BSA) was assayed against Long S6 substrate peptide (KEAKEKRQEQIAKRRRLSSL-RASTSKSGGSQK) (SEQ ID NO: 10) in a final volume of 25.5 μl containing 50 mM Tris pH 7.5, 0.1 mM EGTA, 30 μM Long S6 substrate peptide, 10 mM magnesium acetate and 0.02 mM [33P-g-ATP] (50-1000 cpm/pmole) and incubated for 30 min at room temperature. Assays were stopped by addition of 5 μl of 0.5 M (3%) orthophosphoric acid and then harvested onto P81 Unifilter plates with a wash buffer of 50 mM orthophosphoric acid.

AMPK assay: AMPK (5-20 mU diluted in 50 mM Hepes pH 7.5, 1 mM DTT, 0.02% Brij35) was assayed against SAMS substrate peptide (HMRSAMSGLHLVKRR) (SEQ ID NO: 11) in a final volume of 25.5 μl containing 50 mM Hepes pH 7.5, 1 mM DTT, 0.02% Brij35, 0.4 mM SAMS peptide, 0.196 mM AMP, 10 mM magnesium acetate and 0.05 mM [33P-g-ATP] (50-1000 cpm/pmole) and incubated for 30 min at room temperature. Assays were stopped by addition of 5 μl of 0.5 M (3%) orthophosphoric acid and then harvested onto P81 Unifilter plates with a wash buffer of 50 mM orthophosphoric acid.

CHK1 assay: CHK1 (5-20 mU diluted in 20 mM MOPS pH 7.5, 1 mM EDTA, 0.1% b-mercaptoethanol, 0.01% Brij-35, 5% glycerol, 1 mg/ml BSA) was assayed against CHKtide substrate peptide (KKKVSRSGLYRSPSMPENLNRPR) (SEQ ID NO: 12) in a final volume of 25.5 μl containing 8 mM MOPS pH 7.0, 0.2 mM EDTA, 200 μM CHKtide, 10 mM magnesium acetate and 0.02 mM [33P-g-ATP] (50-1000 cpm/pmole) and incubated for 30 min at room temperature Assays were stopped by addition of 5 μl of 0.5 M (3%) orthophosphoric acid and then harvested onto P81 Unifilter plates with a wash buffer of 50 mM orthophosphoric acid.

CK2 assay: CK2 (5-20 mU diluted in 20 mM Hepes pH7.5, 0.15 M NaCl, 0.1 mM EGTA, 0.1% Triton X-100, 5 mM DTT, 50% glycerol) was assayed against CKII peptide (RRRDDDSDDD) (SEQ ID NO: 13) in a final volume of 25.5 μl containing 20 mM Hepes pH 7.5, 0.15 M NaCl, 0.1 mM EDTA, 5 mM DTT, 0.1% Triton-X 100, CKII peptide (0.165 mM), 10 mM magnesium acetate and 0.005 mM [33P-g-ATP] (500-1000 cpm/pmole) and incubated for 30 min at room temperature. Assays were stopped by addition of 5 μl of 0.5 M (3%) orthophosphoric acid and then harvested onto P81 Unifilter plates with a wash buffer of 50 mM orthophosphoric acid.

PBK assay: PBK (5-20 mU diluted in 50 mM Na-b-glycerophosphate pH 7.0, 0.1% b-mercaptoethanol) was assayed against phosphorylase b peptide (KRKQISVRGL) (SEQ ID NO: 14) in a final volume of 25.5 μl containing 50 mM Tris pH 8.6, 50 mM Na-b-glycerophosphate, 0.04 mM CaCl2, phosphorylase b peptide (0.196 mM), 10 mM magnesium acetate, 0.02 mM [33P-g-ATP] (500-1000 cpm/pmole) then incubated for 15 min at room temperature. Assays were stopped by addition of 5 μl of 0.5 M (3%) orthophosphoric acid and then harvested onto P81 Unifilter plates with a wash buffer of 50 mM orthophosphoric acid.

LCK assay: LCK (5-20 mU diluted in 20 mM MOPS pH 7.5, 1 mM EDTA, 0.01% Brij35, 5% glycerol, 0.1% b-mercaptoethanol, 1 mg/ml BSA) was assayed against Cdc2 peptide (KVEKIGEGTYGVVYK) (SEQ ID NO: 15) in a final volume of 25.5 μl containing 50 mM Tris pH 7.5, 0.1 mM EGTA, 0.1 mM Na3Vo4, Cdc2 peptide (0.25 mM), 10 mM magnesium acetate and 0.05 mM [33P-g-ATP] (500-1000 cpm/pmole) and incubated for 15 min at room temperature Assays were stopped by addition of 5 μl of 0.5 M (3%) orthophosphoric acid and then harvested onto P81 Unifilter plates with a wash buffer of 50 mM orthophosphoric acid.

CSK assay: CSK (5-20 mU diluted in 20 mM MOPS pH7.5, 1 mM EDTA, 0.01% Brij35, 5% glycerol, 0.1% b-mercaptoethanol, 1 mg/ml BSA) was assayed against Cdc2 peptide (KVEKIGEGTYGVVYK) (SEQ ID NO: 15) in a final volume of 25.5 μl containing 8 mM MOPS pH7.0, 0.2 mM EDTA, Cdc2 peptide (0.25 mM), 10 mM magnesium acetate and 0.02 mM [33P-g-ATP] (500-1000 cpm/pmole) and incubated for 30 min at room temperature Assays were stopped by addition of 5 μl of 0.5 M (3%) orthophosphoric acid and then harvested onto P81 Unifilter plates with a wash buffer of 50 mM orthophosphoric acid.

CDK2/cyclin A assay: CDK2/cyclin A (5-20 mU diluted in 50 mM Hepes pH 7.5, 1 mM DTT, 0.02% Brij35, 100 mM NaCl) was assayed against Histone H1 in a final volume of 25.5 μl containing 50 mM Hepes pH7.5, 1 mM DTT, 0.02% Brij35, 100 mM NaCl, Histone H1 (1 mg/ml), 10 mM magnesium acetate and 0.02 mM [33P-g-ATP] (500-1000 cpm/pmole) and incubated for 30 min at room temperature. Assays were stopped by addition of 5 μl of 0.5 M (3%) orthophosphoric acid and then harvested onto P81 Unifilter plates with a wash buffer of 50 mM orthophosphoric acid.

DYRK 1A assay: DYRK 1A (5-20 mU of diluted in 50 mM Tris pH7.5, 0.1 mM EGTA) was assayed against Woodtide (KKISGRLSPIMTEQ) (SEQ ID NO: 16) in a final volume of 25.5 μl containing 50 mM Tris pH 7.5, 0.1 mM EGTA, 350 μM substrate peptide, 10 mM Magnesium acetate and 0.05 mM [33P-g-ATP] (50-1000 cpm/pmole) and incubated for 30 min at room temperature. Assays were stopped by addition of 5 μl of 0.5 M (3%) orthophosphoric acid and then harvested onto P81 Unifilter plates with a wash buffer of 50 mM orthophosphoric acid.

CK1 assay: CK1 (5-20 mU diluted in 20 mM Hepes pH7.5, 0.15 M NaCl, 0.1 mM EGTA, 0.1% Triton X-100, 5 mM DTT, 50% glycerol) was assayed against CKI peptide (RRKDLHDDEEDEAMSITA) (SEQ ID NO: 17) in a final volume of 25.5 μl containing 20 mM Hepes pH 7.5, 0.15 M NaCl, 0.1 mM EDTA, 5 mM DTT, 0.1% Triton-X 100, CKI peptide (0.5 mM), 10 mM magnesium acetate and 0.02 mM [33P-g-ATP] (500-1000 cpm/pmole) and incubated for 30 min at room temperature. Assays were stopped by addition of 5 μl of 0.5 M (3%) orthophosphoric acid and then harvested onto P81 Unifilter plates with a wash buffer of 50 mM orthophosphoric acid.

NEK6 assay: NEK6 (5-20 mU diluted in 50 mM Tris (pH 7.5), 0.1 mM EGTA, 1 mg/ml BSA, 0.1%, b-Mercaptoethanol) was assayed against NEK6 peptide (FLAKSFGSPN-RAYKK) (SEQ ID NO: 18) in a final volume of 25.5 µl containing 50 mM Tris (pH 7.5), 0.1 mM EGTA, 0.01% Brij, 0.1%, b-Mercaptoethanol, NEK6 peptide (0.3 mM), 10 mM magnesium acetate and 0.05 mM [33P-g-ATP] (500-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

NEK2a assay: 5-20 mU of NEK2a (diluted in 50 mM Tris (pH 7.5), 0.1 mM EGTA, 1 mg/ml BSA, 0.1%, b-Mercaptoethanol) was assayed against NEK2a peptide (RFRRSRRMI) (SEQ ID NO: 19) in a final volume of 25.5 µl containing 50 mM Tris (pH 7.5), 0.1 mM EGTA, 0.01% Brij, 0.1%, b-Mercaptoethanol, 300 µM NEK2a peptide, 10 mM magnesium acetate and 0.05 mM [33P-g-ATP] (500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

MAPKAP-K1b/RSK2 assay: MAPKAP-K1b (5-20 mU diluted in 20 mM MOPS pH 7.5, 1 mM EDTA, 0.01% Brij35, 5% glycerol, 0.1% b-mercaptoethanol, 1 mg/ml BSA) was assayed against substrate peptide (KKLNRTLSVA) (SEQ ID NO: 3) in a final volume of 25.5 l containing 50 mM Na-b-glycerophosphate (pH 7.5), 0.5 mM EDTA, 30 µM substrate peptide, 10 mM magnesium acetate and 0.05 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

IKKb assay: 5-20 mU of IKKb (diluted in 50 mM Tris (pH 7.5), 0.1 mM EGTA, 1 mg/ml BSA, 0.1%, b-Mercaptoethanol) was assayed against substrate peptide (LDDRHDS-GLDSMKDEEY) (SEQ ID NO: 20) in a final volume of 25.5 µl containing 50 mM Tris (pH 7.5), 0.1 mM EGTA, 0.1%, b-Mercaptoethanol, 300 µM substrate peptide, 10 mM magnesium acetate and 0.005 mM [33P-g-ATP] (500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

smMLCK assay: 5-20 mU of smMLCK (diluted in 50 mM Hepes (pH 7.5), 0.1 mM EGTA, 1 mg/mlBSA, 0.1%, b-Mercaptoethanol) was assayed against substrate peptide (KKRPQRATSNVFA) (SEQ ID NO: 21) in a final volume of 25.5 µl containing 50 mM Hepes (pH 7.5), 0.1 mM EGTA, 5 mM CaCl2, 10 µM Calmodulin, 300 µM substrate peptide, 10 mM magnesium acetate and 0.05 mM [33P-g-ATP] (500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

PRK2 assay: 5-20 mU of PRK2 (diluted in 50 mM Tris (pH 7.5), 0.1 mM EGTA, 1 mg/ml BSA, 0.1%, b-Mercaptoethanol) was assayed against Long S6 peptide (KEAKEKRQE-QIAKRRRLSSLRASTSKSGGSQK) (SEQ ID NO: 10) in a final volume of 25.5 µl containing 50 mM Tris (pH 7.5), 0.1 mM EGTA, 0.1%, b-Mercaptoethanol, 30 µM Long S6 peptide, 10 mM magnesium acetate and 0.005 mM [33P-g-ATP] (500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

MNK2 alpha assay: 5-20 mU of MNK2 (diluted in 50 mM Tris (pH 7.5), 0.1 mM EGTA, 1 mg/ml BSA, 0.1%, b-Mercaptoethanol) was assayed against substrate peptide (eIF4E) in a final volume of 25.5 µl containing 50 mM Tris (pH 7.5), 0.1 mM EGTA, 0.1%, b-Mercaptoethanol, 0.5 mg/ml substrate peptide, 10 mM magnesium acetate and 0.05 mM [33P-g-ATP](500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

CAMK-1 assay: 5-20 mU of CAMK-1 (diluted in 50 mM Tris (pH 7.5), 0.1 mM EGTA, 1 mg/ml BSA, 0.1%, b-Mercaptoethanol) was assayed against substrate peptide (YLR-RRLSDSNF) (SEQ ID NO: 22) in a final volume of 25.5 µl containing 50 mM Tris (pH 7.5), 0.1 mM EGTA, 0.5 mM CaCl2, 0.3 µM calmodulin, 0.1%, b-Mercaptoethanol, 300 µM substrate peptide, 10 mM magnesium acetate and 0.05 mM [33P-g-ATP] (500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

PIM2 assay: 5-20 mU of PIM2 (diluted in 50 mM Tris (pH 7.5), 0.1 mM EGTA, 1 mg/ml BSA, 0.1%, b-Mercaptoethanol) was assayed against substrate peptide (RSRHSSYPAGT) (SEQ ID NO: 23) in a final volume of 25.5 µl containing 50 mM Tris (pH 7.5), 0.1 mM EGTA, 0.5 mM CaCl2, 0.3 µM calmodulin, 0.1%, b-Mercaptoethanol, 300 µM substrate peptide, 10 mM magnesium acetate and 0.005 mM [33P-g-ATP] (500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

NEK7 assay: NEK7 (5-20 mU diluted in 50 mM Tris (pH 7.5), 0.1 mM EGTA, 1 mg/ml BSA, 0.1%, b-Mercaptoethanol) was assayed against substrate peptide (FLAKSFGSPN-RAYKK) (SEQ ID NO: 24) in a final volume of 25.5 µl containing 50 mM Tris (pH 7.5), 0.1 mM EGTA, 0.01% Brij, 0.1%, b-Mercaptoethanol, substrate peptide (0.3 mM), 10 mM magnesium acetate and 0.02 mM [33P-g-ATP] (500-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

JNK3 alpha 1 assay: JNK3 alpha 1(5-20 mU diluted in 50 mM Tris (pH 7.5), 0.1 mM EGTA, 1 mg/ml BSA, 0.1% b-mercaptoethanol) was assayed against ATF2 (activating transcription factor in a final volume of 25.5 µl in 50 mM Tris pH 7.5, 0.1 mM EGTA, 0.1% b-Mercaptoethanol, ATF2 (3 µM), 10 mM magnesium acetate and 0.05 mM [33P-g-ATP] (500-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

MAPKAP-K3 assay: 5-20 mU of MAPKAP-K3 (diluted in 50 mM Tris (pH 7.5), 0.1 mM EGTA, 1 mg/ml BSA, 0.1%, b-Mercaptoethanol) was assayed against substrate peptide (KKLNRTLSVA) (SEQ ID NO: 3) in a final volume of 25.5 µl containing 50 mM Tris (pH 7.5), 0.1 mM EGTA, 0.1%, b-Mercaptoethanol, 30 µM substrate peptide, 10 mM magnesium acetate and 0.02 mM [33P-g-ATP] (500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

ERK8 assay: 5-20 mU of ERK8 (diluted in 50 mM Tris (pH 7.5), 0.1 mM EGTA, 1 mg/ml BSA, 0.1%, b-Mercaptoethanol) was assayed against MBP in a final volume of 25.5 µl containing 50 mM Tris (pH 7.5), 0.1 mM EGTA, 0.1%, b-Mercaptoethanol, 0.33 mg/ml MBP, 10 mM magnesium acetate and 0.005 mM [33P-g-ATP] (500-1000 cpm/pmole) and incubated for 30 mins at room temperature. Assays were stopped by addition of 5 µl of 0.5% (3%) orthophosphoric acid. Assays were harvested onto P81 Unifilter plates using a wash buffer of 50 mM orthophosphoric acid.

MNK1 assay: 5-20 mU of MNK1 (diluted in 50 mM Tris (pH 7.5), 0.1 mM EGTA, 1 mg/ml BSA, 0.1%, b-Mercaptoethanol) was assayed against substrate peptide (eIF4E) in a final volume of 25.5 µl containing 50 mM Tris (pH 7.5), 0.1 mM EGTA, 0.1%, b-Mercaptoethanol, 0.5 mg/ml substrate peptide, 10 mM magnesium acetate and 0.05 mM [33P-g-ATP](500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

SRPK1 assay: 5-20 mU of SRPK1 (diluted in 50 mM Tris (pH 7.5), 0.1 mM EGTA, 1 mg/ml BSA, 0.1%, b-Mercaptoethanol) was assayed against substrate peptide (RSRSRSRSRSRSRSR) (SEQ ID NO: 25) in a final volume of 25.5 µl containing 50 mM Tris (pH 7.5), 0.1 mM EGTA, 0.1%, b-Mercaptoethanol, 300 µM substrate peptide, 10 mM magnesium acetate and 0.05 mM [33P-g-ATP] (500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

ΔPH-PKBbeta (S474D) assay: ΔPH-PKBbeta-S474D (5-20 mU diluted in 50 mM Tris pH 7.5, 0.1 mM EGTA, 0.1% b-mercaptoethanol, 1 mg/ml BSA) was assayed against a modified Crosstide peptide (GRPRTSSFAEGKK) (SEQ ID NO: 4) in a final volume of 25.5 µl containing 50 mM Tris pH 7.5, 0.05% b-mercaptoethanol, 30 µM substrate peptide, 10 mM magnesium acetate and 0.05 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

Aurora B assay: Aurora B (5-20 mU diluted in 50 mM Tris pH 7.5, 0.1 mM EGTA, 0.1% b-mercaptoethanol, 1 mg/ml BSA) was assayed against a substrate peptide (LRRLSLGL-RRLSLGLRRLSLGLRRLSLG) (SEQ ID NO: 26) in a final volume of 25.5 l containing 50 mM Tris pH 7.5, 0.05% b-mercaptoethanol, 300 µM substrate peptide, 10 mM magnesium acetate and 0.02 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

CHK2 assay: CHK2 (5-20 mU diluted in 20 mM MOPS pH 7.5, 1 mM EDTA, 0.1% b-mercaptoethanol, 0.01% Brij-35, 5% glycerol, 1 mg/ml BSA) was assayed against CHKtide substrate peptide (KKKVSRSGLYRSPSMPENLNRPR) (SEQ ID NO: 12) in a final volume of 25.5 µl containing 8 mM MOPS pH 7.0, 0.2 mM EDTA, 200 µM CHKtide, 10 mM magnesium acetate and 0.02 mM [33P-g-ATP] (50-1000 cpm/pmole) and incubated for 30 min at room temperature Assays were stopped by addition of 5 µl of 0.5 M (3%) orthophosphoric acid and then harvested onto P81 Unifilter plates with a wash buffer of 50 mM orthophosphoric acid.

Src assay: Src (5-20 mU diluted in 50 mM Tris pH 7.5, 0.1 mM EGTA, 0.1% b-mercaptoethanol, 1 mg/ml BSA) was assayed against a substrate peptide (KVEKIGEGTYGV-VYK) (SEQ ID NO: 15) in a final volume of 25.5 µl containing 50 mM Tris pH 7.5, 0.05% b-mercaptoethanol, 300 µM substrate peptide, 10 mM magnesium acetate and 0.05 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

EF2K assay: EF2K (5-20 mU diluted in 50 mM Hepes pH 6.6, 0.1% b-mercaptoethanol, 1 mg/ml BSA) was assayed against a substrate peptide (RKKFGESKTKTKEFL) (SEQ ID NO: 27) in a final volume of 25.5 µl containing 50 mM Hepes pH 6.6, 0.2 mM CaCl2, 0.3 µM Calmodulin, 0.05% b-mercaptoethanol, 300 µM substrate peptide, 10 mM magnesium acetate and 0.005 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

MARK3 assay: MARK3 (5-20 mU diluted in 50 mM Tris pH 7.5, 0.1 mM EGTA, 0.1% b-mercaptoethanol, 1 mg/ml BSA) was assayed against CHKtide substrate (KKKVSRS-GLYRSPSMPENLNRPR) (SEQ ID NO: 12) in a final volume of 25.5 µl containing 50 mM Tris pH 7.5, 0.05% b-mercaptoethanol, 300 µM substrate peptide, 10 mM magnesium acetate and 0.005 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

MST2 assay: MST2 (5-20 mU diluted in 50 mM Tris pH 7.5, 0.1 mM EGTA, 0.1% b-mercaptoethanol, 100 µM Vanadate) was assayed against MBP in a final volume of 25.5 µl containing 50 mM Tris pH 7.5, 0.05% b-mercaptoethanol, 0.33 mg/ml MBP, 10 mM magnesium acetate and 0.02 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

PKD1 assay: PKD1 (5-20 mU diluted in 50 mM Tris pH 7.5, 0.1 mM EGTA, 0.1% b-mercaptoethanol, 1 mg/ml BSA) was assayed substrate peptide (KKLNRTLSVA) (SEQ ID NO: 3) in a final volume of 25.5 µl containing 50 mM Tris pH 7.5, 0.05% b-mercaptoethanol, 30 µM substrate peptide, 10 mM magnesium acetate and 0.05 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

PLK1 assay: PLK1 (5-20 mU diluted in 50 mM Tris pH 7.5, 0.1 mM EGTA, 0.1% b-mercaptoethanol, 1 mg/ml BSA, 100 µM Vanadate) was assayed against a substrate peptide (ISDELMDATFADQEAKKK) (SEQ ID NO: 28) in a final volume of 25.5 µl containing 50 mM Tris pH 7.5, 0.05% b-mercaptoethanol, 10 µM Vanadate, 300 µM substrate peptide, 10 mM magnesium acetate and 0.005 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

DYRK2 assay: DYRK2 (5-20 mU of diluted in 50 mM Tris pH7.5, 0.1 mM EGTA) was assayed against Woodtide (KKISGRLSPIMTEQ) (SEQ ID NO: 29) in a final volume of 25.5 µl containing 50 mM Tris pH 7.5, 0.1 mM EGTA, 350 µM substrate peptide, 10 mM Magnesium acetate and 0.05 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

JNK2 assay: JNK2 1(5-20 mU diluted in 50 mM Tris (pH 7.5), 0.1 mM EGTA, 1 mg/ml BSA, 0.1% b-mercaptoethanol) was assayed against ATF2 (activating transcription factor in a final volume of 25.5 µl in 50 mM Tris pH 7.5, 0.1 mM EGTA, 0.1% b-Mercaptoethanol, ATF2 (3 µM), 10 mM magnesium acetate and 0.02 mM [33P-g-ATP] (500-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

DYRK3 assay: DYRK3 (5-20 mU of diluted in 50 mM Tris pH7.5, 0.1 mM EGTA) was assayed against Woodtide (KKISGRLSPIMTEQ) (SEQ ID NO: 29) in a final volume of 25.5 µl containing 50 mM Tris pH 7.5, 0.1 mM EGTA, 350 µM substrate peptide, 10 mM Magnesium acetate and 0.005 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

HIPK2 assay: 5-20 mU of HIPK2 (diluted in 50 mM Tris (pH 7.5), 0.1 mM EGTA, 1 mg/ml BSA, 0.1%, b-Mercaptoethanol) was assayed against MBP in a final volume of 25.5 µl containing 50 mM Tris (pH 7.5), 0.1 mM EGTA, 0.1%, b-Mercaptoethanol, 0.33 mg/ml MBP, 10 mM magnesium acetate and 0.005 mM [33P-g-ATP] (500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

HIPK3 assay: 5-20 mU of HIPK3 (diluted in 50 mM Tris (pH 7.5), 0.1 mM EGTA, 1 mg/ml BSA, 0.1%, b-Mercaptoethanol) was assayed against MBP in a final volume of 25.5 µl containing 50 mM Tris (pH 7.5), 0.1 mM EGTA, 0.1%, b-Mercaptoethanol, 0.33 mg/ml MBP, 10 mM magnesium acetate and 0.02 mM [33P-g-ATP] (500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

PAK4 assay: PAK4 (5-20 mU diluted in 50 mM Tris pH 7.5, 0.1 mM EGTA, 0.1% b-mercaptoethanol, 1 mg/ml BSA) was assayed against a substrate peptide (RRRLSFAEPG) (SEQ ID NO: 30) in a final volume of 25.5 µl containing 50 mM Tris pH 7.5, 0.05% b-mercaptoethanol, 300 µM substrate peptide, 10 mM magnesium acetate and 0.005 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

PAK5 (PAK7) assay: PAK5 (PAK7)(5-20 mU diluted in 50 mM Tris pH 7.5, 0.1 mM EGTA, 0.1% b-mercaptoethanol, 1 mg/ml BSA) was assayed against a substrate peptide (RRRLSFAEPG) (SEQ ID NO: 30) in a final volume of 25.5 µl containing 50 mM Tris pH 7.5, 0.05% b-mercaptoethanol, 300 µM substrate peptide, 10 mM magnesium acetate and 0.02 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

PAK6 assay: PAK6 (5-20 mU diluted in 50 mM Tris pH 7.5, 0.1 mM EGTA, 0.1% b-mercaptoethanol, 1 mg/ml BSA) was assayed against a substrate peptide (RRRLSFAEPG) (SEQ ID NO: 30) in a final volume of 25.5 µl containing 50 mM Tris pH 7.5, 0.05% b-mercaptoethanol, 300 µM substrate peptide, 10 mM magnesium acetate and 0.02 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

CAMKKa assay: 5-20 mU of CAMKKa (diluted in 50 mM Tris (pH 7.5), 0.1 mM EGTA, 1 mg/ml BSA, 0.1%, b-Mercaptoethanol) was assayed against substrate peptide (AKPKGNKDYHLQTCCGSLAYRRR) (SEQ ID NO: 31) in a final volume of 25.5 µl containing 50 mM Tris (pH 7.5), 0.1 mM EGTA, 0.5 mM CaCl2, 0.3 µM calmodulin, 0.1%, b-Mercaptoethanol, 300 µM substrate peptide, 10 mM magnesium acetate and 0.02 mM [33P-g-ATP] (500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

CAMKKb assay: 5-20 mU of CAMKKb (diluted in 50 mM Tris (pH 7.5), 0.1 mM EGTA, 1 mg/ml BSA, 0.1%, b-Mercaptoethanol) was assayed against substrate peptide (DGEFLRTSCGSPNYAARRR) (SEQ ID NO: 32) in a final volume of 25.5 µl containing 50 mM Tris (pH 7.5), 0.1 mM EGTA, 0.5 mM CaCl2, 0.3 µM calmodulin, 0.1%, b-Mercaptoethanol, 300 µM substrate peptide, 10 mM magnesium acetate and 0.02 mM [33P-g-ATP] (500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

PIM1 assay: PIM1 (5-20 mU diluted in 50 mM Tris pH 7.5, 0.1 mM EGTA, 0.1% b-mercaptoethanol, 1 mg/ml BSA) was assayed against a substrate peptide (RSRHSSYPAGT) (SEQ ID NO: 23) in a final volume of 25.5 µl containing 50 mM Tris pH 7.5, 0.05% b-mercaptoethanol, 300 µM substrate peptide, 10 mM magnesium acetate and 0.02 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

PIM3 assay: PIM3 (5-20 mU diluted in 50 mM Tris pH 7.5, 0.1 mM EGTA, 0.1% b-mercaptoethanol, 1 mg/ml BSA) was assayed against a substrate peptide (RSRHSSYPAGT) (SEQ ID NO: 23) in a final volume of 25.5 µl containing 50 mM Tris pH 7.5, 0.05% b-mercaptoethanol, 300 µM substrate peptide, 10 mM magnesium acetate and 0.02 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

PLK1 assay: PLK1 (5-20 mU diluted in 50 mM Tris pH 7.5, 0.1 mM EGTA, 0.1% b-mercaptoethanol, 1 mg/ml BSA, 100 µM Vanadate) was assayed against a substrate peptide (ISDELMDATFADQEAKKK) (SEQ ID NO: 28) in a final volume of 25.5 µl containing 50 mM Tris pH 7.5, 0.05% b-mercaptoethanol, 10 µM Vanadate, 300 µM substrate peptide, 10 mM magnesium acetate and 0.005 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

BRSK2 assay: BRSK2 (5-20 mU diluted in 50 mM Tris pH 7.5, 0.1 mM EGTA, 0.1% b-mercaptoethanol, 1 mg/ml BSA) was assayed against a substrate peptide (KKLNRTLSFAEPG) (SEQ ID NO: 33) in a final volume of 25.5 µl containing 50 mM Tris pH 7.5, 0.05% b-mercaptoethanol, 300 µM substrate peptide, 10 mM magnesium acetate and 0.05 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

MELK assay: MELK (5-20 mU diluted in 50 mM Tris pH 7.5, 0.1 mM EGTA, 0.1% b-mercaptoethanol, 1 mg/ml BSA) was assayed against a substrate peptide (KKLNRTLSFAEPG) (SEQ ID NO: 33) in a final volume of 25.5 µl containing 50 mM Tris pH 7.5, 0.05% b-mercaptoethanol, 200 µM substrate peptide, 10 mM magnesium acetate and 0.05 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

PKC zeta assay: PKC zeta (5-20 mU diluted in 50 mM Tris pH 7.5, 0.1 mM EGTA, 0.1% b-mercaptoethanol, 1 mg/ml BSA, 100 µM Vanadate) was assayed against a substrate peptide (ERMRPRKRQGSVRRV) (SEQ ID NO: 34) in a final volume of 25.5 µl containing 50 mM Tris pH 7.5, 0.05% b-mercaptoethanol, 10 µM Vanadate, 300 µM substrate peptide, 10 mM magnesium acetate and 0.005 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

Aurora C assay: Aurora C (5-20 mU diluted in 50 mM Tris pH 7.5, 0.1 mM EGTA, 0.1% b-mercaptoethanol, 1 mg/ml BSA) was assayed against a substrate peptide (LRRLSLGLRRLSLGLRRLSLGLRRLSLG) (SEQ ID NO: 26) in a final volume of 25.5 µl containing 50 mM Tris pH 7.5, 0.05% b-mercaptoethanol, 300 µM substrate peptide, 10 mM magnesium acetate and 0.005 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

ERK1 assay: 5-20 mU of ERK1 (diluted in 50 mM Tris (pH 7.5), 0.1 mM EGTA, 1 mg/ml BSA, 0.1%, b-Mercaptoethanol) was assayed against MBP in a final volume of 25.5 µl containing 50 mM Tris (pH 7.5), 0.1 mM EGTA, 0.1%, b-Mercaptoethanol, 0.33 mg/ml MBP, 10 mM magnesium acetate and 0.005 mM [33P-g-ATP] (500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

FGF-R1 assay: FGF-R1 (5-20 mU diluted in 50 mM Tris pH 7.5, 0.1 mM EGTA, 1 mg/ml BSA) was assayed against a substrate peptide (Poly Glut Tyr) in a final volume of 25.5 µl containing 50 mM Tris pH 7.5, 1 mg/ml substrate peptide, 10 mM magnesium acetate and 0.02 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

IRR assay: 5-20 mU of IRR (diluted in 50 mM Hepes (pH 7.5), 0.1 mM EGTA) was assayed against MBP in a final volume of 25.5 µl containing 50 mM Hepes (pH 7.5), 0.1 mM EGTA, 0.33 mg/ml MBP, 10 mM magnesium acetate and 0.005 mM [33P-g-ATP](500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

EPH-A2 assay: EPH-A2 (5-20 mU diluted in 50 mM Tris pH 7.5, 0.1 mM EGTA, 1 mg/ml BSA) was assayed against a substrate peptide (Poly Glut Tyr) in a final volume of 25.5 µl containing 50 mM Tris pH 7.5, 0.1 mg/ml substrate peptide, 10 mM magnesium acetate and 0.05 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

MST4 assay: 5-20 mU of MST4 (diluted in 50 mM Tris (pH 7.5), 0.1 mM EGTA) was assayed against MBP in a final volume of 25.5 µl containing 50 mM Tris (pH 7.5), 0.1 mM EGTA, 0.33 mg/ml MBP, 10 mM magnesium acetate and 0.02 mM [33P-g-ATP] (500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

SYK assay: SYK (5-20 mU diluted in 50 mM Tris pH 7.5, 0.1 mM EGTA, 1 mg/ml BSA) was assayed against a substrate peptide (Poly Glut Tyr) in a final volume of 25.5 µl containing 50 mM Tris pH 7.5, 1 mg/ml substrate peptide, 10 mM magnesium acetate and 0.02 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

YES1 assay: YES1 (5-20 mU diluted in 50 mM Tris pH 7.5, 0.1 mM EGTA, 1 mg/ml BSA) was assayed against a substrate peptide (Poly Glut Tyr) in a final volume of 25.5 µl containing 50 mM Tris pH 7.5, 1 mg/ml substrate peptide, 10 mM magnesium acetate and 0.02 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

IKKe assay: 5-20 mU of IKKe (diluted in 50 mM Tris (pH 7.5), 0.1 mM EGTA, 1 mg/ml BSA) was assayed against MBP in a final volume of 25.5 µl containing 50 mM Tris (pH 7.5), 0.1 mM EGTA, 0.33 mg/ml MBP, 10 mM magnesium acetate and 0.05 mM [33P-g-ATP] (500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

TBK1 assay: TBK1 (5-20 mU diluted in 50 mM Tris pH 7.5, 0.1 mM EGTA, 1 mg/ml BSA) was assayed against a substrate peptide (AKPKGNKDYHLQTCCGSLAYRRR) (SEQ ID NO: 31) in a final volume of 25.5 µl containing 50 mM Tris pH 7.5, 300 µM substrate peptide, 10 mM magnesium acetate and 0.05 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

IGF-1R assay: IGF-1R (5-20 mU diluted in 50 mM Tris pH 7.5, 0.1 mM EGTA, 1 mg/ml BSA) was assayed against a substrate peptide (KKKSPGEYVNIEFG) (SEQ ID NO: in a final volume of 25.5 µl containing 50 mM Tris pH 7.5, 300 µM substrate peptide, 10 mM magnesium acetate and 0.005 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

VEG-FR assay: VEG-FR (5-20 mU diluted in 50 mM Tris pH 7.5, 0.1 mM EGTA, 1 mg/ml BSA) was assayed against a substrate peptide (KKKSPGEYVNIEFG) (SEQ ID NO: 35) in a final volume of 25.5 µl containing 50 mM Tris pH 7.5, 300 µM substrate peptide, 10 mM magnesium acetate and 0.02 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

BTK assay: BTK (5-20 mU diluted in 50 mM Tris pH 7.5, 0.1 mM EGTA, 1 mg/ml BSA) was assayed against a substrate peptide (KVEKIGEGTYGVVYK) (SEQ ID NO: 15) in a final volume of 25.5 µl containing 50 mM Tris pH 7.5, 300 µM substrate peptide, 10 mM magnesium acetate and 0.05 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

IR-HIS assay: IR-HIS (5-20 mU diluted in 50 mM Tris pH 7.5, 0.1 mM EGTA, 1 mg/ml BSA) was assayed against a substrate peptide (KKSRGDYMTMQIG) (SEQ ID NO: 36) in a final volume of 25.5 µl containing 50 mM Tris pH 7.5, 300 µM substrate peptide, 10 mM magnesium acetate and 0.02 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

EPH-B3 assay: EPH-B3 (5-20 mU diluted in 50 mM Tris pH 7.5, 0.1 mM EGTA, 1 mg/ml BSA) was assayed against a substrate peptide (Poly Glut Tyr) in a final volume of 25.5 µl containing 50 mM Tris pH 7.5, 1 mg/ml substrate peptide, 10 mM magnesium acetate and 0.005 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

TBK1 (DU12569) assay: TBK1 (DU12569) (5-20 mU diluted in 50 mM Tris pH 7.5, 0.1 mM EGTA, 1 mg/ml BSA) was assayed against a substrate peptide (KKKKERLLD-DRHDSGLDSMKDEE) (SEQ ID NO: 37) in a final volume of 25.5 µl containing 50 mM Tris pH 7.5, 300 µM substrate peptide, 10 mM magnesium acetate and 0.05 mM [33P-g-ATP] (50-1000 cpm/pmole) and incubated for 30 min at room temperature. Assays were stopped by addition of 5 µl of 0.5 M (3%) orthophosphoric acid and then harvested onto P81 Unifilter plates with a wash buffer of 50 mM orthophosphoric acid.

IKKepsilon (DU14231) assay: 5-20 mU of IKKepsilon (DU14231)(diluted in 50 mM Tris (pH 7.5), 0.1 mM EGTA, 1 mg/ml BSA) was assayed against MBP in a final volume of 25.5 µl containing 50 mM Tris (pH 7.5), 0.1 mM EGTA, 0.33 mg/ml MBP, 10 mM magnesium acetate and 0.05 mM [33P-g-ATP] (500-1000 cpm/pmole) and incubated for 30 mins at room temperature. Assays were stopped by addition of 5 µl of 0.5M (3%) orthophosphoric acid. Assays were harvested onto P81 Unifilter plates using a wash buffer of 50 mM orthophosphoric acid.

Example 19

This example provides in vitro kinase inhibition data for various compounds within the scope of the invention versus CDK 2, CDK 4, CDK, 5, CDK 7 and CDK 9. The protocol was similar to that shown in Example 14 Inhibition of the protein kinases was performed in triplicate using each compound at 100 nM. Table 6 shows are the percentage of kinase activity remaining, following incubation with the compounds at a concentration of 100 nM.

TABLE 6

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
|---|---|---|---|---|---|---|
| | | CDK7 | CDK2 | CDK4 | CDK5 | CDK9 |
| ICEC0057 (BS-151) | 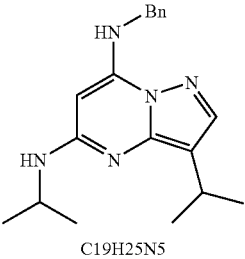 C19H25N5 | 75% (5.0) | 55.5% (9.9%) | 75.5% (1.4) | 84% (3.2) | 93% (2.8) |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
|---|---|---|---|---|---|---|
| | | CDK7 | CDK2 | CDK4 | CDK5 | CDK9 |
| ICEC0060 (BS-181) | 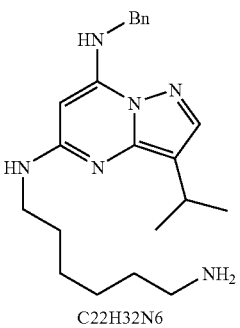 C22H32N6 | 17% (0.24) | 90% (8.0) | 99% (0.3) | 92% (1.3) | 91% (0.6) |
| ICEC0063 (BS-178) | 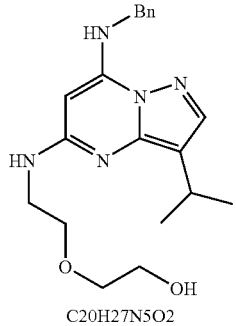 C20H27N5O2 | 25% (3.1) | 88% (7.4) | 83% (0.4) | 90% (1.1) | 90% (1.1) |
| ICEC0067 (BS-193) | 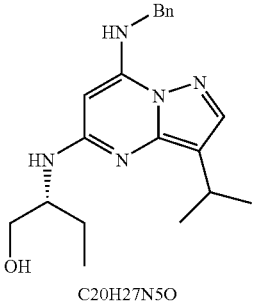 C20H27N5O | 49% (3.6) | 100% (9.5) | 88% (0.5) | 84% (3.2) | 85% (2.6) |
| ICEC0065 (BS-189) | 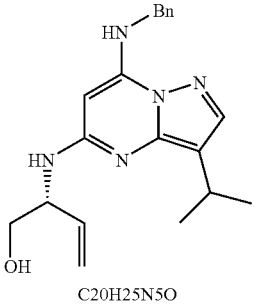 C20H25N5O | 80% (3.4) | 95% (3.2) | 77% (1.4) | 83% (1.6) | 100% (1.2) |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
|---|---|---|---|---|---|---|
| | | CDK7 | CDK2 | CDK4 | CDK5 | CDK9 |
| ICEC0318 (BS-194) | 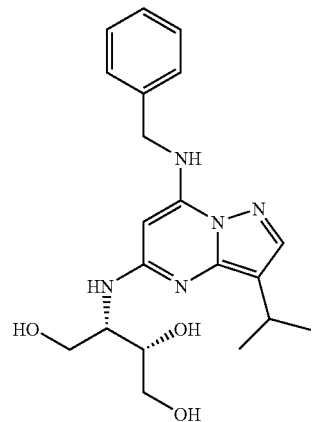 C20H27N5O3 | ND | 76% (4.9%) | 88% (3.5) | 14% (6.7) | 56% (0.9) |
| ICEC0319 (BS-195) | 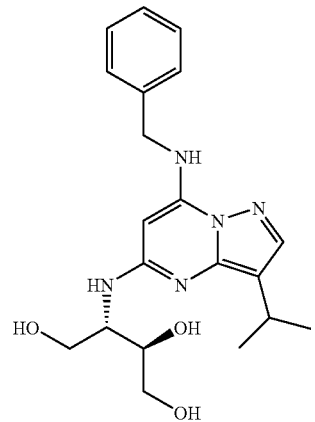 C20H27N5O3 | 81% (3.3) | 66% (6.8) | 71% (1.7) | 26% (7.4) | 57% (1.1) |
| ICEC0048 (BS-182) | 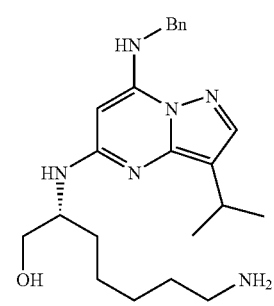 C23H34N6O | 74% (10.1) | 88% (7.0) | 75% (4.1) | 86% (1.1) | 86% (2.9) |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
|---|---|---|---|---|---|---|
| | | CDK7 | CDK2 | CDK4 | CDK5 | CDK9 |
| ICEC0050 (BS-211) | C24H36N6O | 81% (3.5) | 77% (2.3) | 80% (0.04) | 97% (1.2) | 65% (2.6) |
| ICEC0052 (BS-217) | C24H35FN6O | 34% (0.8) | 88% (10.0) | 90% (2.5) | 90% (2.6) | 85% (1.6) |
| ICEC0055 (BS-222) | C23H33FN6O | 55% (3.3) | 73% (10.7) | 84% (1.5) | 90% (0.7) | 75% (5.7) |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
|---|---|---|---|---|---|---|
| | | CDK7 | CDK2 | CDK4 | CDK5 | CDK9 |
| ICEC0138 (AS-473) | 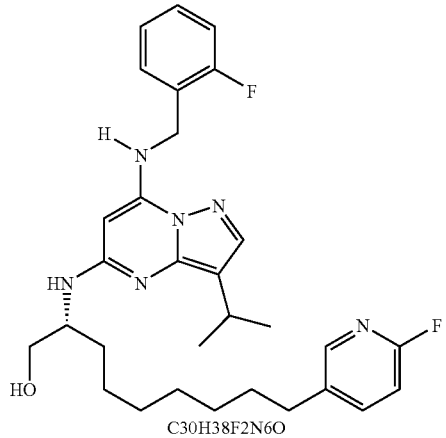 C30H38F2N6O | ND | 100% (0.25) | 92% (1.1) | 98% (1.4) | 100% (0.1) |
| ICEC0141 (AS-481) | 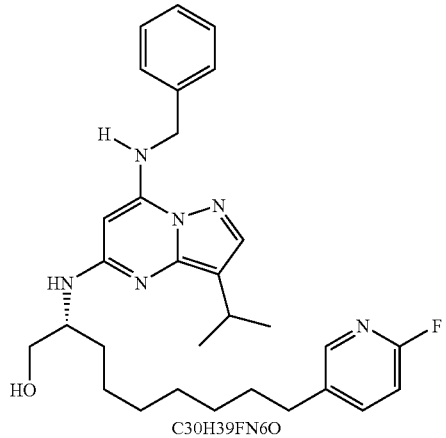 C30H39FN6O | ND | 84% (0.34) | 99% (0.1) | 95% (1.0) | 95% (0.02) |
| ICEC0159 (AS-524) | 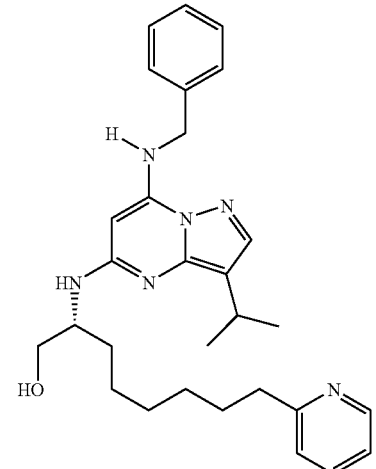 C29H38N6O | ND | 84% (0.47) | 98% (0.2) | 89% (0.4) | 100% (0.1) |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
|---|---|---|---|---|---|---|
| | | CDK7 | CDK2 | CDK4 | CDK5 | CDK9 |
| ICEC0160 (AS-525) | 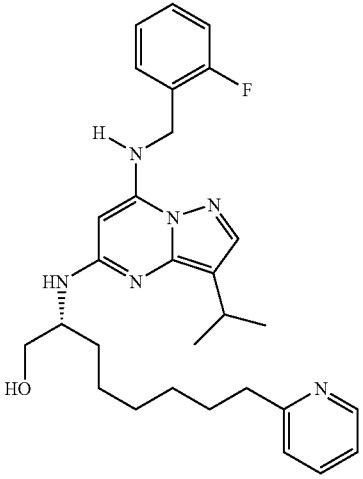 C29H37FN6O | ND | 97% (1.5) | 99% (0.1) | 92% (2.8) | 100% (0.1) |
| ICEC0161 (AS-528) | 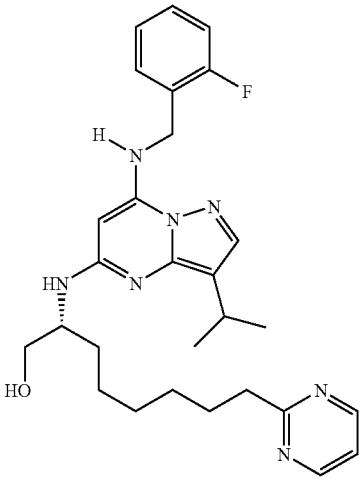 C28H36FN7O | ND | 71% (1.0) | 99% (0.1) | 92% (2.2) | 100% (0.1) |
| ICEC0167 (AS-540) | 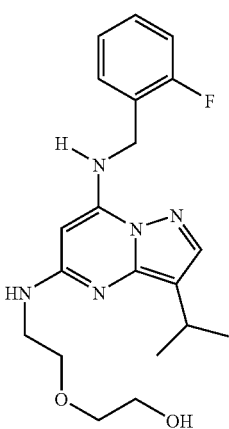 | ND | 24% (0.2) | 96% (0.3) | 92% (3.2) | 100% (0.1) |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
|---|---|---|---|---|---|---|
| | | CDK7 | CDK2 | CDK4 | CDK5 | CDK9 |
| ICEC0168 (AS-541) | C20H26FN5O2 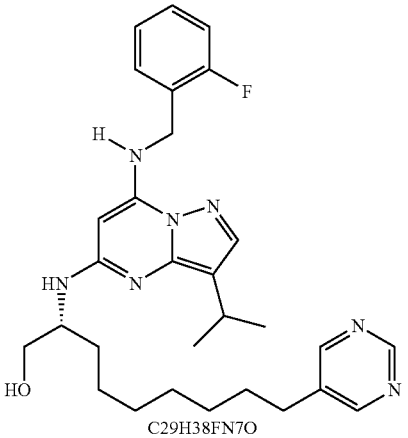 C29H38FN7O | ND | 83% (0.4) | 96% (0.3) | 97% (2.2) | 91% (0.1) |
| ICEC0179 (JAB-012) | 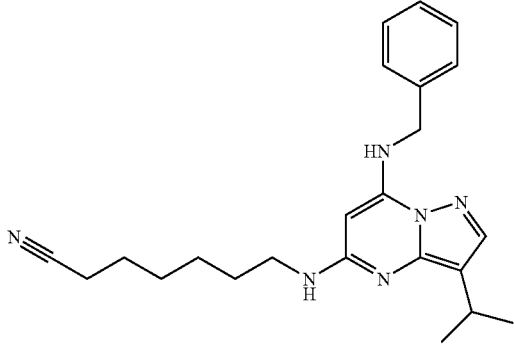 C23H30N6 | ND | 52% (0.9) | 99% (0.3) | 94% (1.6) | 97% (0.1) |
| ICEC-0174 (AS-552) | 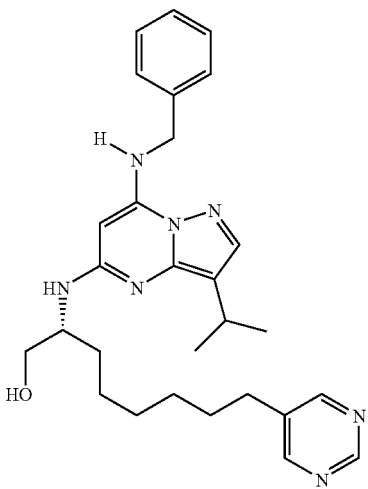 C28H37N7O | ND | 31.5% (1.0) | 99% (0.2) | 97% (3.5) | 92% (0.4) |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
|---|---|---|---|---|---|---|
| | | CDK7 | CDK2 | CDK4 | CDK5 | CDK9 |
| ICEC-0325 (AS-570) | 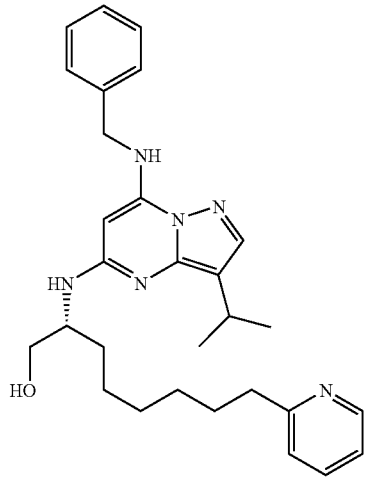 C29H38N6O | ND | 24% (0.4) | 100% (0.4) | 96% (4.3) | 99% (0.1) |
| ICEC-0326 (AS-576) | 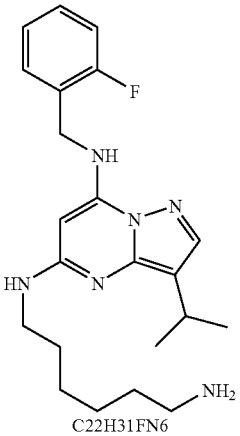 C22H31FN6 | ND | 25% (1.6) | 99% (0.2) | 91% (1.2) | 99% (0.1) |
| ICEC-0327 (AS-585) | 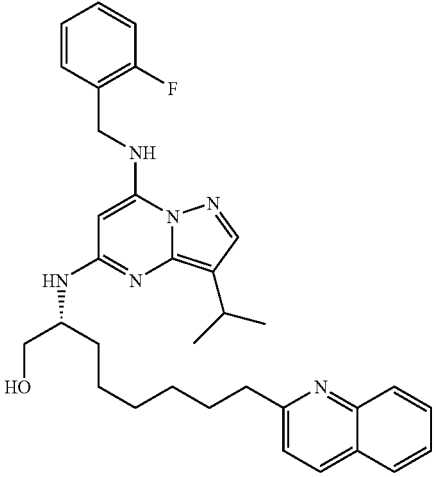 C33H39FN6O | ND | 16% (1.4) | 99% (0.1) | 96% (4.9) | 51% (3.5) |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
|---|---|---|---|---|---|---|
| | | CDK7 | CDK2 | CDK4 | CDK5 | CDK9 |
| ICEC-0186 | C23H29FN6 | ND | 9.3% (2.46) | 95% (0.2) | 94% (2.7) | 98% (0.01) |
| ICEC-0187 | C23H33N7 | ND | 9.3% (0.86) | 98% (0.1) | 93% (3.1) | 99% (0.1) |
| ICEC0192 | C23H34N6 | 18% (0.9) | ND | ND | ND | ND |
| ICEC0193 | C23H33FN6 | 8% (1.9) | ND | ND | ND | ND |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
|---|---|---|---|---|---|---|
| | | CDK7 | CDK2 | CDK4 | CDK5 | CDK9 |
| ICEC0200 | 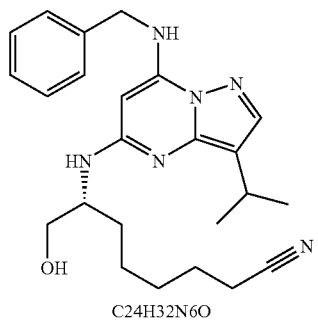 C24H32N6O | 90% (5.9) | ND | ND | ND | ND |
| ICEC0201 | 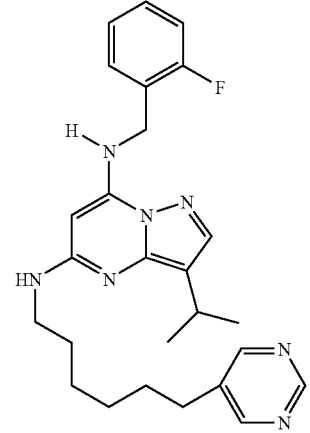 C26H32FN7 | 66% (5.2) | ND | ND | ND | ND |
| ICEC0202 | 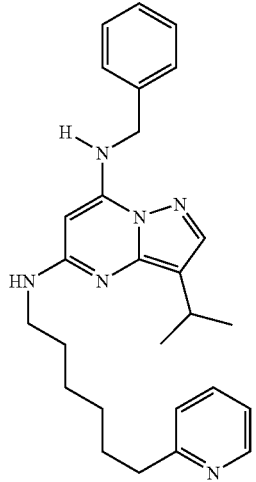 C27H34N6 | 69% (1.4) | ND | ND | ND | ND |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
| --- | --- | --- | --- | --- | --- | --- |
| | | CDK7 | CDK2 | CDK4 | CDK5 | CDK9 |
| ICEC0203 | C27H33FN6 | 96% (3.1) | ND | ND | ND | ND |
| ICEC0204 | C20H26FN5O | 42% (4.0) | ND | ND | ND | ND |
| ICEC0205 | | 83% (2.4) | ND | ND | ND | ND |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
| --- | --- | --- | --- | --- | --- | --- |
| | | CDK7 | CDK2 | CDK4 | CDK5 | CDK9 |
| ICEC0206 | C29H37FN6O | 81% (2.2) | ND | ND | ND | ND |
| ICEC0207 | C30H31F2N5O | 73% (4.7) | ND | ND | ND | ND |
| | C27H33FN6 | | | | | |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
|---|---|---|---|---|---|---|
| | | CDK7 | CDK2 | CDK4 | CDK5 | CDK9 |
| ICEC0208 | 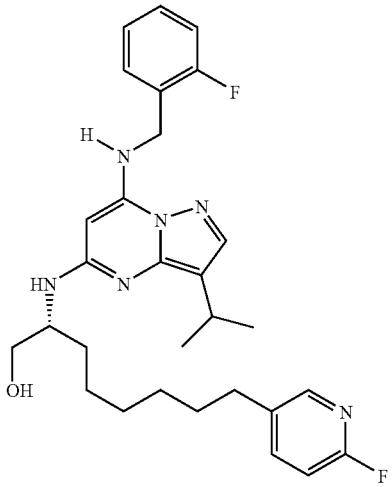 C29H36F2N6O | 79% (3.3) | ND | ND | ND | ND |
| ICEC0209 | 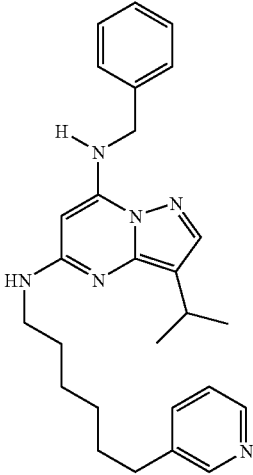 C27H34N6 | 78% (4.4) | ND | ND | ND | ND |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
| --- | --- | --- | --- | --- | --- | --- |
| | | CDK7 | CDK2 | CDK4 | CDK5 | CDK9 |
| ICEC0210 | 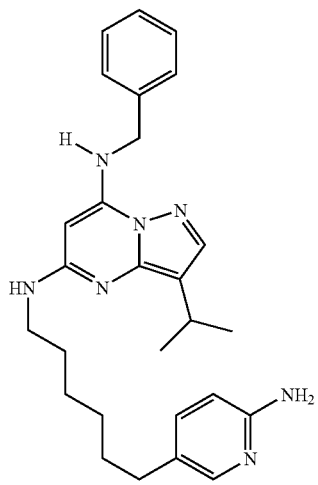 C27H35N7 | 81% (2.6) | 97% (1.8) | ND | ND | ND |
| ICEC0211 | 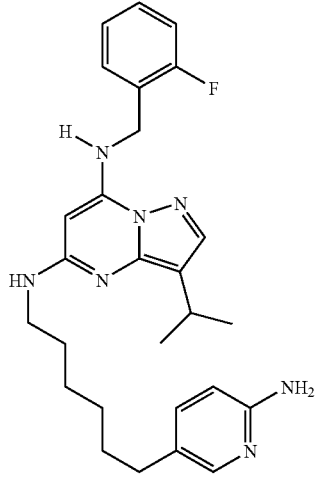 C27H34FN7 | 83% (1.2) | 96% (2.5) | ND | ND | ND |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
| --- | --- | --- | --- | --- | --- | --- |
| | | CDK7 | CDK2 | CDK4 | CDK5 | CDK9 |
| ICEC0212 | C24H35FN6O2S | 63% (3.0) | 91% (0.6) | ND | ND | ND |
| ICEC0213 | C24H34FN6 | 81% (0.2) | 90% (1.0) | ND | ND | ND |
| ICEC0214 | C24H33FN6 | 60% (5.1) | 74% (3.3) | ND | ND | ND |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
|---|---|---|---|---|---|---|
| | | CDK7 | CDK2 | CDK4 | CDK5 | CDK9 |
| ICEC0216 | 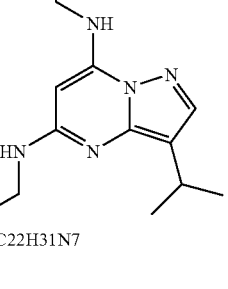 C22H31N7 | 50% (2.3) | 68% (0.4) | ND | ND | ND |
| ICEC0218 | 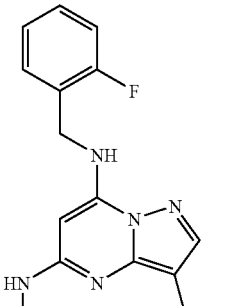 C22H30FN7 | 60% (2.9) | 75% (2.2) | ND | ND | ND |
| ICEC0222 | 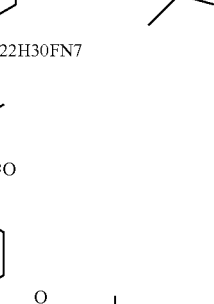 C23H30ClN5O4S | 63% (9.0) | ND | ND | ND | ND |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
|---|---|---|---|---|---|---|
| | | CDK7 | CDK2 | CDK4 | CDK5 | CDK9 |
| ICEC0229 | C22H29FN6 | 54% (11.0) | 60% (2.9) | ND | ND | ND |
| ICEC0232 | C21H29FN6 | 40% (11.1) | 84% (5.6) | 99% (0.1) | 15% (3.5) | 98% (1.3) |
| ICEC0235 | C23H34N6 | 56% (10.7) | 81% (3.3) | ND | ND | ND |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
| --- | --- | --- | --- | --- | --- | --- |
| | | CDK7 | CDK2 | CDK4 | CDK5 | CDK9 |
| ICEC0236 | C40H52N10 | 91% (5.2) | 68% (8.7) | ND | ND | ND |
| ICEC0238 | C30H40N6O | 77% (4.4) | 67% (1.2) | ND | ND | ND |
| ICEC0006 | C16H17ClN4 | 65% (2.4) | 75% (4.4) | ND | ND | ND |
| ICEC0239 | C16H15Cl3N4 | 82% (3.4) | 85% (1.5) | ND | ND | ND |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
| --- | --- | --- | --- | --- | --- | --- |
| | | CDK7 | CDK2 | CDK4 | CDK5 | CDK9 |
| ICEC0240 | 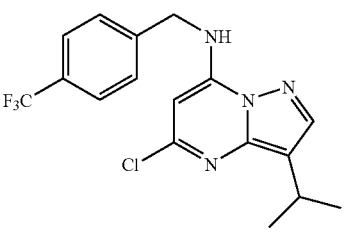<br>C17H16ClF3N4 | 75% (3.3) | 82% (2.6) | ND | ND | ND |
| ICEC0241 | 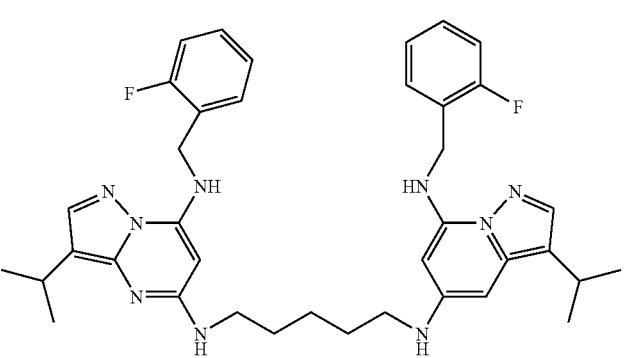<br>C37H44F2N10 | 73% (3.7) | 77% (11.2) | ND | ND | ND |
| ICEC0244 | 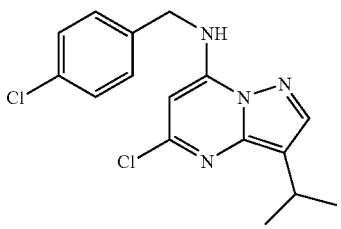<br>C16H16Cl2N4 | 81% (0.9) | 73% (8.2) | ND | ND | ND |
| ICEC0245 | 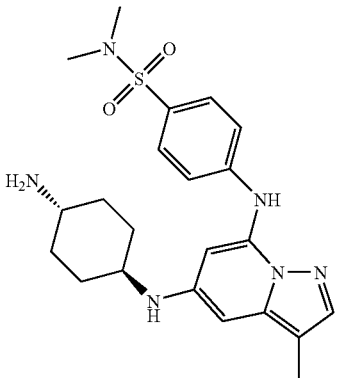<br>C23H33N7O2S | 61% (1.9) | 21% (4.9) | ND | ND | ND |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
|---|---|---|---|---|---|---|
| | | CDK7 | CDK2 | CDK4 | CDK5 | CDK9 |
| ICEC0259 | C22H30N6O | 54% (8.5) | 88% (1.3) | ND | ND | ND |
| ICEC0274 | C23H34N6 | 100% (1.2) | 96% (1.9) | ND | ND | ND |
| ICEC0277 | C20H28N6 | 12.6% (7.7) | 89% (1.9) | ND | ND | ND |
| ICEC0278 | C22H30N6 | 21% (7.6) | 72% (1.8) | ND | ND | ND |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
|---|---|---|---|---|---|---|
| | | CDK7 | CDK2 | CDK4 | CDK5 | CDK9 |
| ICEC0289 | 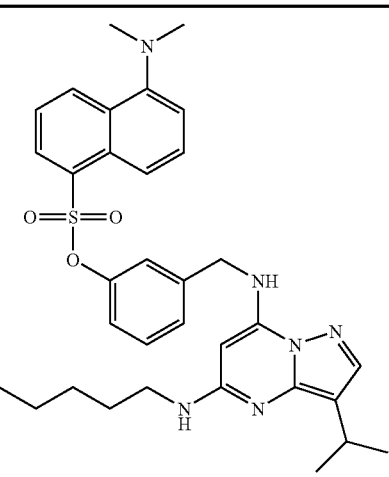 C33H41N7O3S | 47% (10.2) | 79% (2.5) | ND | ND | ND |
| ICEC0291 | 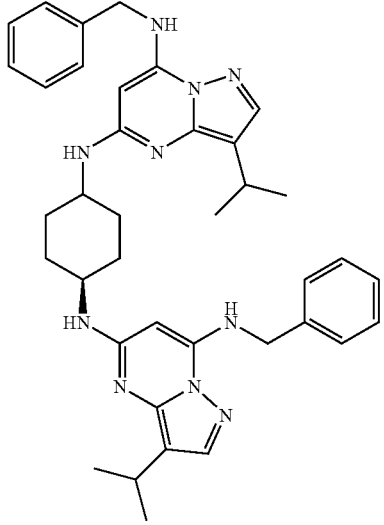 | 99% (0.4) | 98% (0.1) | 98% (0.3) | 99% (0.1) | 90% (1.8) |
| ICEC0295 | 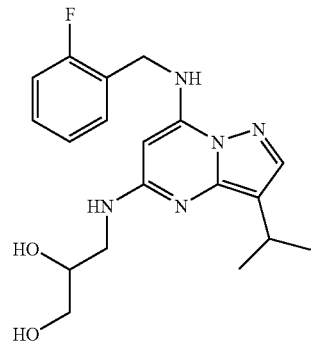 | 88% (0.1) | 98% (0.1) | 99% (0.3) | 57% (1.2) | 57% (1.5) |

TABLE 6-continued

Comparison of the in vitro kinase inhibition data for various compounds within the scope of the invention versus CDK 2, CDK 4, CDK, 5, CDK 7 and CDK 9. Each data point is the mean of three experiments. The standard deviation is also provided, set off with parentheses, below each data point.

| Compound Name | Formula and Structure | Kinase inhibition in vitro (% remaining kinase activity after incubation with 100 nM of compound) | | | | |
|---|---|---|---|---|---|---|
| | | CDK7 | CDK2 | CDK4 | CDK5 | CDK9 |
| ICEC0297 | | 98% (0.4) | 98% (0.3) | 100% (0.1) | 76% (1.0) | 78% (0.9) |
| ICEC0298 | | 89% (0.2) | 98% (0.4) | 101% (0.2) | 57% (0.4) | 63% (2.3) |

Example 20

This example provides in vitro kinase inhibition data for various compounds within the scope of the invention versus CDK 2, CDK 4, CDK, 5, CDK 7 and CDK 9. The data are reported in terms of $IC_{50}$ values, as shown in Table 7. The protocol that was used to obtain this data is similar to that reported in Example 14.

TABLE 7

Comparison of the in vitro kinase inhibition data for various compounds within the scope of the invention versus CDK 2, CDK 4, CDK, 5, CDK 7 and CDK 9. Each data point is the mean of three experiments.

| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| ICEC0057 (BS-151) | C19H25N5 | >1000 nM | 100 nM | >1000 nM | ND | >1000 nM |

TABLE 7-continued

Comparison of the in vitro kinase inhibition data for various compounds within the scope of the invention versus CDK 2, CDK 4, CDK, 5, CDK 7 and CDK 9. Each data point is the mean of three experiments.

| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| ICEC0060 (BS-181) | 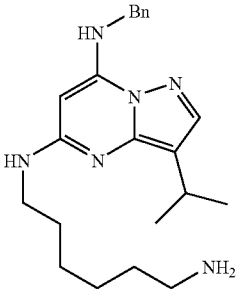 C22H32N6 | 18 nM | 750 nM | >1000 nM | >1000 nM | >1000 nM |
| ICEC0063 (BS-178) | 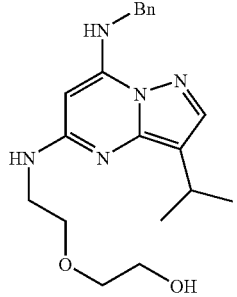 C20H27N5O2 | 32 nM | >1000 nM | >1000 nM | ND | 100 nM |
| ICEC0067 (BS-193) | 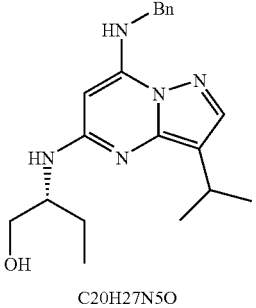 C20H27N5O | 70 nM | >1000 nM | >1000 nM | ND | 100 nM |
| ICEC0065 (BS-189) | 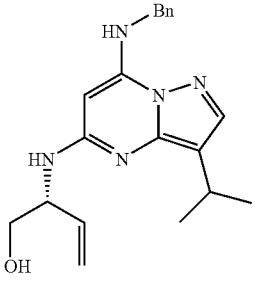 C20H25N5O | >1000 nM | >1000 nM | >1000 nM | >1000 nM | >1000 nM |

TABLE 7-continued

Comparison of the in vitro kinase inhibition data for various compounds within the scope of the invention versus CDK 2, CDK 4, CDK, 5, CDK 7 and CDK 9. Each data point is the mean of three experiments.

| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| ICEC0318 (BS-194) | 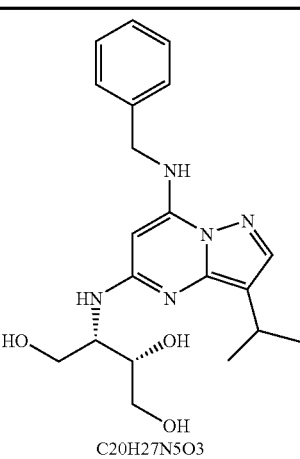 C20H27N5O3 | 350 nM | 580 nM | >1000 nM | 30 nM | 50 nM |
| ICEC0319 (BS-195) | 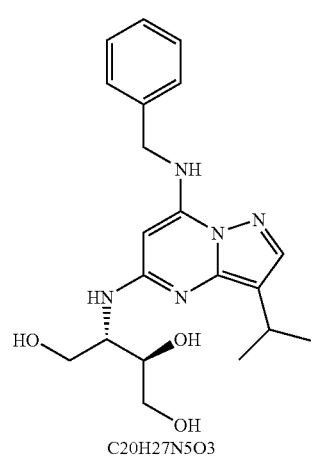 C20H27N5O3 | 300 nM | ND | ND | 45 nM | 75 nM |
| ICEC0048 (BS-182) | 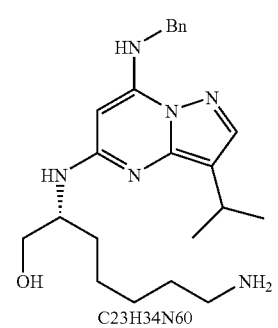 C23H34N6O | >1000 nM | ND | ND | ND | ND |
| ICEC0050 (BS-211) | 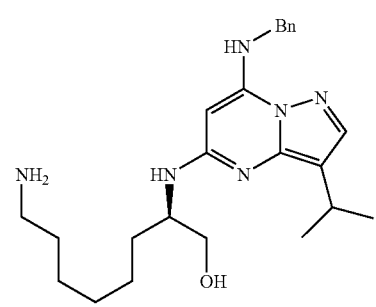 | 320 nM | ND | >1000 nM | ND | ND |

TABLE 7-continued

Comparison of the in vitro kinase inhibition data for various compounds within the scope of the invention versus CDK 2, CDK 4, CDK, 5, CDK 7 and CDK 9. Each data point is the mean of three experiments.

| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| | C24H36N6O | | | | | |
| ICEC0052 (BS-217) | 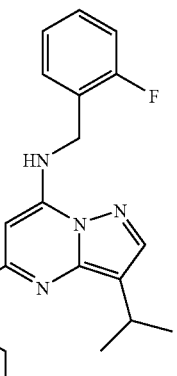 C24H35FN6O | 60 nM | >1000 nM | >1000 nM | ND | ND |
| ICEC0055 (BS-222) | 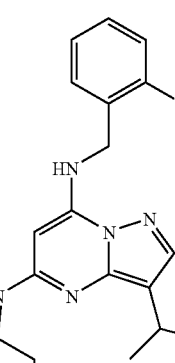 C23H33FN6O | 180 nM | ND | >1000 nM | ND | ND |
| ICEC0138 (AS-473) |  C30H38F2N6O | 46 nM | ND | >1000 nM | ND | ND |

TABLE 7-continued

Comparison of the in vitro kinase inhibition data for various compounds within the scope of the invention versus CDK 2, CDK 4, CDK, 5, CDK 7 and CDK 9. Each data point is the mean of three experiments.

| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| ICEC0141 (AS-481) | 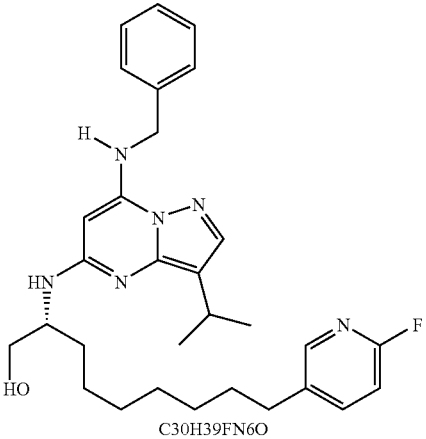 C30H39FN6O | 80 nM | ND | >1000 nM | ND | ND |
| ICEC0159 (AS-524) | 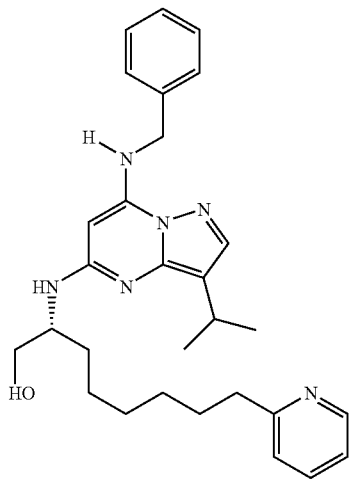 C29H38N6O | 42 nM | ND | >1000 nM | ND | ND |
| ICEC0161 (AS-528) | 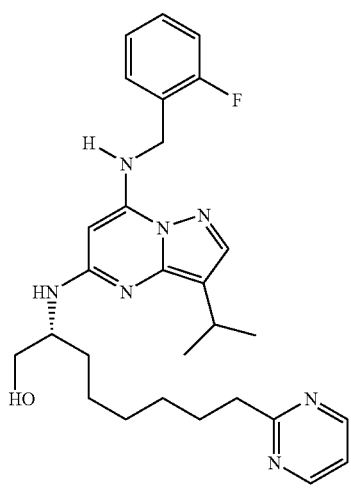 C28H36FN7O | 44 nM | ND | >1000 nM | ND | ND |

TABLE 7-continued

Comparison of the in vitro kinase inhibition data for various compounds within the scope of the invention versus CDK 2, CDK 4, CDK, 5, CDK 7 and CDK 9. Each data point is the mean of three experiments.

| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| ICEC0167 (AS-540) | 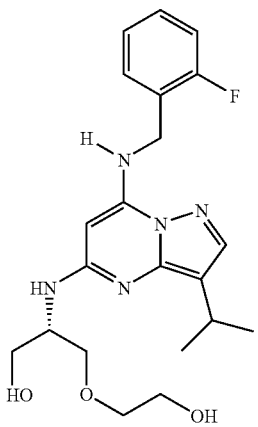 C20H26FN5O2 | 55 nM | ND | >1000 nM | ND | ND |
| ICEC0168 (AS-541) | 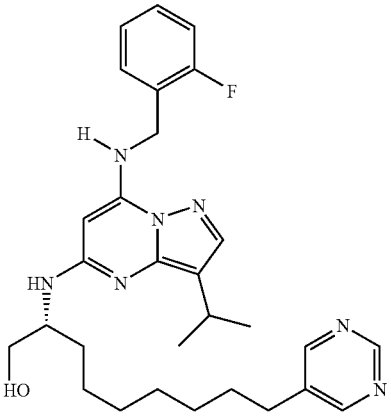 C29H38FN7O | 18 nM | <100 nM | >1000 nM | ND | ND |
| ICEC0179 (JAB-012) | 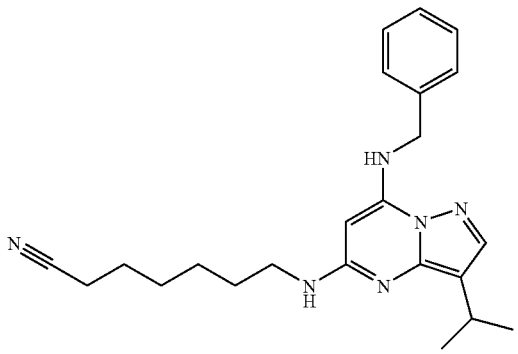 C23H30N6 | 120 nM | ND | >1000 nM | ND | ND |

TABLE 7-continued

Comparison of the in vitro kinase inhibition data for various compounds within the scope of the invention versus CDK 2, CDK 4, CDK, 5, CDK 7 and CDK 9. Each data point is the mean of three experiments.

| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| ICEC-0174 (AS-552) | 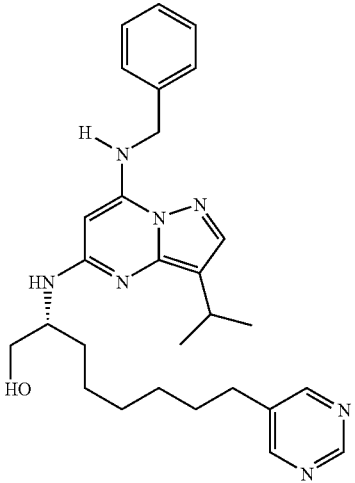 C28H37N7O | 20 nM | 100 nM | >1000 nM | ND | ND |
| ICEC-0325 (AS-570) | 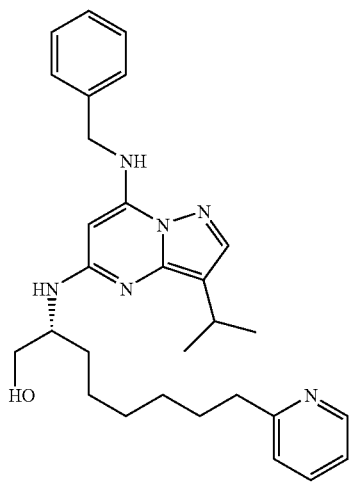 C29H38N6O | >1000 nM | ND | ND | ND | ND |
| ICEC-0326 (AS-576) | 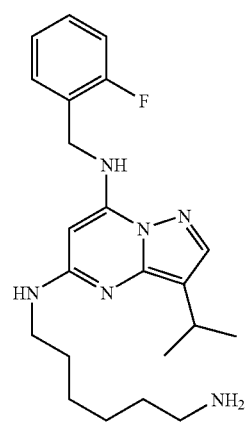 C22H31FN6 | >1000 nM | ND | ND | ND | ND |

TABLE 7-continued

Comparison of the in vitro kinase inhibition data for various compounds within the scope of the invention versus CDK 2, CDK 4, CDK, 5, CDK 7 and CDK 9. Each data point is the mean of three experiments.

| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| ICEC-0327 (AS-585) | 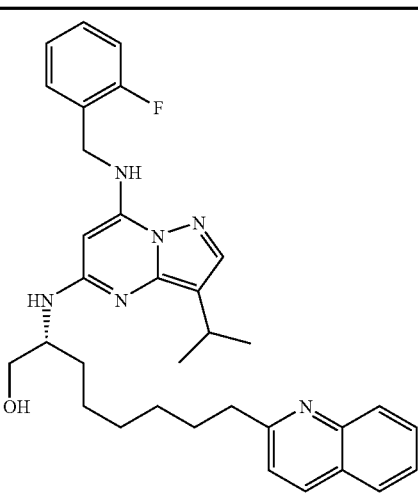 C33H39FN6O | 24 nM | ND | ND | ND | ND |
| ICEC-0186 | 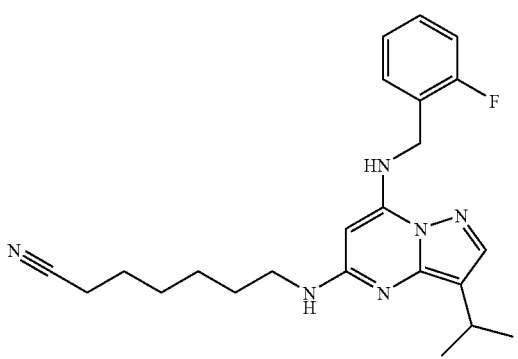 C23H29FN6 | >1000 nM | ND | ND | ND | 160 nM |
| ICEC-0187 | 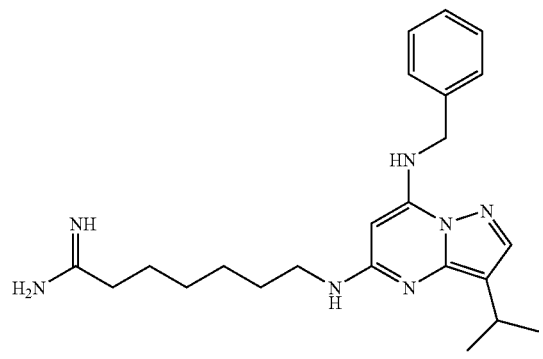 C23H33N7 | 40 nM | ND | ND | ND | ND |
| ICEC0192 | 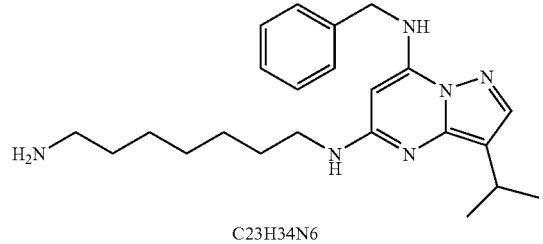 C23H34N6 | 654 nM | ND | ND | ND | ND |

TABLE 7-continued

Comparison of the in vitro kinase inhibition data for various compounds within the scope of the invention versus CDK 2, CDK 4, CDK, 5, CDK 7 and CDK 9. Each data point is the mean of three experiments.

| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| ICEC0193 | 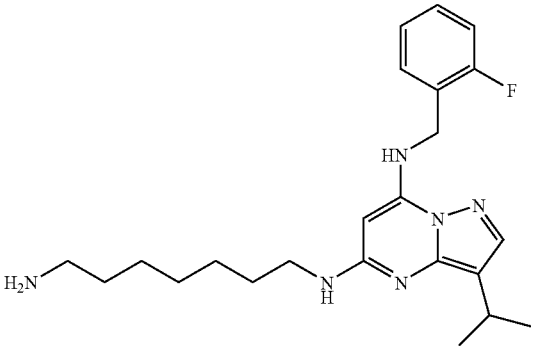<br>C23H33FN6 | 27 nM | ND | ND | ND | ND |
| ICEC0200 | 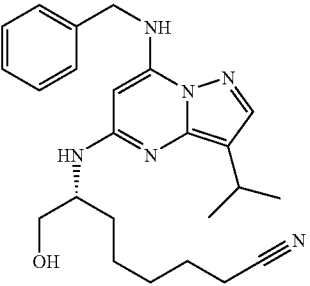<br>C24H32N6O | 18 nM | ND | ND | ND | ND |
| ICEC0201 | 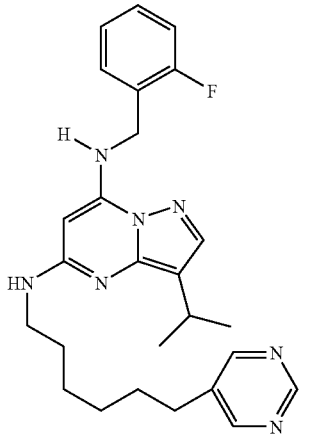<br>C26H32FN7 | >1000 nM | ND | ND | ND | ND |

TABLE 7-continued
Comparison of the in vitro kinase inhibition data for various compounds within the scope of the invention versus CDK 2, CDK 4, CDK, 5, CDK 7 and CDK 9. Each data point is the mean of three experiments.
| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| ICEC0202 | 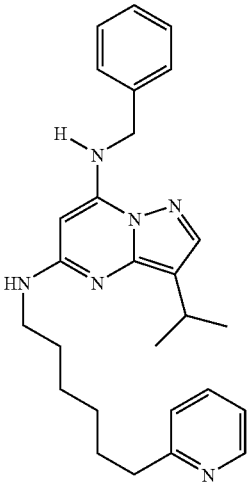 C27H34N6 | 604 nM | ND | ND | ND | ND |
| ICEC0203 | 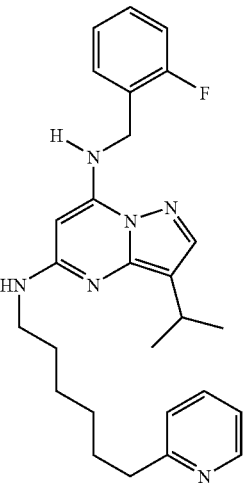 C27H33FN6 | 704 nM | ND | ND | ND | ND |
| ICEC0204 | 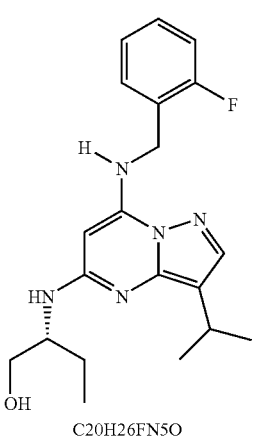 C20H26FN5O | >1000 nM | ND | ND | ND | ND |

TABLE 7-continued
Comparison of the in vitro kinase inhibition data for various compounds within the scope of the invention versus CDK 2, CDK 4, CDK, 5, CDK 7 and CDK 9. Each data point is the mean of three experiments.
| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| ICECO205 | 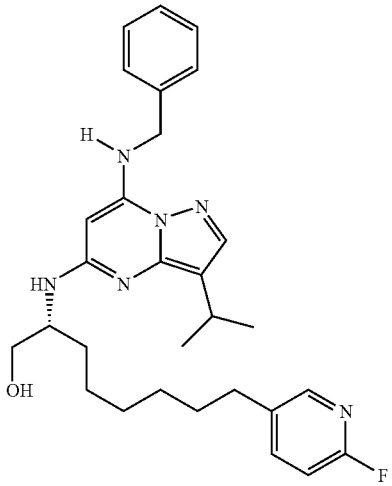 C29H37FN6O | 183 nM | ND | ND | ND | ND |
| ICEC0206 | 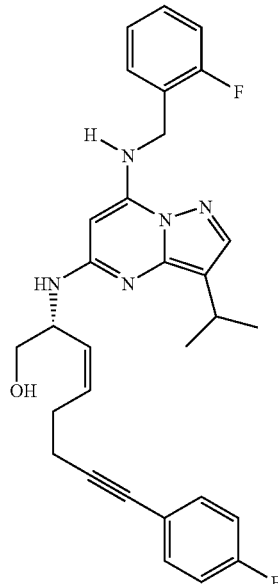 C30H31F2N5O | >1000 nM | ND | ND | ND | ND |

TABLE 7-continued
Comparison of the in vitro kinase inhibition data for various compounds within the scope of the invention versus CDK 2, CDK 4, CDK, 5, CDK 7 and CDK 9. Each data point is the mean of three experiments.
| Compound Name | Formula and Structure | Kinase inhibition in vitro (IC50) in nM | | | | |
| --- | --- | --- | --- | --- | --- | --- |
| | | CDK7 | CDK2 | CDK4 | CDK5 | CDK9 |
| ICEC0207 | 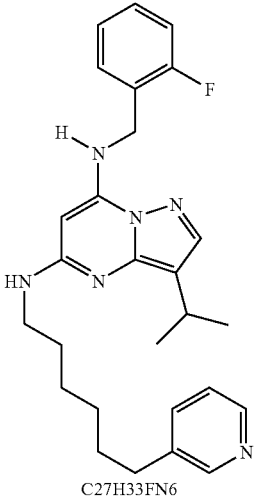 C27H33FN6 | >1000 nM | ND | ND | ND | ND |
| ICEC0208 | 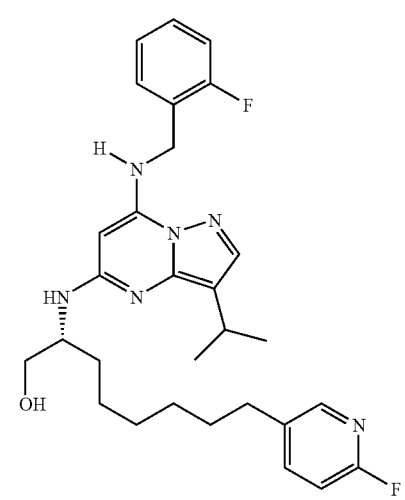 C29H36F2N6O | >1000 nM | ND | ND | ND | ND |
| ICEC0209 | 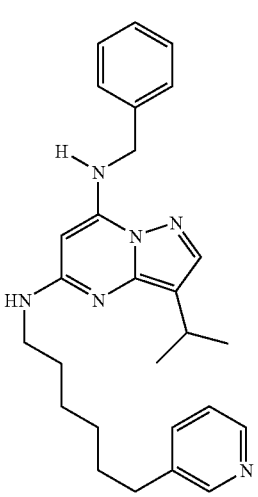 C27H34N6 | >1000 nM | ND | ND | ND | ND |

TABLE 7-continued
Comparison of the in vitro kinase inhibition data for various compounds within the scope of the invention versus CDK 2, CDK 4, CDK, 5, CDK 7 and CDK 9. Each data point is the mean of three experiments.
| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| ICEC0210 | 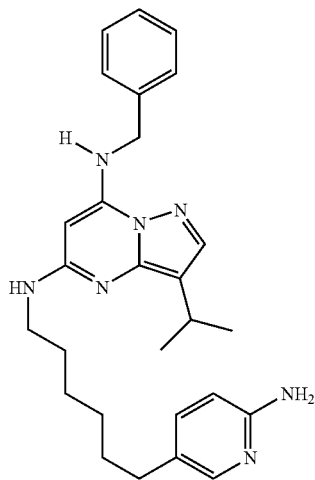 C27H35N7 | >1000 nM | ND | ND | ND | ND |
| ICEC0211 | 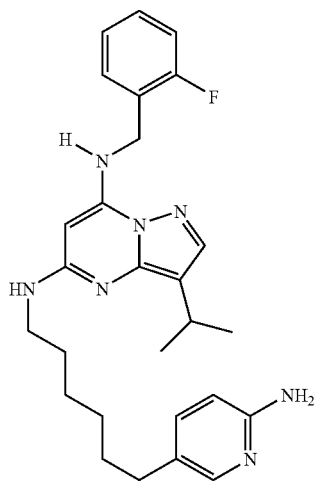 C27H34FN7 | >1000 nM | ND | ND | ND | ND |

TABLE 7-continued
Comparison of the in vitro kinase inhibition data for various compounds within the scope of the invention versus CDK 2, CDK 4, CDK, 5, CDK 7 and CDK 9. Each data point is the mean of three experiments.
| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| ICEC0212 | 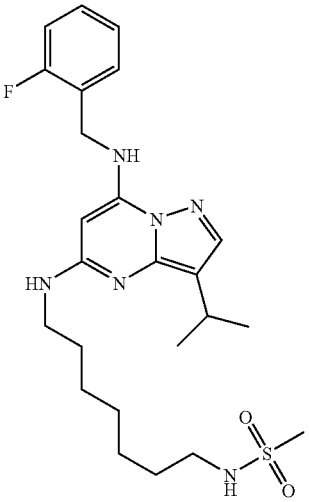 C24H35FN6O2S | >1000 nM | ND | ND | ND | ND |
| ICEC0213 | 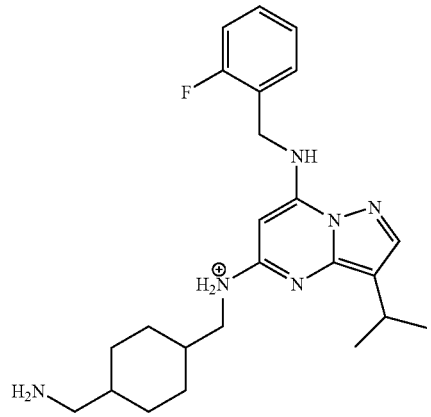 C24H34FN6 | >1000 nM | ND | ND | ND | ND |
| ICEC0214 | 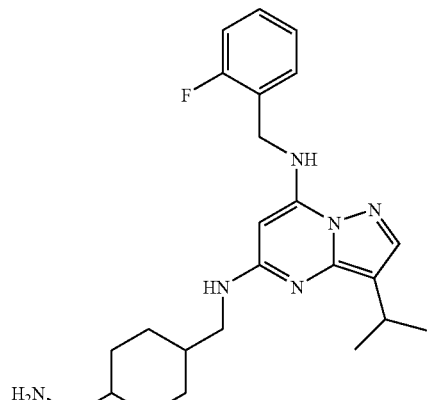 C24H33FN6 | >1000 nM | ND | ND | ND | ND |

TABLE 7-continued

Comparison of the in vitro kinase inhibition data for various compounds within the scope of the invention versus CDK 2, CDK 4, CDK, 5, CDK 7 and CDK 9. Each data point is the mean of three experiments.

| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| ICEC0216 | C22H31N7 | 76 nM | ND | ND | ND | ND |
| ICEC0222 | C23H30ClN5O4S | 48 nM | ND | ND | ND | ND |
| ICEC0229 | C22H29FN6 | 48 nM | ND | ND | ND | ND |

TABLE 7-continued

Comparison of the in vitro kinase inhibition data for various compounds within the scope of the invention versus CDK 2, CDK 4, CDK, 5, CDK 7 and CDK 9. Each data point is the mean of three experiments.

| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| ICEC0232 | 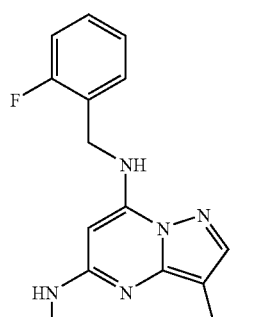<br>C21H29FN6 | 564 nM | 310 nM | ND | ND | ND |
| ICEC0235 | 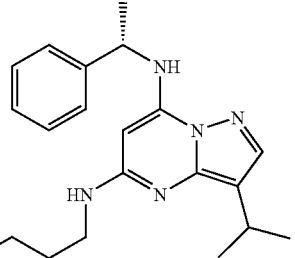<br>C23H34N6 | 6 nM | 180 nM | ND | ND | ND |
| ICEC0236 | 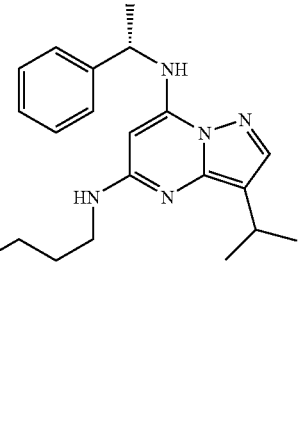<br>C40H52N10 | 7 nM | ND | ND | ND | ND |
| ICEC0238 | 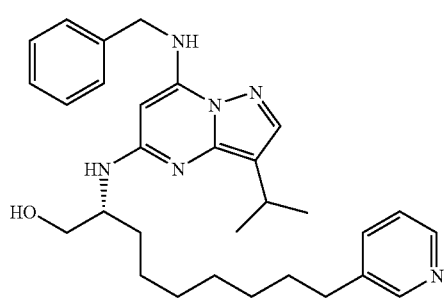<br>C30H40N6O | 520 nM | ND | ND | ND | ND |

TABLE 7-continued

Comparison of the in vitro kinase inhibition data for various compounds within the scope of the invention versus CDK 2, CDK 4, CDK, 5, CDK 7 and CDK 9. Each data point is the mean of three experiments.

| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| ICEC0006 | 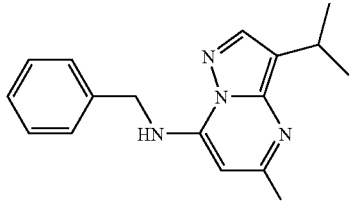 C16H17ClN4 | 664 nM | ND | ND | ND | ND |
| ICEC0239 | 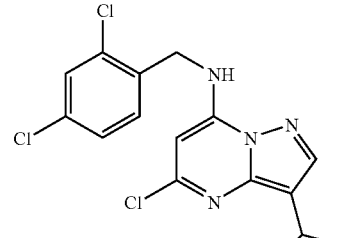 C16H15Cl3N4 | 620 nM | ND | ND | ND | ND |
| ICEC0240 | 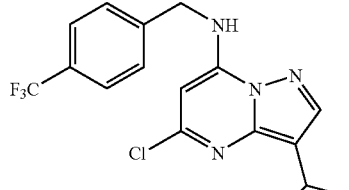 C17H16ClF3N4 | 725 nM | ND | ND | ND | ND |
| ICEC0241 | 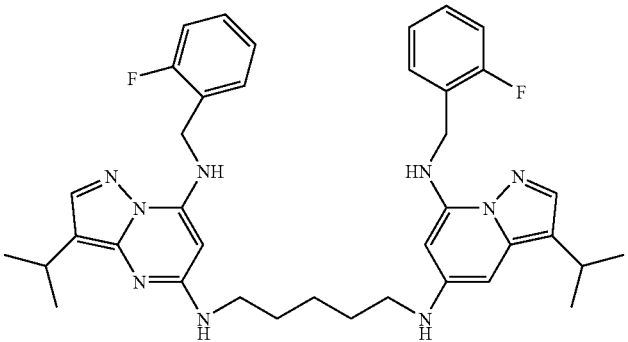 C37H44F2N10 | >1000 nM | ND | ND | ND | ND |
| ICEC0244 | 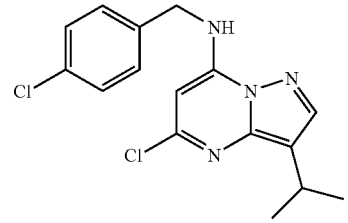 C16H16Cl2N4 | >1000 nM | ND | ND | ND | ND |

TABLE 7-continued

Comparison of the in vitro kinase inhibition data for various compounds within the scope of the invention versus CDK 2, CDK 4, CDK, 5, CDK 7 and CDK 9. Each data point is the mean of three experiments.

| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| ICEC0245 | C23H33N7O2S | >1000 nM | ND | ND | ND | ND |
| ICEC0259 | C22H30N6O | >1000 nM | ND | ND | ND | ND |
| ICEC0274 | C23H34N6 | 520 nM | 30 nM | ND | ND | ND |
| ICEC0277 | C20H28N6 | 225 nM | ND | ND | ND | ND |
| ICEC0278 | C22H30N6 | 963 nM | ND | ND | ND | ND |

TABLE 7-continued

Comparison of the in vitro kinase inhibition data for various compounds within the scope of the invention versus CDK 2, CDK 4, CDK, 5, CDK 7 and CDK 9. Each data point is the mean of three experiments.

| Compound Name | Formula and Structure | Kinase inhibition in vitro (IC50) in nM | | | | |
|---|---|---|---|---|---|---|
| | | CDK7 | CDK2 | CDK4 | CDK5 | CDK9 |
| ICEC0289 | 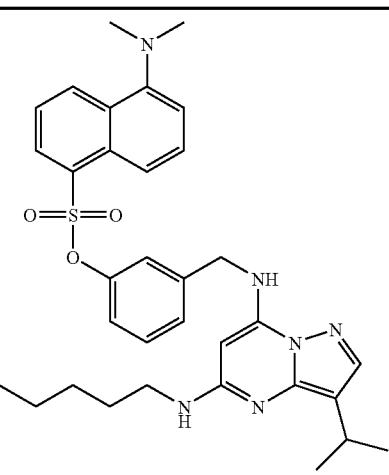 C33H41N7O3S | 30 nM | ND | ND | ND | ND |
| ICEC0291 | 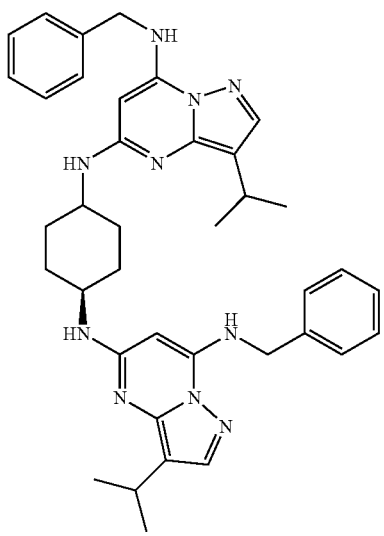 | 43 nM | ND | ND | ND | ND |
| ICEC0295 | 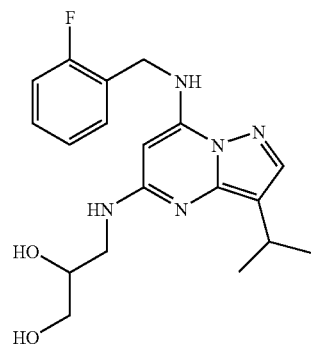 | 155 nM | ND | ND | ND | ND |

Example 21

Table 8, shown below, provides growth inhibition data for the MCF-7 cell line obtained using the SRB assay. In the SRB assay, sixteen hours following seeding of $3\times10^3$ MCF-7 cells in 96-well plates in DMEM containing 10% FCS, the medium was replaced with fresh medium supplemented with the compound of interest, or an equivalent volume of the vehicle control (DMSO), at concentrations, ranging from 0.1 to 100 µM. The compounds were added to three well to provide replicates. The cells were fixed after 24 hours, using 40% (w/v) TCA, for one hour at 4° C., washed five times with distilled, deionised H₂O, followed by incubation with 0.4% (w/v) sulphorhodamine B (SRB) in 1% acetic acid for one hour at room temperature. Excess dye was removed with five washes with 1% acetic acid and drying at room temperature. Absorbance at 480 nm was determined following solubilisation of the dye by the addition of 100 μl of 10 mM Tris base to each well.

SRB values (absorbance at 480 nm) for the vehicle control (DMSO) were set at 100% and absorbance at 480 nm for the compound treatments were calculated relative to the control. Growth inhibition (GI50), total growth inhibition (TGI) and lethal concentration (LC50) were determined GI50 is the concentration at which cell growth is inhibited by 50%, TGI represents the concentration of compound at which there is no growth and LC50 is the concentration of compound at which 50% of seeded cells are lost (death).

TABLE 8

Growth inhibition data for the MCF-7 cell line. Each IC50 data point is the mean of three experiments.

| Compound Name | Formula and Structure | LC50 (μm) | TGI (μm) | IC50 (μm) |
|---|---|---|---|---|
| ICEC0057 (BS-151) | 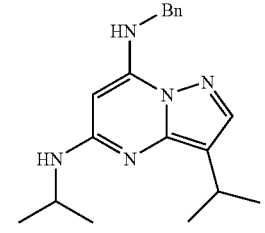 C19H25N5 | 20.3 μM | 36.5 μM | >100 μM |
| ICEC0060 (BS-181) | 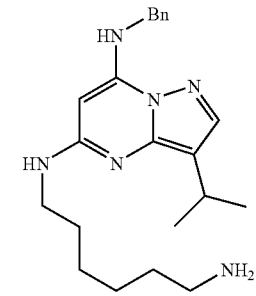 C22H32N6 | 21 μM | 32 μM | 48 μM |
| ICEC0063 (BS-178) | 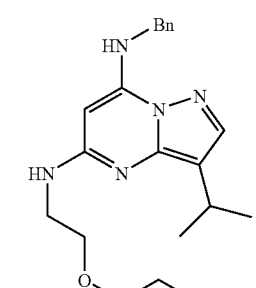 C20H27N5O2 | 40.5 μM | 76.5 μM | >100 μM |
| ICEC0067 (BS-193) | 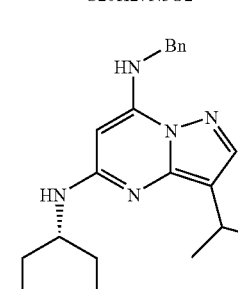 C20H27N5O | 8.5 μM | 13 μM | >100 μM |

TABLE 8-continued
Growth inhibition data for the MCF-7 cell line. Each IC50 data point is the mean of three experiments.
| Compound Name | Formula and Structure | LC50 (μm) | TGI (μm) | IC50 (μm) |
|---|---|---|---|---|
| ICEC0065 (BS-189) | 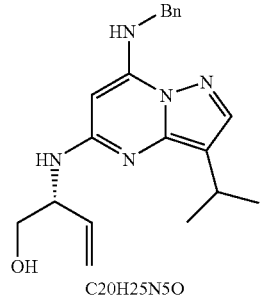 C20H25N5O | 8.5 μM | 12 μM | >100 μM |
| ICEC0318 (BS-194) | 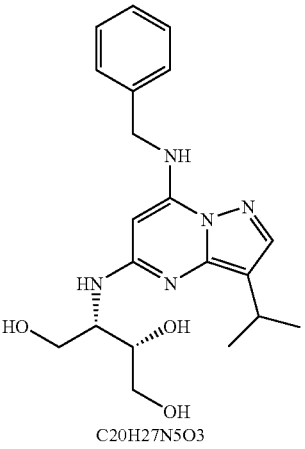 C20H27N5O3 | 0.3 μM | <2 μM | <2 μM |
| ICEC0319 (BS-195) | 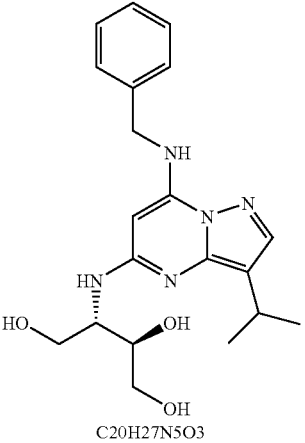 C20H27N5O3 | 0.5 μM | <2 μM | <2 μM |
| ICEC0048 (BS-182) | 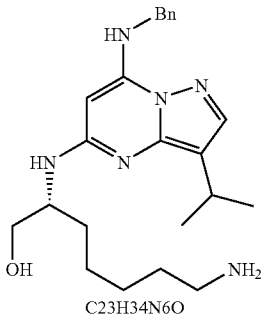 C23H34N6O | 17 μM | 32 μM | >100 μM |

TABLE 8-continued
Growth inhibition data for the MCF-7 cell line. Each IC50 data point is the mean of three experiments.
| Compound Name | Formula and Structure | LC50 (μm) | TGI (μm) | IC50 (μm) |
|---|---|---|---|---|
| ICEC0050 (BS-211) | 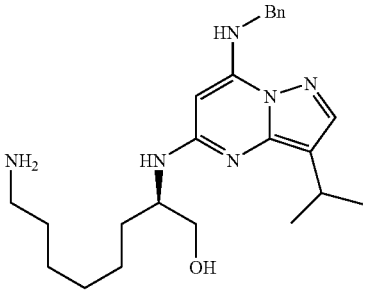<br>C24H36N6O | 21 μM | 56 μM | >100 μM |
| ICEC0052 (BS-217) | 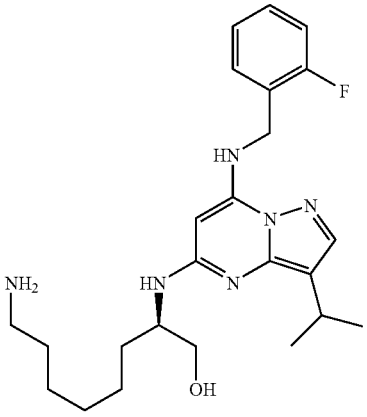<br>C24H35FN6O | 21 μM | 32 μM | 47 μM |
| ICEC0055 (BS-222) | 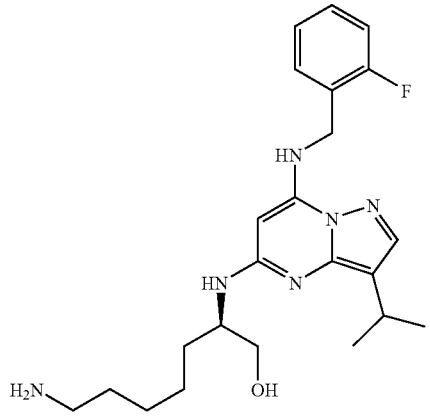<br>C23H33FN6O | 16 μM | 26 μM | 44 μM |

TABLE 8-continued
Growth inhibition data for the MCF-7 cell line. Each IC50 data point is the mean of three experiments.
| Compound Name | Formula and Structure | LC50 (μm) | TGI (μm) | IC50 (μm) |
|---|---|---|---|---|
| ICEC0141 (AS-481) | 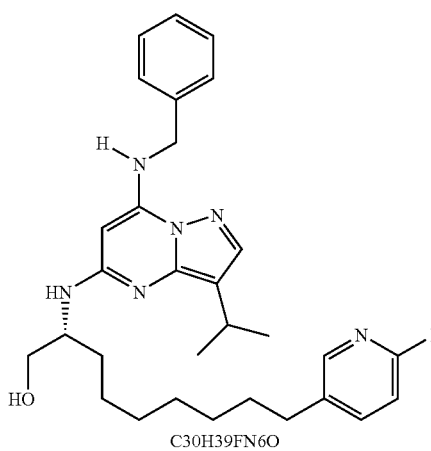 C30H39FN6O | 42 μM | >100 μM | >100 μM |
| ICEC0159 (AS-524) | 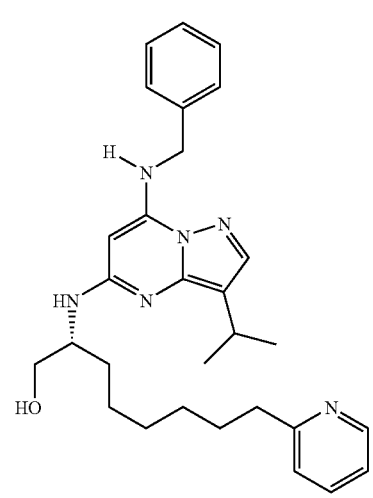 C29H38N6O | 87 μM | >100 μM | >100 μM |
| ICEC0161 (AS-528) | 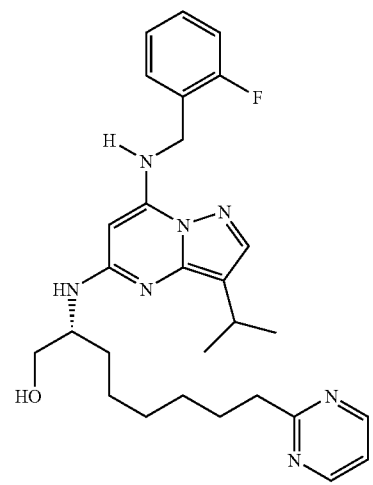 C28H36FN7O | 55 μM | >100 μM | >100 μM |

TABLE 8-continued
Growth inhibition data for the MCF-7 cell line. Each IC50 data point is the mean of three experiments.
| Compound Name | Formula and Structure | LC50 (μm) | TGI (μm) | IC50 (μm) |
|---|---|---|---|---|
| ICEC0167 (AS-540) | 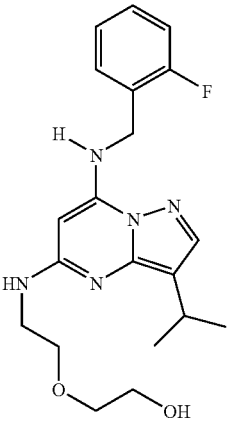<br>C20H26FN5O2 | 23 μM | 36 μM | >100 μM |
| ICEC0168 (AS-541) | 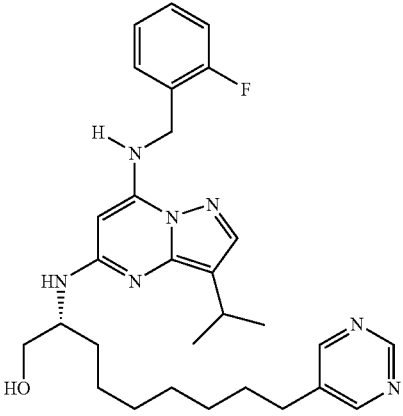<br>C29H38FN7O | 25 μM | 55 μM | >100 μM |
| ICEC0179 (JAB-012) | 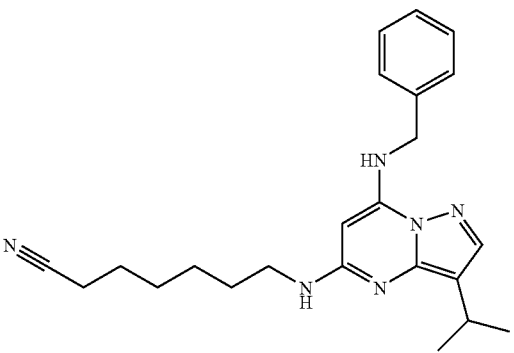<br>C23H30N6 | 16 μM | 26 μM | 44 μM |

TABLE 8-continued
Growth inhibition data for the MCF-7 cell line. Each IC50 data point is the mean of three experiments.
| Compound Name | Formula and Structure | LC50 (μm) | TGI (μm) | IC50 (μm) |
|---|---|---|---|---|
| ICEC-0174 (AS-552) | 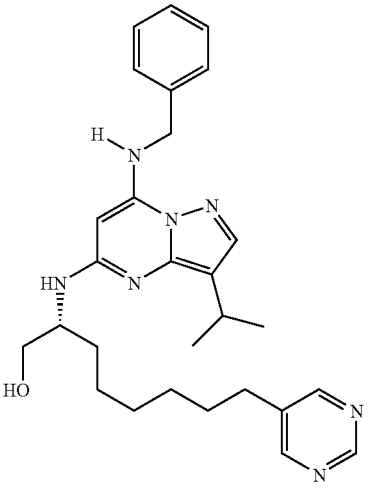 C28H37N7O | 35 μM | >100 μM | >100 μM |
| ICEC-0325 (AS-570) | 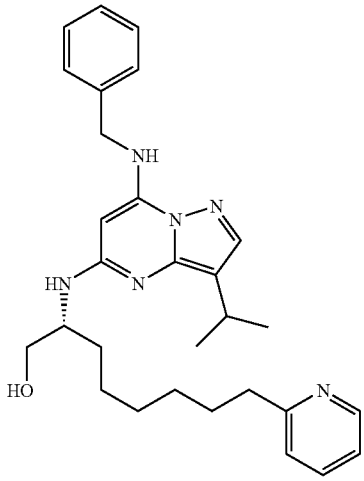 C29H38N6O | 17 μM | 32 μM | >100 μM |
| ICEC-0326 (AS-576) | 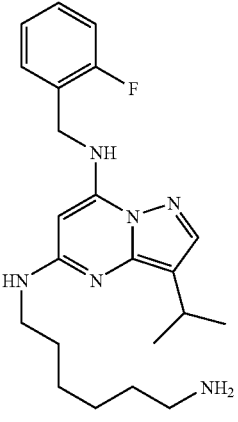 C22H31FN6 | 92 μM | >100 μM | >100 μM |

TABLE 8-continued
Growth inhibition data for the MCF-7 cell line. Each IC50 data point is the mean of three experiments.
| Compound Name | Formula and Structure | LC50 (μm) | TGI (μm) | IC50 (μm) |
|---|---|---|---|---|
| ICEC-0327 (AS-585) | 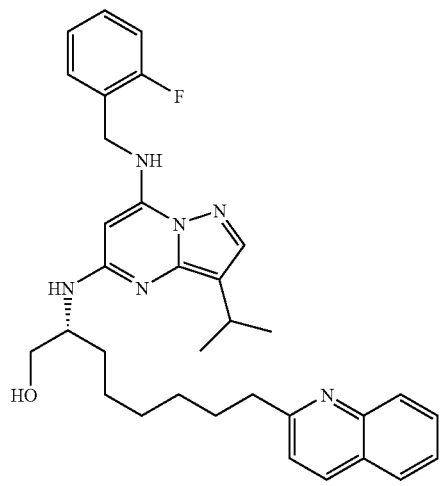 C33H39FN6O | 29 μM | 36 μM | 47 μM |
| ICEC-0186 | 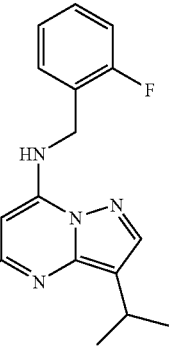 C23H29FN6 | 20 μM | 50 μM | >100 μM |
| ICEC-0187 | 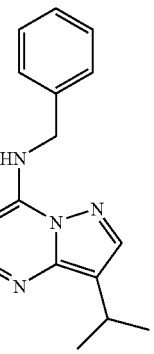 C23H33N7 | 23 μM | >100 μM | >100 μM |
| ICEC0192 | 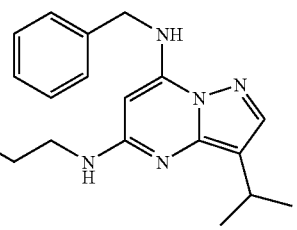 C23H34N6 | 28 μM | >100 μM | >100 μM |

160
TABLE 8-continued
Growth inhibition data for the MCF-7 cell line. Each IC50 data point is the mean of three experiments.
| Compound Name | Formula and Structure | LC50 (μm) | TGI (μm) | IC50 (μm) |
|---|---|---|---|---|
| ICEC0193 | 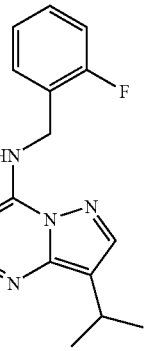 C23H33FN6 | >200 μM | >200 μM | >200 μM |
| ICEC0200 | 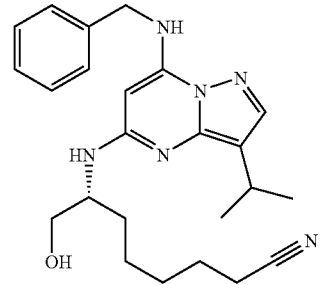 C24H32N6O | 87 μM | 167 μM | >200 μM |
| ICEC0201 | 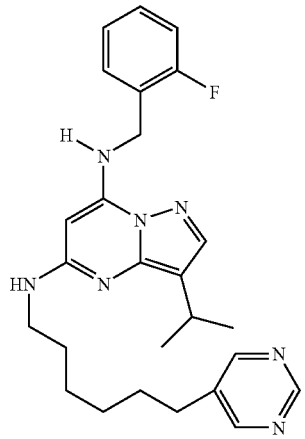 C26H32FN7 | >200 μM | >200 μM | >200 μM |

TABLE 8-continued
Growth inhibition data for the MCF-7 cell line. Each IC50 data point is the mean of three experiments.
| Compound Name | Formula and Structure | LC50 (µm) | TGI (µm) | IC50 (µm) |
|---|---|---|---|---|
| ICEC0202 | 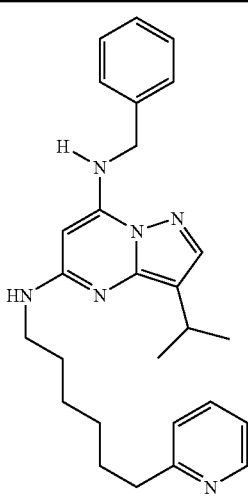 C27H34N6 | 70 µM | >200 µM | >200 µM |
| ICEC0203 | 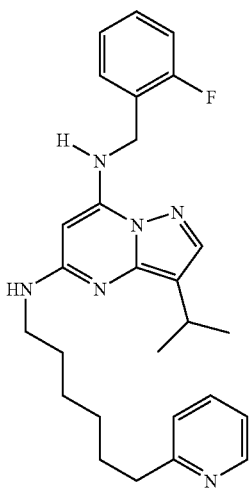 C27H33FN6 | 37 µM | 165 µM | >200 µM |
| ICEC0204 | 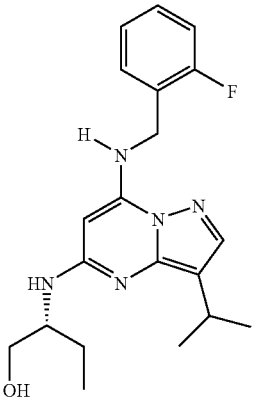 C20H26FN5O | 57 µM | 70 µM | >200 µM |

TABLE 8-continued
Growth inhibition data for the MCF-7 cell line. Each IC50 data point is the mean of three experiments.
| Compound Name | Formula and Structure | LC50 (μm) | TGI (μm) | IC50 (μm) |
|---|---|---|---|---|
| ICEC0205 | 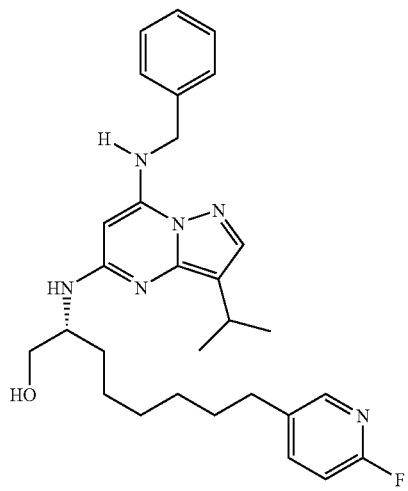<br>C29H37FN6O | 22 μM | 142 μM | >200 μM |
| ICEC0206 | 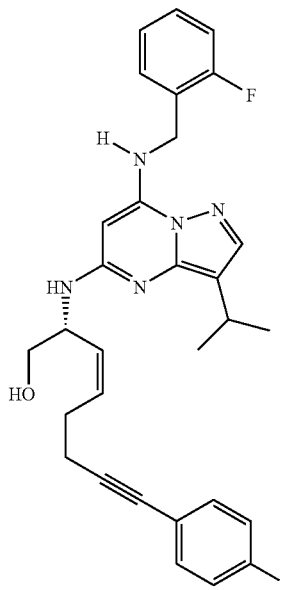<br>C30H31F2N5O | 174 μM | >200 μM | >200 μM |

TABLE 8-continued
Growth inhibition data for the MCF-7 cell line. Each IC50 data point is the mean of three experiments.
| Compound Name | Formula and Structure | LC50 (μm) | TGI (μm) | IC50 (μm) |
|---|---|---|---|---|
| ICEC0207 | 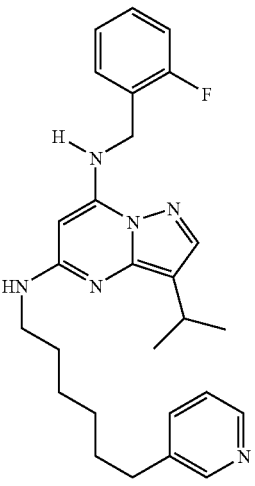<br>C27H33FN6 | 53 μM | 111 μM | >200 μM |
| ICEC0211 | 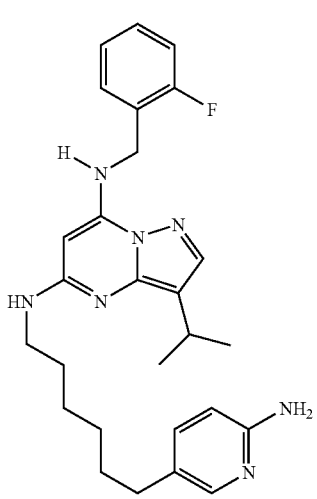<br>C27H34FN7 | 39 μM | 79 μM | >200 μM |
| ICEC0212 | 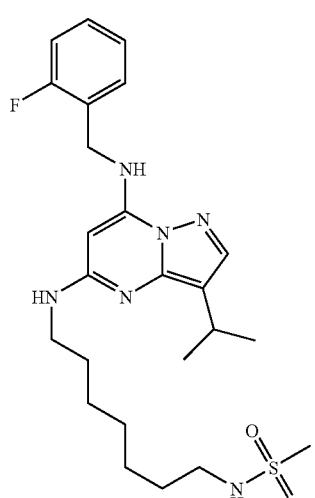<br>C24H35FN6O2S | 41 μM | 71 μM | 192 μM |

TABLE 8-continued

Growth inhibition data for the MCF-7 cell line. Each IC50 data point is the mean of three experiments.

| Compound Name | Formula and Structure | LC50 (μm) | TGI (μm) | IC50 (μm) |
|---|---|---|---|---|
| ICEC0213 | C24H34FN6 | 31 μM | 119 μM | >200 μM |
| ICEC0214 | C24H33FN6 | 140 μM | >200 μM | >200 μM |
| ICEC0216 | C22H31N7 | 26 μM | 42 μM | >200 μM |

TABLE 8-continued
Growth inhibition data for the MCF-7 cell line. Each IC50 data point is the mean of three experiments.
| Compound Name | Formula and Structure | LC50 (μm) | TGI (μm) | IC50 (μm) |
|---|---|---|---|---|
| ICEC0222 | 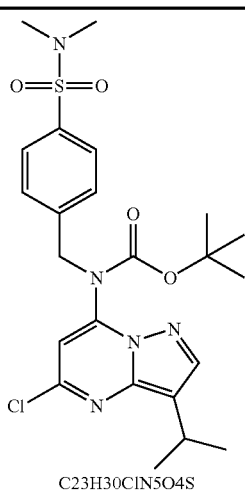 C23H30ClN5O4S | 16 μM | 31 μM | 51 μM |
| ICEC0229 | 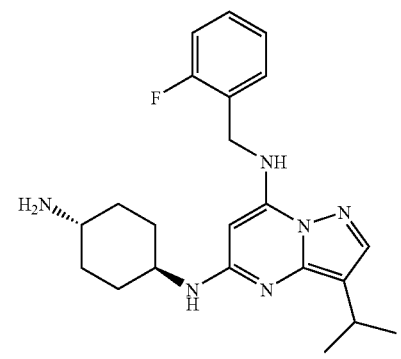 C22H29FN6 | 27 μM | 42 μM | 109 μM |
| ICEC0232 | 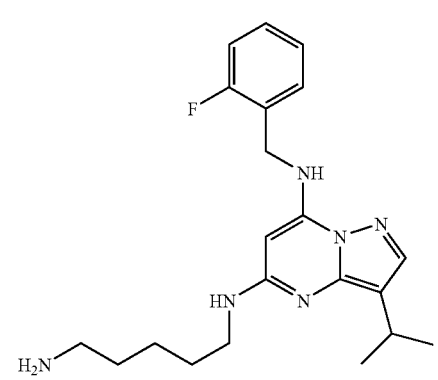 C21H29FN6 | 16 μM | 31 μM | >200 μM |
| ICEC0235 | 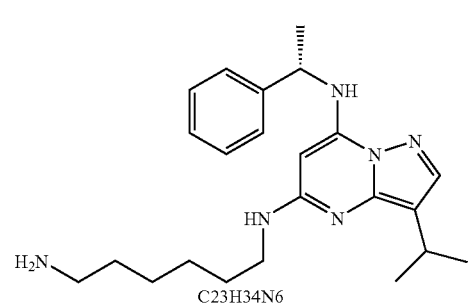 C23H34N6 | 43 μM | 67 μM | 95 μM |

TABLE 8-continued
Growth inhibition data for the MCF-7 cell line. Each IC50 data point is the mean of three experiments.
| Compound Name | Formula and Structure | LC50 (μm) | TGI (μm) | IC50 (μm) |
|---|---|---|---|---|
| ICEC0236 | 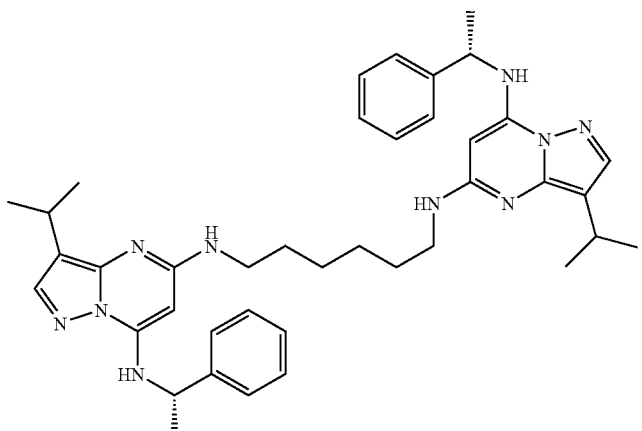 C40H52N10 | 11 μM | 28 μM | 46 μM |
| ICEC0238 | 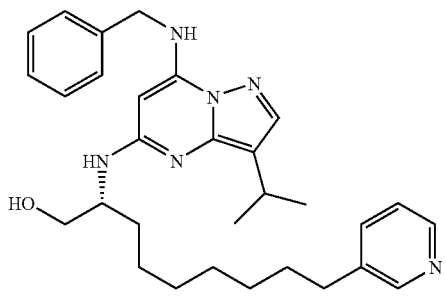 C30H40N6O | 11 μM | 28 μM | 46 μM |
| ICEC0006 | 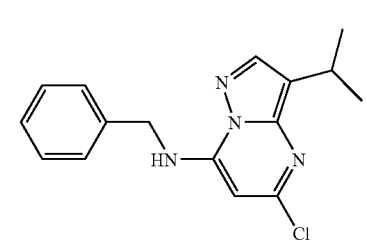 C16H17ClN4 | 139 μM | >200 μM | >200 μM |
| ICEC0239 | 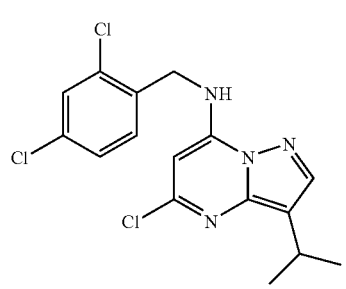 C16H15Cl3N4 | 59 μM | 200 μM | >200 μM |

TABLE 8-continued
Growth inhibition data for the MCF-7 cell line. Each IC50 data point is the mean of three experiments.
| Compound Name | Formula and Structure | LC50 (μm) | TGI (μm) | IC50 (μm) |
|---|---|---|---|---|
| ICEC0240 | 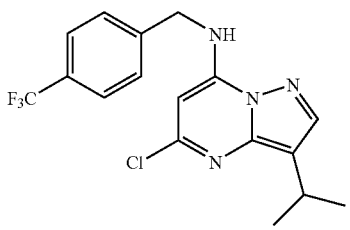 C17H16ClF3N4 | 48 μM | 97 μM | >200 μM |
| ICEC0241 | 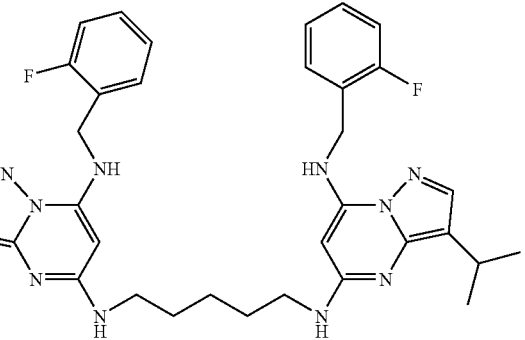 C37H44F2N10 | 75 μM | >200 μM | >200 μM |
| ICEC0244 | 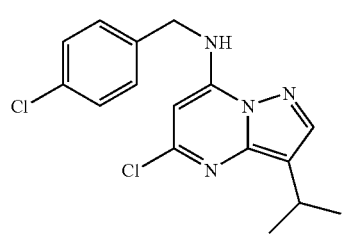 C16H16Cl2N4 | 59 μM | 117 μM | >200 μM |
| ICEC0245 | 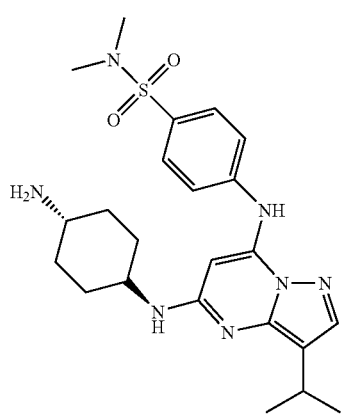 C23H33N7O2S | 172 μM | >200 μM | >200 μM |

TABLE 8-continued
Growth inhibition data for the MCF-7 cell line. Each IC50 data point is the mean of three experiments.
| Compound Name | Formula and Structure | LC50 (μm) | TGI (μm) | IC50 (μm) |
|---|---|---|---|---|
| ICEC0259 | 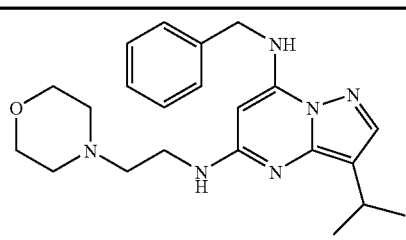 C22H30N6O | 41 μM | 79 μM | >200 μM |
| ICEC0274 | 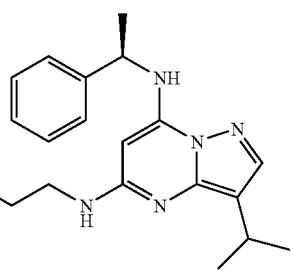 C23H34N6 | 8 μM | 23 μM | 200 μM |
| ICEC0277 | 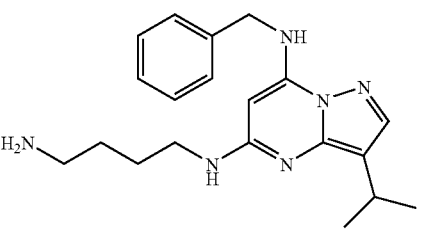 C20H28N6 | 40 μM | ND | ND |
| ICEC0278 | 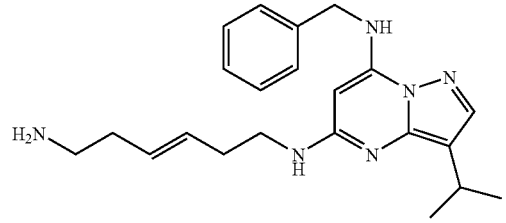 | 45 μM | ND | ND |

TABLE 8-continued
Growth inhibition data for the MCF-7 cell line. Each IC50 data point is the mean of three experiments.
| Compound Name | Formula and Structure | LC50 (μm) | TGI (μm) | IC50 (μm) |
|---|---|---|---|---|
| ICEC0289 | C22H30N6 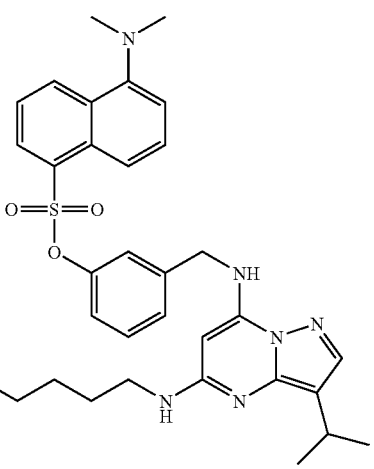 C33H41N7O3S | 19 μM | ND | ND |
| ICEC0291 | 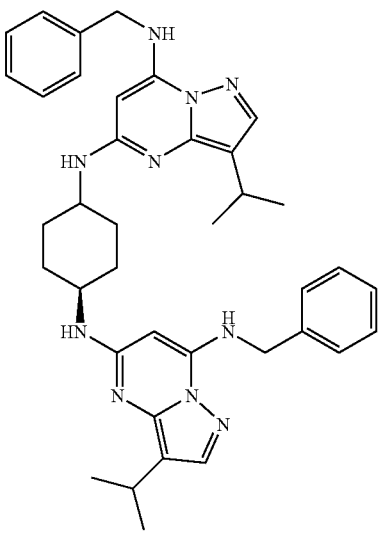 | 20 μM | ND | ND |
| ICEC0295 | 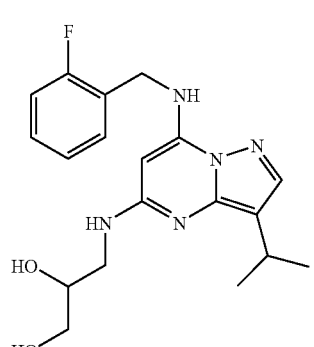 | 15 μM | ND | ND |

Example 22

Synthesis of BS-194 and Analogs

As shown by the data above, BS-194 shows promise as a compound for specifically inhibiting more than one cyclin-dependent kinase (particularly CDK 5 and CDK 9). The following experimental protocols and equipment were used for the preparation of BS-194, BS-195 and corresponding analogs shown in Table 9.

TABLE 9

Analogs of BS-194

| Compound Reference Name | Structure |
|---|---|
| ICEC0302 | 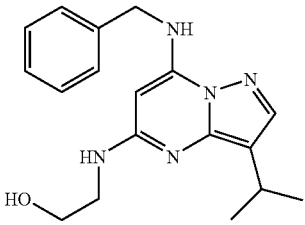 |
| ICEC0305 | 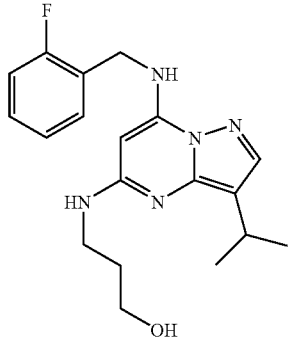 |
| ICEC0314 | 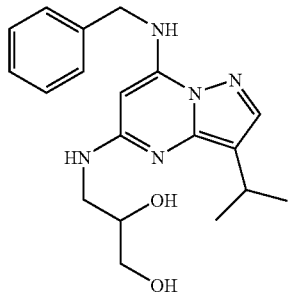 |
| ICEC0315 | 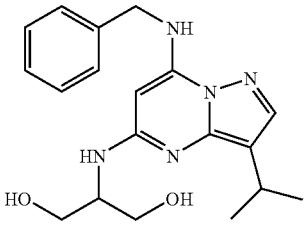 |
| ICEC0317 | 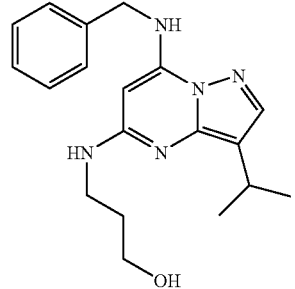 |
| ICEC0323 | 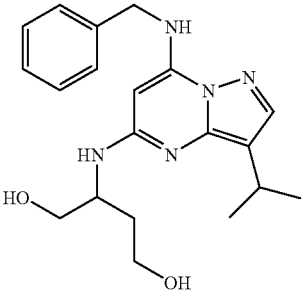 |
| ICEC0324 | 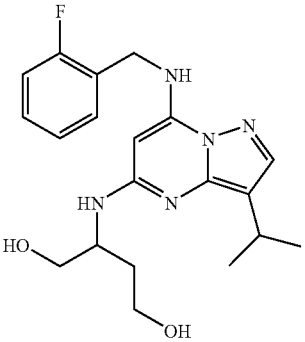 |
| ICEC0329 | 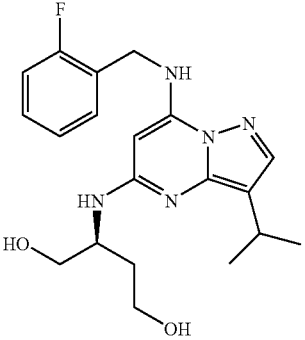 |

TABLE 9-continued

Analogs of BS-194

| Compound Reference Name | Structure |
|---|---|
| ICEC0331 | 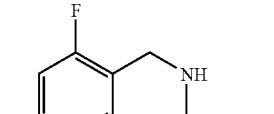 |

Melting points were obtained on a Reichert-Thermovar melting point apparatus and are uncorrected. Optical rotations were recorded at 25° C. on a Perkin-Elmer 241 polarimeter with a path length of 1 dm, using the 589.3 nm D-line of sodium. Concentrations (c) are quoted in g/100 mL. For bulb-to-bulb distillation a Büchi B-580 Kugelrohr was used. Boiling points (bp.) correspond to the uncorrected recorded air bath temperatures Infrared spectra were recorded on a Unicam FTIR spectrometer with automated background subtraction. Samples were prepared as thin films on sodium chloride plates. Reported absorptions are strong or medium strength unless stated otherwise and given in wavenumbers ($cm^{-1}$). $^1$H NMR spectra were recorded on a Bruker DRX-400 spectrometer operating at 400 MHz. $^{13}$C NMR spectra were recorded on a Bruker DRX-400 spectrometer operating at 100 MHz. Chemical shifts (δ) are quoted in parts per million (ppm) and are referenced to a residual solvent peak. CDCl$_3$ ($\delta_H$: 7.25, $\delta_C$: 77.0), C$_6$D$_6$ ($\delta_H$: 7.15, $\delta_{C:\ 128.0}$), DMSO-d$_6$ ($\delta_H$: 2.50, $\delta_C$: 39.4). Coupling constants (J) are quoted in Hertz (Hz) to the nearest 0.5 Hz. Spectra recorded at 400 ($^1$H NMR) and 100 ($^{13}$C NMR) were carried out by the Imperial College London Department of Chemistry NMR Service. Low and high resolution mass spectrometry (EI, CI, FAB) were recorded by the Imperial College London Department of Chemistry Mass Spectrometry Service using a Micromass Platform II and Micromass AutoSpec-Q spectrometer. Elemental analyses were determined by the University of North London Analytical Service.

All manipulations of air or moisture sensitive materials were carried out in oven or flame dried glassware under an inert atmosphere of nitrogen or argon. Syringes, which were used to transfer reagents and solvents, were purged with nitrogen prior to use. Reaction solvents were distilled from CaH$_2$ (dichloromethane, toluene, triethylamine, pyridine, n-hexane), Na/Ph$_2$CO (tetrahydrofuran, diethyl ether) or obtained as dry or anhydrous from Aldrich Chemical Company (N,N-dimethylformamide, acetonitrile) or BDH (ethanol). Other solvents and all reagents were obtained from commercial suppliers (Fluka; Aldrich Chemical Company; Lancaster Chemicals) and were used as obtained if purity was >98%. All flash column chromatography was carried out on BDH silica gel 60, particle size 0.040-0.063 mm unless otherwise stated. Thin layer chromatography (TLC) was performed on pre-coated aluminium backed or glass backed plates (Merck Kieselgel 60 F$_{254}$), and visualised with ultraviolet light (254 nm) or potassium permanganate (KMnO$_4$), vanillin or phosphomolybdic acid (PMA) stains as deemed appropriate.

1) Synthesis of the Aromatic Core

The synthesis of the aromatic cores ICEC0012 (BS-96) and ICEC0013 (BS-107) was carried out in the same way as for the BS-181 Synthesis, Scheme1.1.

Scheme 1.1: Synthesis of the aromatic cores ICEC0012 and ICEC0013.

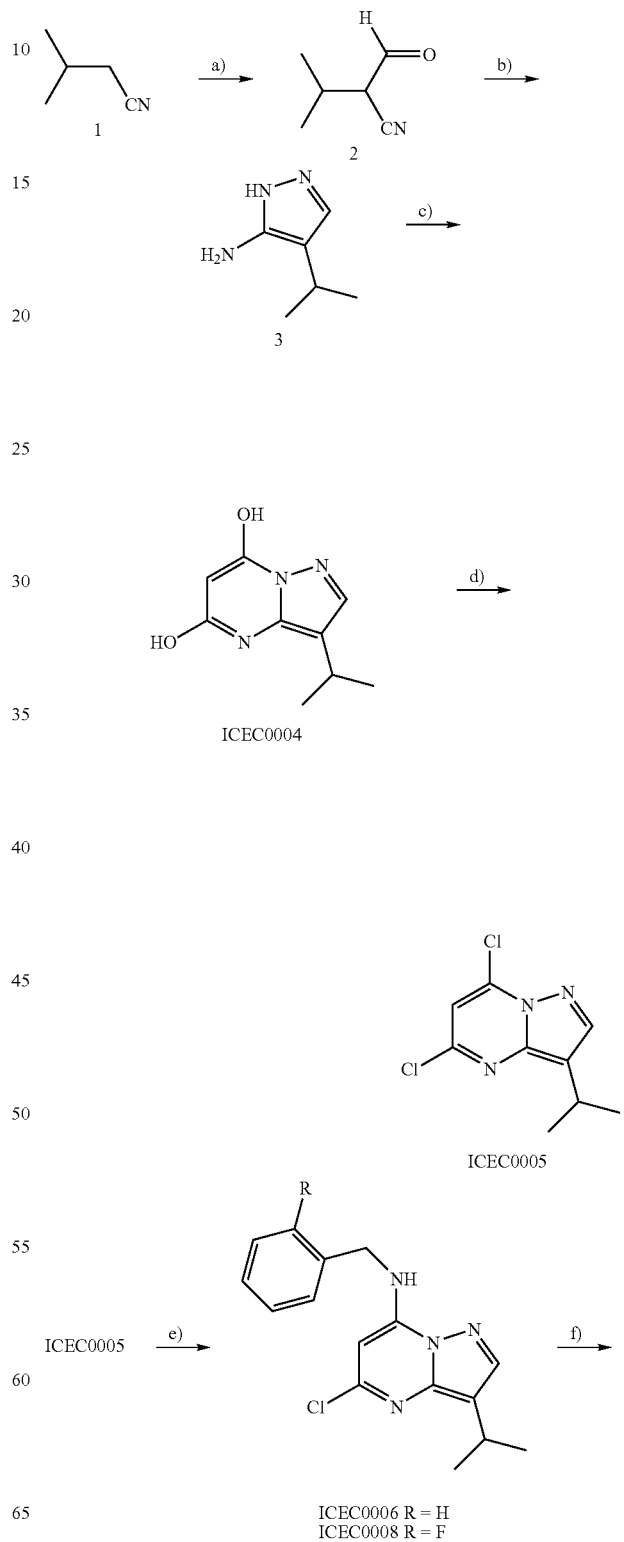

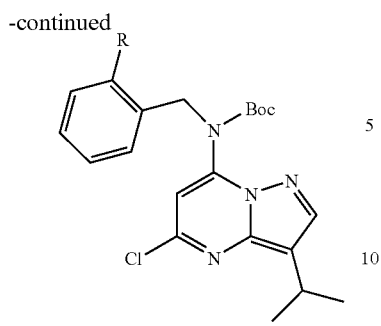

ICEC0012 R = H
ICEC0013 R = F a) HCO₂Et, LDA, -78° C. to rt, o/n, 75%;
b) N₂H₄•H₂O, EtOH, reflux, o/n, 64%;
c) Diethylmalonic ester, EtOH, NaOEt, reflux, o/n, 35% over three steps
d) POCl₃ reflux, o/n, 81%;
e) ICEC0006 R = H, BnNH₂, EtOH, reflux, o/n, 97%;
   ICEC0008 R = F, o-F BnNH₂, EtOH, reflux, o/n, 98%;
f) ICEC0012 R = H, Boc₂O, THF, DMAP$_{(cat)}$, rt, o/n, 96%;
   ICEC0013 R = F, Boc₂O, THF, DMAP$_{(cat)}$, rt, o/n, 99%;

3-Isopropyl-5,7-dihydroxypyrazolo[1,5-a]pyrimidine
(ICEC0004)

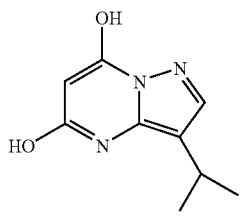

A solution of LDA (60.2 mL, 120 mmol, 2 M in THF) in THF (40 mL) was cooled to −78° C. Isovaleronitrile (1) (10 g, 120 mmol) was added and the solution stirred for 10 min at −78° C. The reaction mixture was added to a solution of ethyl formate (10.2 mL, 126 mmol) in THF (50 mL) at −78° C. The solution was stirred for 30 min at this temperature and then allowed to warm to rt and stirred for additional 16 h. 1 M Hydrochloric acid was added until the pH was approximately pH=3. The red organic phase was separated and the aqueous phase extracted with ethyl acetate (3×75 mL). The combined organic phases were dried over MgSO₄ and the solvent evaporated in vacuo. The resulting residue was purified by column chromatography on silica (diethyl ether:hexanes=1:2) to yield 2-formyl-3-methylbutanenitrile (2) as a yellow oil (9.97 g, 75%).

Next, 2-formyl-3-methylbutanenitrile 2 (9.97 g, 90 mmol), hydrazine hydrate (5.68 mL, 117 mmol) and glacial acetic acid (9.02 mL, 158 mmol) were dissolved in EtOH (250 mL) and the mixture was heated under reflux for 16 h. The reaction was then concentrated to approximately one third of the original volume. The residue was diluted with sat. NaHCO₃ (100 mL) and the product extracted with CH₂Cl₂ (3×100 mL). The combined organic fractions were washed with brine, dried over MgSO₄ and the solvent was removed in vacuum. Crude 4-isopropyl-1H-pyrazol-5-amine (3) was obtained as a yellow oil (7.17 g, 64%).

Sodium (1.58 g, 68.7 mmol) was dissolved in EtOH (250 mL) and to this solution was added 4-isopropyl-1H-pyrazol-5-amine (3) (7.17 g, 57 mmol) and diethyl malonate (10.2 mL, 63 mmol). The solution was heated under reflux for 16 h, cooled to rt and concentrated in vacuo. The residue was dissolved in water (60 mL) and acidified to pH=3 with 2 M HCl and the formed precipitate collected by filtration. The title compound ICEC0004 was obtained as an off-white solid (8.10 g, 35% over three steps). M.p. 242-243° C. (ethanol).

5,7-Dichloro-3-isopropylpyrazolo[1,5-a]pyrimidine
(ICEC0005)

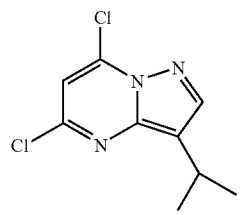

To a suspension of 3-Isopropyl-5,7-dihydroxypyrazolo[1,5-a]pyrimidine (ICEC0004) (3.95 g, 20.4 mmol) in POCl₃ (38.2 mL, 410 mmol) was added N,N-dimethylaniline (1.73 mL, 13.6 mmol) and the mixture was heated under reflux for 16 h. During this time the pyrimidine went into solution. The POCl₃ was distilled off and the concentrate poured onto ice (~50 g). The product was extracted with extracted with CH₂Cl₂ (3×50 mL) and the combined organic fractions were washed with brine and dried over Na₂SO₄. After concentration the crude product was purified by column chromatography on silica (ethyl acetate:hexanes=1:20) to yield the title compound ICEC0005 as a yellow solid (3.81 g, 81%).

M.p. 43-44° C. (ethyl acetate). ¹H NMR (CDCl₃, 300 MHz) δ 8.10 (s, 1H), 6.93 (s, 1H), 3.31 (hep, J=6.8 Hz, 1H), 1.37 (d, J=6.8 Hz, 6H). ¹³C NMR (CDCl₃, 75 MHz) δ 147.3, 144.6, 143.9, 139.4, 119.4, 107.9, 23.6, 23.2. IR (neat) $v_{max}$=2963, 1641, 1496, 1098, 618. MS m/z (CI) 230 (M+H). HRMS (CI) Calc.: 230.0252. Found: 230.0248 Microanalysis Calc: C, 46.98; H, 3.94; N, 18.26. Found: C, 47.02; H, 3.87; N, 18.28.

General Procedure for the Substitution of the Chloride in Position 7

A solution of 3-Isopropyl-5,7-dichloropyrazolo[1,5-a]pyrimidine ICEC0005 (2.17 mmol) and the amine (4.56 mmol) in EtOH (20 mL) was heated under reflux for 3 h. The reaction mixture was cooled to rt and concentrated in vacuo. The remaining residue was purified by flash chromatography on silica (methanol/ethyl acetate) to yield the desired products in analytically pure form.

N-Benzyl-5-chloro-3-isopropylpyrazolo[1,5-a]pyrimidin-7-amine (ICEC0006)

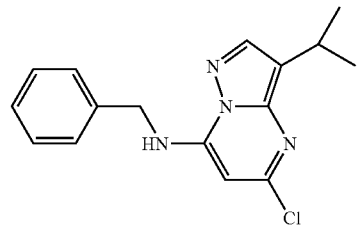

Following the general procedure above, the dichloride ICEC0005 (500 mg, 2.17 mmol) and benzyl amine (0.52 mL, 4.78 mmol) were reacted in EtOH (20 mL). The title compound ICEC006 was obtained as a white solid (630 mg, 97%).

M.p. 74-75° C. (CHCl$_3$). $^1$H NMR (CDCl$_3$, 300 MHz) δ 7.82 (m, 1H), 7.32 (m, 5H), 7.01 (m, 1H), 5.90 (m, 1H), 4.53 (m, 2H), 3.27 (hep, J=6.9 Hz, 1H), 1.32 (d, J=6.9 Hz, 6H). $^{13}$C NMR (CDCl$_3$, 75 MHz) δ 150.1, 146.8, 144.1, 141.5, 135.7, 129.0, 128.1, 127.1, 116.9, 84.6, 46.0, 23.4, 23.3. IR (neat) $v_{max}$=1617, 1583, 1455, 1168, 740. MS m/z (CI) 301 (M+H), 267, 177, 52. HRMS (CI) Calc.: 301.1220. Found: 301.1230. Microanalysis Calc: C, 63.89; H, 5.70; N, 18.63. Found: C, 63.95; H, 5.78; N, 18.59.

N-(2-fluorobenzyl)-5-chloro-3-isopropylpyrazolo[1,5-a]pyrimidin-7-amine (ICEC0008)

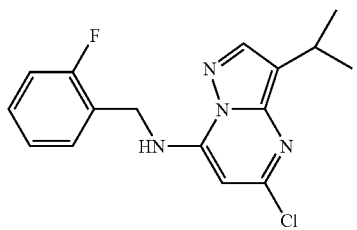

Following the general procedure above, the dichloride ICEC0005 (500 mg, 2.17 mmol) and 2-Fluorobenzyl amine (0.5 mL, 4.34 mmol) were reacted in EtOH (20 mL). The title compound ICEC0008 was obtained as a light yellow solid (681 mg, 98%).

M.p. 83-84° C. (CHCl$_3$). $^1$H NMR (CDCl$_3$, 300 MHz) δ 7.84 (s, 1H), 7.30 (m, 2H), 7.11 (m, 2H), 6.86 (m, 1H), 5.95 (s, 1H), 4.61 (m, 2H), 3.27 (hep, J=6.9 Hz, 1H), 1.32 (d, J=6.9 Hz, 6H). $^{13}$C NMR (CDCl$_3$, 75 MHz) δ 160.7 (J=247.5 Hz), 150.1, 146.7, 144.1, 141.6, 130.1 (J=8.3 Hz), 129.2, 129.1, 124.6 (J=3.2 Hz), 122.9 (J=14.2 Hz), 117.0, 115.8 (J=21.2 Hz), 84.5, 40.0, 23.5, 23.3. IR (neat) $v_{max}$=1616, 1601, 1491, 1458, 1225, 757. MS m/z (CI) 319 (M+H), 285, 211, 177, 124. HRMS (CI) Calc.: 319.1126. Found: 319.1123. Microanalysis Calc: C, 60.28; H, 5.06; N, 17.58. Found: C, 60.36; H, 4.94; N, 17.57.

tert-Butyl-benzyl-5-chloro-3-isopropylpyrazolo[1,5-a]pyrimidin-7-ylcarbamate (ICEC0012)

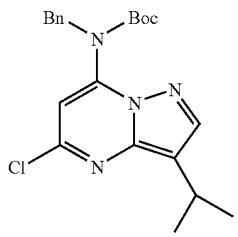

A flask was charged with the amine ICEC0006 (300 mg, 1 mmol), Boc$_2$O (284 mg, 1.3 mmol), DMAP (24 mg, 0.2 mmol) and THF (6 mL). The mixture was stirred for 1.5 h at rt. Ethyl acetate (10 mL) was added and the organic phase washed with water (3×20 mL), NaHCO$_3$ (20 mL) and dried over Na$_2$SO$_4$. The crude product was purified after concentration by column chromatography on silica (ethyl acetate: hexanes=1:20) to yield the product ICEC0012 as a pale yellow solid (385 mg, 96%).

M.p. 93-94° C. (ethyl acetate). $^1$H NMR (CDCl$_3$, 300 MHz) δ 8.03 (s, 1H), 7.25 (m, 5H), 6.49 (s, 1H), 5.04 (s, 2H), 3.31 (hep, J=6.8 Hz, 1H), 1.37 (d, J=6.8 Hz, 6H). $^{13}$C NMR (CDCl$_3$, 75 MHz) δ 152.6, 147.9, 144.9, 144.0, 142.5, 136.7, 128.5, 127.7, 127.6, 118.2, 106.1, 82.9, 51.3, 27.8, 23.5, 23.3. IR (neat) $v_{max}$=2967, 1727, 1612, 1518, 1454, 1154, 699. MS m/z (CI) 401 (M+H), 301, 179, 123, 52. HRMS (CI) Calc.: 401.1744. Found: 401.1747. Microanalysis Calc: C, 62.91; H, 6.29; N, 13.98. Found: C, 62.87; H, 6.19; N, 13.94.

tert-Butyl-2-fluorobenzyl-5-chloro-3-isopropylpyrazolo[1,5-a]pyrimidin-7-ylcarbamate (ICEC0013)

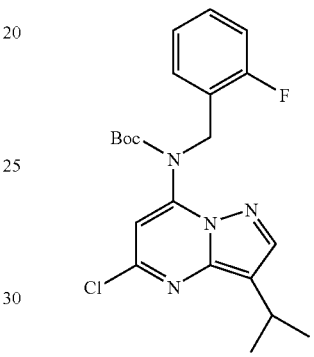

A flask was charged with the amine ICEC0008 (644 mg, 2.02 mmol), Boc$_2$O (573 g, 2.63 mmol), DMAP (49 mg, 0.40 mmol) and THF (12 mL). The mixture was stirred for 1.5 h at rt. Ethyl acetate (20 mL) was added and the organic phase washed with water (3×20 mL), NaHCO$_3$ (40 mL) and dried over Na$_2$SO$_4$. The crude product was purified after concentration by column chromatography on silica (ethyl acetate: hexanes=1:20) to yield the product ICEC0013 as a pale yellow solid (837 mg, 99%).

M.p. 120-121° C. (ethyl acetate). $^1$H NMR (CDCl$_3$, 300 MHz) δ 8.02 (s, 1H), 7.28, (m, 2H), 7.03 (m, 2H), 6.57 (s, 1H), 5.12 (s, 2H), 3.31 hep, J=6.8 Hz, 1H), 1.40 (s, 9H), 1.37 (d, J=6.8 Hz, 6H). $^{13}$C NMR (CDCl$_3$, 75 MHz) δ 162.3, 159.0, 152.5, 148.0, 145.0, 143.9, 142.5, 130.1, 130.1, 129.7, 129.6, 124.1, 124.1, 123.7, 123.5, 118.2, 115.5, 115.2, 106.2, 83.0, 45.4, 27.8, 23.5, 23.3. IR (neat) $v_{max}$=2967, 1728, 1613, 1456, 1155, 877, 758. MS m/z (CI) 419 (M+H), 363, 319, 303, 211, 126, 109. HRMS (CI) Calc.: 419.1650. Found: 419.1635. Microanalysis Calc: C, 60.21; H, 5.77; N, 13.37. Found: C, 60.37; H, 5.68; N, 13.30.

2) Synthesis of the BS-194 Side-Chain

The synthesis for the side-chain started at L-serine, in order to have the desired stereochemistry in place. The whole sequence is outlined in scheme 2.1.

Scheme 2.1: Synthesis of the BS-194 side-chain.

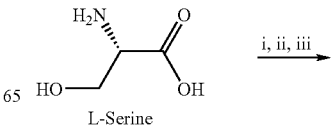

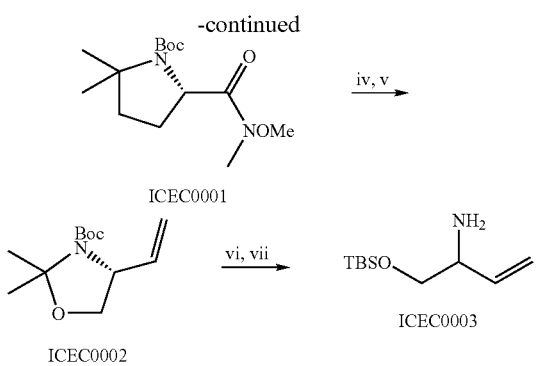

i: Boc₂O, NaOH, dioxane, water, 48 h, rt; ii: EDCI, HN(Me)OMe, CH₂Cl₂, 1.5 h, -15° C.; iii: DMP, BF₃·OEt₂, acetone, 1.5 h, RT; iv: LiAlH₄ (solution in THF), THF, 30 min, 0° C.; v: Ph₃P=CH₂, THF, 2 h, -78° C. → rt; vi: HCl, 30 min, RT; vii: TBSCl, Et₃N, DMAP, CH₂Cl₂, rt, 12 h;

(S)-3-(tert-Butoxycarbonyl)-N-methoxy-2,2,N-trimethyloxazolidine-4-carboxamide (ICEC0001)

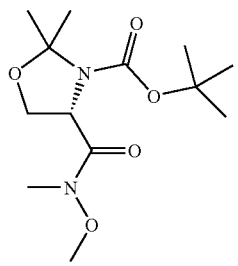

A solution of L-serine (20.56 g, 192 mmol) in 1 M NaOH (400 mL) and dioxane (200 mL) at 0° C., was treated with di-tert-butyl dicarbonate (50.29 g, 230 mmol) and the mixture was allowed to warm to rt and stirred for two days with readjustment to pH 9. The dioxane was removed in vacuo and the aqueous layer washed with diethyl ether (200 mL). Ethyl acetate (400 mL) was added to the aqueous mixture and 1 M H₂SO₄ added until pH 2-3 was reached. The organic phase was separated, the aqueous layer saturated with NaCl and extracted with ethyl acetate (4×200 mL). The combined organic layers were filtered, dried (MgSO₄) and the solvent was removed under vacuum, to give Boc-Serine as thick, colourless syrup, which was used without purification.

The crude boc-protected amino acid was dissolved in CH₂Cl₂ (600 mL), cooled to -15° C., followed by addition of N,O-dimethylhydroxyamine hydrochloride (19.65 g, 201 mmol) and NMM (22.1 mL, 201 mmol). EDCI (38.57 g, 201 mmol) was added portion-wise as a solid over 30 min. The reaction was stirred for 30 min at this temperature and then ice cold 1 M HCl (120 mL) was added. The aqueous layer was extracted with CH₂Cl₂ (400 mL) and the combined organic phases were washed with sat. NaHCO₃. The aqueous layer was washed with CH₂Cl₂ (200 mL) and the combined organic phases were dried over MgSO₄ and the solvent evaporated to yield the N,O-dimethylhydroxamic acid (Weinreb-amide) as a white solid, which was used without purification.

The solid was dissolved in acetone (500 mL) and 2,2-dimethoxypropane (200 mL) and BF₃.OEt₂ (1.6 mL) were added until there was a permanent change in colour (colourless to dark yellow) and the reaction was stirred for 90 min. Et₃N (4 mL) was added to quench the reaction and the solvent was evaporated to give a solid which was purified by column chromatography on silica (ethyl acetate:hexanes=1:4). The product ICEC0001 was obtained as a white solid (48.20 g, 87% over three steps).

M.p. 63-64° C. (ethyl acetate). [α]$_D$ (c 2.36, CHCl₃)-36.1. ¹H NMR (CDCl₃, 300 MHz) δ 4.73 (m, 1H), 4.15 (m, 1H), 3.92 (m, 1H), 3.70 (m, 3H), 3.19 (s, 3H), 1.66 (m, 3H), 1.54-1.39 (m, 12H). ¹³C NMR (CDCl₃, 75 MHz) δ 171.2, 170.5, 152.1, 151.2, 94.9, 94.3, 80.5, 79.9, 66.1, 65.8, 61.1, 57.8, 57.6, 32.5, 32.4, 28.3, 25.6, 25.3, 24.6, 24.5.

(R)-tert-butyl 2,2-dimethyl-4-vinyloxazolidine-3-carboxylate (ICEC0002)

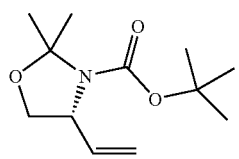

The hydroxamate ICEC0001 (1 g, 3.47 mmol) was dissolved in anhyd. THF (15 mL) and cooled to 0° C. 1.0 M LiAlH₄ in THF (0.87 mL, 1.73 mmol) was added drop-wise and the mixture was stirred for 30 min. The reaction was then cooled further to -15° C. and sat. aq. KHSO₄ (10 mL) was added carefully, the solution diluted with diethyl ether (25 mL) and stirred vigorously for 30 min. The organic layer was dried over MgSO₄, filtered and the solvent removed in vacuo to give the corresponding aldehyde as a pale yellow oil, which was directly used in the next step.

Methyltriphenylphosphonium bromide (2.17 g, 6.07 mmol) was suspended in THF (20 mL) at rt and 0.5 M KHMDS in toluene (11.66 mL, 5.83 mmol) was added. The resultant suspension was stirred at rt for 1 h, then cooled to -78° C. and a solution of the aldehyde in THF (10 mL) was added drop-wise. The cooling bath was removed and the mixture was stirred for further 2 h. The reaction was quenched with MeOH (3 mL) and the resulting mixture poured into a mixture of sat. potassium sodium tatrate and water (1:1, 50 mL). Extraction with diethyl ether (2×25 mL), drying (MgSO₄) and evaporation of the solvent in vacuo gave a colourless oil which was purified by column chromatography on silica (ethyl acetate:hexanes=1:9) to give the alkene ICEC0002 as a colourless oil (492 mg, 62%).

[α]$_D$ (c 0.54, CHCl₃) +11.1. ¹H NMR (CDCl₃, 300 MHz) δ 5.80 (m, 1H), 5.19 (m, 2H), 4.33 (m, 1H), 4.05 (m, 1H), 3.75 (m, 1H), 1.61-1.44 (m, 15H). ¹³C NMR (CDCl₃, 75 MHz) δ 162.3, 137.3, 136.7, 116.0, 115.8, 93.9, 68.0, 59.6, 28.4, 26.5, 23.6.

(2R)-2-Aminobut-3-enol Hydrochloride (ICEC0003)

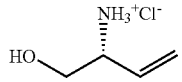

The alkene ICEC0002 (492 mg, 2.16 mmol) was dissolved in 6 M HCl (3 mL) and stirred at rt for 30 min and the solvent was evaporated under high vacuum to give a waxy white solid, ICEC0003 (260 mg, 97%).

M.p. 54-55° C. (MeOH). $[\alpha]_D$ (c 0.54, MeOH) −11.8. $^1$H NMR (CD$_3$OD, 300 MHz) δ 5.85 (m, 1H), 5.40 (m, 2H), 3.73 (m, 2H), 3.55 (m, 1H). $^{13}$C NMR (CD$_3$OD, 75 MHz) δ 132.3, 121.6, 62.9, 56.7. MS m/z (CI) 124 (M+H), 120, 106, 92, 73, 61.

(R)-1-(tert-Butyldimethylsilanyloxymethyl)-allylamine (ICEC0035)

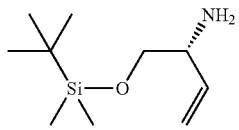

To a solution of the amino-alcohol ICEC0003 (2.0 g, 16.2 mmol) in CH$_2$Cl$_2$ (80 mL) was added Et$_3$N (5.0 mL, 35.6 mmol), DMAP (20 mg) and TBSCl (2.7 g, 17.8 mmol). The mixture was stirred over night at rt. Water (80 mL) was added and the mixture vigorously stirred for 10 min. The org. layer was separated, washed with water (60 mL), brine (60 mL) and dried over Na$_2$SO$_4$. The amine ICEC0035 was obtained after removal of the solvent analytically pure (3.27 g, 100%).

$[\alpha]_D$ (c 1.09, CH$_2$Cl$_2$): +22.8. $^1$H NMR (CDCl$_3$, 300 MHz) δ 5.80 (m, 1H), 5.14 (m, 2H), 3.60 (m, 1H), 3.42 (m, 2H), 1.61 (m, 2H), 0.89 (s, 9H), 0.05 (s, 6H). $^{13}$C NMR (CDCl$_3$, 75 MHz) δ 139.2, 115.1, 67.8, 55.8, 25.9, 18.3, −5.4. IR (neat) $v_{max}$=2954, 2930, 2887, 2857, 1471, 1254, 1095, 776. MS m/z (CI) 202 (M+H). HRMS (CI) Calc.: 202.1627. Found: 202.1622.

3) BS-194 Synthesis

The formation of BS-194 was carried out analogously to the BS-181 synthesis and is displayed in scheme 2.2:

Scheme 2.2: BS-194 and BS-195 Synthesis.

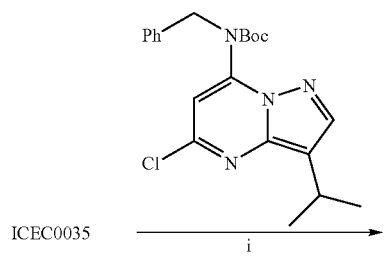

ICEC0035

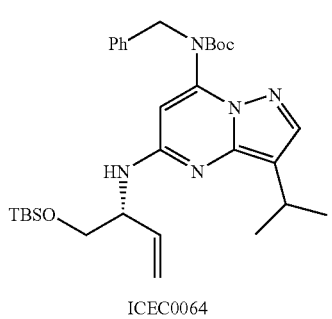

ICEC0064

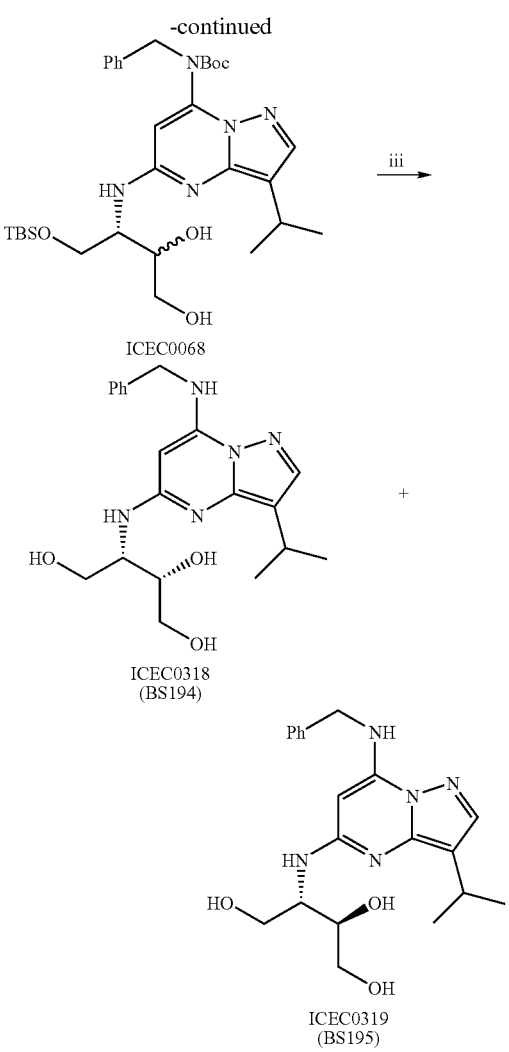

i: Pd$_2$dba$_3$, rac-BINAP, NaO$^t$Bu, toluene, 16 h, 100° C.; ii: OsO$_4$ (5-15 mol %), NMO, acetone: water 4:1, 16 h, rt, 75%; iii: MeOH/HCl 2-5M, 3 h, rt, 79% (BS-194), 67% (BS-195).

Benzyl-{5-[(R)-(tert-butyldimethylsilanyloxymethyl)-allylamino]-3-isopropyl-pyrazolo[1,5-a]pyrimidin-7-yl}-carbamic acid tert-butyl ester (ICEC064)

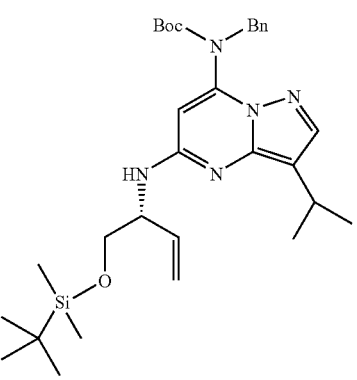

The heteroaryl chloride ICEC0012 (100 mg, 0.25 mmol), Pd$_2$dba$_3$ (12 mg, 5 mol %), rac-BINAP (24 mg, 15 mol %), and NaO$^t$Bu (36 mg, 0.38 mmol) were suspended in toluene (0.5 mL). After 5 min of stirring the amine ICEC0035 (60 mg, 0.30 mmol) was added and the red mixture heated for 12 h at 100° C. The reaction mixture was cooled to rt and poured into water (10 mL). The aqueous phase was extracted with ethyl acetate (3×10 mL) and the combined organic phases were dried over Na$_2$SO$_4$. After concentration the crude product was purified by column chromatography on silica (ethyl acetate:hexanes=10:1) to yield the product ICEC0064 as a yellow syrup (72 mg, 51%).

[α]$_D$ (c 0.59, CH$_2$Cl$_2$): +16.3. $^1$H NMR (CDCl$_3$, 300 MHz) δ 7.75 (s, 1H), 7.27 (m, 5H), 5.85 (m, 1H), 5.71 (s, 1H), 5.19 (m, 2H), 4.95 (m, 3H), 4.54 (m, 1H), 3.75 (m, 2H), 3.08 (m, 1H), 1.40-1.31 (m, 15H), 0.88 (s, 9H), 0.05 (s, 6H). $^{13}$C NMR (CDCl$_3$, 75 MHz) δ 154.0, 153.5, 146.1, 142.8, 141.5, 137.7, 136.4, 128.4, 127.9, 127.4, 116.2, 113.3, 97.2, 82.0, 65.0, 54.6, 51.3, 28.0, 25.9, 23.8, 23.1, 18.3, −5.4. IR (neat) ν$_{max}$=3370, 2956, 2929, 2858, 1722, 1642, 1581, 1516, 1368, 1158, 1107, 837, 777, 699. MS m/z (CI) 566 (M+H). HRMS (CI) Calc.: 566.3526. Found: 566.3538.

Bis-Hydroxylation and Global Deprotection

Method 1

Benzyl-{5-[(S)-(tert-butyldimethylsilanyloxymethyl)-2,3-dihydroxypropylamino]-3-isopropylpyrazolo[1,5-a]pyrimidin-7-yl}-carbamic acid tert-butyl ester (ICEC0068)

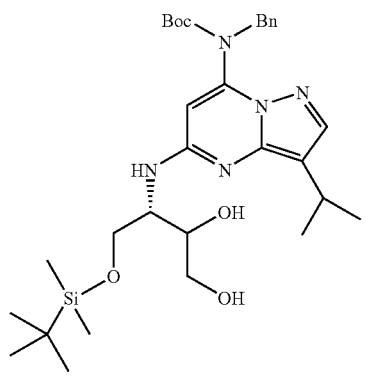

To a solution of the alkene ICEC0064 (30 mg, 0.053 mmol) and NMO.H$_2$O (14 mg, 0.11 mmol) in acetone/water (1.5 mL, 4:1) was added a solution of OsO$_4$ in $^t$BuOH (0.03 mL, 5 mol %, 2.5% w in $^t$BuOH) at rt. The solution was stirred for 14 h at ambient temperature and quenched by addition of a sat. solution of Na$_2$SO$_3$ (10 mL). The mixture was stirred for 45 min at rt and the aqueous phase was extracted with ethyl acetate (3×10 mL). The combined org. phases were dried over Na$_2$SO$_4$, concentrated and the crude product purified by column chromatography on silica (hexanes:ethyl acetate=4:1) to yield both diastereomers of ICEC0068 as white solids (each 10 mg, 31%, 62% combined yield).

Diastereomer 1:

[α]$_D$ (c 0.50, CH$_2$Cl$_2$): −3.2. $^1$H NMR (CDCl$_3$, 300 MHz) δ 7.78 (s, 1H), 7.26 (m, 5H), 5.71 (s, 1H), 5.22 (m, 1H), 4.96 (m, 3H), 4.15 (m, 1H), 3.89 (m, 1H), 3.75 (m, 1H), 3.58 (m, 3H), 3.08 (m, 1H), 2.83 (m, 1H), 1.42-1.28 (m, 15H), 0.92 (s, 9H), 0.11 (s, 6H). $^{13}$C NMR (CDCl$_3$, 75 MHz) δ 154.8, 153.4, 141.7, 137.6, 128.5, 127.9, 127.6, 113.8, 97.4, 83.8, 82.5, 70.4, 62.5, 61.8, 53.5, 51.7, 28.0, 25.9, 23.6, 23.5, 23.2, −5.4. IR (neat) ν$_{max}$=3363, 2955, 2929, 2857, 1721, 1644, 1518, 1368, 1157, 836, 778. MS m/z (CI) 600 (M+H). HRMS (CI) Calc.: 600.3581. Found: 600.3578.

Diastereomer 2:

[α]$_D$ (c 0.50, CH$_2$Cl$_2$): −28.4. $^1$H NMR (CDCl$_3$, 300 MHz) δ 7.77 (s, 1H), 7.28 (m, 5H), 5.73 (s, 1H), 5.10 (m, 1H), 4.95 (m, 2H), 4.31 (m, 2H), 4.13 (m, 1H), 4.00 (m, 2H), 3.58 (m, 2H), 3.36 (m, 1H), 3.07 (m, 1H), 1.41-1.26 (m, 15H), 0.90 (s, 9H), 0.08 (s, 6H). $^{13}$C NMR (CDCl$_3$, 75 MHz) δ 141.7, 137.6, 128.5, 127.9, 113.8, 97.4, 83.8, 74.1, 65.8, 62.6, 51.6, 28.0, 25.8, 23.6, −5.5. IR (neat) ν$_{max}$=3361, 2955, 2931, 2860, 1719, 1644, 1518, 1254, 1158, 836, 777. MS m/z (CI) 600 (M+H). HRMS (CI) Calc.: 600.3581. Found: 600.3574.

(3S)-3-(7-(Benzylamino)-3-isopropylpyrazolo[1,5-a]pyrimidin-5-ylamino)butane-1,2,4-triol (ICEC0318 and ICEC0319)

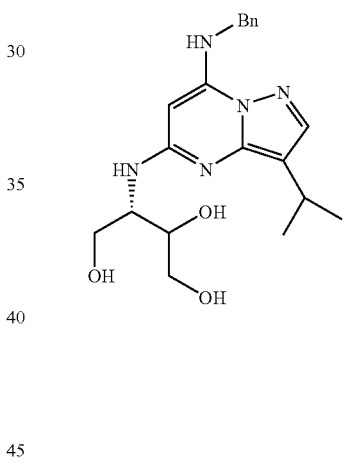

The enantiomeric carbamate ICEC0068 (each 9 mg, 0.015 mmol) was dissolved in MeOH/HCl (5 mL, 1.25M) and stirred at rt for 2 h. The solvent was evaporated and the residues dissolved in CH$_2$Cl$_2$ (10 mL) and washed with NaHCO$_3$ (10 mL). The organic phases were dried over Na$_2$SO$_4$ and the solvent removed in vacuo. The crude products were purified by column chromatography on silica (ethyl acetate) to yield white solids (each 4 mg, 69%).

Diastereomer 1, ICEC0318:

[α]$_D$ (c 0.20, CH$_3$OH): +38.0. $^1$H NMR (CD$_3$OD, 300 MHz) δ 7.66 (s, 1H), 7.34 (m, 5H), 5.29 (s, 1H), 4.54 (s, 2H), 4.03 (m, 1H), 3.83 (m, 2H), 3.57 (m, 3H), 3.04 (m, 1H), 1.28 (m, 7H). $^{13}$C NMR (CD$_3$OD, 75 MHz) δ 129.8, 128.5, 128.1, 85.1, 74.5, 74.3, 73.6, 64.5, 63.2, 55.9, 24.7, 24.0, 23.7. IR (neat) ν$_{max}$=3291, 1638, 1579, 1445, 1077.

Diastereomer, ICEC0319:

[α]$_D$ (c 0.20, CH$_3$OH): −53.0. $^1$H NMR (CD$_3$OD, 300 MHz) δ 7.66 (s, 1H), 7.34 (m, 5H), 5.32 (s, 1H), 4.54 (s, 2H), 4.17 (m, 1H), 3.89 (m, 1H), 3.75 (m, 2H), 3.50 (m, 1H), 3.36 (m, 1H), 3.01 (m, 1H), 1.28 (m, 8H). $^{13}$C NMR (CD$_3$OD, 75

MHz) δ 129.8, 128.5, 128.1, 63.5, 24.7, 24.0, 23.7. IR (neat) $v_{max}$=3305, 1638, 1579, 1443, 1069.

Method 2

Benzyl-{5-[(S)-(tert-butyldimethylsilanyloxymethyl)-2,3-dihydroxypropylamino]-3-isopropylpyrazolo[1,5-a]pyrimidin-7-yl}-carbamic acid tert-butyl ester (ICEC0068)

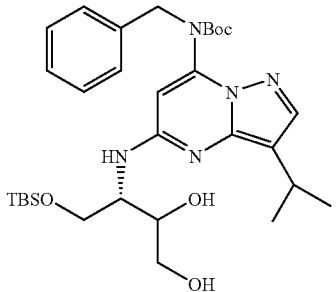

To a solution of the alkene ICEC064 (1.64 g, 2.9 mmol) and NMO.H$_2$O (0.71 g, 6.02 mmol) in acetone/water (60 mL, 4:1) was added a solution of OsO$_4$ in $^t$BuOH (1.00 mL, 5 mol %, 2.5% w in $^t$BuOH) at rt. The solution was stirred for 18 h at ambient temperature and quenched by addition of a sat. solution of Na$_2$SO$_3$ (10 mL). The mixture was stirred for 45 min at rt and the aqueous phase was extracted with ethyl acetate (3×100 mL). The combined org. phases were dried over Na$_2$SO$_4$, concentrated and the crude product purified by column chromatography on silica (hexanes:ethyl acetate=4:1) to yield both enantiomers ICEC0068 as white solids (each 590 mg, 34% (Diastereomer 1), 480 mg, 27% (Diastereomer 2)).

Diastereomer 1:

[α]$_D$ (c 0.50, CH$_2$Cl$_2$): −3.2. $^1$H NMR (CDCl$_3$, 300 MHz) δ 7.78 (s, 1H), 7.26 (m, 5H), 5.71 (s, 1H), 5.22 (m, 1H), 4.96 (m, 3H), 4.15 (m, 1H), 3.89 (m, 1H), 3.75 (m, 1H), 3.58 (m, 3H), 3.08 (m, 1H), 2.83 (m, 1H), 1.42-1.28 (m, 15H), 0.92 (s, 9H), 0.11 (s, 6H). $^{13}$C NMR (CDCl$_3$, 75 MHz) δ 154.8, 153.4, 141.7, 137.6, 128.5, 127.9, 127.6, 113.8, 97.4, 83.8, 82.5, 70.4, 62.5, 61.8, 53.5, 51.7, 28.0, 25.9, 23.6, 23.5, 23.2, −5.4. IR (neat) $v_{max}$=3363, 2955, 2929, 2857, 1721, 1644, 1518, 1368, 1157, 836, 778. MS m/z (CI) 600 (M+H). HRMS (CI) Calc.: 600.3581. Found: 600.3578.

Diastereomer 2:

[α]$_D$ (c 0.50, CH$_2$Cl$_2$): −28.4. $^1$H NMR (CDCl$_3$, 400 MHz) δ 7.77 (s, 1H), 7.28 (m, 5H), 5.73 (s, 1H), 5.10 (m, 1H), 4.95 (m, 2H), 4.31 (m, 2H), 4.13 (m, 1H), 4.00 (m, 2H), 3.58 (m, 2H), 3.36 (m, 1H), 3.07 (m, 1H), 1.41-1.26 (m, 15H), 0.90 (s, 9H), 0.08 (s, 6H). $^{13}$C NMR (CDCl$_3$, 75 MHz) δ 141.7, 137.6, 128.5, 127.9, 113.8, 97.4, 83.8, 74.1, 65.8, 62.6, 51.6, 28.0, 25.8, 23.6, −5.5. IR (neat) $v_{max}$=3361, 2955, 2931, 2860, 1719, 1644, 1518, 1254, 1158, 836, 777. MS m/z (CI) 600 (M+H). HRMS (CI) Calc.: 600.3581. Found: 600.3574.

(3S)-3-(7-(Benzylamino)-3-isopropylpyrazolo[1,5-a]pyrimidin-5-ylamino)butane-1,2,4-triol (ICEC 0318)

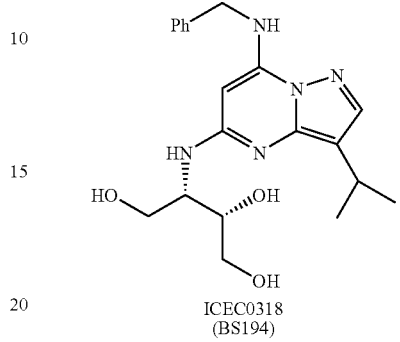

ICEC0318
(BS194)

The carbamate ICEC0068 (Diastereomer 1; 590 mg, 0.98 mmol) was dissolved in MeOH/HCl (20 mL, 1.5 M) and stirred at rt for 6 h. The solvent was evaporated and the residues dissolved in K$_2$CO$_{3aq}$ (10%, 10 mL) and washed with CH$_2$Cl$_2$ (3×30 mL) and EtOAc (3×30 mL). The organic phases were dried over Na$_2$SO$_4$ and the solvent removed in vacuo. The crude product was purified by column chromatography on silica (ethyl acetate) to yield ICEC0318 as white solid (178.8 mg, 69%).

[α]$_D$ (c 0.20, CH$_3$OH): +38.0. $^1$H NMR (CD$_3$OD, 300 MHz) δ 7.66 (s, 1H), 7.34 (m, 5H), 5.29 (s, 1H), 4.54 (s, 2H), 4.03 (m, 1H), 3.83 (m, 2H), 3.57 (m, 3H), 3.04 (m, 1H), 1.28 (m, 7H). $^{13}$C NMR (CD$_3$OD, 75 MHz) δ 129.8, 128.5, 128.1, 85.1, 74.5, 74.3, 73.6, 64.5, 63.2, 55.9, 24.7, 24.0, 23.7. IR (neat) $v_{max}$=3291, 1638, 1579, 1445, 1077. MS (CI): m/z 386 (M+H). HRMS (CI) Calc.: 386.2192. Found: 386.2181 (M+H).

(3S)-3-(7-(Benzylamino)-3-isopropylpyrazolo[1,5-a]pyrimidin-5-ylamino)butane-1,2,4-triol (ICEC0319)

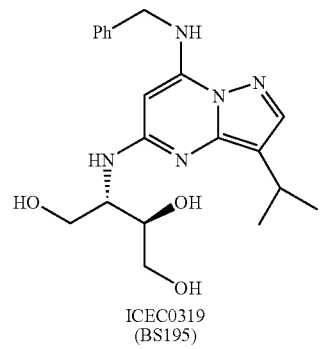

ICEC0319
(BS195)

The carbamates ICEC0068 (Diastereomer 1; 480 mg, 0.80 mmol) was dissolved in MeOH/HCl (20 mL, 1.5 M) and stirred at rt for 6 h. The solvent was evaporated and the residues dissolved in aqueous K$_2$CO$_3$ (10%, 10 mL) and washed with CH$_2$Cl$_2$ (3×30 mL) and EtOAc (3×30 mL). The organic phases were dried over Na$_2$SO$_4$ and the solvent removed in vacuo. The crude product was purified by column chromatography on silica (ethyl acetate) to yield ICEC0319 as white solid (178.8 mg, 69%).

[α]$_D$ (c 0.20, CH$_3$OH): −53.0 $^1$H NMR (CD$_3$OD, 300 MHz) δ 7.66 (s, 1H), 7.34 (m, 5H), 5.32 (s, 1H), 4.54 (s, 2H), 4.17 (m, 1H), 3.89 (m, 1H), 3.75 (m, 2H), 3.50 (m, 1H), 3.36 (m, 1H), 3.01 (m, 1H), 1.28 (m, 8H). $^{13}$C NMR (CD$_3$OD, 75 MHz) δ 129.8, 128.5, 128.1, 63.5, 24.7, 24.0, 23.7. IR (neat) ν$_{max}$=3305, 1638, 1579, 1443, 1069. MS (CI): m/z 386 (M+H); HRMS (CI) Calc.: 386.2192. Found: 386.2186 (M+H).

Method 3

Benzyl-{5-[(S)-(tert-butyldimethylsilanyloxymethyl)-2,3-dihydroxypropylamino]-3-isopropylpyrazolo[1,5-a]pyrimidin-7-yl}-carbamic acid tert-butyl ester (ICEC0068)

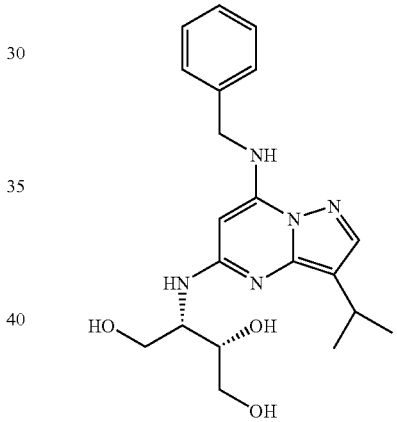

To a solution of the alkene ICEC0064 (2.27 g, 4.0 mmol) and NMO.H$_2$O (0.97 g, 8.3 mmol) in acetone/water (80 mL, 4:1) was added a solution of OsO$_4$ in $^t$BuOH (5.40 mL, 15 mol %, 2.5% w in $^t$BuOH) at rt. The solution was stirred for 16 h at ambient temperature and quenched by addition of a sat. solution of Na$_2$SO$_3$ (20 mL). The mixture was stirred for 45 min at rt and the aqueous phase was extracted with ethyl acetate (3×200 mL). The combined organic layers were dried over Na$_2$SO$_4$, concentrated and the crude product purified by column chromatography on silica (20:1=PE: EtOAc to 4:1=PE: EtOAc) to yield both diastereomers of ICEC0068 as white solids (1.0 g, 42% (Diastereomer 1), 0.8 mg, 33% (Diastereomer 2)).

Diastereomer 1 (protected ICEC0318):
$^1$H NMR (CDCl$_3$, 400 MHz) δ 7.80 (s, 1H), 7.36-7.27 (m, 5H), 5.72 (s, 1H), 5.24-5.22 (m, 1H), 4.98-4.94 (m, 3H), 4.18-4.11 (m, 1H), 3.95-3.90 (m, 1H), 3.79-3.76 (m, 1H), 3.64-3.57 (m, 3H), 3.10 (hept, J=6.9 Hz, 1H), 2.84-2.81 (m, 1H), 1.43 (s, 9H), 1.33 (d, J=6.9 Hz, 6H), 0.93 (s, 9H), 0.13-0.12 (m, 6H); $^{13}$C NMR (CDCl$_3$, 100 MHz) δ 154.8, 153.4, 141.7, 137.6, 128.5, 127.9, 127.6, 113.8, 97.4, 83.8, 82.5, 70.4, 62.5, 61.8, 53.5, 51.7, 28.0, 25.9, 23.6, 23.5, 23.2, −5.4. MS m/z (CI) 600 (M+H).

Diastereomer 2 (protected ICEC0319):
$^1$H NMR (CDCl$_3$, 400 MHz) δ 7.77 (s, 1H), 7.32-7.23 (m, 5H), 5.78 (s, 1H), 5.27-5.25 (m, 1H), 4.98-4.89 (m, 2H), 4.41-4.31 (m, 2H), 4.14-4.09 (m, 1H), 4.00-3.90 (m, 2H), 3.79-3.75 (m, 1H), 3.61-3.57 (m, 1H), 3.40-3.36 (m, 1H), 3.11-3.04 (m, 1H), 1.40 (s, 9H), 1.32-1.28 (m, 6H), 0.89 (s, 9H), 0.08-0.06 (m, 6H); $^{13}$C NMR (CDCl$_3$, 100 MHz) δ 154.8, 153.5, 141.7, 137.6, 128.5, 127.9, 127.6, 113.8, 97.4, 82.5, 70.4, 62.4, 61.8, 60.4, 53.5, 51.6, 28.0, 25.9, 23.6, −5.4; MS m/z (CI) 600 (M+H).

(3S)-3-(7-(Benzylamino)-3-isopropylpyrazolo[1,5-a]pyrimidin-5-ylamino)butane-1,2,4-triol (ICEC0318)

The carbamate ICEC0068 (Diastereomer 1; 992 mg, 1.67 mmol) was dissolved in MeOH/HCl (200 mL, 5 M) and stirred at rt for 3 h. The solvent was evaporated and the crude product was purified by column chromatography on silica (ethyl acetate) to yield a white solid ICEC0318 (310 mg, 79%).

[α]$^{25}_D$ (c (0.20, CH$_3$OH): −25.0, (Lit.+38.0); m.p. 182-184° C.; $^1$H NMR (CD$_3$OD, 400 MHz) δ 7.69 (s, 1H), 7.42-7.27 (m, 5H), 5.32 (s, 1H), 4.56 (s, 2H), 4.10-4.04 (m, 1H), 3.86-3.83 (m, 2H), 3.63-3.56 (m, 3H), 3.05 (hept, J=6.9 Hz, 1H), 1.30 (d, J=6.9 Hz, 6H); $^{13}$C NMR (CD$_3$OD, 100 MHz) δ 157.6, 146.9, 144.9, 144.6, 140.1, 137.7, 128.4, 127.1, 126.6, 112.1, 72.8, 70.2, 63.0, 61.7, 54.3, 45.1, 23.3, 22.6, 22.2; IR (neat) $v_{max}$=3295, 2956, 2931, 2869, 1639, 1581; MS (ESI): m/z 386 (M+H). HRMS (ESI) Calc.: ($C_{20}H_{27}N_5O_3$) 386.2192. Found: 386.2202.

The absolute configuration of ICEC0318 (BS194) was assigned by X-ray diffraction studies. The amine and the secondary alcohol are in syn geometry.

(3S)-3-(7-(Benzylamino)-3-isopropylpyrazolo[1,5-a]pyrimidin-5-ylamino)butane-1,2,4-triol (ICEC0319)

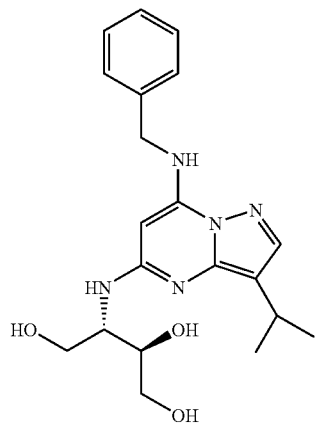

The carbamate ICEC0068 (Diastereomer 2; 757 mg, 1.3 mmol) was dissolved in MeOH/HCl (100 mL, 5 M) and stirred at rt for 3.5 h. The solvent was evaporated and the crude product was purified by column chromatography on silica (ethyl acetate) to yield a white solid ICEC0319 (338 mg, 67%).

$[\alpha]^{25}_D$ (c (0.20, $CH_3OH$): −60.0; m.p. 78-82° C.; $^1H$ NMR ($CD_3OD$, 400 MHz) δ 7.68 (s, 1H), 7.40-7.25 (m, 5H), 5.34 (s, 1H), 4.54 (s, 2H), 4.23-4.20 (m, 1H), 3.93-3.89 (m, 1H), 3.82-3.75 (m, 2H), 3.54-3.50 (m, 1H), 3.42-3.37 (m, 1H), 3.03 (hept, J=6.9 Hz, 1H), 1.30 (d, J=6.9 Hz, 6H); $^{13}C$ NMR ($CD_3OD$, 100 MHz) δ 158.0, 146.9, 144.5, 140.1, 137.7, 128.3, 127.1, 126.7, 112.0, 72.8, 70.8, 62.2, 62.0, 53.4, 45.1, 23.2, 22.6, 22.2; IR (neat) $v_{max}$=3307, 2954, 2931, 2867, 1637, 1579, 1444; MS (ESI): m/z 386 (M+H); HRMS (ESI) Calc.: 386.2192. Found: 386.2209.

4) Synthesis of Analogues

The activity of structurally related analogues of ICEC0318 (BS-194) was investigated. The structures of analogues of ICEC0318 (BS-194) is shown below.

BS-194 related analogues.

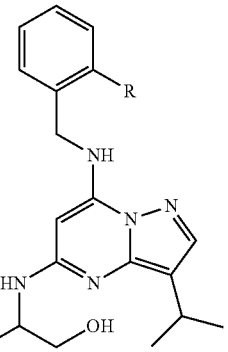

R = H: ICEC0315
R = F: ICEC0298

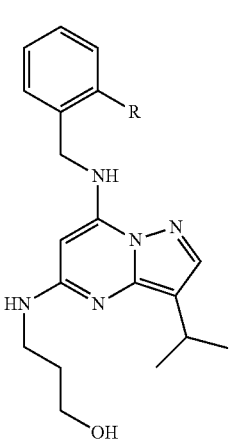

R = H: ICEC0317
R = F: ICEC0305

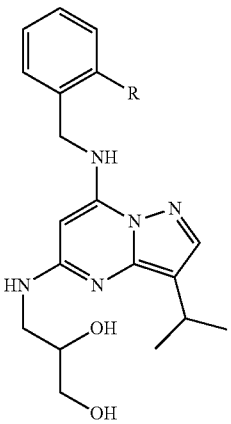

R = H: ICEC0314
R = F: ICEC0295

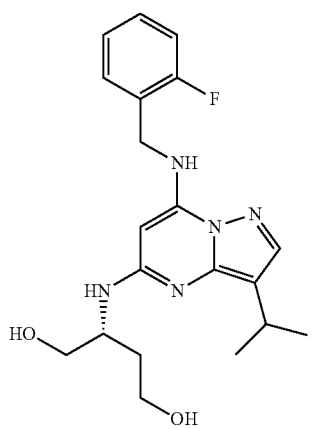

ICEC0331

-continued

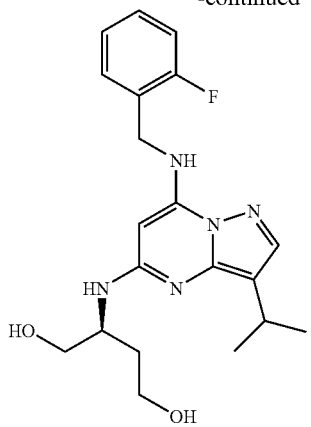

ICEC0329

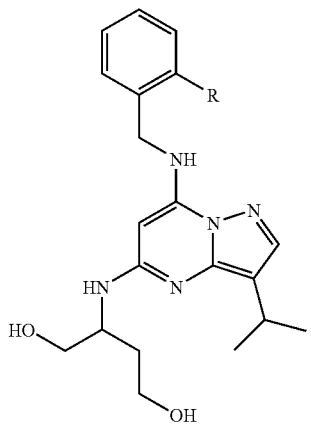

R = H: ICEC0323
R = H: ICEC0324

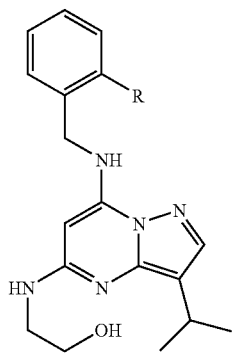

R = H: ICEC0302
R = F: ICEC0297

4.1) Synthesis of the Side-chains

Most of the required amino-alcohols for this small focus library were commercially available. The free alcohols were appropriately protected before the Pd-cross coupling reaction. TBS-protection of amino-ethanol, amino-propanol and 2-amino-propanediol was carried out by treatment of the amino-alcohol with TBSCl in DCM in the presence of NEt₃ and catalytic DMAP. 1-aminopropanediol was used as a racemate in its commercially available form where the diol is protected as an acetonide.

The only alcohol not commercially available was 2-aminobutane-1,4-diol. However it was available from the reduction of aspartic acid (L, D, DL-form) with LAH. TBS-protection was carried in DCM with TBSCl in the presence of NEt₃ and catalytic DMAP.

2-(tert-butyldimethylsilyloxy)ethanamine (ICEC0293)

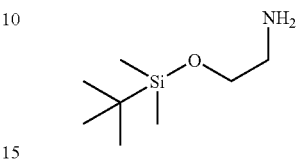

Ethanolamine (2.0 g, 32.7 mmol) was dissolved in CH$_2$Cl$_2$ (50 mL) and NEt$_3$ (5 mL). The mixture was treated with TBSCl (5.40 g, 36 mmol) and DMAP (50 mg). After 12 h water (20 mL) was added and the resulting mixture stirred for 30 min. The aqueous phase was washed with CH$_2$Cl$_2$ (3×50 mL). The crude product was purified by column chromatography on silica (EtOAc) to give ICEC0293 as colourless oil (5.13 g, 89%; Palomo et al., *Org. Lett.*, 2007, 9, 101-104).

$^1$H NMR (400 MHz, CDCl$_3$): $\delta_H$ 0.07 (m, 6H), 0.90 (s, 9H), 2.78 (t, J=7.4 Hz, 2H), 3.63 (t, J=7.4 Hz, 2H); $^{13}$C NMR (CDCl$_3$, 75 MHz) $\delta_C$ −5.3, 18.3, 25.9, 44.3, 65.3; MS (CI): m/z 176 (M+H); HRMS (CI) Calc.: 176.1471. Found: 176.1476 (M+H).

2,2,3,3,9,9,10,10-octamethyl-4,8-dioxa-3,9-disilaundecan-6-amine (ICEC0292)

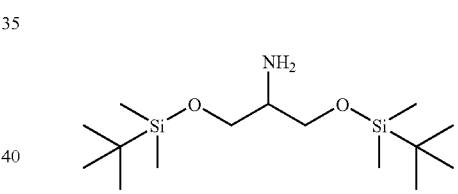

2-aminopropane-1,3-diol (2.0 g, 22.0 mmol) was dissolved in CH$_2$Cl$_2$ (50 mL) and NEt$_3$ (5 mL). The mixture was treated with TBSCl (7.20 g, 48 mmol) and DMAP (50 mg). After 12 h water (20 mL) was added and the resulting mixture stirred for 30 min. The aqueous phase was washed with CH$_2$Cl$_2$ (3×50 mL). The crude product was purified by column chromatography on silica (EtOAc) to give ICEC0292 as colourless oil (5.82 g, 82%).

$^1$H NMR (400 MHz, CDCl$_3$): $\delta_H$ 0.06 (m, 12H), 0.90 (s, 18H), 2.89-2.95 (m, 1H), 3.52-3.57 (m, 2H), 3.61-3.65 (m, 2H); $^{13}$C NMR (CDCl$_3$, 75 MHz) $\delta_C$ −5.4, 18.3, 25.9, 54.3, 64.7; MS (CI): m/z 320 (M+H). HRMS (CI) Calc.: 320.2441. Found: 320.2433.

4.3.6 3-(tert-butyldimethylsilyloxy)propan-1-amine (ICEC0312)

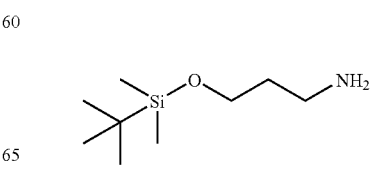

3-aminopropanol (0.3 mL, 10.0 mmol) was stirred in $CH_2Cl_2$ (20 mL). Imidazole (2.04 g, 30.0 mmol), DMAP (8.0 mg, 0.07 mmol) and TBSC1 (4.50 g, 30.0 mmol) were added and the reaction mixture was stirred at rt for 16 h. Brine (50 mL) was added and the organic phase was extracted with $CH_2Cl_2$ (3×50 mL) and dried over $Na_2SO_4$. The crude product was purified by column chromatography on silica (EtOAc) to give ICEC0312 as colourless oil (1.0 g, 50%; Dufour et al., *Synth. Comm.*, 1992, 22, 189-200).

$^1$H NMR (400 MHz, CDCl$_3$): $\delta_H$ 0.08 (m, 6H), 0.92 (s, 9H), 1.70 (q, 2H, J=3.4 Hz), 2.75 (br s 2H), 2.84 (t, 2H, J=3.4 Hz, 2H), 3.73 (t, 2H, J=3.4 Hz); $^{13}$C NMR (CDCl$_3$, 100 MHz) $\delta_C$ −5.4, 18.3, 25.9, 36.0, 39.4, 61.4; IR (neat) $v_{max}$=3432, 2948, 2929, 2856, 1646, 1575; MS (CI): m/z 190 (M+H); HRMS (CI) Calc.: 189.1549. Found: 190.1629 (M+H).

4.3.7 2-aminobutane-1,4-diol (ICEC0320)

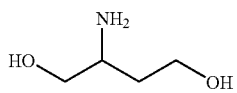

DL-aspartic acid (13.3 g, 100 mmol) was stirred in EtOH (200 mL) and cooled to −78° C. SOCl$_2$ (15 mL, 210 mmol) was added drop-wise and the reaction mixture was allowed to warm to rt and stirred for additional 16 h. The solvent was evaporated and the residue was re-dissolved in EtOAc (100 mL). The organic layer was washed with brine (100 mL) and the aqueous layer was extracted with EtOAc (3×50 mL). The solvent was evaporated to give 12.75 g, 67% of the corresponding diester, which was used without further purification (Lakanen et al., *J. Med. Chem.*, 1995, 38, 2714).

LAH (12.8 mL, 30.0 mmol, 2.4 M in THF) was cooled to 0° C. The diester (1.89 g, 10.0 mmol) was dissolved in THF (10 mL) and added drop-wise to the LAH-suspension. After the complete addition of the diester, the reaction mixture was heated to reflux for 30 min. Then it was cooled to 0° C. and iPrOH (13 mL) was added drop-wise, and water (3.4 mL) was added. The grey slurry was stirred for 15 min and the solvent was evaporated. The powdered residue was extracted using a soxleth in refluxing iPrOH (250 mL) for 16 h. The solvent was evaporated and the crude product was dried under high vacuum. ICEC0320 was received as a yellow oil (746 mg, 71%).

$^1$H NMR (400 MHz, d$_6$-DMSO): $\delta_H$ 1.19-128 (m, 1H), 1.46-1.55 (m, 1H), 2.68-2.74 (m, 1H), 3.10-3.15 (m, 1H), 3.23-3.27 (m, 1H), 3.30 (br s, 1H), 3.50 (t, 2H), 4.35 (d, 1H); $^{13}$C NMR (100 MHz, d$_6$-DMSO) $\delta_C$ 37.0, 51.5, 59.5, 67.6; IR (neat) $v_{max}$=3432, 2948, 2929, 2856, 1646, 1575; MS (ESI): m/z 106 (M+H), 146 (M+2H+K); HRMS (ESI) Calc.: ($C_4H_{11}NO_2$) 105.1356. Found: 106.0863.

(R)-perfluorophenyl 3,3,3-trifluoro-2-methoxy-2-phenylpropanoate (4)

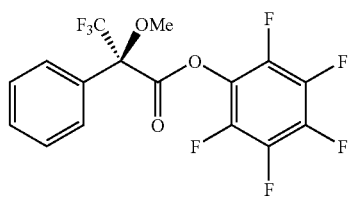

(R)-(+)-3,3,3-trifluoro-2-methoxy-2-phenylpropanoic acid (Mosher Acid) (936 mg, 3.9 mmol) and pentafluorophenol (1.10 g, 6.0 mmol) were stirred in anhydrous MeCN (6 mL) and cooled to 0° C. DCC (803 mg, 3.9 mmol) was added at one portion and the reaction mixture was stirred at 0° C. for 1 h and then allowed to warm to rt and stirred for additions 16 h. The suspension was filtered and washed with cold MeCN. The filtrated were evaporated and dried on high vacuum. The crude product was purified by column chromatography (20:1=PE: EtOAc) to yield 4 as a colourless oil (1.52 g, 97%; Campbell et al., *J. Org. Chem.*, 1995, 60, 4602).

$^1$H NMR (400 MHz, CDCl$_3$): $\delta$ 7.66-7.64 (m, 2H), 7.53-7.50 (m, 3H), 3.74 (s, 3H); $^{13}$C NMR (100 MHz, CDCl$_3$) $\delta$ 130.9, 130.3, 128.7, 127.1, 86.9, 56.1; $^{19}$F NMR (400 MHz, CDCl$_3$) $\delta$ −71.9 (CF$_3$), −151.44 (C$_{aro}$F), −155.9 (C$_{aro}$F), −161.2 (C$_{aro}$F); MS (EI): m/z 189 (M-C$_7$F$_5$O$^+$);

The TBS-protected aminodiol (ICEC0321, ICEC0328, ICEC0330) (17.0 mg, 0.05 mmol) was stirred with ester 4 (20.0 mg, 0.05 mmol) and DMAP (6.4 mg, 0.05 mg) in CDCl$_3$ (1 mL) for 16 h at rt. The resulting reaction mixture was analysed by $^{19}$F NMR to determine the enantiomeric excess by integration of the corresponding signals.

2,2,3,3,10,10,11,11-octamethyl-4,9-dioxa-3,10-disiladodecan-6-amine (ICEC0321)

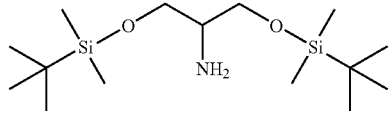

DL-aspartic acid (13.3 g, 100 mmol) was stirred in EtOH (200 mL) and cooled to −78° C. SOCl$_2$ (15 mL, 210 mmol) was added drop-wise and the reaction mixture was allowed to warm to rt and stirred for additional 16 h. The solvent was evaporated and the residue was re-dissolved in EtOAc (100 mL). The organic layer was washed with brine (100 mL) and the aqueous layer was extracted with DCM (3×50 mL). The solvent was evaporated to give 12.75 g of the corresponding diester, which was used without further purification.

LAH (18.8 mL, 45.0 mmol, 2.4 M in THF) was added to THF (25 mL) and cooled to 0° C. The diester (2.84 g, 15.0 mmol) was dissolved in THF (10 mL) and added drop-wise to the LAH-suspension. After the complete addition of the diester, the reaction mixture was heated to reflux for 30 min. Then it was cooled to 0° C. and iPrOH (20 mL) was added drop-wise, and water (5.13 mL) was added. The grey slurry was stirred for 15 min and the solvent was evaporated. The powdered residue was extracted using a soxleth in refluxing iPrOH (250 mL) for 16 h. The solvent was evaporated and the crude product was dried under high vacuum to give the crude 2-amino-diol (1.28 g).

The 2-amino-diol (840 mg, 8 mmol) was added to a solution of diisopropylethylamine (8.8 mL, 48 mmol) and DCM (10 mL) and cooled to 0° C. TBSOTf (9.2 mL, 40 mmol) was added and the reaction mixture was stirred for 16 at rt. The reaction was quenched by adding brine (75 mL). The aqueous layer was extracted with DCM (3×75 mL) and dried over Mg$_2$SO$_4$. Column chromatography (EtOAc) gave ICEC0321 as light yellow solid (2.02 g, 76%).

$^1$H NMR (400 MHz, CDCl$_3$): δ 3.77-3.72 (m, 1H), 3.60-3.54 (m, 1H), 2.03-1.94 (m, 1H), 1.85-1.82 (m, 1H), 0.93-0.92 (m, 18H), 0.12-0.11 (m, 12H); $^{13}$C NMR (100 MHz, CDCl$_3$) δ 62.4, 61.1, 54.0, 30.7, 25.9, 25.8, 18.2, 18.1, −5.7; IR (neat) ν$_{max}$=2954, 2931, 2886, 2859, 1471, 1257; MS (ESI): m/z 334 (M+H); HRMS (ESI) Calc.: (C$_4$K$_1$NO$_2$) 333.2519. Found: 334.2596.

(R)-2,2,3,3,10,10,11,11-octamethyl-4,9-dioxa-3,10-disiladodecan-6-amine (ICEC0330)

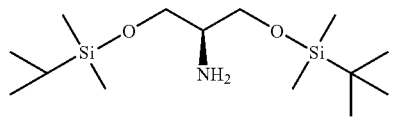

D-aspartic acid (4.0 g, 30 mmol) was stirred in EtOH (60 mL) and cooled to −78° C. SOCl$_2$ (4.5 mL, 63 mmol) was added drop-wise and the reaction mixture was allowed to warm to rt and stirred for additional 16 h. The solvent was evaporated and the residue was re-dissolved in EtOAc (40 mL). The organic layer was washed with brine (50 mL) and the aqueous layer was extracted with DCM (3×20 mL). The solvent was evaporated to give 3.26 g of the corresponding diester, which was used without further purification.

LAH (18.8 mL, 45.0 mmol, 2.4 M in THF) was added to THF (25 mL) and cooled to 0° C. The diester (2.84 g, 15.0 mmol) was dissolved in THF (10 mL) and added drop-wise to the LAH-suspension. After the complete addition of the diester, the reaction mixture was heated to reflux for 30 min. Then it was cooled to 0° C. and iPrOH (20 mL) was added drop-wise, and water (5.13 mL) was added. The grey slurry was stirred for 15 min and the solvent was evaporated. The powdered residue was extracted using a soxleth in refluxing iPrOH (250 mL) for 16 h. The solvent was evaporated and the crude product was dried under high vacuum to give the crude (R)-2-amino-diol (1.49 g).

(R)-2-amino-diol (840 mg, 8 mmol) was added to a solution of diisopropylethylamine (7.3 mL, 40 mmol) and DCM (10 mL) and cooled to 0° C. TBSOTf (7.4 mL, 32 mmol) was added and the reaction mixture was stirred for 16 at rt. The reaction was quenched by adding brine (75 mL). The aqueous layer was extracted with DCM (3×75 mL) and dried over Mg$_2$SO$_4$. Column chromatography (EtOAc) gave ICEC0330 as pale oil (1.14 g, 42%, 99% ee).

The enantiomeric excess was determined by forming an amide of with (R)-(+)-3,3,3-trifluoro-2-methoxy-2-phenyl-propanoic acid (Mosher acid), as described above.

[α]$^{25}_D$ (c 0.21, CH$_2$Cl$_2$): −1.0; $^1$H NMR (400 MHz, CDCl$_3$): δ 3.78-3.75 (m, 2H), 3.63-3.59 (m, 1H), 3.43-3.36 (m, 1H), 3.04-2.99 (m, 1H), 1.69-1.61 (m, 3H), 1.53-1.45 (m, 1H), 0.92-0.91 (m, 18H), 0.08-0.07 (m, 12H); $^{13}$C NMR (100 MHz, CDCl$_3$) δ 68.4, 61.1, 51.2, 36.4, 26.1, 26.1, 18.5, 18.4, −5.2; IR (neat) ν$_{max}$=2950, 2931, 2886, 2858, 1471, 1255; MS (ESI): m/z 334 (M+H); HRMS (ESI) Calc.: (C$_4$H$_{11}$NO$_2$) 333.2519. Found: 334.2593.

(S)-2,2,3,3,10,10,11,11-octamethyl-4,9-dioxa-3,10-disiladodecan-6-amine (ICEC0328)

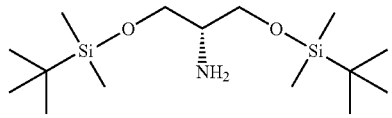

L-aspartic acid (13.3 g, 100 mmol) was stirred in EtOH (200 mL) and cooled to −78° C. SOCl$_2$ (15 mL, 210 mmol) was added drop-wise and the reaction mixture was allowed to warm to rt and stirred for additional 16 h. The solvent was evaporated and the residue was re-dissolved in EtOAc (100 mL). The organic layer was washed with brine (100 mL) and the aqueous layer was extracted with DCM (3×50 mL). The solvent was evaporated to give 12.75 g of the corresponding diester, which was used without further purification.

LAH (18.8 mL, 45.0 mmol, 2.4 M in THF) was added to THF (25 mL) and cooled to 0° C. The diester (284 mg, 15.0 mmol) was dissolved in THF (10 mL) and added drop-wise to the LAH-suspension. After the complete addition of the diester, the reaction mixture was heated to reflux for 30 min. Then it was cooled to 0° C. and iPrOH (20 mL) was added drop-wise, and water (5.13 mL) was added. The grey slurry was stirred for 15 min and the solvent was evaporated. The powdered residue was extracted using a soxlet in refluxing iPrOH (250 mL) for 16 h. The solvent was evaporated and the crude product was dried under high vacuum to give the crude (S)-2-amino-diol (1.35 g).

(S)-2-amino-diol (840 mg, 8 mmol) was added to a solution of diisopropylethylamine (7.3 mL, 40 mmol) and DCM (10 mL) and cooled to 0° C. TBSOTf (7.4 mL, 32 mmol) was added and the reaction mixture was stirred for 16 at RT. The reaction was quenched by adding brine (75 mL). The aqueous layer was extracted with DCM (3×75 mL) and dried over Mg$_2$SO$_4$. Column chromatography (EtOAc) gave ICEC0328 as pale oil (1.45 g, 54%, 92% ee).

The enantiomeric excess was determined by forming an amide with the Mosher acid, as described above.

[α]$^{25}_D$ (c (0.21, CH$_2$Cl$_2$): +2.0; $^1$H NMR (400 MHz, CDCl$_3$): δ 3.78-3.75 (m, 2H), 3.62-3.59 (m, 1H), 3.41-3.37 (m, 1H), 3.04-2.98 (m, 1H), 1.69-1.60 (m, 3H), 1.52-1.43 (m, 1H), 0.93-0.92 (m, 18H), 0.09-0.08 (m, 12H); $^{13}$C NMR (100 MHz, CDCl$_3$) δ 68.5, 60.9, 50.8, 36.5, 25.9, 18.3, 18.3, −5.3; IR (neat) ν$_{max}$=2954, 2931, 2894, 1471, 1255; MS (ESI): m/z 334 (M+H); HRMS (ESI) Calc.: (C$_4$H$_{11}$NO$_2$) 333.2519. Found: 334.2610.

4.2) Synthesis of the New Analogues

The synthesis was carried out according to the method used for previous coupling reactions.

Scheme 4.1: General reaction scheme to BS-194 analogues.

Protected amino-alcohols

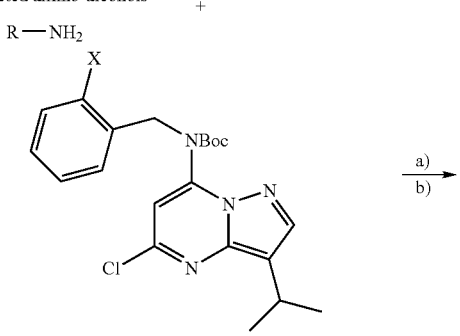

X = H, F

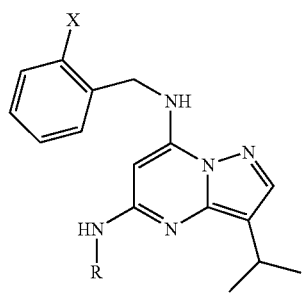

X = H, F a) Pd$_2$(dba)$_3$, BINAP, NaO$^t$Bu, tol. reflux, o/n
b) HCl MeOH, rt, 2 h tert-butyl benzyl(5-(2-(tert-butyldimethylsilyloxy)ethylamino)-3-isopropylpyrazolo[1,5-a]pyrimidin-7-yl)carbamate (ICEC0301)

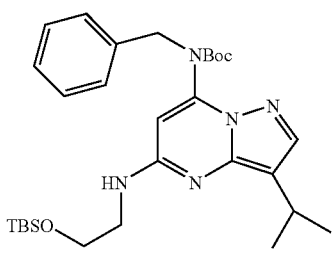

The heteroaryl chloride ICEC0012 (241 mg, 0.60 mmol), Pd$_2$dba$_3$ (18 mg, 5 mol %), rac-BINAP (37 mg, 10 mol %), and NaO$^t$Bu (56 g, 0.90 mmol), were suspended in toluene (1.3 ml). After 5 min of stirring the amine ICEC0293 (126 mg, 0.72 mmol) was added and the red mixture heated for 12 h at 100° C. The reaction mixture was cooled to rt, diluted with EtOAc (5 mL) and poured into brine (5 mL). The aqueous phase was extracted with ethyl acetate (3×10 mL) and the combined organic phases were dried over Na$_2$SO$_4$. After concentration the crude product was purified by column chromatography on silica (PE:EtOAc=20:1) to yield the protected coupling product ICEC0301 (102 mg, 32%) as a colourless oil.

$^1$H NMR (CDCl$_3$, 400 MHz) δ 0.07 (s, 6H), 0.92 (s, 9H), 1.36 (d, J=6.9 Hz, 6H), 1.42 (s, 9H), 3.16 (h, J=6.9 Hz, 1H), 3.51-3.55 (m, 2H), 3.79-3.81 (m, 2H), 3.79-3.82 (m, 1H), 4.92-5.00 (m, 1H), 5.68 (s, 1H), 7.27-7.36 (m, 5H), 7.77 (s, 1H); $^{13}$C NMR (CDCl$_3$, 100 MHz) δ −5.3, 18.4, 23.2, 23.8, 26.0, 28.1, 43.5, 51.4, 61.6, 82.1, 97.4, 113.4, 127.5, 128.1, 128.5, 137.8, 141.5, 142.8, 146.3, 153.6, 154.5. IR (neat) ν$_{max}$=3380, 2956, 2929, 2859, 1720; MS m/z (ESI) 540 (M+H). HRMS (ESI) Calc.: (C$_{29}$H$_{45}$N$_5$O$_3$Si) 539.3292. Found: 540.3367.

tert-butyl 5-(2-(tert-butyldimethylsilyloxy)ethylamino)-3-isopropylpyrazolo[1,5-a]pyrimidin-7-yl(2-fluorobenzyl)carbamate (ICEC0296)

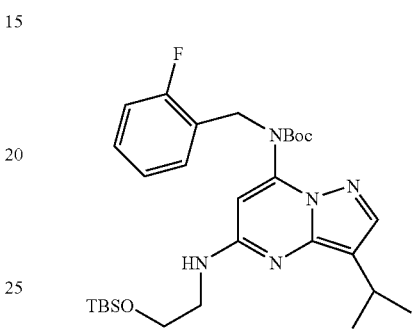

The heteroaryl chloride ICEC0013 (264 mg, 0.63 mmol), Pd$_2$dba$_3$ (27.5 mg, 5 mol %), rac-BINAP (40 mg, 10 mol %), and NaO$^t$Bu (96 g, 1.00 mmol), were suspended in toluene (1.3 ml). After 5 min of stirring the amine ICEC0293 (144 mg, 0.82 mmol) was added and the red mixture heated for 12 h at 100° C. The reaction mixture was cooled to rt, diluted with EtOAc (5 mL) and poured into brine (5 mL). The aqueous phase was extracted with ethyl acetate (3×10 mL) and the combined organic phases were dried over Na$_2$SO$_4$. After concentration the crude product was purified by column chromatography on silica (PE:EtOAc=20:1) to yield the protected coupling product ICEC0296 (68 mg, 24%) as a colourless oil.

$^1$H NMR (CDCl$_3$, 400 MHz) δ 0.07 (s, 6H), 0.92 (s, 9H), 1.35 (d, J=6.9 Hz, 6H), 1.42 (s, 9H), 3.16 (h, J=6.9 Hz, 1H), 3.53-3.57 (m, 2H), 3.80-3.83 (m, 2H), 5.05 (br s, 1H), 5.76 (s, 1H), 6.99-7.11 (m, 2H), 7.23-727 (m, 1H), 7.36-7.40 (m, 1H), 7.77 (s, 1H); $^{13}$C NMR (CDCl$_3$, 100 MHz) δ-5.3, 18.4, 23.2, 23.8, 26.0, 28.0, 43.6, 45.6, 51.4, 61.6, 82.3, 96.9, 113.3, 115.3, 124.2, 124.6, 129.4, 130.5, 141.5, 143.0, 153.4, 159.6, 162.1. IR (neat) ν$_{max}$=3374, 2956, 2929, 2858, 1722; MS m/z (ESI) 558 (M+H). HRMS (ESI) Calc.: (C$_{29}$H$_{44}$FN$_5$O$_3$Si) 557.3197. Found: 558.3262.

2-(7-(benzylamino)-3-isopropylpyrazolo[1,5-a]pyrimidin-5-ylamino)ethanol (ICEC0302)

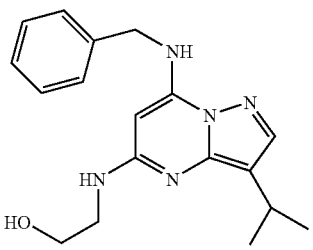

ICEC0301 (102 mg, 0.19 mmol) was dissolved in MeOH/HCl (10 mL, 5M) and stirred for 2 h at rt. The crude product was purified by column chromatography on silica (EtOAc). ICEC0302 was obtained as a pale yellow solid (52 mg, 84%).

$^1$H NMR (CDCl$_3$, 400 MHz) δ 1.32 (d, J=6.9 Hz, 6H), 3.12 (h, J=6.9 Hz, 1H), 3.51-3.56 (m, 2H), 3.80-3.83 (m, 2H), 4.50 (d, J=5.7 Hz, 2H), 5.06 (s, 1H), 5.18 (br s, 1H), 5.47 (br s 1H), 6.71-6.73 (m, 1H), 7.31-7.39 (m, 5H), 7.68 (s, 1H); $^{13}$C NMR (CDCl$_3$, 100 MHz) δ 23.3, 23.5, 45.7, 46.1, 64.3, 72.5, 113.1, 127.1, 127.9, 128.9, 136.5, 140.8, 143.9, 147.0, 157.3. IR (neat) $v_{max}$=3299, 2958, 2923, 2865, 1639; MS m/z (ESI) 326 (M+H). HRMS (ESI) Calc.: (C$_{18}$H$_{23}$N$_5$O) 325.1903. Found: 326.1981.

2-(7-(2-fluorobenzylamino)-3-isopropylpyrazolo[1,5-a]pyrimidin-5-ylamino)ethanol (ICEC0297)

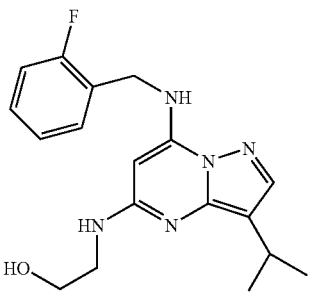

ICEC0296 (68 mg, 0.15 mmol) was dissolved in MeOH/HCl (10 mL, 5M) and stirred for 2 h at rt. The crude product was purified by column chromatography on silica (EtOAc). ICEC0297 was obtained as a pale yellow solid (20.4 mg, 40%).

$^1$H NMR (CDCl$_3$, 400 MHz) δ 1.32 (d, J=6.9 Hz, 6H), 3.10 (h, J=6.9 Hz, 1H), 3.57-3.60 (m, 2H), 3.81-3.83 (m, 2H), 4.56 (d, J=6.1 Hz, 2H), 4.94-4.97 (m, 1H), 5.10 (s, 1H), 6.50 (t, J=6.1 Hz, 1H), 7.08-7.15 (m, 2H), 7.30-7.37 (m, 2H), 7.68 (s, 1H); $^{13}$C NMR (CDCl$_3$, 100 MHz) δ 23.3, 23.6, 39.7, 45.8, 64.8, 72.7, 113.3, 115.6, 123.7, 124.5, 129.0, 129.7, 140.8, 144.4, 146.6, 157.3, 159.4. IR (neat) $v_{max}$=3307, 3286, 2958, 2925, 2867, 1639; MS m/z (ESI) 344 (M+H). HRMS (CI) Calc.: (C$_{18}$H$_{22}$FN$_5$O) 343.1808. Found: 344.1887.

2-(7-(benzylamino)-3-isopropylpyrazolo[1,5-a]pyrimidin-5-ylamino)propane-1,3-diol (ICEC0315)

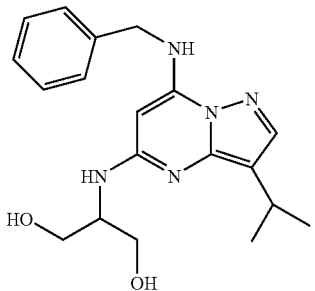

The heteroaryl chloride ICEC0012 (100 mg, 0.25 mmol), Pd$_2$dba$_3$ (12 mg, 5 mol %), rac-BINAP (16 mg, 10 mol %), and NaO$^t$Bu (36 g, 0.38 mmol), were suspended in toluene (1.0 ml). After 5 min of stirring the amine ICEC0292 (116 mg, 0.30 mmol) was added and the red mixture heated for 12 h at 100° C. The reaction mixture was cooled to rt and poured into brine (5 mL). The aqueous phase was extracted with ethyl acetate (3×10 mL) and the combined organic phases were dried over Na$_2$SO$_4$. After concentration the crude product was liberated from by-products, the catalyst and excess amine by column chromatography on silica (PE:EtOAc=4:1) to yield a mixture of the protected and deprotected diol (49 mg). This mixture was dissolved in MeOH/HCl (5 mL, 5M) and stirred for 2 h at rt. The crude product was purified by column chromatography on silica (EtOAc). The diol ICEC0315 was obtained as a pale yellow solid (14.6 mg, 17%).

$^1$H NMR (CDCl$_3$, 400 MHz) δ 1.31 (d, J=6.9 Hz, 6H), 3.04 (h, J=6.9 Hz, 1H), 3.73-3.78 (m, 2H), 3.83-3.87 (m, 2H), 3.96-4.02 (m, 1H), 4.46 (d, J=5.4 Hz, 2H), 5.08, (s, 1H), 5.24 (d, J=5.4 Hz, 1H), 6.52 (t, J=5.8 Hz, 1H), 7.29-7.38 (m, 5H), 7.67 (s, 1H); $^{13}$C NMR (CDCl$_3$, 100 MHz) δ 23.3, 23.6, 46.1, 56.5, 64.2, 73.2, 113.2, 127.2, 127.9, 128.9, 136.6, 140.7, 144.3, 146.8, 156.8. IR (neat) $v_{max}$=3390, 2956, 2925, 2867, 1727, 1639, 1581; MS m/z (ESI) 356 (M+H). HRMS (ESI) Calc.: (C$_{19}$H$_{25}$N$_5$O$_2$) 355.2008. Found: 356.2093.

2-(7-(2-fluorobenzylamino)-3-isopropylpyrazolo[1,5-a]pyrimidin-5-ylamino)propane-1,3-diol (ICEC0298)

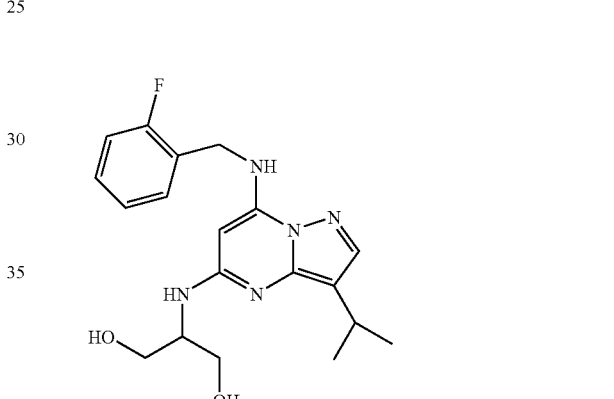

The heteroaryl chloride ICEC0013 (264 mg, 0.63 mmol), Pd$_2$dba$_3$ (27.5 mg, 5 mol %), rac-BINAP (40 mg, 10 mol %), and NaO$^t$Bu (96 g, 1.00 mmol), were suspended in toluene (1.3 ml). After 5 min of stirring the amine ICEC0292 (262 mg, 0.82 mmol) was added and the red mixture heated for 12 h at 100° C. The reaction mixture was cooled to rt and poured into brine (10 mL). The aqueous phase was extracted with ethyl acetate (3×20 mL) and the combined organic phases were dried over Na$_2$SO$_4$. After concentration the crude product was liberated from by-products, the catalyst and excess amine by column chromatography on silica (PE:EtOAc=9:1) to yield a mixture of the protected and deprotected diol (167 mg). This mixture was dissolved in MeOH/HCl (5 mL, 5M) and stirred for 3 h at rt. The solvent was evaporated and the residue dissolved in EtOAc (100 mL) and washed with sat. K$_2$CO$_3$ sol. (20 mL). After concentration the crude product was purified by column chromatography on silica (EtOAc). The diol ICEC0298 was obtained as a pale yellow solid (32.2 mg, 14%).

$^1$H NMR (CDCl$_3$, 400 MHz) δ 1.26 (d, J=6.8 Hz, 6H), 3.04 (h, J=6.8 Hz, 1H), 3.70-3.72 (m, 2H), 3.73-3.75 (m, 2H), 3.79-3.82 (m, 1H), 4.47 (d, J=6.0 Hz, 2H), 5.10, (s, 1H), 5.37 (d, J=6.0 Hz, 1H), 6.54 (t, J=6.4 Hz, 1H), 7.02-7.08 (m, 2H), 7.22-7.30 (m, 3H), 7.64 (s, 1H); $^{13}$C NMR (CDCl$_3$, 100 MHz) δ 23.2, 23.6, 39.8, 56.4, 64.1, 73.0, 113.2, 115.6, 123.8, 124.5, 129.1, 129.6, 140.8, 144.2, 146.7, 156.8, 161.9. MS m/z (CI) 374 (M+H). HRMS (CI) Calc.: (C$_{19}$H$_{25}$FN$_5$O$_2$) 374.1978. Found: 374.1992.

tert-butyl benzyl(5-((2,2-dimethyl-1,3-dioxolan-4-yl)methylamino)-3-isopropylpyrazolo[1,5-a]pyrimidin-7-yl)carbamate (ICEC0313)

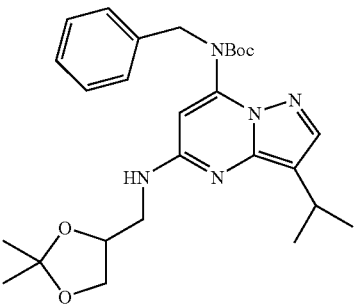

The heteroaryl chloride ICEC0012 (241 mg, 0.60 mmol), Pd$_2$dba$_3$ (27.5 mg, 5 mol %), rac-BINAP (40 mg, 10 mol %), and NaO$^t$Bu (56 g, 0.90 mmol), were suspended in toluene (1.3 ml). After 5 min of stirring the amine ((2,2-dimethyl-1,3-dioxolan-4-yl)methanamine, 84 mg, 0.72 mmol) was added and the red mixture heated for 12 h at 100° C. The reaction mixture was cooled to rt, diluted with EtOAc (5 mL) and poured into brine (5 mL). The aqueous phase was extracted with ethyl acetate (3×10 mL) and the combined organic phases were dried over Na$_2$SO$_4$. After concentration the crude product was purified by column chromatography on silica (PE:EtOAc=20:1) to yield the protected coupling product ICEC0313 (67 mg, 23%) as a yellow oil.

$^1$H NMR (CDCl$_3$, 400 MHz) δ 1.34 (d, J=6.9 Hz, 6H), 1.36 (s, 3H), 1.41 (s, 9H), 1.43 (s, 3H), 3.13 (h, J=6.9 Hz, 1H), 3.42-3.47 (m, 1H), 3.66-3.73 (m, 2H), 4.05-4.10 (m, 1H), 4.29-4.35 (m, 1H), 3.79-3.82 (m, 1H), 4.94 (br s, 2H), 5.72 (s, 1H), 7.24-7.33 (m, 5H), 7.77 (s, 1H); $^{13}$C NMR (CDCl$_3$, 100 MHz) δ 23.2, 23.8, 25.4, 26.9, 28.1, 43.5, 51.4, 67.0, 74.6, 82.2, 97.5, 109.3, 113.5, 127.5, 127.9, 128.5, 137.7, 141.6, 142.8, 146.1, 153.6, 154.4. IR (neat) ν$_{max}$=3370, 2979, 2960, 2933, 2869, 1720; MS m/z (ESI) 496 (M+H). HRMS (ESI) Calc.: (C$_{22}$H$_{37}$N$_5$O$_4$) 495.2846. Found: 496.2924.

tert-butyl 5-((2,2-dimethyl-1,3-dioxolan-4-yl)methylamino)-3-isopropylpyrazolo[1,5-a]pyrimidin-7-yl(2-fluorobenzyl)carbamate (ICEC0294)

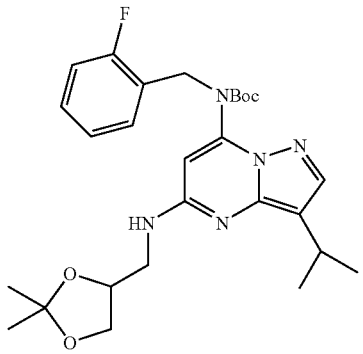

The heteroaryl chloride ICEC0013 (264 mg, 0.63 mmol), Pd$_2$dba$_3$ (27.5 mg, 5 mol %), rac-BINAP (40 mg, 10 mol %), and NaO$^t$Bu (96 g, 1.00 mmol), were suspended in toluene (1.3 ml). After 5 min of stirring the amine ((2,2-dimethyl-1,3-dioxolan-4-yl)methanamine, 96 mg, 0.82 mmol) was added and the red mixture heated for 12 h at 100° C. The reaction mixture was cooled to rt, diluted with EtOAc (5 mL) and poured into brine (5 mL). The aqueous phase was extracted with ethyl acetate (3×10 mL) and the combined organic phases were dried over Na$_2$SO$_4$. After concentration the crude product was purified by column chromatography on silica (PE:EtOAc=20:1) to yield the protected coupling product ICEC0294 (120 mg, 40%) as a colourless oil.

$^1$H NMR (CDCl$_3$, 400 MHz) δ 1.34 (d, J=6.9 Hz, 6H), 1.37 (s, 3H), 1.42 (s, 9H), 1.44 (s, 3H), 3.13 (h, J=6.9 Hz, 1H), 3.45-3.52 (m, 1H), 3.68-3.75 (m, 2H), 4.06-4.10 (m, 1H), 4.31-4.37 (m, 1H), 5.04 (br s, 3H), 5.82 (s, 1H), 6.99-7.10 (m, 2H), 7.22-7.28 (m, 1H), 7.34-7.38 (m, 1H), 7.77 (s, 1H); $^{13}$C NMR (CDCl$_3$, 100 MHz) δ 23.2, 23.8, 25.4, 26.9, 28.0, 43.4, 45.7, 67.0, 74.6, 82.4, 97.2, 109.3, 113.5, 115.3, 124.1, 124.5, 129.3, 130.3, 141.6, 142.9, 153.4, 154.5, 159.6, 162.0. IR (neat) ν$_{max}$=3372, 2964, 2933, 2871, 1724; MS m/z (ESI) 514 (M+H). HRMS (CI) Calc.: (C$_{27}$H$_{36}$FN$_5$O$_4$) 513.2751. Found: 514.2823.

3-(7-(benzylamino)-3-isopropylpyrazolo[1,5-a]pyrimidin-5-ylamino)propane-1,2-diol (ICEC0314)

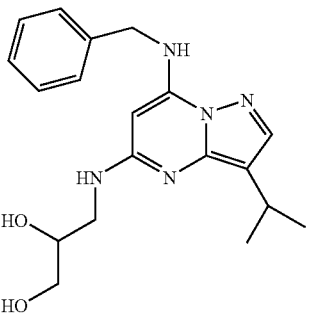

ICEC0313 (67.0 mg, 0.14 mmol) was dissolved in MeOH/HCl (10 mL, 5M) and stirred for 2 h at rt. The crude product was purified by column chromatography on silica (EtOAc:MeOH=9:1). The diol ICEC0314 was obtained as a pale yellow solid (48.7 mg, 98%).

$^1$H NMR (CDCl$_3$, 400 MHz) δ 1.31 (d, J=6.9 Hz, 6H), 3.10 (h, J=6.9 Hz, 1H), 3.52-3.66 (m, 4H), 3.76-3.81 (m, 1H), 4.46-4.48 (m, 2H), 5.04 (s, 1H), 6.58-6.64 (m, 1H), 7.30-7.38 (m, 5H), 7.68 (s, 1H); $^{13}$C NMR (CDCl$_3$, 100 MHz) δ 23.3, 23.5, 44.5, 46.1, 63.2, 72.2, 72.8, 113.3, 127.1, 128.0, 129.0, 136.5, 140.8, 144.0, 146.8, 157.3. IR (neat) ν$_{max}$=3326, 2958, 2925, 2867, 1637; MS m/z (ESI) 356 (M+H). HRMS (ESI) Calc.: ($C_{19}H_{25}N_5O_2$) 355.208. Found: 356.2097.

3-(7-(2-fluorobenzylamino)-3-isopropylpyrazolo[1,5-a]pyrimidin-5-ylamino)propane-1,2-diol (ICEC0295)

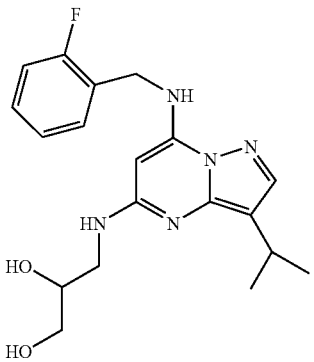

ICEC0294 (120 mg, 0.23 mmol) was dissolved in MeOH/HCl (10 mL, 5M) and stirred for 2 h at rt. The crude product was purified by column chromatography on silica (EtOAc). The diol ICEC0295 was obtained as a pale yellow solid (18.8 mg, 22%).

$^1$H NMR (CDCl$_3$, 400 MHz) δ 1.31 (d, J=6.9 Hz, 6H), 3.09 (h, J=6.9 Hz, 1H), 3.53-3.66 (m, 4H), 3.77-3.82 (m, 1H), 4.55 (d, J=6.1 Hz, 2H), 4.86-4.89 (m, 1H), 5.09 (s, 1H), 6.57 (t, J=6.1 Hz, 1H), 7.08-7.15 (m, 2H), 7.30-7.36 (m, 2H), 7.68 (s, 1H); $^{13}$C NMR (CDCl$_3$, 100 MHz) δ 23.3, 23.5, 39.7, 44.5, 63.2, 72.3, 72.8, 113.4, 115.6, 123.6, 124.6, 129.0, 129.7, 140.8, 144.2, 146.4, 157.4, 160.6. IR (neat) ν$_{max}$=3315, 2958, 2925, 2869, 1639; MS m/z (ESI) 374 (M+H). HRMS (ESI) Calc.: ($C_{19}H_{24}FN_5O_2$) 373.1914. Found: 374.2004.

tert-butyl benzyl(5-(3-(tert-butyldimethylsilyloxy)propylamino)-3-isopropylpyrazolo[1,5-a]pyrimidin-7-yl)carbamate (ICEC0316)

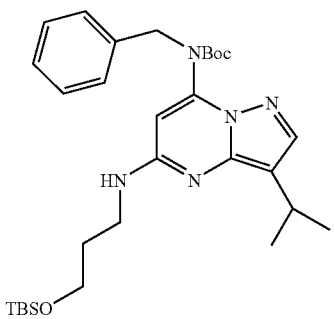

The heteroaryl chloride ICEC0012 (100 mg, 0.25 mmol), Pd$_2$dba$_3$ (12 mg, 5 mol %), rac-BINAP (16 mg, 10 mol %), and NaO$^t$Bu (36 g, 0.38 mmol), were suspended in toluene (1.0 ml). After 5 min of stirring the amine ICEC0312 (57 mg, 0.30 mmol) was added and the red mixture heated for 12 h at 100° C. The reaction mixture was cooled to rt, diluted with EtOAc (5 mL) and poured into brine (5 mL). The aqueous phase was extracted with ethyl acetate (3×10 mL) and the combined organic phases were dried over Na$_2$SO$_4$. After concentration the crude product was purified by column chromatography on silica (PE:EtOAc=20:1) to yield the protected coupling product ICEC0316 (22.6 mg, 16%) as a colourless oil.

$^1$H NMR (CDCl$_3$, 400 MHz) δ 0.07 (s, 6H), 0.91 (s, 9H), 1.35 (d, J=6.9 Hz, 6H), 1.42 (s, 9H), 1.79-1.85 (m, 2H), 3.14 (h, J=6.9 Hz, 1H), 3.48-3.53 (m, 2H), 3.76-378 (m, 2H), 4.94 (br s, 1H), 5.23 (br s, 1H), 5.61 (s, 1H), 7.25-7.33 (m, 5H), 7.75 (s, 1H); $^{13}$C NMR (CDCl$_3$, 100 MHz) δ −5.4, 18.2, 23.2, 23.8, 26.0, 28.1, 31.4, 40.2, 51.3, 62.4, 82.0, 97.2, 113.2, 127.5, 127.9, 128.5, 137.8, 141.5, 142.7, 153.7, 154.6. IR (neat) ν$_{max}$=3378, 2956, 2929, 2859, 1720; MS m/z (ESI) 554 (M+H). HRMS (ESI) Calc.: ($C_{30}H_{47}N_5O_3Si$) 553.3448. Found: 554.3545.

tert-butyl 5-(3-(tert-butyldimethylsilyloxy)propylamino)-3-isopropylpyrazolo[1,5-a]pyrimidin-7-yl(2-fluorobenzyl)carbamate (ICEC0304)

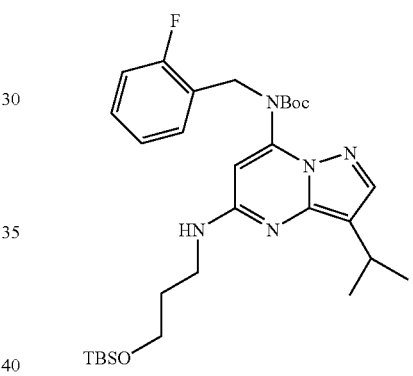

The heteroaryl chloride ICEC0013 (251 mg, 0.60 mmol), Pd$_2$dba$_3$ (27.5 mg, 5 mol %), rac-BINAP (40 mg, 10 mol %), and NaO$^t$Bu (86 g, 0.90 mmol), were suspended in toluene (1.3 ml). After 5 min of stirring the amine ICEC0312 (136 mg, 0.72 mmol) was added and the red mixture heated for 12 h at 100° C. The reaction mixture was cooled to rt, diluted with EtOAc (5 mL) and poured into brine (5 mL). The aqueous phase was extracted with ethyl acetate (3×10 mL) and the combined organic phases were dried over Na$_2$SO$_4$. After concentration the crude product was purified by column chromatography on silica (PE:EtOAc=20:1) to yield the protected coupling product ICEC0304 (51 mg, 15%) as a colourless oil.

$^1$H NMR (CDCl$_3$, 400 MHz) δ 0.07 (s, 6H), 0.92 (s, 9H), 1.34 (d, J=6.9 Hz, 6H), 1.41 (s, 9H), 1.80-1.86 (m, 2H), 3.14 (h, J=6.9 Hz, 1H), 3.50-3.54 (m, 2H), 3.76-3.79 (m, 2H), 5.03 (br s, 1H), 5.72 (s, 1H), 6.98-7.10 (m, 2H), 7.22-7.27 (m, 1H), 7.34-7.38 (m, 1H), 7.75 (s, 1H); $^{13}$C NMR (CDCl$_3$, 100 MHz) δ −5.4, 18.2, 23.2, 23.8, 25.9, 28.0, 31.4, 40.3, 45.6, 62.3, 82.0, 113.1, 115.3, 124.0, 124.6, 129.3, 130.3, 131.3, 141.5, 153.5, 154.7. IR (neat) ν$_{max}$=3378, 2956, 2931, 2859, 1724;

MS m/z (ESI) 572 (M+H). HRMS (ESI) Calc.: (C$_{30}$H$_{46}$FN$_5$O$_3$Si) 571.3354. Found: 572.3441.

3-(7-(benzylamino)-3-isopropylpyrazolo[1,5-a]pyrimidin-5-ylamino)propan-1-ol (ICEC0317)

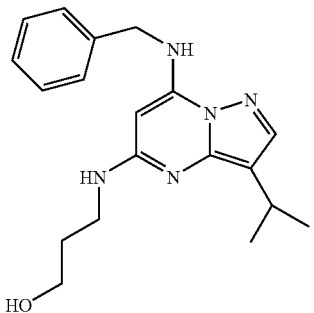

ICEC0316 (22.6 mg, 0.04 mmol) was dissolved in MeOH/HCl (10 mL, 5M) and stirred for 2 h at rt. The crude product was purified by column chromatography on silica (EtOAc). ICEC0317 was obtained as a pale yellow solid (9.4 mg, 69%).

$^1$H NMR (CDCl$_3$, 400 MHz) δ 1.32 (d, J=6.9 Hz, 6H), 1.68-1.74 (m, 2H), 3.13 (h, J=6.9 Hz, 1H), 3.53-3.66 (m, 4H), 3.60-3.66 (m, 4H), 4.50 (d, J=5.7 Hz, 2H), 4.71 (br s, 1H), 5.01 (s, 1H), 6.50 (t, J=5.7 Hz, 1H), 7.31-7.40 (m, 5H), 7.68 (s, 1H); $^{13}$C NMR (CDCl$_3$, 100 MHz) δ 23.4, 23.5, 33.7, 37.0, 46.1, 57.8, 72.6, 113.2, 127.1, 127.9, 129.0, 136.6, 140.7, 146.4, 146.7, 157.4. IR (neat) $\nu_{max}$=3311, 2956, 2927, 2867, 1639; MS m/z (ESI) 340 (M+H). HRMS (ESI) Calc.: (C$_{19}$H$_{25}$N$_5$O) 339.2059. Found: 340.2146.

3-(7-(2-fluorobenzylamino)-3-isopropylpyrazolo[1,5-a]pyrimidin-5-ylamino)propan-1-ol (ICEC0305)

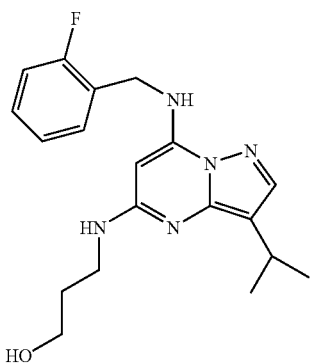

ICEC0304 (51 mg, 0.09 mmol) was dissolved in MeOH/HCl (10 mL, 5M) and stirred for 2 h at rt. The crude product was purified by column chromatography on silica (EtOAc). ICEC0305 was obtained as a pale yellow solid (23 mg, 72%).

$^1$H NMR (CDCl$_3$, 400 MHz) δ 1.32 (d, J=6.9 Hz, 6H), 1.67-1.74 (m, 2H), 3.13 (h, J=6.9 Hz, 1H), 3.60-3.68 (m, 4H), 4.55 (d, J=6.1 Hz, 2H), 4.68-4.75 (m, 1H), 5.06 (s, 1H), 6.52 (t, J=6.1 Hz, 1H), 7.08-7.15 (m, 2H), 7.30-7.37 (m, 2H), 7.68 (s, 1H); $^{13}$C NMR (CDCl$_3$, 100 MHz) δ 23.3, 23.4, 33.6, 37.1, 39.8, 57.8, 72.3, 113.2, 115.6, 123.7, 124.6, 129.1, 129.8, 140.9, 146.6, 157.2, 159.4, 161.9. IR (neat) $\nu_{max}$=3311, 2956, 2925, 2867, 1639; MS m/z (ESI) 358 (M+H). HRMS (ESI) Calc.: (C$_{19}$H$_{24}$FN$_5$O) 357.1965. Found: 358.2055.

tert-butyl benzyl(3-isopropyl-5-(2,2,3,3,10,10,11,11-octamethyl-4,9-dioxa-3,10-disiladodecan-6-ylamino)pyrazolo[1,5-a]pyrimidin-7-yl)carbamate (ICEC0322)

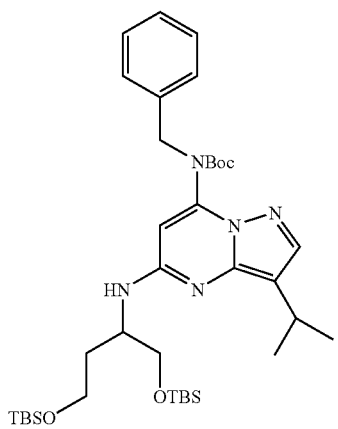

The heteroaryl chloride ICEC0012 (112 mg, 0.28 mmol), Pd$_2$dba$_3$ (13 mg, 5 mol %), rac-BINAP (17 mg, 10 mol %), and NaO$^t$Bu (40 mg, 0.42 mmol), were suspended in toluene (1.0 mL). After 5 min of stirring the amine ICEC0321 (112 mg, 0.33 mmol) was added and the red mixture heated for 12 h at 100° C. The reaction mixture was cooled to rt, diluted with EtOAc (2 mL) and poured into brine (5 mL). The aqueous phase was extracted with ethyl acetate (3×5 mL) and the combined organic phases were dried over Na$_2$SO$_4$. After concentration of the crude, the product was purified by column chromatography on silica (20:1=PE:EtOAc) to yield the protected coupling product ICEC0322 (102 mg, 52%) as a colourless oil.

$^1$H NMR (CDCl$_3$, 400 MHz) δ 7.76 (s, 1H), 7.34-7.27 (m, 5H), 5.63 (s, 1H), 5.25-5.23 (m, 1H), 4.96 (s$_{br}$, 2H), 4.21 (s$_{br}$, 1H), 3.88-3.83 (m, 2H), 3.77-3.72 (m, 1H), 3.67-3.63 (m, 1H), 3.15 (hept, J=6.9 Hz, 1H), 1.96-1.81 (m, 2H), 1.42 (s, 9H), 1.39 (d, J=6.9 Hz, 6H), 0.90 (s, 9H), 0.90 (s, 9H), 0.07-0.03 (m, 12H); $^{13}$C NMR (CDCl$_3$, 100 MHz) 154.2, 153.7, 146.4, 142.7, 141.4, 137.8, 128.5, 127.9, 127.5, 113.2, 97.5, 82.0, 63.5, 60.6, 51.4, 50.6, 33.4, 28.1, 25.9, 23.8, 23.3, 23.2, 18.3, 18.2, -5.29. IR (neat) $\nu_{max}$=3374, 2956, 2929, 2858, 1724, 1643; MS m/z (ESI) 698 (M+H). HRMS (ESI) Calc.: ($C_{37}H_{63}N_5O_4Si_2$) 697.4419. Found: 698.4489.

2-(7-(benzylamino)-3-isopropylpyrazolo[1,5-a]pyrimidin-5-ylamino)butane-1,4-diol (ICEC 0323)

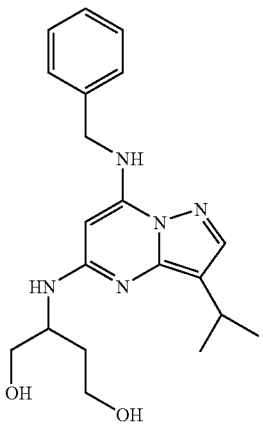

ICEC0322 (150 mg, 0.21 mmol) was dissolved in MeOH/HCl (25 mL, 5M) and stirred for 2 h at rt. The crude product was purified by column chromatography on silica (EtOAc) and recrystallized from CHCl$_3$. ICEC0323 was obtained as a pale solid (20.7 mg, 27%).

m.p. 102° C.; $^1$H NMR (d$_6$-DMSO, 400 MHz) δ 7.92 (s, 1H), 7.65 (s, 1H), 7.38-7.24 (m, 5H), 6.53 (s, 1H), 5.22 (s, 1H), 4.83 (s$_{br}$, 1H), 4.46-4.45 (m, 2H), 4.00 (s, 1H), 3.47-3.3 (m, 4H), 2.94 (hept, J=6.9 Hz, 1H), 1.79-1.70 (m, 1H), 1.50-1.42 (m, 1H), 1.24 (d, J=6.9 Hz, 6H); $^{13}$C NMR (d$_6$-DMSO, 100 MHz) δ 157.1, 146.7, 140.2, 139.0, 128.9, 127.5, 127.3, 111.1, 72.9, 64.2, 58.3, 49.7, 45.1, 35.4, 31.2, 23.8, 23.6, 23.6. IR (neat) ν$_{max}$=3293, 2954, 2927, 2867, 1631, 1575; MS m/z (ESI) 370 (M+H). HRMS (ESI) Calc.: ($C_{20}H_{27}N_5O_2$) 369.2165. Found: 370.2245.

2-(7-(2-fluorobenzylamino)-3-isopropylpyrazolo[1,5-a]pyrimidin-5-ylamino)butane-1,4-diol (ICEC0324)

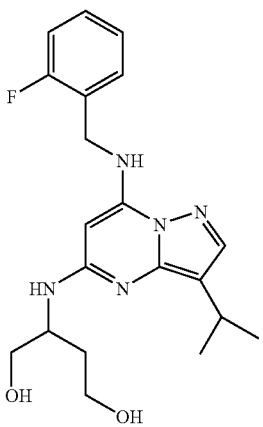

The heteroaryl chloride ICEC0013 (251 mg, 0.60 mmol), Pd$_2$dba$_3$ (27.5 mg, 5 mol %), rac-BINAP (38 mg, 10 mol %), and NaO$^t$Bu (86 mg, 0.9 mmol), were suspended in toluene (1.3 ml). After 5 min of stirring the amine ICEC0321 (240 mg, 0.72 mmol) was added and the red mixture heated for 12 h at 100° C. The reaction mixture was cooled to RT, diluted with EtOAc (2 mL) and poured into brine (5 mL). The aqueous phase was extracted with ethyl acetate (3×5 mL) and the combined organic phases were dried over Na$_2$SO$_4$. After concentration of the crude, the product was separated from other impurities by column chromatography on silica (20:1=PE:EtOAc) to yield a mixture of unprotected and protected coupling product, a colourless oil (450 mg).

The crude product was dissolved in MeOH/HCl (50 mL, 5M) and stirred for 2 h at rt. The crude product was purified by column chromatography on silica (EtOAc). ICEC0324 was obtained as a white solid and recrystallized from EtOAc (42 mg, 18%).

m.p. 123-126° C.; $^1$H NMR (CDCl$_3$, 400 MHz) δ 7.62 (s, 1H), 7.36-7.24 (m, 2H), 7.12-7.04 (m, 2H), 5.14 (s, 1H), 4.53 (s, 2H), 4.22-4.16 (m, 1H), 3.76-3.73 (m, 1H), 3.66-3.37 (m, 3H), 3.07-2.97 (m, 1H), 1.84-1.76 (m, 1H), 1.63-1.55 (m, 1H), 1.28-1.24 (m, 6H); $^{13}$C NMR (CDCl$_3$, 100 MHz) δ 161.7, 159.2, 157.1, 146.5, 140.3, 129.5, 128.9, 125.5, 125.0, 115.7, 111.1, 64.2, 58.3, 49.7, 35.3, 23.8, 23.7, 23.6; IR (neat) ν$_{max}$=3295, 2954, 2869, 1639, 1579; MS m/z (ESI) 388 (M+H). HRMS (ESI) Calc.: ($C_{20}H_{26}FN_5O_2$) 387.2071. Found: 388.2157.

(R)-2-(7-(2-fluorobenzylamino)-3-isopropylpyrazolo[1,5-a]pyrimidin-5-ylamino)butane-1,4-diol (ICEC 0331)

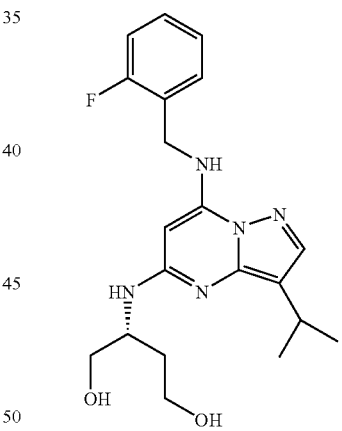

The heteroaryl chloride ICEC0013 (112 mg, 0.28 mmol), Pd$_2$dba$_3$ (13.0 mg, 5 mol %), rac-BINAP (17 mg, 10 mol %), and NaO$^t$Bu (40 mg, 0.42 mmol), were suspended in toluene (1.0 ml). After 5 min of stirring the amine ICEC0330 (112 mg, 0.33 mmol) was added and the red mixture heated for 12 h at 100° C. The reaction mixture was cooled to rt, diluted with EtOAc (2 mL) and poured into brine (5 mL). The aqueous phase was extracted with ethyl acetate (3×5 mL) and the combined organic phases were dried over Na$_2$SO$_4$. After concentration of the crude, the product was separated from other impurities by column chromatography on silica (20:1=PE:EtOAc) to yield a mixture of unprotected and protected coupling product, a colourless oil (158 mg).

The crude product was dissolved in MeOH/HCl (40 mL, 5M) and stirred for 2 h at rt. The crude product was purified by column chromatography on silica (EtOAc). ICEC0331 was obtained as a white solid and recrystallized from EtOAc (44.5 mg, 41%).

$[\alpha]^{25}_D$ (c (0.23, CH$_3$OH): −10.0; m.p. 60-65° C.; $^1$H NMR (CDCl$_3$, 400 MHz) δ 7.67 (s, 1H), 7.36-7.29 (m, 2H), 7.15-7.08 (m, 2H), 6.54-6.51 (m, 1H), 5.09 (s, 1H), 5.05-5.03 (m, 1H), 4.54-4.52 (m, 2H), 4.42-4.33 (m, 1H), 3.87-3.84 (m, 1H), 3.73-3.59 (m, 3H), 3.09 (hept, J=6.9 Hz, 1H), 1.91-1.83 (m, 1H), 1.67-1.59 (m, 1H), 1.30 (d, J=6.9 Hz, 6H); $^{13}$C NMR (CDCl$_3$, 100 MHz) δ 161.9, 159.4, 157.1, 146.6, 144.4, 140.8, 129.7, 129.0, 124.5, 123.7, 115.6, 113.2, 72.9, 66.5, 58.4, 49.9, 39.8, 35.3, 23.5, 23.4, 23.2; IR (neat) ν$_{max}$=3297, 2956, 2869, 1639, 1581; MS m/z (ESI) 388 (M+H). HRMS (ESI) Calc.: (C$_{20}$H$_{26}$FN$_5$O$_2$) 387.2071. Found: 388.2148.

(S)-2-(7-(2-fluorobenzylamino)-3-isopropylpyrazolo[1,5-a]pyrimidin-5-ylamino)btane-1,4-diol (ICEC0329)

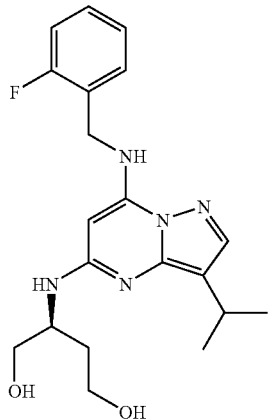

The heteroaryl chloride ICEC0013 (251 mg, 0.60 mmol), Pd$_2$dba$_3$ (25.0 mg, 5 mol %), rac-BINAP (38 mg, 10 mol %), and NaO$^t$Bu (86 mg, 0.42 mmol), were suspended in toluene (1.0 ml). After 5 min of stirring the amine ICEC0328 (240 mg, 0.76 mmol) was added and the red mixture heated for 12 h at 100° C. The reaction mixture was cooled to rt, diluted with EtOAc (2 mL) and poured into brine (5 mL). The aqueous phase was extracted with ethyl acetate (3×5 mL) and the combined organic phases were dried over Na$_2$SO$_4$. After concentration the crude product was separated from other impurities by column chromatography on silica (20:1=PE:EtOAc) to yield a mixture of unprotected and protected coupling product, a colourless oil (205 mg).

The crude product was dissolved in MeOH/HCl (50 mL, 5M) and stirred for 2 h at rt. The crude product was purified by column chromatography on silica (EtOAc). ICEC0329 was obtained as a white solid and recrystallized from EtOAc (38.0 mg, 16%).

$[\alpha]^{25}_D$ (c (0.24 CH$_3$OH): +12.0; m.p. 69-72° C.; $^1$H NMR (CDCl$_3$, 400 MHz) δ 7.67 (s, 1H), 7.36-7.28 (m, 2H), 7.14-7.07 (m, 2H), 6.54-6.51 (m, 1H), 5.08 (s, 1H), 5.06-5.04 (m, 1H), 4.53-4.51 (m, 2H), 4.40-4.32 (m, 1H), 3.87-3.83 (m, 1H), 3.72-3.59 (m, 3H), 3.08 (hept, J=6.9 Hz, 1H), 1.91-1.82 (m, 1H), 1.66-1.59 (m, 1H), 1.30 (d, J=6.9 Hz, 6H); $^{13}$C NMR (CDCl$_3$, 100 MHz) δ 161.8, 159.4, 157.1, 146.6, 144.4, 140.7, 129.7, 129.0, 124.5, 123.7, 115.6, 113.2, 72.9, 66.4, 58.4, 49.9, 39.7, 35.3, 23.5, 23.4, 23.2; IR (neat) ν$_{max}$=3293, 2954, 2869, 1639, 1579; MS m/z (ESI) 388 (M+H). HRMS (ESI) Calc.: (C$_{20}$H$_{26}$FN$_5$O$_2$) 387.2071. Found: 388.2151.

Example 23

Inhibition of MCF-7 Tumor Growth in Nude Mice by BS-194

This example demonstrates the capability of BS-194 to inhibit the growth of MCF-7 tumors in nude mice. In all, 32 female 8- to 10-week Balb/c nude mice (Harlan UK) were randomly divided into three groups. The mice received 0.72 mg 60-day release E2 pellets (Innovative Research of America, USA), subcutaneously implanted in one flank. MCF7 cells, were trypsinized and 5×10$^6$ cells in 0.1 ml of PBS were subcutaneously injected into the other flank of each mouse and tumor volumes were measured every 2-3 days, according to the formula (tumor width squared×tumor length)/2. Animal weight was also recorded throughout the course of the study. The animals were injected subcutaneously with BS-194, prepared in 10% DMSO, 50 mM HCl, 5% Tween 20, and 85% Saline, twice daily for 14 days, at which point the animals were sacrificed. The xenograft experiments were conducted after appropriate ethical approval and licensing was obtained in accordance with the UK 'Guidance on the operation of animals (Scientific Procedure) Act 1986 (HMSO, London, UK, 1990).

Figure 4A:
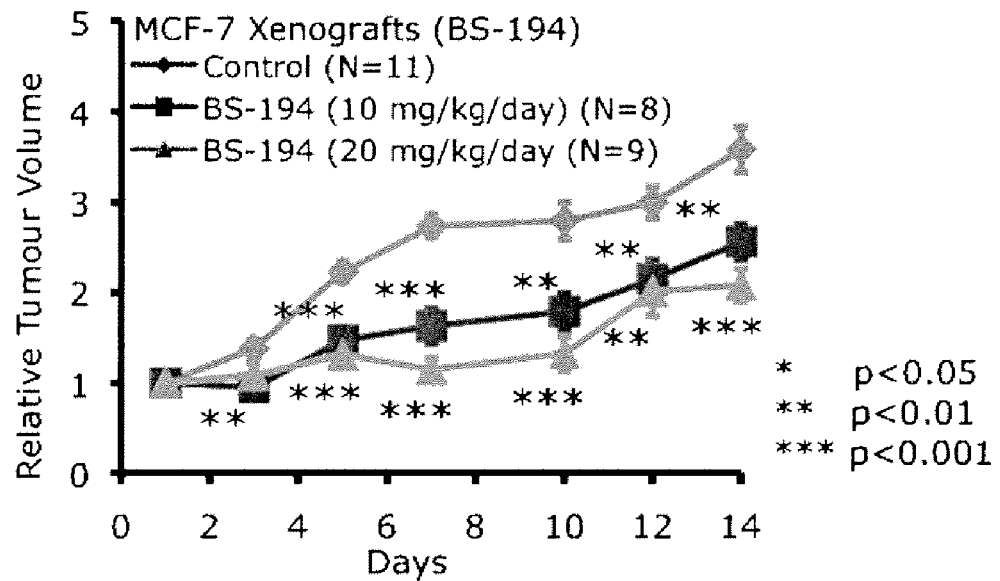
FIG. 4a shows the tumour volume increases over the 14-day course of BS-194 injection, relative to the tumour volume on day 1.
Figure 4B:
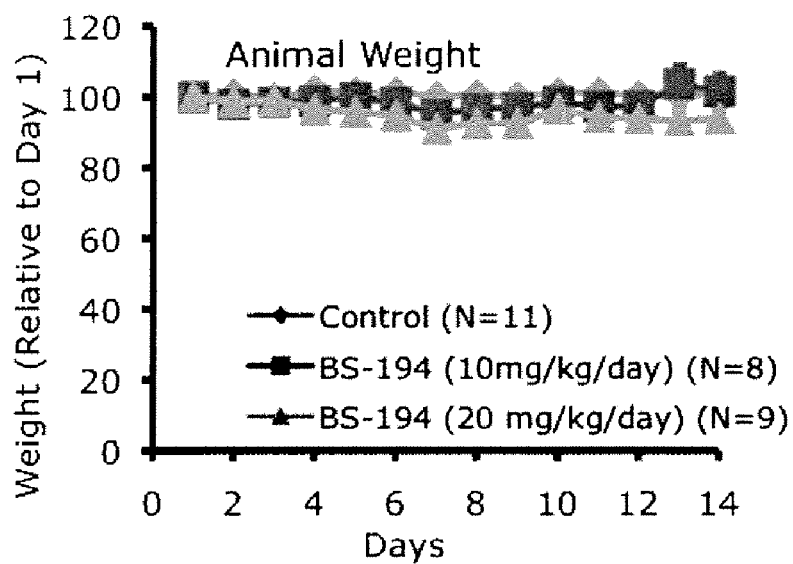
FIG. 4b shows changes in animal weight relative to animal weight on day 1 of the study. Control refers to injections carried out with the solvent alone. The unpaired Student's t-test was used to determine statistical significance. The significance of the differences between the control group and each of the BS-194 treatment groups is depicted by asterisks.
Figure 5A:
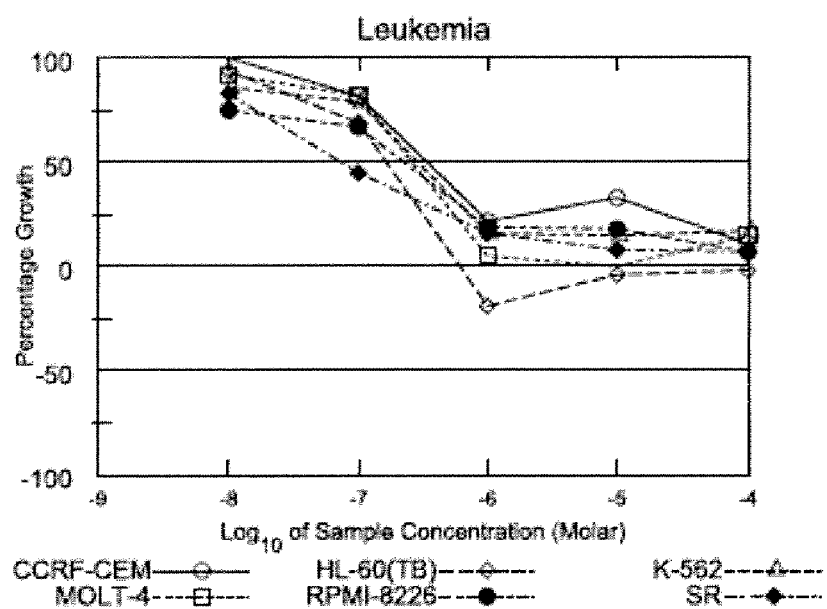
FIG. 5: Plots of percent growth versus log$_{10}$ sample concentation of BS-194 for various cell lines: (a) leukemia; (b) non-small cell lung cancer; (c) colon cancer; (d) CNS cancer; (e) melanoma; (f) ovarian cancer; (g) renal cancer; (h) prostate cancer; (i) breast cancer.
Figure 5B:
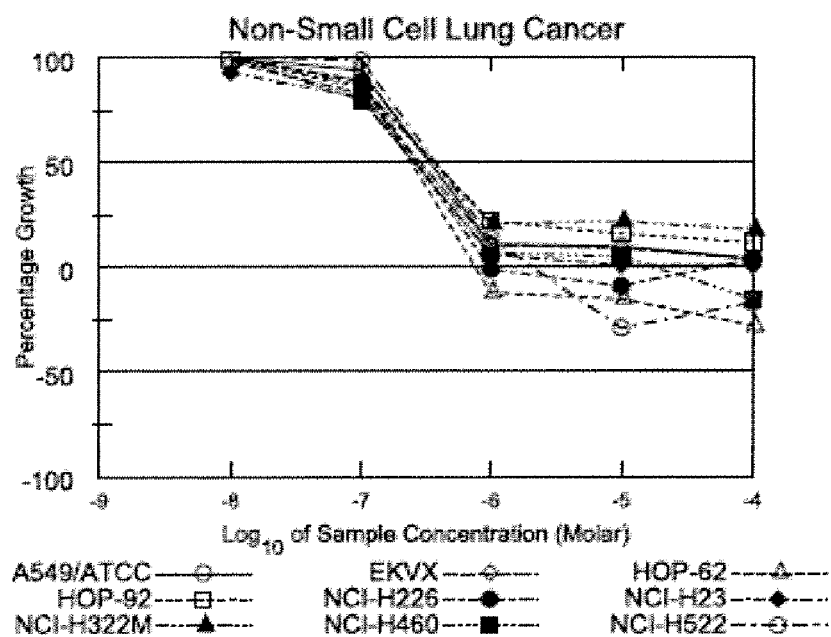
Figure 5C:
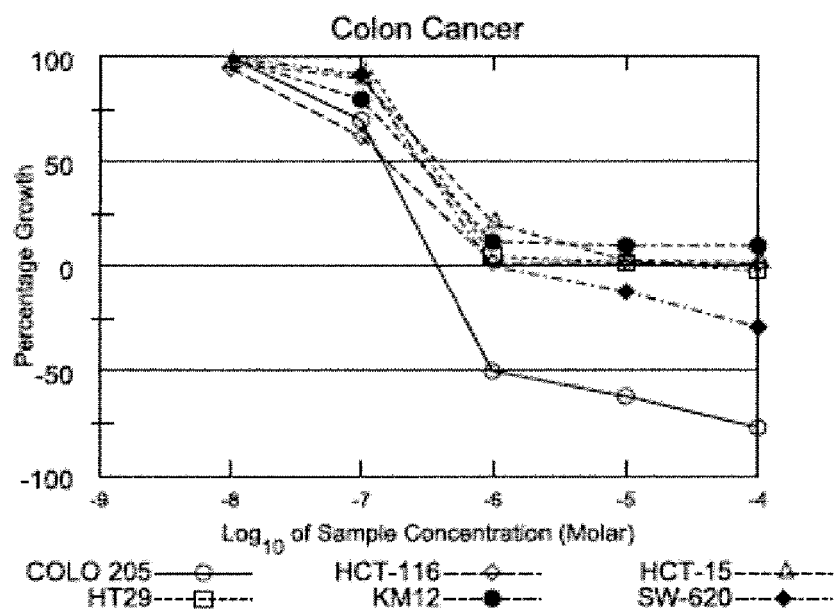
Figure 5D:
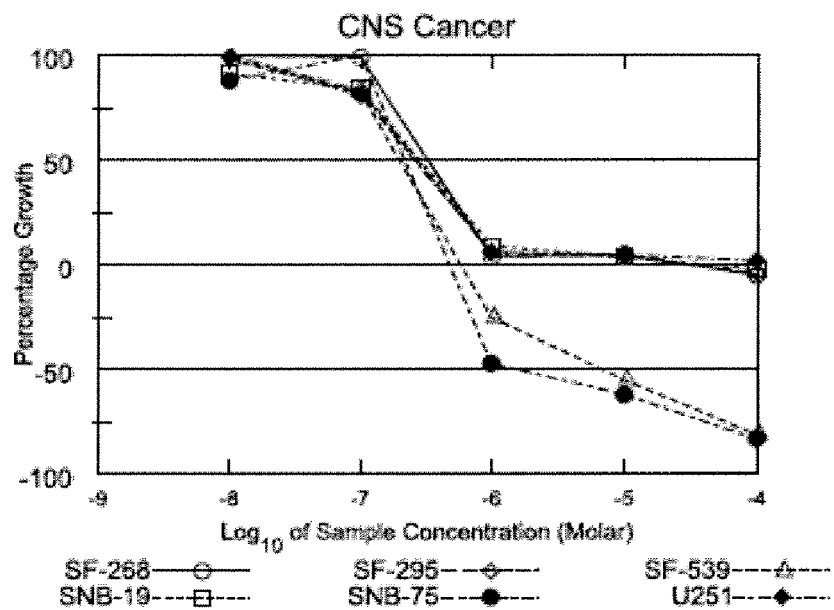
Figure 5E:
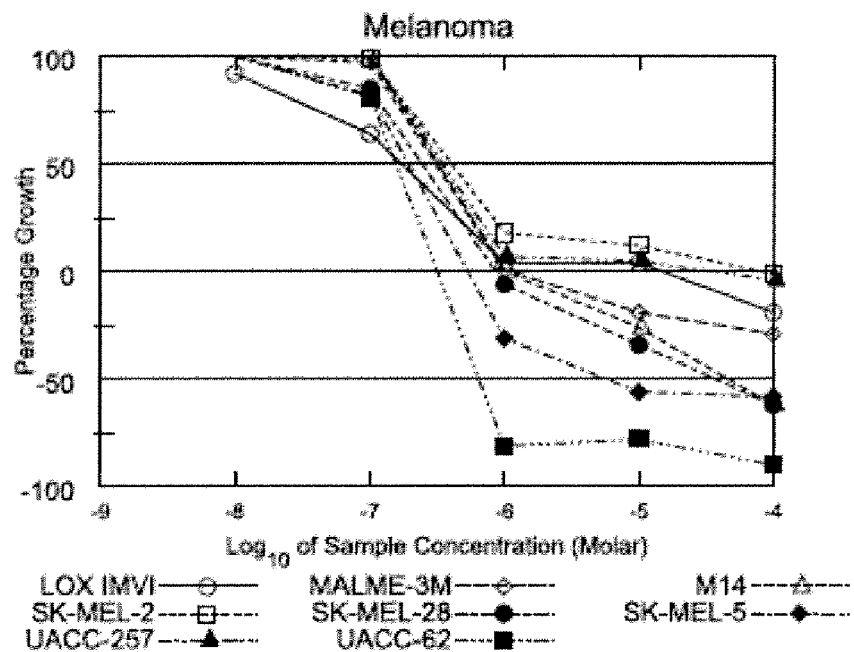
Figure 5F:
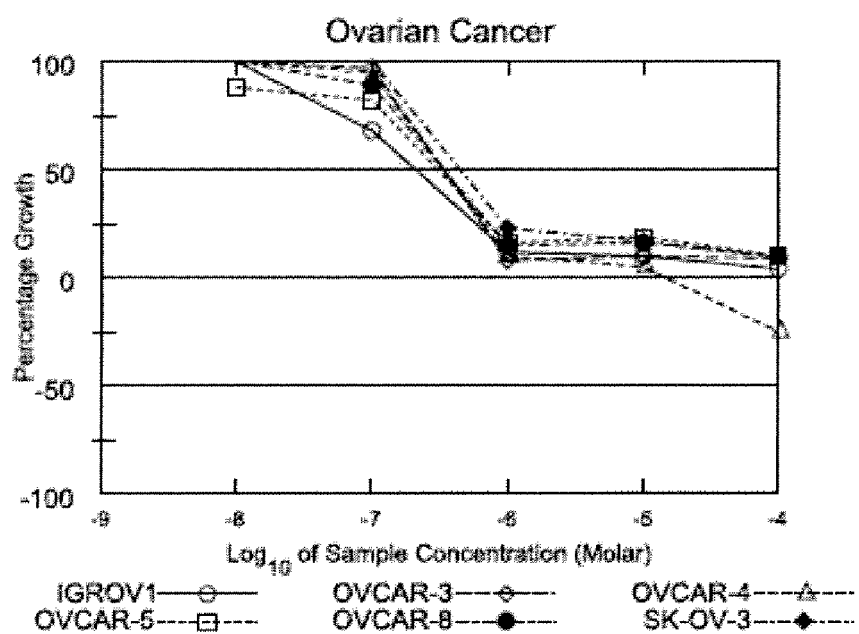
Figure 5G:
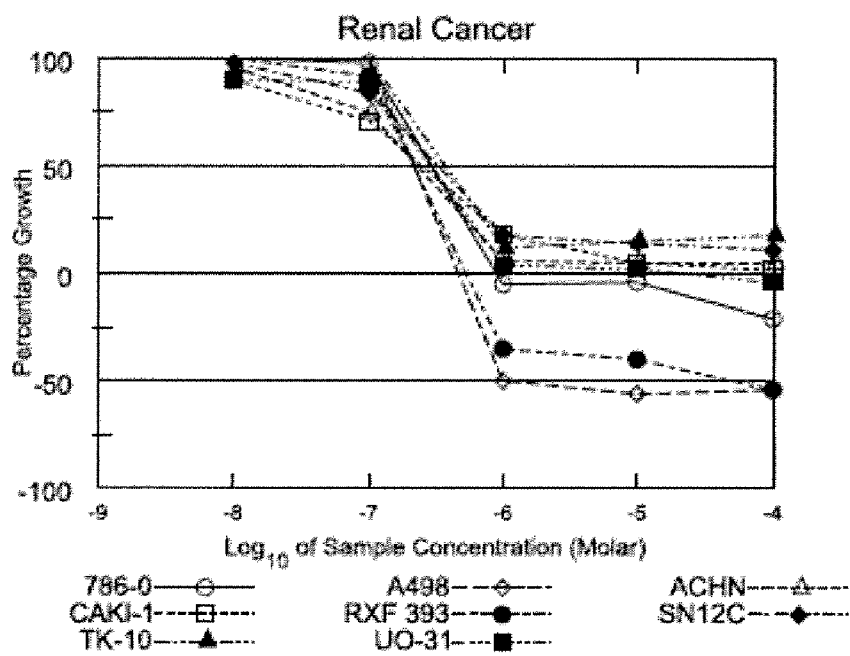
Figure 5H:
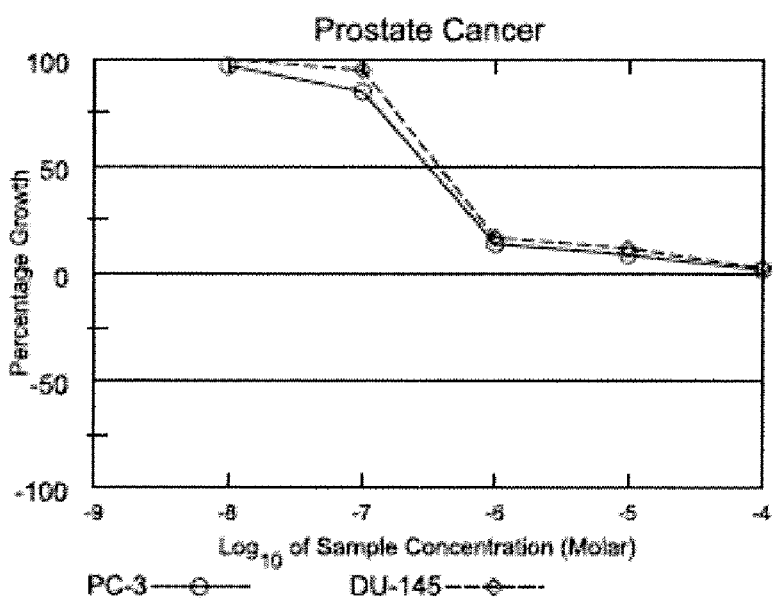
Figure 5I:
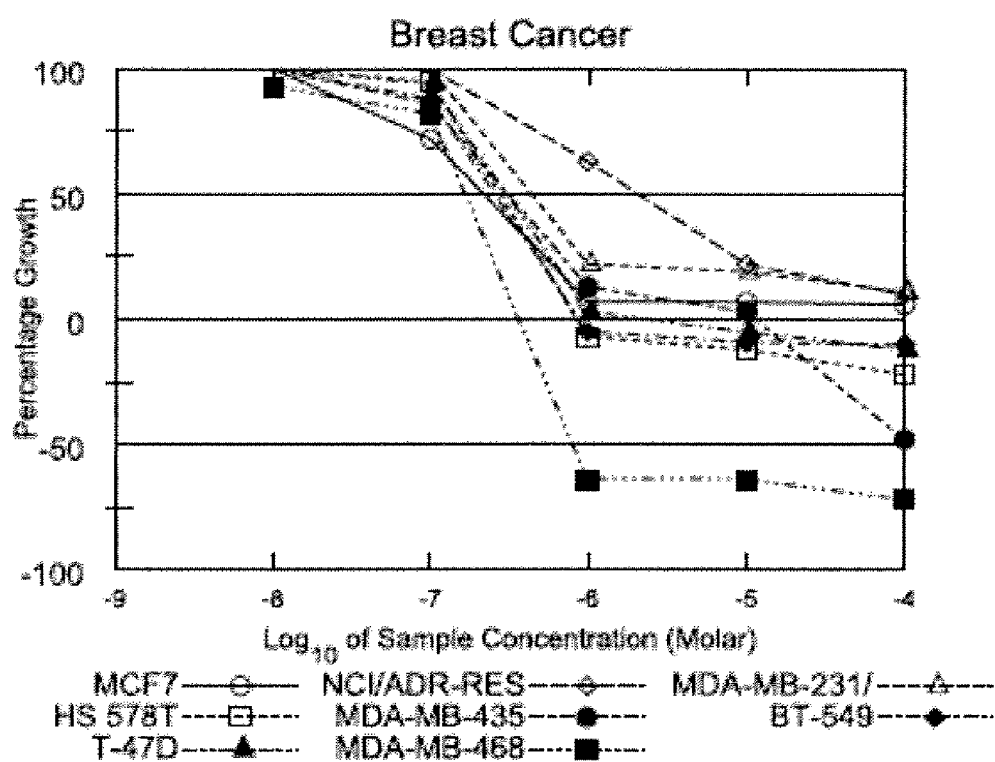

FIG. 4a shows the increase in tumor volume over a 14-day course of BS-194 injection, at different doses relative to the tumor volume on day one. The control curve refers to injections carried out with the solvent alone. FIG. 4b shows the corresponding change in animal weight during the same 14-day course of BS-194 injection. From these data, it is evident that the tumor volume increased more slowly with increasing dosage of BS-194, indicating that BS-194 is capable of inhibiting the growth of MCF-7 tumors. Furthermore, the corresponding animal weight was nearly constant during the 14-day course of BS-194 injection.

Example 24

In Vitro Human Tumor Cell Line Screening for BS-194

This example provides the results of in vitro human tumor cell line screening for BS-194, performed in accordance with the protocols set forth in the National Cancer Institute (NCI)/National Institute of Health (NIH) (see e.g., http://dtp.nci.nih.gov/branches/btb/ivclsp.html).

The human tumor cell lines of the cancer screening panel were grown in RPMI 1640 medium containing 5% fetal bovine serum and 2 mM L-glutamine. For a typical screening experiment, cells were inoculated into 96 well microtiter plates in 100 μL at plating densities ranging from 5,000 to 40,000 cells/well depending on the doubling time of individual cell lines. After cell inoculation, the microtiter plates were incubated at 37° C., 5% CO2, 95% air and 100% relative humidity for 24 h prior to addition of experimental drugs.

After 24 h, two plates of each cell line were fixed in situ with TCA, to represent a measurement of the cell population for each cell line at the time of BS-194 addition (Tz). BS-194 was solubilized in dimethyl sulfoxide at 400-fold the desired final maximum test concentration and stored frozen prior to use. At the time of BS-194 addition, an aliquot of frozen concentrate was thawed and diluted to twice the desired final maximum test concentration with complete medium containing 50 μg/ml gentamicin. Additional four, 10-fold or ½ log serial dilutions were made to provide a total of five BS-194 concentrations plus control. Aliquots of 100 μl of these different BS-194 dilutions were added to the appropriate microtiter wells already containing 100 μl of medium, resulting in the required final drug concentrations.

Following BS-194 addition, the plates were incubated for an additional 48 h at 37° C., 5% CO2, 95% air, and 100% relative humidity. For adherent cells, the assay was terminated by the addition of cold TCA. Cells were fixed in situ by the gentle addition of 50 μl of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 μl) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 μl of 80% TCA (final concentration, 16% TCA). Using the seven absorbance measurements [time zero, (Tz), control growth, (C), and test growth in the presence of BS-194 at the five concentration levels (Ti)], the percentage growth was calculated at each of the drug concentrations levels. Percentage growth inhibition was calculated as:

[(Ti−Tz)/(C−Tz)]×100 for concentrations for which Ti>/=Tz

[(Ti−Tz)/Tz]×100 for concentrations for which Ti<Tz.

Three dose response parameters were calculated. Growth inhibition of 50% (GI50) was calculated from [(Ti−Tz)/(C−Tz)]×100=50, which was the drug concentration resulting in a 50% reduction in the net protein increase (as measured by SRB staining) in control cells during the drug incubation. The drug concentration resulting in total growth inhibition (TGI) was calculated from Ti=Tz. The LC50 (concentration of drug resulting in a 50% reduction in the measured protein at the end of the drug treatment as compwered to that at the beginning) indicating a net loss of cells following treatment was calculated from [(Ti−Tz)/Tz]×100=−50. Values were calculated for each of these three parameters if the level of activity was reached; however, if the effect was not reached or was exceeded, the value for that parameter was expressed as greater or less than the maximum or minimum concentration tested.

TABLE 10

Mean optical densities recorded as a function of dilution of BS-194, for different cell lines.

| Panel/Cell Line | Time Zero | Ctrl | Mean Optical Densities | | | | |
|---|---|---|---|---|---|---|---|
| | | | −8.0 | −7.0 | −6.0 | −5.0 | −4.0 |
| Leukemia | | | | | | | |
| CCRF-CEM | 0.173 | 0.651 | 0.769 | 0.565 | 0.279 | 0.330 | 0.227 |
| HL-60(TB) | 0.504 | 1.121 | 1.084 | 0.932 | 0.407 | 0.484 | 0.495 |
| K-562 | 0.166 | 1.212 | 1.064 | 0.991 | 0.334 | 0.325 | 0.341 |
| MOLT-4 | 0.325 | 1.137 | 1.072 | 0.987 | 0.368 | 0.329 | 0.449 |
| RPMI-8226 | 0.211 | 0.726 | 0.595 | 0.556 | 0.311 | 0.302 | 0.249 |
| SR | 0.209 | 0.615 | 0.548 | 0.394 | 0.275 | 0.244 | 0.239 |
| Non-Small Cell Lung Cancer | | | | | | | |
| A549/ATCC | 0.302 | 1.433 | 1.447 | 1.369 | 0.422 | 0.417 | 0.346 |
| EKVX | 0.691 | 2.066 | 2.035 | 1.830 | 0.841 | 0.817 | 0.740 |
| HOP-62 | 0.465 | 1.255 | 1.312 | 1.165 | 0.412 | 0.393 | 0.336 |
| HOP-92 | 0.529 | 1.052 | 1.050 | 0.981 | 0.645 | 0.612 | 0.594 |
| NCI-H226 | 0.670 | 2.068 | 2.076 | 1.920 | 0.662 | 0.613 | 0.725 |
| NCI-H23 | 0.546 | 1.897 | 1.802 | 1.639 | 0.633 | 0.563 | 0.562 |
| NCI-H322M | 0.698 | 1.807 | 1.904 | 1.663 | 0.927 | 0.941 | 0.893 |
| NCI-H460 | 0.111 | 1.118 | 1.138 | 0.919 | 0.181 | 0.158 | 0.094 |
| NCI-H522 | 0.896 | 2.174 | 2.185 | 2.156 | 1.075 | 0.640 | 0.741 |
| Colon Cancer | | | | | | | |
| COLO 205 | 0.130 | 0.474 | 0.499 | 0.372 | 0.065 | 0.050 | 0.030 |
| HCT-116 | 0.160 | 1.104 | 1.058 | 0.749 | 0.182 | 0.179 | 0.170 |
| HCT-15 | 0.250 | 1.374 | 1.354 | 1.262 | 0.481 | 0.286 | 0.268 |
| HT29 | 0.193 | 1.340 | 1.394 | 1.345 | 0.247 | 0.216 | 0.190 |
| KM12 | 0.235 | 0.943 | 1.036 | 0.802 | 0.318 | 0.304 | 0.305 |
| SW-620 | 0.142 | 0.839 | 0.839 | 0.782 | 0.412 | 0.125 | 0.101 |
| CNS Cancer | | | | | | | |
| SF-268 | 0.423 | 1.243 | 1.291 | 1.234 | 0.452 | 0.460 | 0.404 |
| SF-295 | 0.386 | 1.476 | 1.492 | 1.288 | 0.447 | 0.427 | 0.371 |
| SF-539 | 0.724 | 2.214 | 2.183 | 1.950 | 0.540 | 0.327 | 0.138 |
| SNB-19 | 0.501 | 1.390 | 1.309 | 1.247 | 0.580 | 0.537 | 0.492 |
| SNB-75 | 0.425 | 0.904 | 0.848 | 0.911 | 0.226 | 0.162 | 0.072 |
| U251 | 0.240 | 1.175 | 1.168 | 0.999 | 0.299 | 0.289 | 0.262 |
| Melanoma | | | | | | | |
| LOX IMVI | 0.275 | 1.728 | 1.614 | 1.208 | 0.326 | 0.328 | 0.224 |
| MALME-3M | 0.562 | 0.917 | 0.958 | 1.008 | 0.565 | 0.458 | 0.398 |
| M14 | 0.333 | 1.054 | 1.074 | 1.032 | 0.333 | 0.246 | 0.125 |
| SK-MEL-2 | 1.073 | 2.282 | 2.282 | 2.275 | 1.290 | 1.218 | 1.061 |
| SK-MEL-28 | 0.300 | 0.807 | 0.816 | 0.733 | 0.284 | 0.198 | 0.114 |
| SK-MEL-5 | 0.617 | 2.348 | 2.375 | 2.036 | 0.427 | 0.275 | 0.260 |
| UACC-257 | 0.880 | 1.890 | 1.906 | 1.891 | 0.948 | 0.933 | 0.848 |
| UACC-62 | 0.745 | 2.079 | 2.110 | 1.821 | 0.142 | 0.165 | 0.078 |
| Ovarian Cancer | | | | | | | |
| IGROV1 | 0.413 | 1.401 | 1.429 | 1.088 | 0.528 | 0.510 | 0.451 |
| OVCAR-3 | 0.272 | 0.713 | 0.795 | 0.700 | 0.306 | 0.317 | 0.313 |
| OVCAR-4 | 0.359 | 1.175 | 1.246 | 1.138 | 0.445 | 0.399 | 0.269 |
| OVCAR-5 | 0.544 | 1.301 | 1.211 | 1.165 | 0.665 | 0.688 | 0.618 |
| OVCAR-8 | 0.557 | 2.145 | 2.165 | 1.975 | 0.803 | 0.810 | 0.723 |
| SK-OV-3 | 0.733 | 1.469 | 1.504 | 1.701 | 0.903 | 0.860 | 0.799 |
| Renal Cancer | | | | | | | |
| 786-0 | 0.621 | 1.793 | 1.824 | 1.769 | 0.592 | 0.598 | 0.491 |
| A498 | 0.836 | 1.279 | 1.280 | 1.321 | 0.414 | 0.365 | 0.386 |
| ACHN | 0.291 | 1.339 | 1.302 | 1.080 | 0.358 | 0.347 | 0.343 |
| CAKI-1 | 0.352 | 0.745 | 0.704 | 0.631 | 0.423 | 0.372 | 0.358 |
| RXF 393 | 0.514 | 0.965 | 0.980 | 0.928 | 0.333 | 0.308 | 0.239 |
| SN12C | 0.385 | 1.724 | 1.702 | 1.515 | 0.620 | 0.578 | 0.531 |
| TK-10 | 0.486 | 1.183 | 1.202 | 1.192 | 0.572 | 0.593 | 0.610 |
| UO-31 | 0.541 | 1.471 | 1.378 | 1.371 | 0.578 | 0.557 | 0.522 |
| Prostate Cancer | | | | | | | |
| PC-3 | 0.164 | 0.542 | 0.532 | 0.486 | 0.218 | 0.200 | 0.173 |
| DU-145 | 0.188 | 0.714 | 0.732 | 0.688 | 0.277 | 0.250 | 0.204 |
| Breast Cancer | | | | | | | |
| MCF7 | 0.181 | 1.042 | 1.098 | 0.805 | 0.244 | 0.237 | 0.229 |
| NCI/ADR-RES | 0.420 | 1.515 | 1.587 | 1.638 | 1.107 | 0.657 | 0.531 |
| MDA-MB-231/ATCC | 0.414 | 1.034 | 1.087 | 1.039 | 0.548 | 0.529 | 0.482 |
| HS 578T | 0.401 | 0.824 | 0.867 | 0.803 | 0.373 | 0.352 | 0.314 |
| MDA-MB-435 | 0.463 | 1.999 | 2.132 | 1.781 | 0.659 | 0.511 | 0.242 |
| BT-549 | 0.888 | 1.884 | 1.968 | 1.769 | 0.843 | 0.805 | 0.803 |
| T-47D | 0.542 | 1.242 | 1.266 | 1.199 | 0.565 | 0.516 | 0.479 |
| MDA-MB-468 | 0.425 | 0.987 | 0.946 | 0.884 | 0.154 | 0.153 | 0.121 |

TABLE 11

Percent growth of cells for various cell lines, at different log₁₀ concentrations of BS-194.

| Panel/Cell Line | Percent Growth | | | | |
|---|---|---|---|---|---|
| | −8.0 | −7.0 | −6.0 | −5.0 | −4.0 |
| Leukemia | | | | | |
| CCRF-CEM | 125 | 82 | 22 | 33 | 11 |
| HL-60(TB) | 94 | 69 | −19 | −4 | −2 |
| K-562 | 86 | 79 | 16 | 15 | 17 |
| MOLT-4 | 92 | 82 | 5 | — | 15 |
| RPMI-8226 | 75 | 67 | 19 | 18 | 7 |
| SR | 83 | 45 | 16 | 8 | 7 |
| Non-Small Cell Lung Cancer | | | | | |
| A549/ATCC | 101 | 94 | 11 | 10 | 4 |
| EKVX | 98 | 83 | 11 | 9 | 4 |
| HOP-62 | 107 | 89 | −12 | −15 | −28 |
| HOP-92 | 99 | 86 | 22 | 16 | 12 |
| NCI-H226 | 101 | 89 | −1 | −9 | 4 |
| NCI-H23 | 93 | 81 | 6 | 1 | 1 |
| NCI-H322M | 109 | 87 | 21 | 22 | 18 |
| NCI-H460 | 102 | 80 | 7 | 5 | −15 |
| NCI-H522 | 101 | 99 | 14 | −29 | −17 |
| Colon Cancer | | | | | |
| COLO 205 | 107 | 70 | −50 | −62 | −77 |
| HCT-116 | 95 | 62 | 2 | 2 | 1 |
| HCT-15 | 98 | 90 | 21 | 3 | 2 |
| HT29 | 105 | 100 | 5 | 2 | −2 |
| KM12 | 113 | 80 | 12 | 10 | 10 |
| SW-620 | 100 | 92 | — | −12 | −29 |
| CNS Cancer | | | | | |
| SF-268 | 106 | 99 | 4 | 5 | −5 |
| SF-295 | 101 | 83 | 6 | 4 | −4 |
| SF-539 | 98 | 82 | −25 | −55 | −81 |
| SNB-19 | 91 | 84 | 9 | 4 | −2 |
| SNB-75 | 88 | 101 | −47 | −62 | −83 |
| U251 | 99 | 81 | 6 | 5 | 2 |
| Melanoma | | | | | |
| LOX IMVI | 92 | 64 | 4 | 4 | −19 |
| MALME-3M | 112 | 126 | 1 | −19 | −29 |
| M14 | 103 | 97 | — | −26 | −62 |
| SK-MEL-2 | 100 | 99 | 18 | 12 | −1 |
| SK-MEL-28 | 102 | 85 | −6 | −34 | −62 |
| SK-MEL-5 | 102 | 82 | −31 | −56 | −58 |
| UACC-257 | 102 | 100 | 7 | 5 | −4 |
| UACC-62 | 102 | 81 | −81 | −78 | −90 |
| Ovarian Cancer | | | | | |
| IGROV1 | 103 | 68 | 12 | 10 | 4 |
| OVCAR-3 | 118 | 97 | 8 | 10 | 9 |
| OVCAR-4 | 109 | 95 | 10 | 5 | −25 |
| OVCAR-5 | 88 | 82 | 16 | 19 | 10 |
| OVCAR-8 | 101 | 89 | 15 | 16 | 10 |
| SK-OV-3 | 105 | 132 | 23 | 17 | 9 |
| Renal Cancer | | | | | |
| 786-0 | 103 | 98 | −5 | −4 | −21 |
| A498 | 100 | 109 | −50 | −56 | −54 |
| ACHN | 96 | 75 | 6 | 5 | 5 |
| CAKI-1 | 90 | 71 | 18 | 5 | 2 |
| RXF 393 | 103 | 92 | −35 | −40 | −54 |
| SN12C | 98 | 84 | 18 | 14 | 11 |
| TK-10 | 103 | 101 | 12 | 15 | 18 |
| UO-31 | 90 | 89 | 4 | 2 | −4 |
| Prostate Cancer | | | | | |
| PC-3 | 97 | 85 | 14 | 9 | 2 |
| DU-145 | 103 | 95 | 17 | 12 | 3 |
| Breast Cancer | | | | | |
| MCF7 | 107 | 72 | 7 | 7 | 6 |
| NCI/ADR-RES | 107 | 111 | 63 | 22 | 10 |
| MDA-MB-231/ | 109 | 101 | 22 | 19 | 11 |
| ATCC | | | | | |
| HS 578T | 110 | 95 | −7 | −12 | −22 |
| MDA-MB-435 | 109 | 86 | 13 | 3 | −48 |
| BT-549 | 108 | 88 | −5 | −9 | −10 |
| T-47D | 103 | 94 | 3 | −5 | −12 |
| MDA-MB-468 | 93 | 82 | −64 | −64 | −72 |

TABLE 12

GI50, TGI, and LC50 values of BS-194 for various cell lines.

| Panel | Cell Line | | |
|---|---|---|---|
| | GI50 | TGI | LC50 |
| Leukemia | | | |
| CCRF-CEM | 3.42E-7 | >1.00E-4 | >1.00E-4 |
| HL-60(TB) | 1.66E-7 | 6.07E-7 | >1.00E-4 |
| K-562 | 2.88E-7 | >1.00E-4 | >1.00E-4 |
| MOLT-4 | 2.59E-7 | >1.00E-4 | >1.00E-4 |
| RPMI-8226 | 2.27E-7 | >1.00E-4 | >1.00E-4 |
| SR | 7.58E-8 | >1.00E-4 | >1.00E-4 |
| Non-Small Cell Lung Cancer | | | |
| A549/ATCC | 3.38E-7 | >1.00E-4 | >1.00E-4 |
| EKVX | 2.86E-7 | >1.00E-4 | >1.00E-4 |
| HOP-62 | 2.43E-7 | 7.68E-7 | >1.00E-4 |
| HOP-92 | 3.69E-7 | >1.00E-4 | >1.00E-4 |
| NCI-H226 | 2.72E-7 | — | >1.00E-4 |
| NCI-H23 | 2.60E-7 | >1.00E-4 | >1.00E-4 |
| NCI-H322M | 3.61E-7 | >1.00E-4 | >1.00E-4 |
| NCI-H460 | 2.58E-7 | 1.71E-5 | >1.00E-4 |
| NCI-H522 | 3.75E-7 | 2.13E-6 | >1.00E-4 |
| Colon Cancer | | | |
| COLO 205 | 1.47E-7 | 3.82E-7 | 9.93E-7 |
| HCT-116 | 1.61E-7 | >1.00E-4 | >1.00E-4 |
| HCT-15 | 3.77E-7 | >1.00E-4 | >1.00E-4 |
| HT29 | 3.36E-7 | 3.66E-5 | >1.00E-4 |
| KM12 | 2.75E-7 | >1.00E-4 | >1.00E-4 |
| SW-620 | 2.85E-7 | 1.00E-6 | >1.00E-4 |
| CNS Cancer | | | |
| SF-268 | 3.26E-7 | 3.12E-5 | >1.00E-4 |
| SF-295 | 2.66E-7 | 3.10E-5 | >1.00E-4 |
| SF-539 | 1.99E-7 | 5.81E-7 | 6.85E-6 |
| SNB-19 | 2.83E-7 | 4.89E-5 | >1.00E-4 |
| SNB-75 | 2.22E-7 | 4.82E-7 | 1.60E-6 |
| U251 | 2.61E-7 | >1.00E-4 | >1.00E-4 |
| Melanoma | | | |
| LOX IMVI | 1.71E-7 | 1.46E-5 | >1.00E-4 |
| MALME-3M | 4.04E-7 | 1.09E-6 | >1.00E-4 |
| M14 | 3.05E-7 | 1.00E-6 | 4.52E-5 |
| SK-MEL-2 | 4.04E-7 | 8.22E-5 | >1.00E-4 |
| SK-MEL-28 | 2.45E-7 | 8.70E-7 | 3.71E-5 |
| SK-MEL-5 | 1.92E-7 | 5.33E-7 | 5.98E-6 |
| UACC-257 | 3.44E-7 | 3.88E-5 | >1.00E-4 |
| UACC-62 | 1.55E-7 | 3.16E-7 | 6.44E-7 |
| Ovarian Cancer | | | |
| IGROV1 | 2.10E-7 | >1.00E-4 | >1.00E-4 |
| OVCAR-3 | 3.35E-7 | >1.00E-4 | >1.00E-4 |
| OVCAR-4 | 3.43E-7 | 1.45E-5 | >1.00E-4 |
| OVCAR-5 | 3.05E-7 | >1.00E-4 | >1.00E-4 |
| OVCAR-8 | 3.40E-7 | >1.00E-4 | >1.00E-4 |
| SK-OV-3 | 5.65E-7 | >1.00E-4 | >1.00E-4 |

TABLE 12-continued

GI50, TGI, and LC50 values of BS-194 for various cell lines.

| Panel | G150 | TGI | LC50 |
|---|---|---|---|
| Renal Cancer | | | |
| 786-0 | 2.93E−7 | 8.99E−7 | >1.00E−4 |
| A498 | 2.35E−7 | 4.83E−7 | 9.93E−7 |
| ACHN | 2.33E−7 | >1.00E−4 | >1.00E−4 |
| CAKI-1 | 2.49E−7 | >1.00E−4 | >1.00E−4 |
| RXF 393 | 2.13E−7 | 5.27E−7 | 5.46E−5 |
| SN12C | 3.27E−7 | >1.00E−4 | >1.00E−4 |
| TK-10 | 3.77E−7 | >1.00E−4 | >1.00E−4 |
| UO-31 | 2.89E−7 | 2.07E−5 | >1.00E−4 |
| Prostate Cancer | | | |
| PC-3 | 3.14E−7 | >1.00E−4 | >1.00E−4 |
| DU-145 | 3.77E−7 | >1.00E−4 | >1.00E−4 |
| Breast Cancer | | | |
| MCF7 | 2.21E−7 | >1.00E−4 | >1.00E−4 |
| NCI/ADR-RES | 2.04E−6 | >1.00E−4 | >1.00E−4 |
| MDA-MB-231/ATCC | 4.38E−7 | >1.00E−4 | >1.00E−4 |
| HS 578T | 2.76E−7 | 8.54E−7 | >1.00E−4 |
| MDA-MB-435 | 3.09E−7 | 1.15E−5 | >1.00E−4 |
| BT-549 | 2.58E−7 | 8.82E−7 | >1.00E−4 |
| T-47D | 3.05E−7 | 2.55E−6 | >1.00E−4 |
| MDA-MB-468 | 1.65E−7 | 3.64E−7 | 8.03E−7 |

Example 25

Kinase Screen for BS-193, BS-194, BS-189, and ICEC-0232

In this example, recombinant kinases were tested in duplicate for enzyme activity. Assays were done using the protocols set forth in Example 18. Table 13 shows the mean activities remaining (as a percentage of the original activity) following the addition of 10 μM of BS-193, BS-194, BS-189, or ICEC-0232. For each labelled column reporting mean activities, the unlabelled column immediately to the right corresponds to the respective standard deviations of the mean activity measurement. From these experiments, the two kinases that showed the greatest degree of inhibition were determined to be CDK2 and CK1.

TABLE 13

Kinase assays for BS-103, BS-194, BS-189, and ICEC-0232. The values reported are mean activities remaining (as a percentage of the original activity) following the

| Concentration (micromolar) | BS-193 10 | | BS-194 10 | | BS-189 10 | | ICEC-0232 10 | |
|---|---|---|---|---|---|---|---|---|
| MKK1 | 44 | 13 | 65 | 15 | 107 | 2 | 83 | 2 |
| ERK1 | 69 | 11 | 42 | 15 | 84 | 6 | 90 | 32 |
| ERK2 | 59 | 5 | 26 | 4 | 59 | 13 | 70 | 53 |
| JNK1 | 98 | 10 | 93 | 3 | 95 | 5 | 87 | 5 |
| JNK2 | 97 | 1 | 94 | 12 | 88 | 9 | 89 | 2 |
| p38a2 MAPK | 99 | 11 | 98 | 12 | 94 | 6 | 86 | 10 |
| p38b MAPK | 98 | 3 | 94 | 3 | 104 | 2 | 102 | 14 |
| p38g MAPK | 82 | 9 | 112 | 14 | 108 | 3 | 91 | 13 |
| p38s MAPK | 86 | 3 | 86 | 0 | 86 | 3 | 78 | 5 |
| ERK8 | 23 | 4 | 26 | 4 | 28 | 1 | 23 | 4 |
| RSK1 | 62 | 12 | 75 | 15 | 79 | 3 | 24 | 15 |
| RSK2 | 76 | 11 | 90 | 1 | 84 | 9 | 19 | 4 |
| PDK1 | 87 | 13 | 84 | 11 | 78 | 6 | 101 | 8 |
| PKBa | 109 | 14 | 103 | 6 | 116 | 8 | 75 | 14 |
| PKBb | 102 | 5 | 105 | 9 | 109 | 15 | 76 | 23 |
| SGK1 | 89 | 6 | 92 | 1 | 84 | 3 | 50 | 14 |
| S6K1 | 74 | 8 | 77 | 0 | 78 | 6 | 42 | 3 |
| PKA | 93 | 10 | 93 | 2 | 107 | 12 | 96 | 6 |
| ROCK 2 | 85 | 10 | 102 | 14 | 95 | 9 | 86 | 2 |
| PRK2 | 96 | 12 | 106 | 3 | 105 | 3 | 106 | 3 |
| PKCa | 93 | 4 | 96 | 4 | 101 | 1 | 80 | 13 |
| PKC zeta | 76 | 2 | 64 | 14 | 84 | 4 | 65 | 5 |
| PKD1 | 87 | 6 | 97 | 15 | 88 | 0 | 32 | 1 |
| MSK1 | 86 | 10 | 96 | 1 | 88 | 8 | 42 | 0 |
| MNK1 | 86 | 2 | 98 | 3 | 90 | 0 | 97 | 8 |
| MNK2 | 84 | 7 | 136 | 15 | 83 | 7 | 88 | 4 |
| MAPKAP-K2 | 110 | 14 | 111 | 14 | 111 | 2 | 88 | 2 |
| PRAK | 94 | 7 | 97 | 8 | 86 | 4 | 97 | 3 |
| CAMK Kb | 29 | 1 | 23 | 1 | 31 | 2 | 18 | 3 |
| CAMK 1 | 84 | 7 | 93 | 5 | 89 | 0 | 29 | 0 |
| SmMLCK | 81 | 15 | 101 | 13 | 92 | 14 | 38 | 3 |
| PHK | 68 | 0 | 62 | 8 | 68 | 12 | 10 | 1 |
| CHK 1 | 100 | 6 | 98 | 8 | 87 | 3 | 87 | 6 |
| CHK 2 | 70 | 12 | 61 | 5 | 81 | 3 | 15 | 1 |
| GSK 3b | 72 | 7 | 63 | 15 | 92 | 10 | 70 | 12 |
| CDK 2 - Cyclin A | 5 | 2 | 3 | 0 | 3 | 0 | 9 | 1 |
| PLK 1 | 64 | 15 | 68 | 4 | 56 | 0 | 55 | 8 |
| PLK 1 (Okadaic Acid) | 93 | 11 | 97 | 14 | 104 | 7 | 125 | 14 |
| AMPK | 84 | 2 | 88 | 1 | 85 | 7 | 75 | 9 |
| MARK 3 | 89 | 2 | 82 | 4 | 93 | 0 | 96 | 13 |
| BRSK 2 | 76 | 4 | 108 | 14 | 76 | 3 | 81 | 8 |
| MELK | 75 | 10 | 88 | 1 | 90 | 1 | 62 | 8 |
| CK 1 | 16 | 2 | 19 | 1 | 19 | 1 | 9 | 1 |
| CK 2 | 87 | 1 | 89 | 7 | 94 | 5 | 92 | 6 |
| DYRK 1A | 27 | 0 | 15 | 3 | 30 | 4 | 11 | 0 |
| DYRK 2 | 90 | 15 | 75 | 1 | 90 | 3 | 68 | 4 |
| DYRK 3 | 90 | 11 | 88 | 1 | 86 | 0 | 60 | 8 |
| NEK 2a | 75 | 4 | 102 | 3 | 96 | 15 | 83 | 6 |
| NEK 6 | 101 | 0 | 87 | 15 | 105 | 1 | 74 | 2 |
| IKKb | 84 | 9 | 80 | 3 | 81 | 9 | 84 | 7 |
| PIM1 | 107 | 7 | 103 | 6 | 113 | 4 | 110 | 11 |
| PIM2 | 92 | 5 | 94 | 1 | 93 | 4 | 102 | 1 |
| PIM3 | 96 | 2 | 101 | 5 | 100 | 1 | 76 | 2 |
| SRPK1 | 50 | 1 | 62 | 14 | 84 | 14 | 38 | 12 |
| MST2 | 89 | 5 | 86 | 8 | 87 | 6 | 82 | 3 |
| EFK2 | 95 | 2 | 92 | 1 | 97 | 10 | 98 | 7 |
| HIPK2 | 70 | 1 | 73 | 6 | 70 | 13 | 49 | 9 |
| PAK4 | 75 | 5 | 55 | 7 | 82 | 15 | 58 | 1 |
| PAK5 | 89 | 15 | 65 | 3 | 81 | 2 | 81 | 11 |
| PAK6 | 78 | 4 | 85 | 6 | 82 | 0 | 85 | 7 |
| Src | 90 | 5 | 95 | 13 | 112 | 13 | 96 | 2 |
| Lck | 70 | 6 | 85 | 2 | 74 | 6 | 62 | 11 |
| CSK | 77 | 5 | 77 | 1 | 77 | 0 | 78 | 12 |
| FGF-R1 | 78 | 0 | 86 | 2 | 87 | 7 | 82 | 9 |
| IRR | 23 | 0 | 32 | 11 | 24 | 2 | 29 | 1 |
| EPH A2 | 101 | 8 | 116 | 10 | 109 | 6 | 92 | 4 |
| MST4 | 103 | 15 | 92 | 14 | 91 | 5 | 85 | 6 |
| SYK | 104 | 6 | 120 | 11 | 104 | 5 | 84 | 8 |
| YES1 | 87 | 10 | 89 | 7 | 90 | 12 | 106 | 15 |
| IKKe | 103 | 1 | 94 | 7 | 101 | 8 | 92 | 7 |
| TBK1 | 85 | 0 | 87 | 8 | 83 | 2 | 91 | 8 |
| IGF1-R | 63 | 14 | 67 | 15 | 63 | 6 | 17 | 7 |
| VEG-FR | 99 | 12 | 92 | 8 | 101 | 1 | 105 | 3 |
| BTK | 84 | 5 | 91 | 8 | 94 | 10 | 90 | 2 |
| IR-HIS | 78 | 4 | 70 | 2 | 71 | 4 | 58 | 6 |
| EPH-B3 | 79 | 6 | 72 | 13 | 83 | 5 | 88 | 1 |

The invention claimed is:

1. A composition comprising a compound of the following general formula:

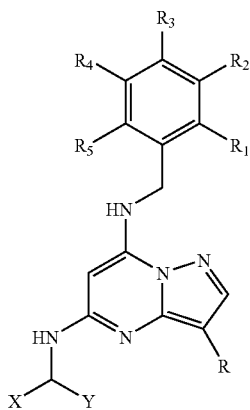

wherein

R represents a hydrocarbyl containing from 1 to 6 carbon atoms;

$R^1$ represents a hydroxyl, alkoxy, hydrogen, or halogen;

$R^2$ represents a hydrogen, an alkanyl, —$NR_aR_b$ where $R_a$ and $R_b$ are independently optionally substituted hydrocarbyls having up to six carbon atoms, an alkoxy chain having from 1 to 6 carbon atoms, —$SR_c$ where $R_c$ is a hydrocarbyl containing from one to six carbon atoms, —$SO_2R_4$ where Rd is a hydrocarbyl containing from one to six carbon atoms, or a halogen;

$R^3$ is hydrogen, —$SO_2NH_2$, —$SO_2NR_eR_f$ where $R_e$ and $R_f$ are independently optionally substituted hydrocarbyls having up to 6 carbon atoms, halogen or a group -$(A)_a$-$Alk^1$ wherein a is 0 or 1, and when a is 1, A is —O—, —S—, or —$NR^6$ wherein $R^6$ is hydrogen or a $C_1$-$C_5$ alkanyl chain, and $Alk^1$ is an optionally substituted divalent hydrocarbyl chain containing from 1 to 6 carbon atoms in length and optionally unsaturated bonds between at least two carbon atoms of $Alk^1$ when $Alk^1$ contains at least two carbon atoms;

$R^4$ represents hydrogen, halogen, alkoxy, hydroxy, or an optionally substituted hydrocarbyl group containing up to 6 carbon atoms;

$R^5$ represents a hydrogen, hydroxyl, alkoxy, a linear, branched, or cyclic chain with between 1 and 8 carbon atoms, or halogen;

X represents a hydrogen, a group -$Alk^2$-Z, $C_1$-$C_4$ hydrocarbyl group or halogen, wherein $Alk^2$ is an optionally substituted divalent alkanyl, alkenyl, or alkynyl chain containing from 1 to 6 carbon atoms in length; and Z represents an —OH, —$OR^7$, —SH, $SR^7$, —CN, —$NH_2$, or $NHR^7$ group, wherein $R^7$ is a $C_1$-$C_6$ hydrocarbyl or heterocyclic group optionally substituted by halogen or alkoxy;

Y represents a group -$Alk^3$-$(Q)_a$-$Alk^4$-B, wherein a is 0 or 1, and wherein $Alk^3$ represents a hydrocarbyl chain containing from 2 to 7 carbon atoms in length, wherein said hydrocarbyl chain optionally comprises double and/or triple bonds in between carbon atoms of said hydrocarbyl chain, and wherein said hydrocarbyl chain is optionally substituted with a halogen, alkoxy, or an alkyl chain that itself is optionally substituted with halogen, hydroxyl, or alkoxy groups;

Q is selected from the group consisting of —CH$_2$—, —O—, —S—, —NR—, —S(O$_2$)—, —C(=O)—, and —S(O)—;

Alk$^4$ is an alkanyl chain; and

B is hydroxyl, alkoxy, halogen, alkylthio, nitro, cyano, amine, an optionally substituted carbocyclic group, an optionally substituted heterocyclic group, and wherein X and Y, along with the carbon atom joining X and Y, do not form an unsubstituted C$_1$ to C$_6$ alkyl.

2. The composition according to claim 1, wherein the compound is selected from the group consisting of:

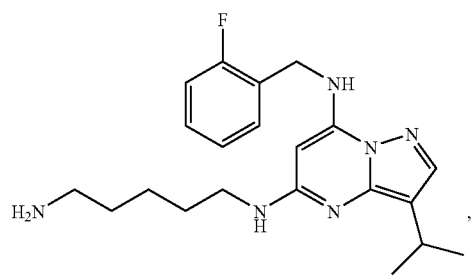
,

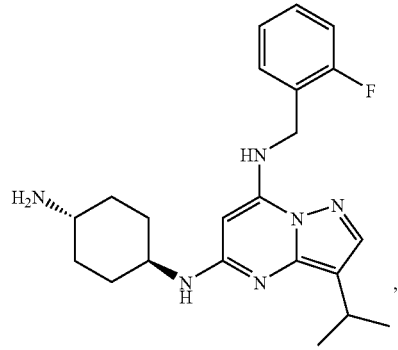
,

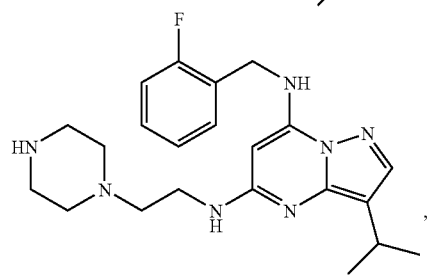
,

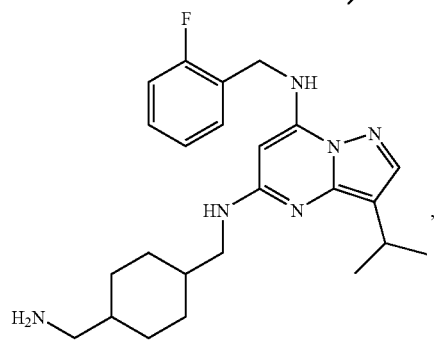
,

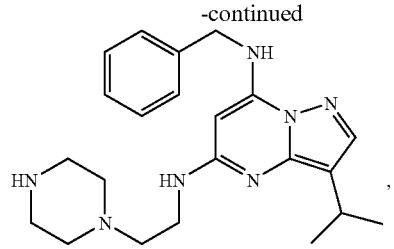
,

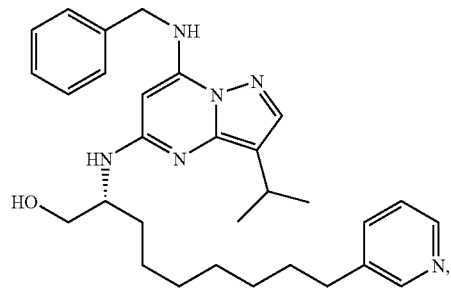
,

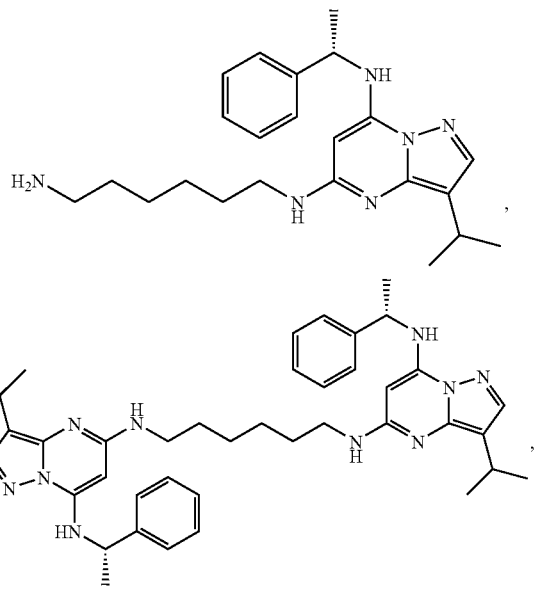
,

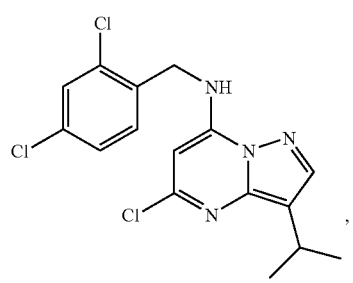
,

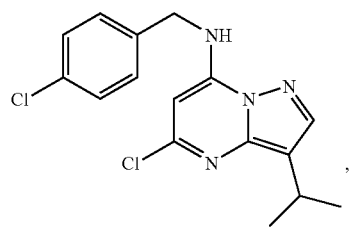
,

241
-continued
242
-continued
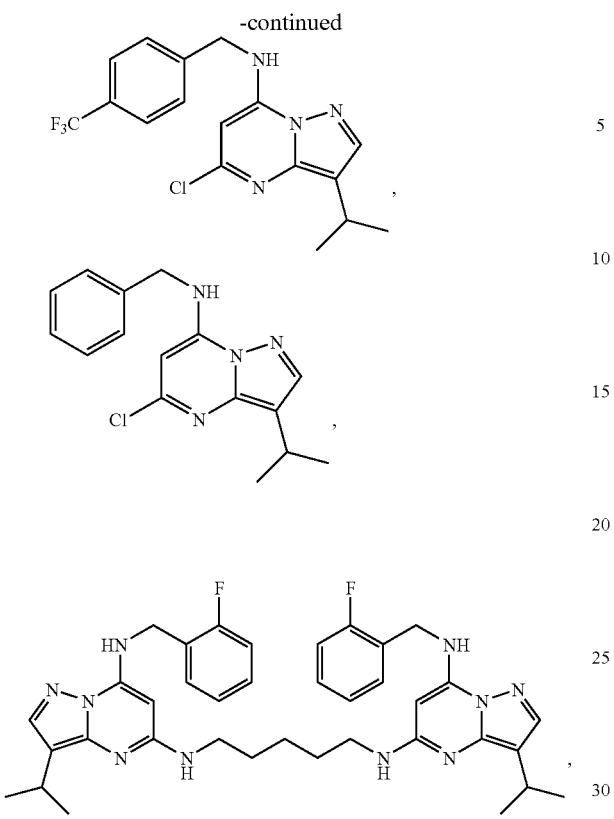
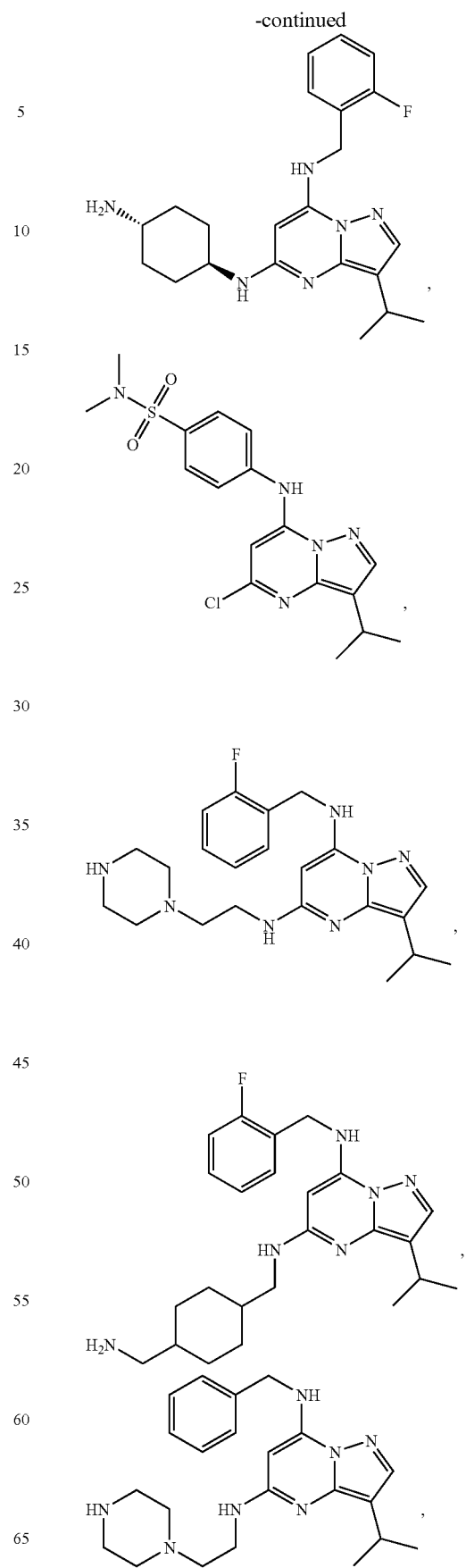

243
-continued
244
-continued
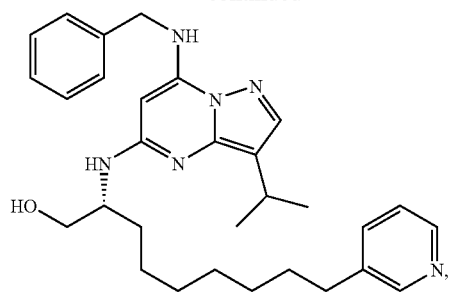
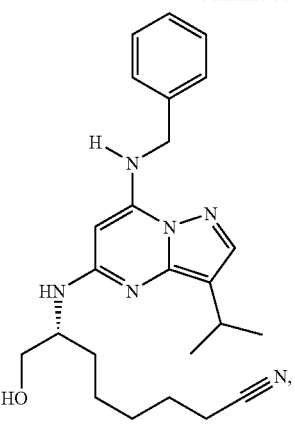
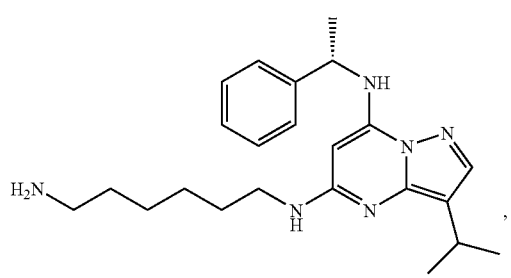
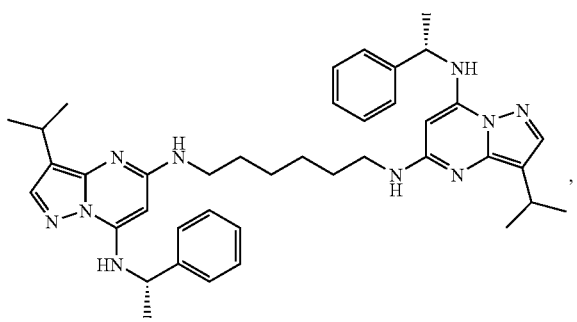
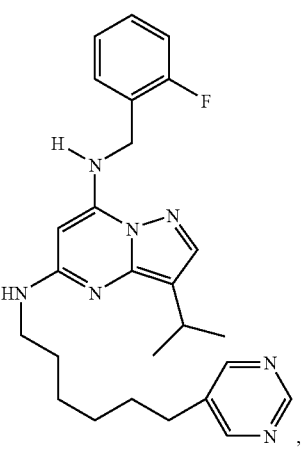

245
-continued
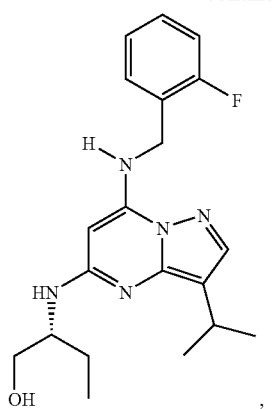
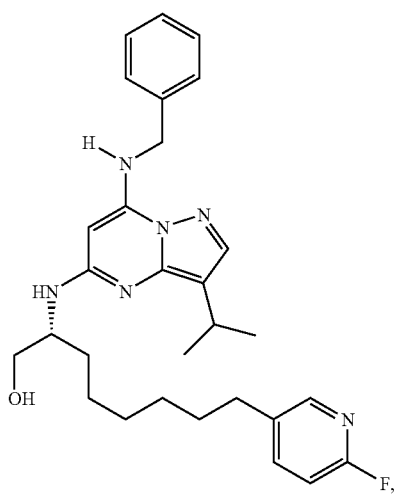
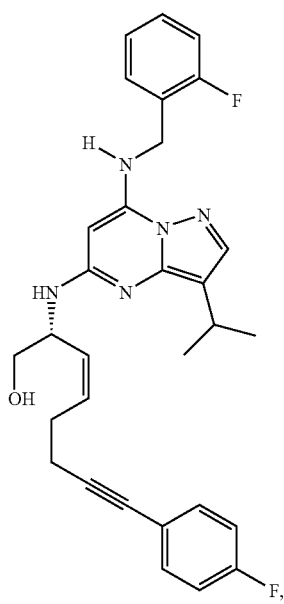
246
-continued
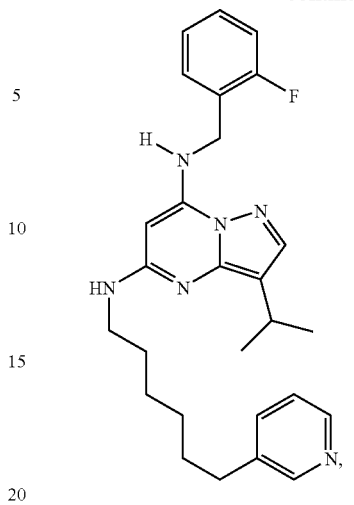
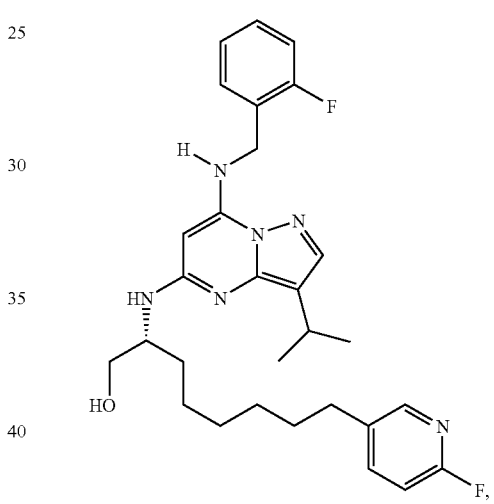
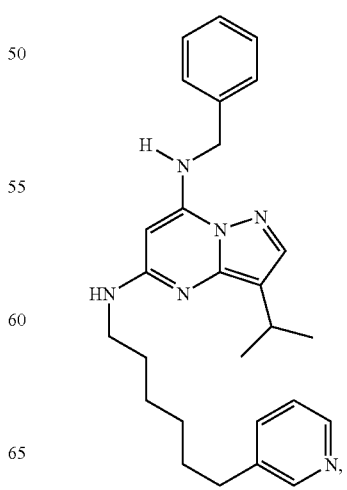

247
-continued
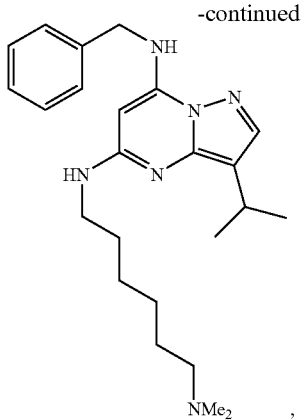
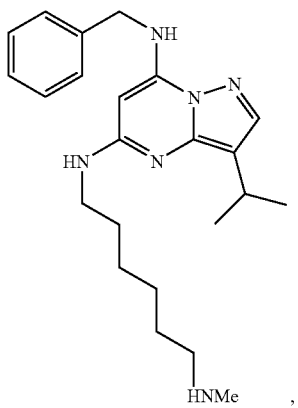
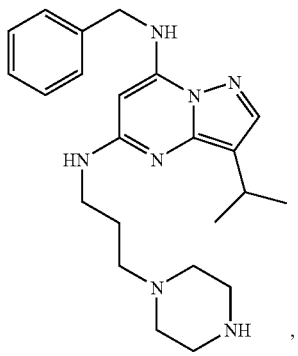
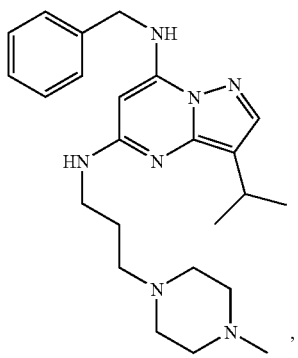
248
-continued
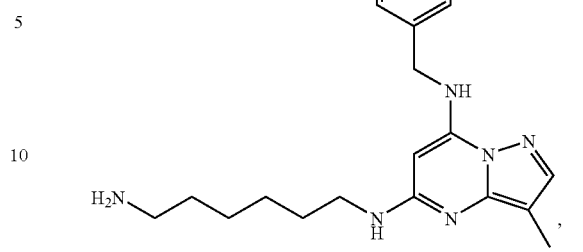
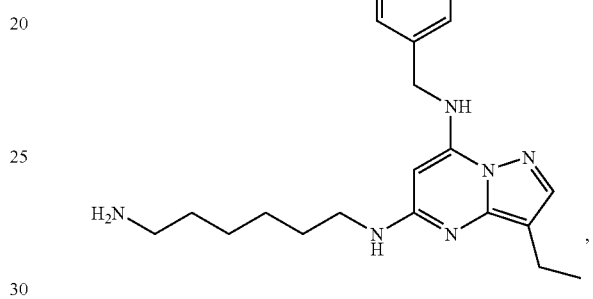
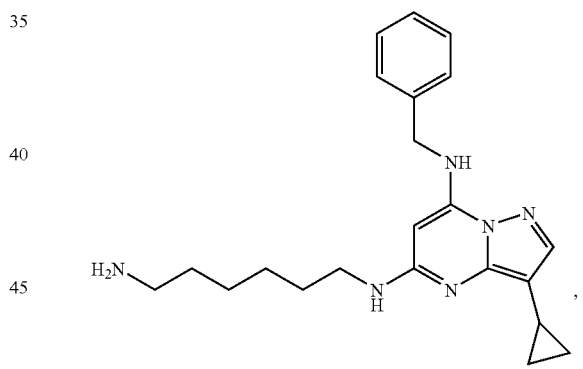
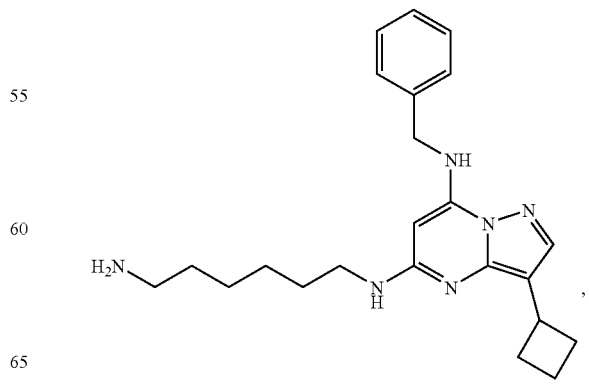

-continued
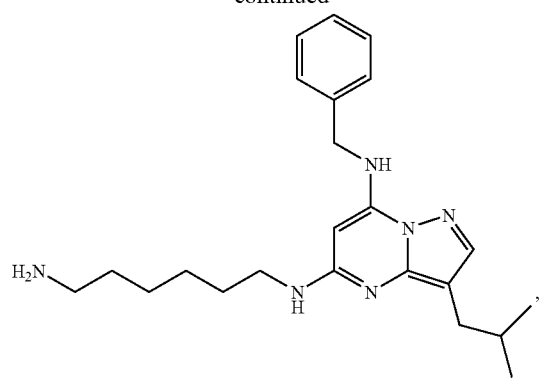
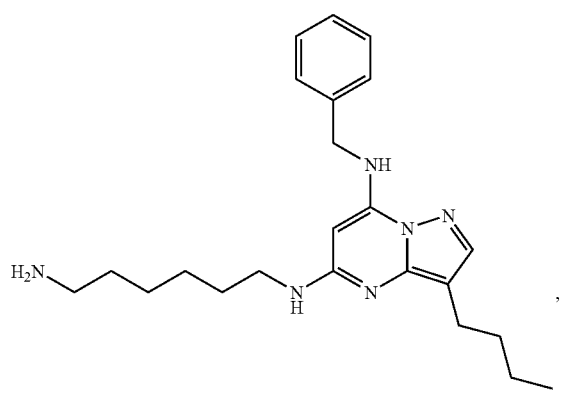
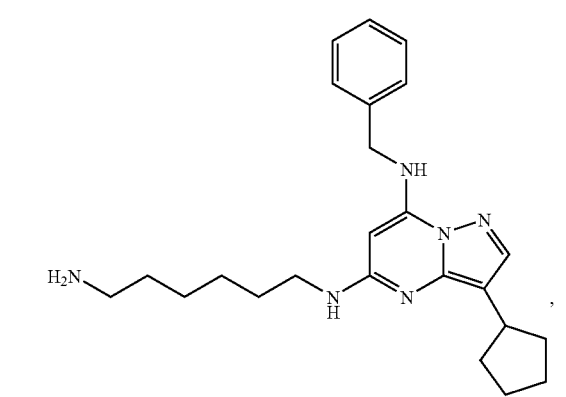
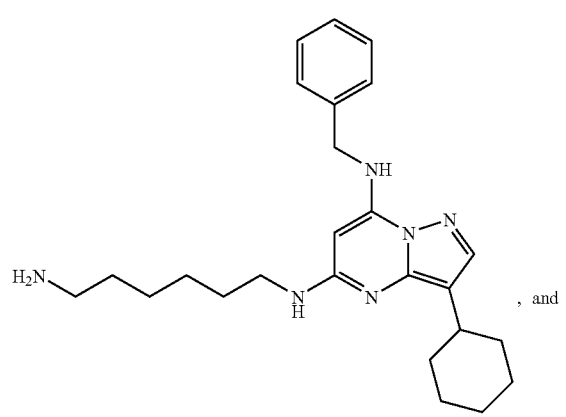
-continued
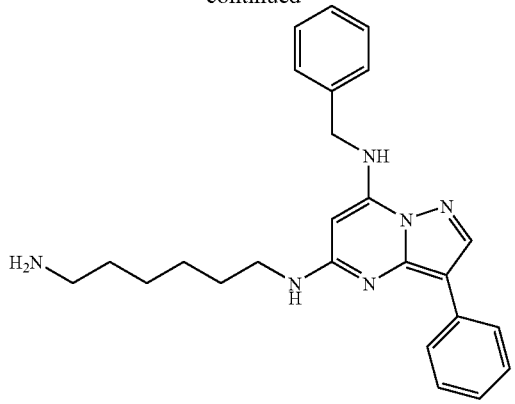
3. The composition according to claim 1, wherein the compound has the following structure:
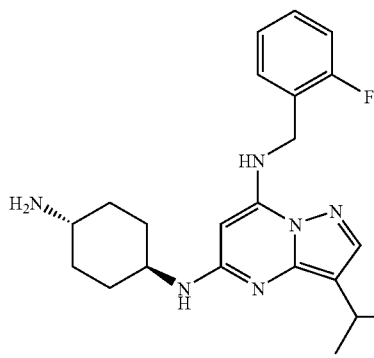
4. The composition according to claim 1, wherein the compound has the following structure:
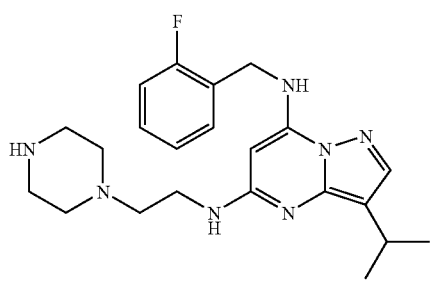

5. The composition according to claim 1, wherein the compound has the following structure:

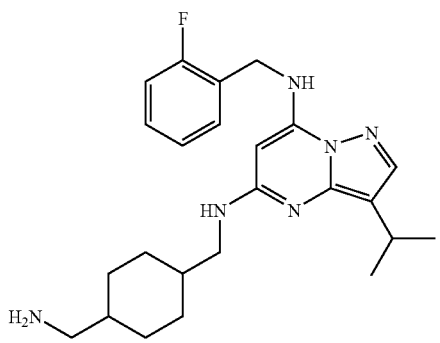

6. The composition according to claim 1, wherein the compound has the following structure:

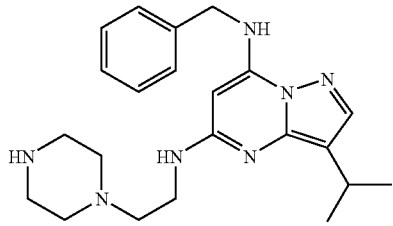

7. The composition according to claim 1, wherein the compound has the following structure:

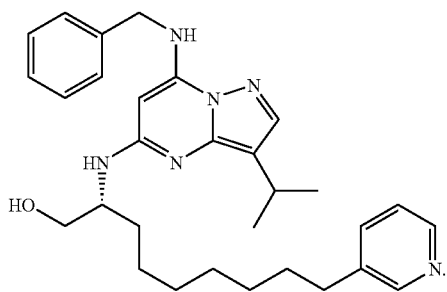

8. The composition according to claim 1, wherein the compound has the following structure:

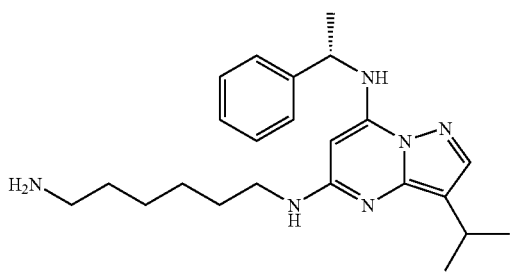

9. The composition according to claim 1, wherein the compound has the following structure:

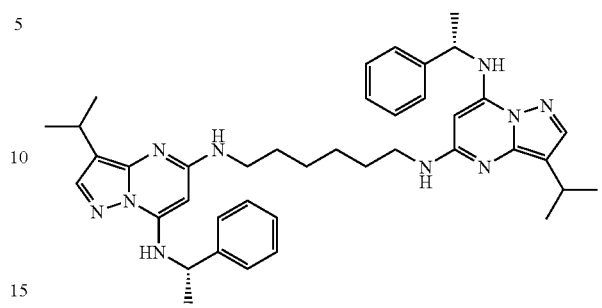

10. The composition according to claim 1, wherein the compound has the following structure:

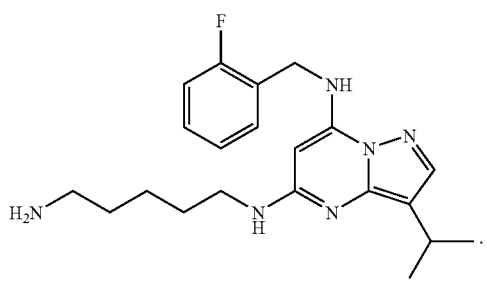

11. The composition according to claim 1, wherein the compound has the following structure:

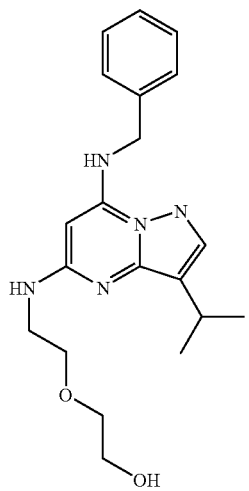

12. The composition according to claim 1, wherein the compound has the following structure:

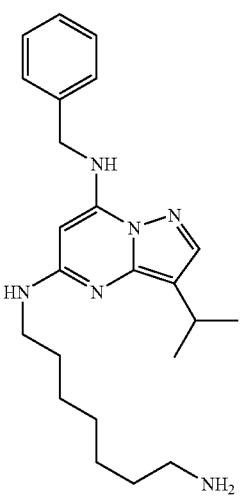

13. The composition according to claim 1, wherein the compound has the following structure:

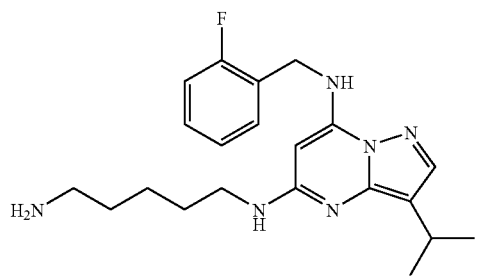

14. A composition comprising a compound with the following structure:

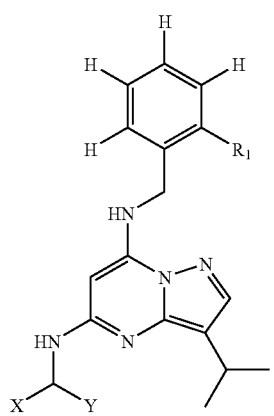

wherein
- $R^1$ is either fluorine or hydrogen;
- X represents a hydrogen or a group -$Alk^2$-Z, wherein $Alk^2$ is an alkanyl containing one or two carbon atoms; and Z represents an —OH group;
- Y represents a group -$Alk^5$, wherein $Alk^5$ comprises one or two carbons, with proviso that $Alk^5$ may be aliphatic or olefinic when it comprises two carbons, and wherein $Alk^5$ is optionally substituted with one hydroxyl group on each carbon atom when $Alk^5$ is not olefinic;

and wherein X and Y, along with the carbon atom joining X and Y, do not form an unsubstituted $C_1$ to $C_6$ alkyl.

15. The composition according to claim 14, wherein the compound is selected from the group consisting of:

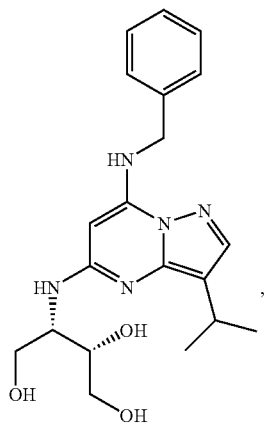

,

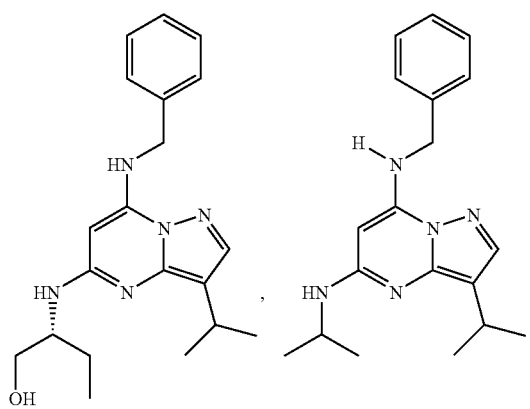

,

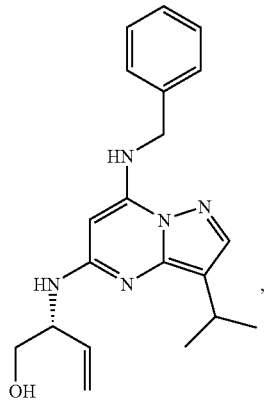

,

255
-continued
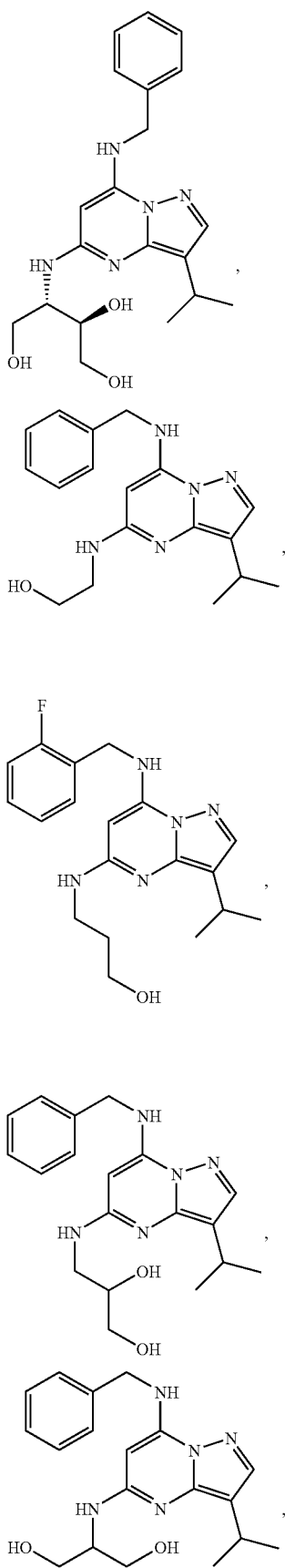
256
-continued
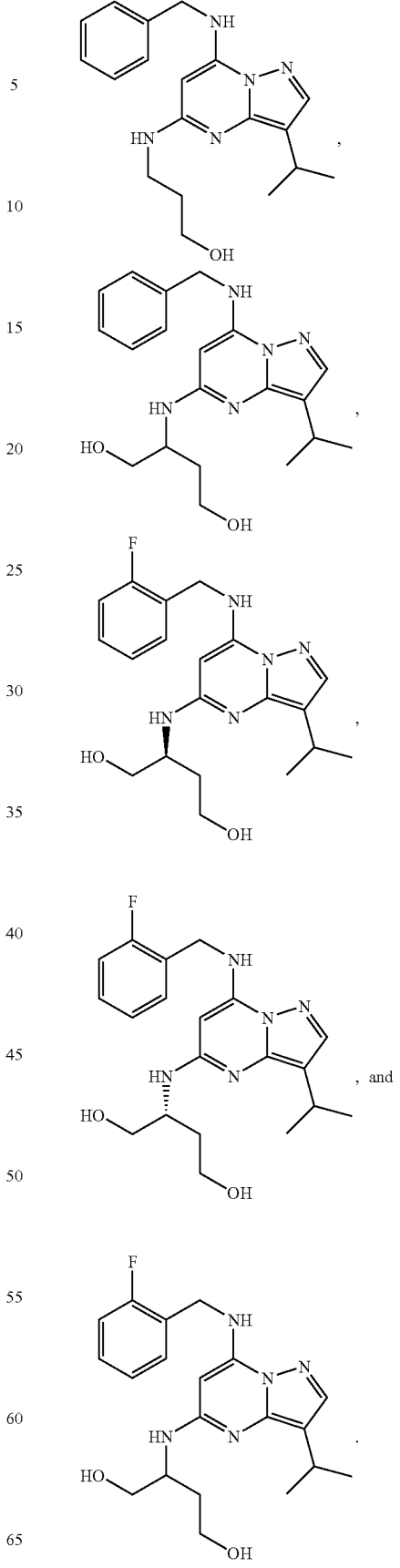

16. A composition comprising a compound with the following structure:

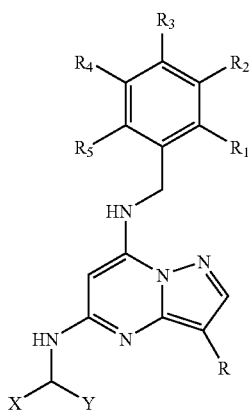

wherein
- R represents a hydrocarbyl containing from 1 to 6 carbon atoms;
- $R^1$ represents a hydroxyl, alkoxy, hydrogen, or halogen;
- $R^2$ represents a hydrogen, an alkanyl, —$NR_aR_b$ where $R_a$ and $R_b$ are independently optionally substituted hydrocarbyls having up to six carbon atoms, an alkoxy chain having from 1 to 6 carbon atoms, —$SR_c$ where $R_c$ is a hydrocarbyl containing from one to six carbon atoms, —$SO_2R_d$ where Rd is a hydrocarbyl containing from one to six carbon atoms, or a halogen;
- $R^3$ is hydrogen, —$SO_2NH_2$, —$SO_2NR_eR_f$ where $R_e$ and $R_f$ are independently optionally substituted hydrocarbyls having up to 6 carbon atoms, halogen or a group -(A)$_a$-$Alk^1$ wherein a is 0 or 1, and when a is 1, A is —O—, —S—, or —$NR^6$ wherein $R^6$ is hydrogen or a $C_1$-$C_5$ alkanyl chain, and $Alk^1$ is an optionally substituted divalent hydrocarbyl chain containing from 1 to 6 carbon atoms in length and optionally unsaturated bonds between at least two carbon atoms of $Alk^1$ when $Alk^1$ contains at least two carbon atoms;
- $R^4$ represents hydrogen, halogen, alkoxy, hydroxy, or an optionally substituted hydrocarbyl group containing up to 6 carbon atoms;
- $R^5$ represents a hydrogen, hydroxyl, alkoxy, a linear, branched, or cyclic chain with between 1 and 8 carbon atoms, or halogen;
- X represents a hydrogen, a group -$Alk^2$-Z, $C_1$-$C_4$ hydrocarbyl group or halogen, wherein $Alk^2$ is an optionally substituted divalent alkanyl, alkenyl, or alkynyl chain containing from 1 to 6 carbon atoms in length; and Z represents an —OH, —$OR^7$, —SH, $SR^7$, —CN, —$NH_2$, or $NHR^7$ group, wherein $R^7$ is a $C_1$-$C_6$ hydrocarbyl or heterocyclic group optionally substituted by halogen or alkoxy;
- Y represents a group -$Alk^3$-(Q)$_a$-($Alk^4$)$_b$-B, wherein a and b are independently 0 or 1, and wherein $Alk^3$ represents a hydrocarbyl chain containing from 2 to 7 carbon atoms in length, wherein said hydrocarbyl chain optionally comprises double and/or triple bonds in between carbon atoms of said hydrocarbyl chain, and wherein said hydrocarbyl chain is optionally substituted with a halogen, hydroxyl, alkoxy, or an alkyl chain that itself is optionally substituted with halogen, hydroxyl, or alkoxy groups;
- Q is selected from the group consisting of —$CH_2$—, —O—, —S—, —NR—, —S(O)—, —C(=O)—, and —S(O)—;
- $Alk^4$ is an alkanyl chain; and
- B is hydroxyl, alkoxy, halogen, alkylthio, nitro, cyano, amine, an optionally substituted carbocyclic group, an optionally substituted heterocyclic group, and wherein X and Y, along with the carbon atom joining X and Y, do not form an unsubstituted $C_1$ to $C_6$ alkyl.

* * * * *